US012655227B2

(12) United States Patent
Wang et al.

(10) Patent No.: US 12,655,227 B2
(45) Date of Patent: Jun. 16, 2026

(54) MODIFIED FC REGION

(71) Applicant: Agency for Science, Technology and Research, Singapore (SG)

(72) Inventors: Cheng-I Wang, Singapore (SG); Patricia Ng, Singapore (SG); John Connolly, Singapore (SG); Chia Yin Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1256 days.

(21) Appl. No.: 17/296,184

(22) PCT Filed: Nov. 21, 2019

(86) PCT No.: PCT/SG2019/050570
§ 371 (c)(1),
(2) Date: May 21, 2021

(87) PCT Pub. No.: WO2020/106220
PCT Pub. Date: May 28, 2020

(65) Prior Publication Data
US 2022/0340684 A1 Oct. 27, 2022

(30) Foreign Application Priority Data

Nov. 22, 2018 (SG) ........................... 10201810463Y

(51) Int. Cl.
| | |
|---|---|
| *C07K 16/40* | (2006.01) |
| *A61P 37/04* | (2006.01) |
| *C07K 14/47* | (2006.01) |
| *A61K 38/00* | (2006.01) |

(52) U.S. Cl.
CPC .............. *C07K 16/40* (2013.01); *A61P 37/04* (2018.01); *C07K 14/47* (2013.01); *A61K 38/00* (2013.01); *C07K 2317/21* (2013.01); *C07K 2317/24* (2013.01); *C07K 2317/31* (2013.01); *C07K 2317/52* (2013.01); *C07K 2317/524* (2013.01); *C07K 2317/526* (2013.01); *C07K 2317/74* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 2018/0037634 A1* | 2/2018 | Viswanathan et al. ..................... C07K 16/00 |
| 2018/0162946 A1* | 6/2018 | Chamberlain ....... C07K 16/082 |
| 2021/0238308 A1 | 8/2021 | Ikawa et al. | |

FOREIGN PATENT DOCUMENTS

| | | | |
|---|---|---|---|
| WO | WO 2016/164480 A1 * | 10/2016 | ......... C07K 16/2875 |
| WO | WO-2019/235426 A1 | 12/2019 | |
| WO | WO-2020/106220 A1 | 5/2020 | |

OTHER PUBLICATIONS

Foss, S. et al., TRIM21 Immune Signaling Is More Sensitive to Antibody Affinity Than Its Neutralization Activity, J. Immunol., 196:3452-3459 (2016).
Gros, M. and Amigorena, S., Regulation of Antigen Export to the Cytosol During Cross-Presentation, Front. Immunol., 10(41):1-9 (2019).
International Search Report for PCT/SG2019/050570, 6 pages (mailed Feb. 11, 2020).
James, L. C. et al., Structural basis for PRYSPRY-mediated tripartite motif (TRIM) protein function, PNAS, 104(15):6200-6205 (2007).
Ng, P. M. L. et al., Enhancing Antigen Cross-Presentation in Human Monocyte-Derived Dendritic Cells by Recruiting the Intracellular Fc Receptor TRIM21, J. Immunol., 202:2307-2319 (2019).
Written Opinion for PCT/SG2019/050570, 7 pages (mailed Feb. 11, 2020).

* cited by examiner

*Primary Examiner* — Joanne Hama
*Assistant Examiner* — Estella M. Gustilo
(74) *Attorney, Agent, or Firm* — Polsinelli PC

(57) ABSTRACT

Fc regions comprising modification to increase the affinity of association between the Fc region and TRIM21 are disclosed. Also disclosed are constituent polypeptides of such Fc regions, antigen-binding molecules and immunogens comprising such Fc regions, and nucleic acids encoding and methods using such Fc regions, antigen-binding molecules and immunogens.

4 Claims, 47 Drawing Sheets

Specification includes a Sequence Listing.

TRIM21
(PRYSPRY domain)

SVFLFPPKPKDTLMISRTPEVTCVVV
DVSHEDPEVKFNWYVDGVEVHNAKTK
PREEQYNSTYRVVSVLTVLHQDWLNG
KEYKCKVSNKALPAPIEKTISKAKGQ
PREPQVYTLPPSREEMTKNQVSLTCL
VKGFYPSDIAVEWESNGQPENNYKTT
PPVLDSDGSFFLYSKLTVDKSRWQQG
NVFSCSVMHEALHNHYTQKSLSLSPG
K (SEQ ID NO: 185)

Sequences of Fc variants from biopanning

|  | Biopanning of FC library | |
|---|---|---|
|  | Round 2 | Round 3 |
| Clone #1 (TRHFTQKI) SEQ ID NO. 187 | 5 hits | 49 hits |
| Clone #2 (HNHYTQQR) SEQ ID NO. 186 | 2 hits | 0 hits |
| Wild type (HNHYTQKS) SEQ ID NO. 188 | 10 hits | 0 hits |
| Single hit sequences | 18 sequences | 1 sequence |
| Nonsense sequences | 15 sequences | 2 sequences |

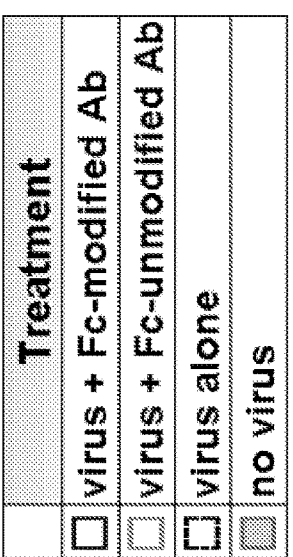
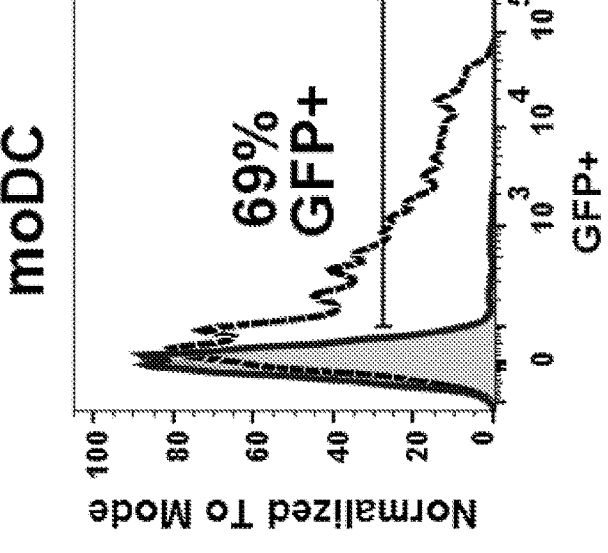
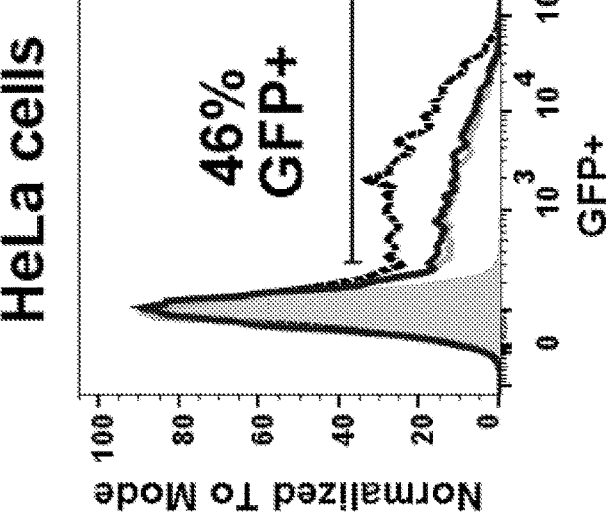
Figure 2A

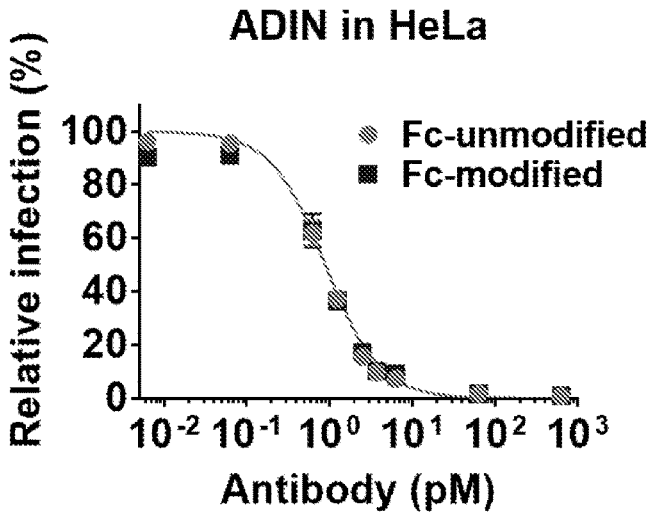
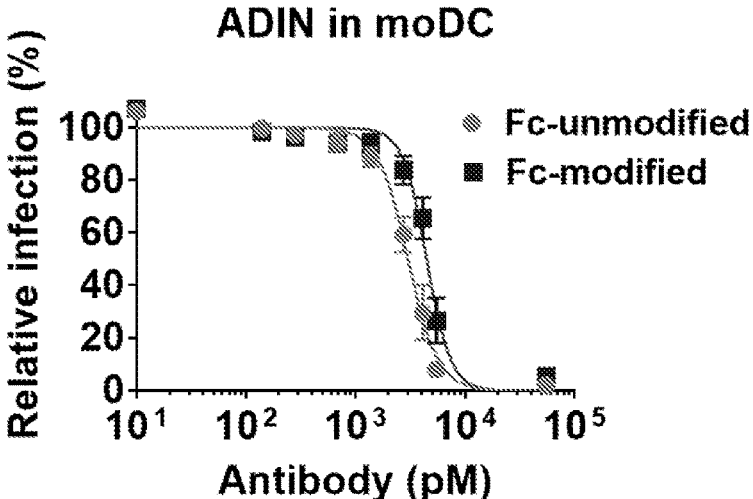
Figure 2B
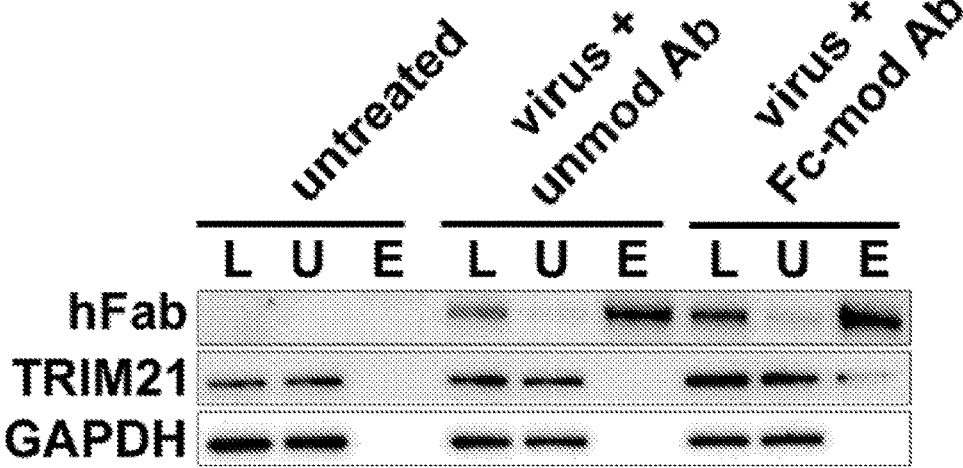
Figure 2C

Fold change of cytokine levels
(modified relative to unmodified)

Relative CD4 T cell count
(7 donors)
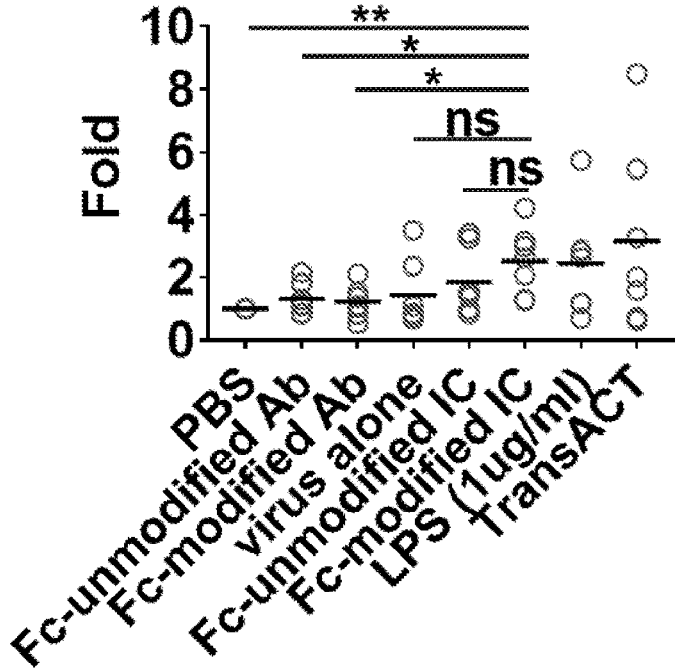
Relative CD8 T cell count
(7 donors)
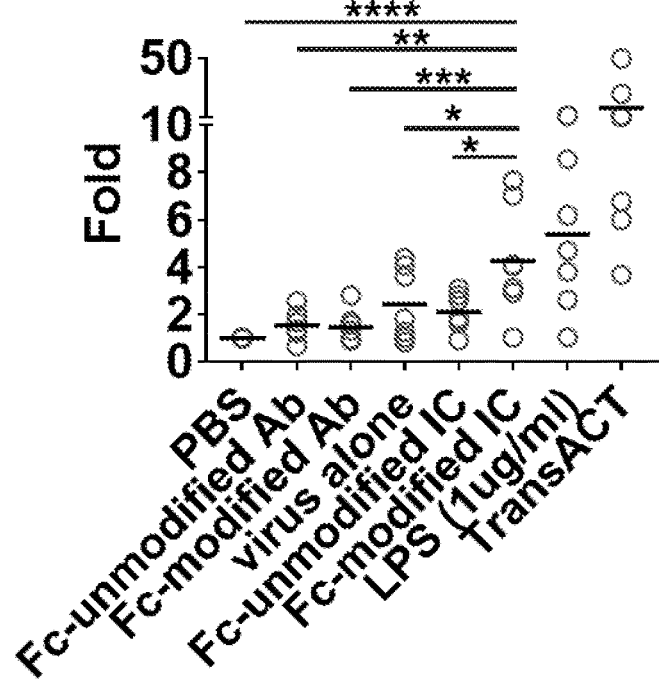
Figure 5C

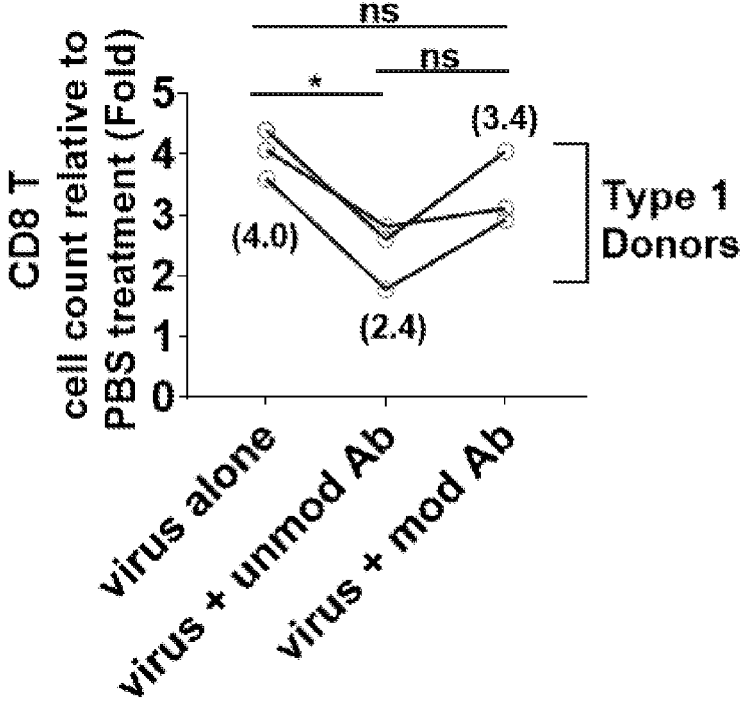
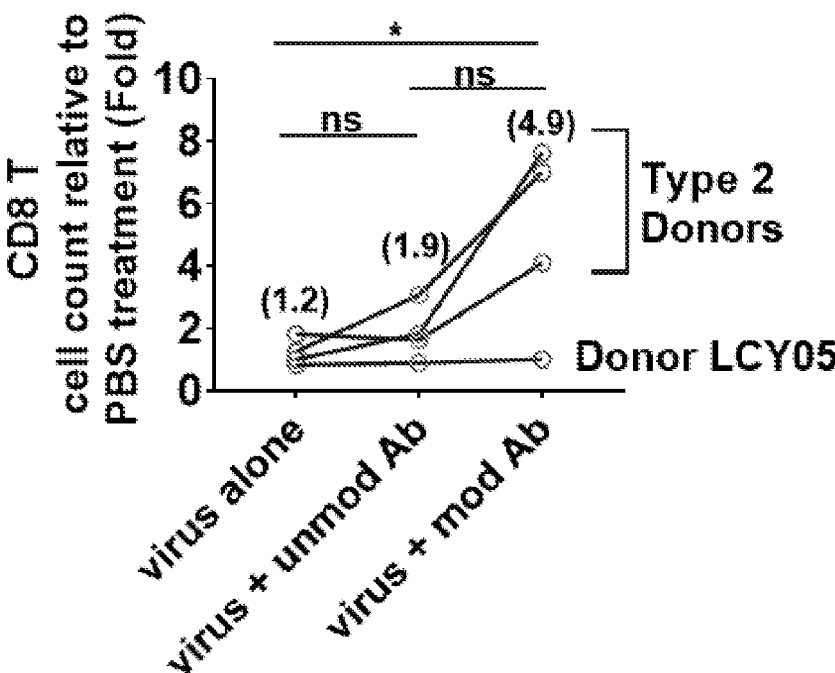
Figure 5D

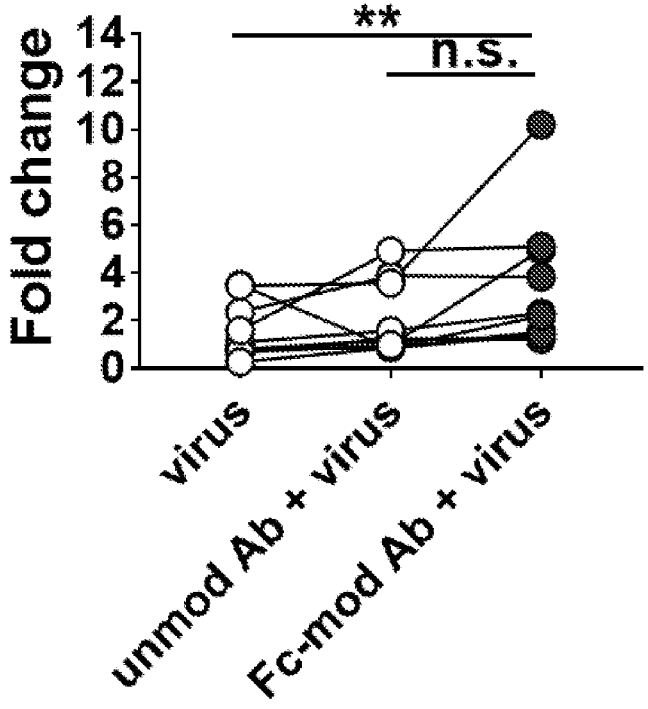
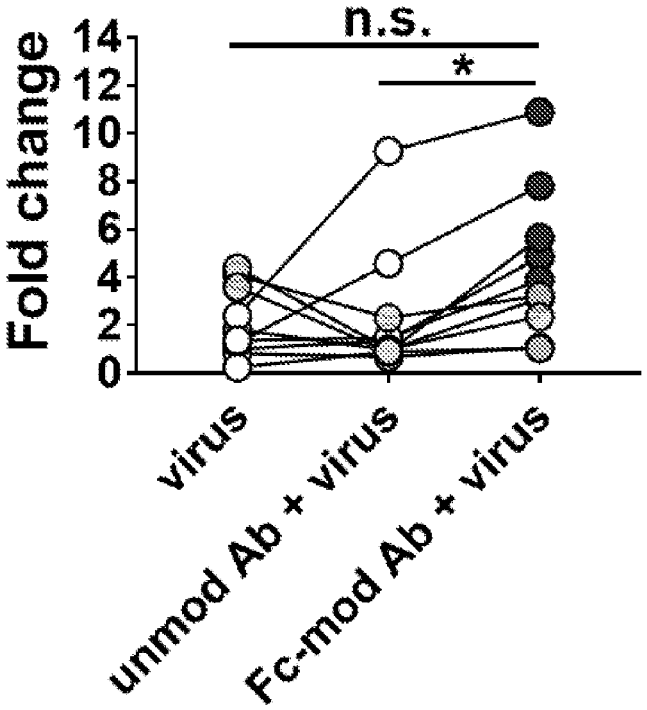
Figure 5E

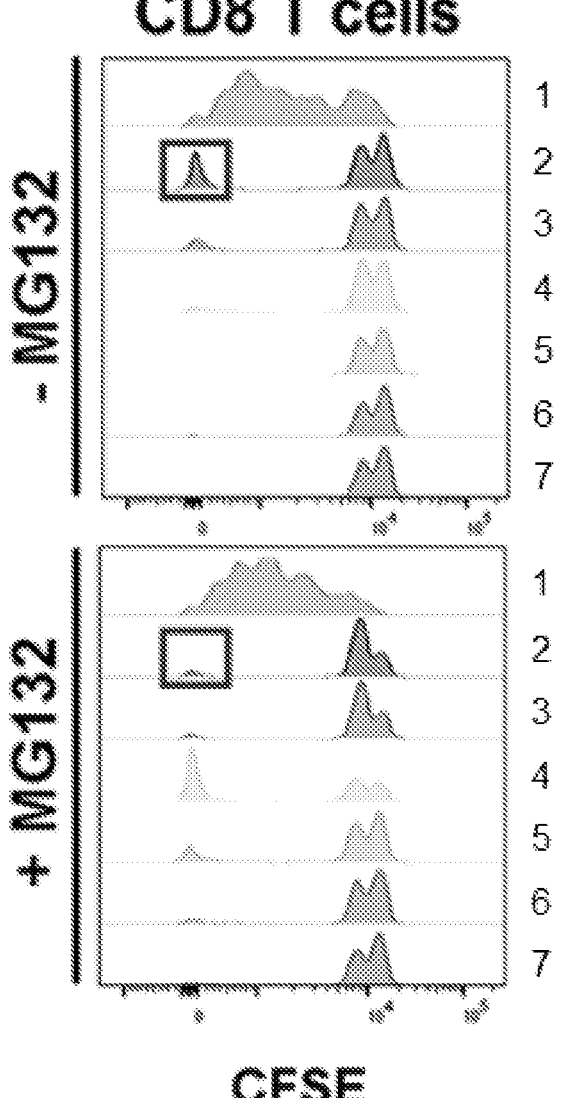
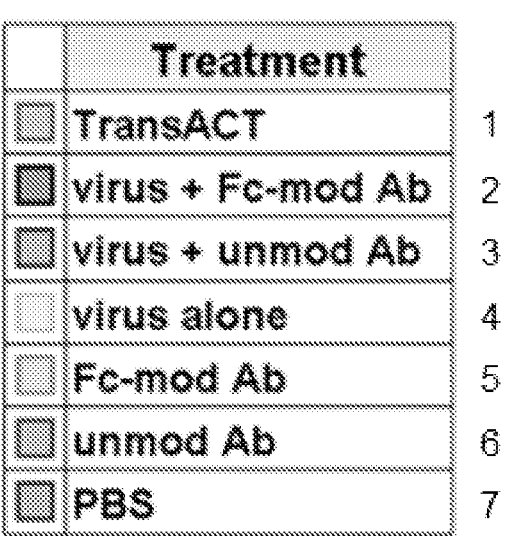
Figure 8E

```
SEQ ID NO: 07 IGHG1   ASTKGPSVFPLAPSSKSTS--GGTAALGCLVKDYFPEP-VTVSWNSGALT--SGVHTFPA 55
SEQ ID NO: 11 IGHG2   ASTKGPSVFPLAPCSRSTS--ESTAALGCLVKDYFPEP-VTVSWNSGALT--SGVHTFPA 55
SEQ ID NO: 15 IGHG3   ASTKGPSVFPLAPCSRSTS--GGTAALGCLVKDYFPEP-VTVSWNSGALT--SGVHTFPA 55
SEQ ID NO: 19 IGHG4   ASTKGPSVFPLAPCSRSTS--ESTAALGCLVKDYFPEP-VTVSWNSGALT--SGVHTFPA 55
SEQ ID NO: 23 IGHA1   ASPTSPKVFPLSLCST-QPDG--NVVIACLVQGFFPQEPLSVTWSESGQG--VTARNFPP 55
SEQ ID NO: 24 IGHA2   ASPTSPKVFPLSLDST-PQDG--NVVVACLVQGFFPQEELSVTWSESGQN--VTARNFPP 55
SEQ ID NO: 25 IGHD    APTKAPDVFPIISGCR-HPKDNSPVVLACLITGYHPTS-VTVTWYMGTQS--QPQRTFPE 56
SEQ ID NO: 26 IGHE    ASTQSPSVFPLTRCCKNIPSNATSVTLGCLATGYFPEP-VMVTWDIGSLN--GTTMTLPA 57
SEQ ID NO: 27 IGHM    GSASAPTLFPLVSCEN-SPSDTSSVAVGCLAQDFLPDS-ITFSWKYKNNSDISSTRGFPS 58
                       .   .* ;**;              ..;.** .; *   ; .;*          ;*

IGHG1   V-LQSSGLYSLSSVVTVPSSSLGT---QTYICNVNHKPSNTKVDKKVE-------------- 99
           IGHG2   V-LQSSGLYSLSSVVTVPSSNFGT---QTYTCNVDHKPSNTKVDKTVERK------------ 101
           IGHG3   V-LQSSGLYSLSSVVTVPSSSLGT---QTYTCNVNHKPSNTKVDKRVELKTPLGDTTHTC 111
           IGHG4   V-LQSSGLYSLSSVVTVPSSSLGT---KTYTCNVDHKPSNTKVDKRVESK----------- 101
           IGHA1   SQDASGDLYTTSSQLTLPA------------------------------------------ 74
           IGHA2   SQDASGDLYTTSSQLTLPA------------------------------------------ 74
           IGHD    I-QRRDSYYMTSSQLSTPLQQWRQ---GEYKCVVQHTASKSKKEIF-------------- 98
           IGHE    TILILSGHYATISLLIV-SGANAK---QMFTCRVAHTPSSTDWVDNKIFSVCSRDFTPPT 113
           IGHM    V---LRGGKYAATSQVLLPSKDVMQGTDEHVVCKVQHPNGNKEK---N---VPLPVIAELPPK 112
                        ..  *    *  ;

IGHG1   ------------------------------------------------------------ 99
           IGHG2   ------------------------------------------------------------ 101
           IGHG3   PKCPEPKSCDTPPPCPR-----CPE-----P-----------K---------------- 133
           IGHG4   ------------------------------------------------------------ 101
           IGHA1   ------------------------------------------------------------ 74
           IGHA2   ------------------------------------------------------------ 74
           IGHD    --------------------------------RWPESPKAQASSVPTAQPQAEGSLA 123
           IGHE    VK-ILQSSCDGGGHFPPTIQLLCLVSGYTPGTINITWLEDGQVMDVDLSTASTTQEGE--- 170
           IGHM    VS-VFVPPRDGFFGNPRKSKLICQATGFSPRQIQVSWLREGKQVGSGVTTDQVQAEAKES 171

IGHG1   ------------------------------PKSCDKTHTCPPCPAPELL----------- 118
           IGHG2   ------------------------------CCVECPPCPAPPV----------------- 114
           IGHG3   ---------------------SCDTPPPCPRCPEPKSCDTPPPCPRCPAPELL-------- 165
           IGHG4   ---------------------------YGPPCPSCPAPEFL------------------- 115
           IGHA1   ----------------TQCLAGKSVTCHVKHYTNP--SQDVTVPCPVESTPPTPSPSTPPT 117
           IGHA2   ----------------TQCPDGKSVTCHVKHYTNS--SQDVTVPCRVPP----------- 105
           IGHD    KATTAPATTRNT------GRGGEEKKK--EKEKEEQEEREIKTPECPSHT---------- 165
           IGHE    ----LASTQSELTLSQKHWLSDRTYTCQVTYQGHT--FEDSTKKCAD-SNP-------- 214
           IGHM    GPTTYKVTSTLTIKESDWLGQSMFTCRVDHRGLT--FQQNASSMCVPDQ--------- 218

IGHG1   ------GGPSVFLFPPKPKDTLMISRTPEVTCVVVDVSHEDPEVKFNWYVDGVEVHN-AKT 172
           IGHG2   ------AGPSVFLFPPKPKDTLMISRTPEVTCVVVDVSHEDPEVQFNWYVDGVEVHN-AKT 168
           IGHG3   ------GGPSVFLFPPKPKDTLMISRTPEVTCVVVDVSHEDPEVQFKWYVDGVEVHN-AKT 219
           IGHG4   ------GGPSVFLFPPKPKDTLMISRTPEVTCVVVDVSQEDPEVQFNWYVDGVEVHN-AKT 169
           IGHA1   PSPSCCHPRLSLHRP-ALEDLLLGSEANLTCTLTGLRDAS-GVTFTWTPSSGKSAV-QGP 174
           IGHA2   -PPPCCHPRLSLHRP-ALEDLLLGSEANLTCTLTGLRDAS-GATFTWTPSSGKSAV-QGP 161
           IGHD    ------QPLGVYLLTP-AVQDLWLRDKATFTCFVVGSDLKD--AHLIWEVAGKVPTGVTE 217
           IGHE    ------RGVSAYLSRPSPF-DLFIRKSPTITCLVVDLAPSKGTVDLTWSRASGKPVN-HST 267
           IGHM    ------DTAIRVFAIPP-SFASIFLTKSTKLTCLVTDLTTYD-SVTISWTRQNGEAVK-THT 271
                          *         ;  ;   .;** ;..   ; .;;.*    ;.
```

Figure 9A

```
SEQ ID NO: 07 IGHG1   KPREEQYNSTYRVVSVLTVLHQDWLNGKEYKCKVSNKALPAPIEKTISKAKGQ-PREPQV 231
SEQ ID NO: 11 IGHG2   KPREEQFNSTFRVVSVLTVVHQDWLNGKEYKCKVSNKGLPAPIEKTISKTKGQ-PREPQV 227
SEQ ID NO: 15 IGHG3   KPREEQYNSTFRVVSVLTVLHQDWLNGKEYKCKVSNKALPAPIEKTISKTKGQ-PREPQV 278
SEQ ID NO: 19 IGHG4   KPREEQFNSTYRVVSVLTVLHQDWLNGKEYKCKVSNKGLPSSIEKTISKAKGQ-PREPQV 228
SEQ ID NO: 23 IGHA1   ---PERDLCGCYSVSSVLPGCAEPWNHGKTFTCTAAYPESKTPLTAILSKS--GNTFRPEV 230
SEQ ID NO: 24 IGHA2   --PERDLCGCYSVSSVLPGCAQPWNHGETFTCTAAHPELKTPLTANITKS--GNTFRPEV 217
SEQ ID NO: 25 IGHD    GLLERHSNGSQSQHSRLTLPRSLWNAGTSVTCTLNHPSLPPQRLMALREPAAQAPVKLSL 277
SEQ ID NO: 26 IGHE    RKEEKQRNGTLTVTSTLPVGTRDWIEGETYQCRVTHPHLPRALMRSTTKTSGP-RAAPEV 326
SEQ ID NO: 27 IGHM    NISESHPNATFSAVGEASICEDDWNSGERFTCTVTHTDLPSPLKQTISRPKGVALHRPDV 331
                       *  .   *       .        *   *    *                     .      .:

IGHG1   YTLPPSRDELT-KNQVSLTCLVKGFYPSDIAVEWESNGQ---PENNYKTTPPVLDSD---G 285
              IGHG2   YTLPPSREEMT-KNQVSLTCLVKGFYPSDISVEWESNGQ--PENNYKTTPPMLDSD---G 281
              IGHG3   YTLPPSREEMT-KNQVSLTCLVKGFYPSDIAVEWESSGQ---PENNYNTTPPMLDSD---G 332
              IGHG4   YTLPPSQEEMT-KNQVSLTCLVKGFYPSDIAVEWESNGQ---PENNYKTTPPVLDSD---G 282
              IGHA1   HLLPPPSEELALNELVTLTCLARGFSPKDVLVRWLQGSQELPREKYLTWASRQEPSQGTT 290
              IGHA2   HLLPPPSEELALNELVTLICLARGFSPKDVLVRWLQGSQELPREKYLTWASRQEPSQGTT 277
              IGHD    NLLASSDPP---EAASWLLCEVSGFSPPNILLMWLEDQREVNTSGFAPARPP--PQPRST 332
              IGHE    YAFATPEWPGS-RDKRTLACLIQNFMPEDISVQWLHNEVQLPDARHSTTQPRKTKG---S 382
              IGHM    YLLPPAREQLNLRESATITCLVTGFSPADVFVQWMQRGQPLSPEKYVTSAPMPEPQAP-G 390
                         :     * *      .       :  *     .* *  ::  :  *          .

IGHG1   SFFLYSKLTVDKSRWQQGNVFSCSVMHEALHN-HYTQKSLSLSPGK---------------- 330
              IGHG2   SFFLYSKLTVDKSRWQQGNVFSCSVMHEALHN-HYTQKSLSLSPGK---------------- 326
              IGHG3   SFFLYSKLTVDKSRWQQGNIFSCSVMHEALHN-RFTQKSLSLSPGK---------------- 377
              IGHG4   SFFLYSRLTVDKSRWQEGNVFSCSVMHEALHN-HYTQKSLSLSLGK---------------- 327
              IGHA1   TFAVTSILRVAAEDWKKGDTFSCMVGHEALPL-AFTQKTIDRLAGKPTHVNVSVVMAEVD 349
              IGHA2   TYAVTSILRVAAEDWKKGETFSCMVGHEALPL-AFTQKTIDRMAGKPTHINVSVVMAEAD 336
              IGHD    TFWAWSVLRVPAPPSPQPATYTCVVSHEDSRTLLNASRSLEVSYVT-----------DH-- 380
              IGHE    GFFVFSRLEVTRAEWEQKDEFICRAVHEAASPSQTVQRAVSVNPGK---------------- 428
              IGHM    RYFAHSILTVSEEEWNTGETYTCVVAHEALPN-RVTERTVDKSTGKPTLYNVSLVMSDTA 449
                        :   * * *        :  *  . **      ..::::.      .

IGHG1   ----- 330
              IGHG2   ----- 326
              IGHG3   ----- 377
              IGHG4   ----- 327
              IGHA1   GTCY  353
              IGHA2   GTCY  340
              IGHD    GPMK  384
              IGHE    ----- 428
              IGHM    GTCY  453
```

Figure 9B

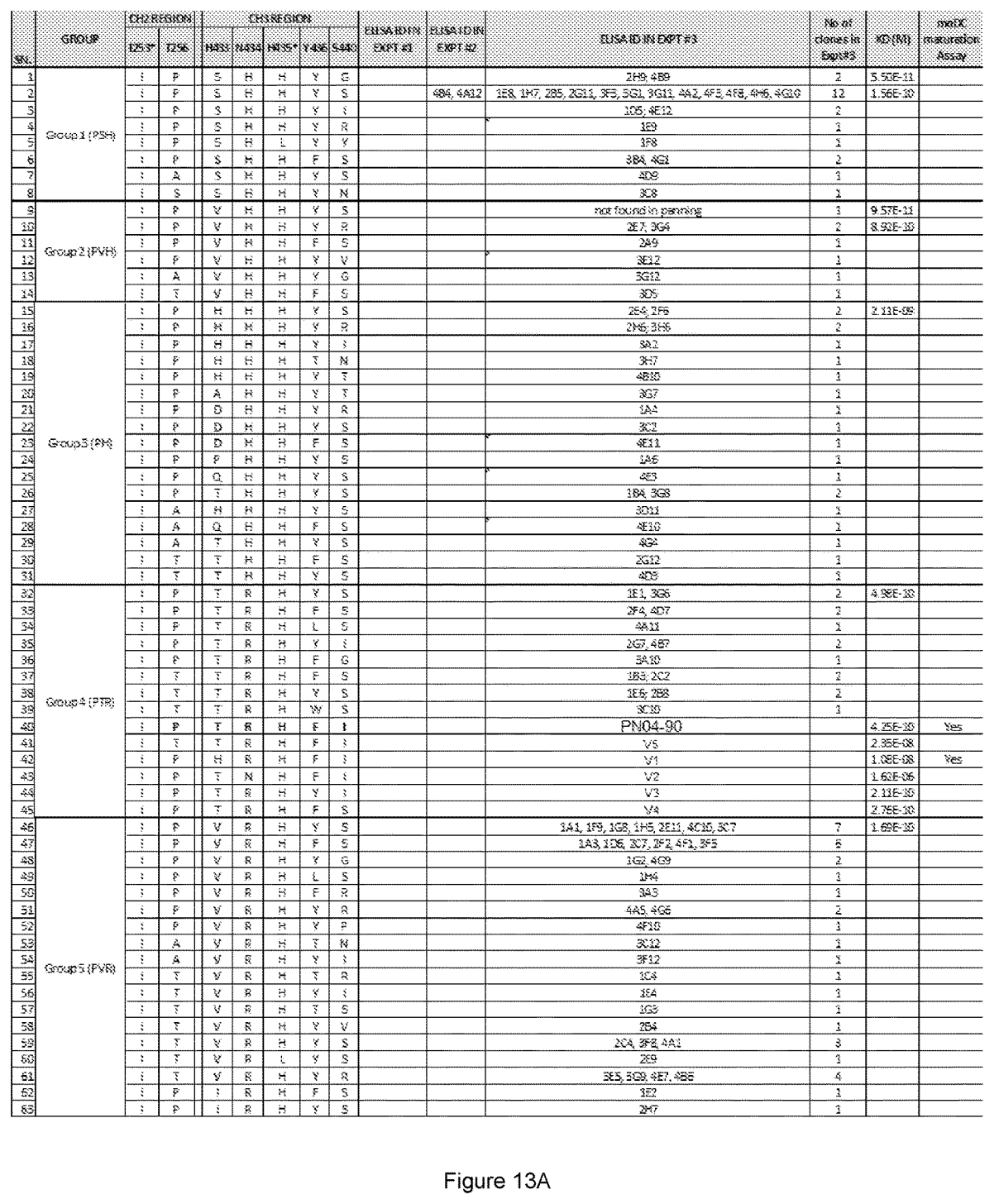

| SN | GROUP | CH2 REGION | | CH3 REGION | | | | | ELISA ID IN EXPT #1 | ELISA ID IN EXPT #2 | ELISA ID IN EXPT #3 | No of clones in Expt#3 | KD (M) | maX maturation Assay |
|---|---|---|---|---|---|---|---|---|---|---|---|---|---|---|
| | | I253* | T256 | N433 | N434 | H435* | Y436 | S440 | | | | | | |
| 1 | Group 1 (PSH) | I | P | S | H | H | Y | G | | | 2H9; 4B9 | 2 | 5.50E-11 | |
| 2 | | I | P | S | H | H | Y | S | | 4B4, 4A12 | 1E8, 1H7, 2B5, 2G11, 3F5, 5G1, 3G11, 4A2, 4F5, 4F8, 4H6, 4G10 | 12 | 1.56E-10 | |
| 3 | | I | P | S | H | H | Y | I | | | 1D5; 4E12 | 2 | | |
| 4 | | I | P | S | H | H | Y | R | | | 1E9 | 1 | | |
| 5 | | I | P | S | H | L | Y | Y | | | 1F8 | 1 | | |
| 6 | | I | P | S | H | H | F | S | | | 3B4, 4G1 | 2 | | |
| 7 | | I | A | S | H | H | Y | S | | | 4D9 | 1 | | |
| 8 | | I | S | S | H | H | Y | N | | | 3C8 | 1 | | |
| 9 | Group 2 (PVH) | I | P | V | H | H | Y | S | | | not found in panning | 1 | 9.57E-11 | |
| 10 | | I | P | V | H | H | Y | R | | | 2E7, 3G4 | 2 | 8.92E-10 | |
| 11 | | I | P | V | H | H | F | S | | | 2A9 | 1 | | |
| 12 | | I | P | V | H | H | Y | V | | | 3E12 | 1 | | |
| 13 | | I | A | V | H | H | Y | G | | | 3G12 | 1 | | |
| 14 | | I | T | V | H | H | F | S | | | 3D5 | 1 | | |
| 15 | Group 3 (PH) | I | P | H | H | H | Y | S | | | 2B4; 2F6 | 2 | 2.11E-09 | |
| 16 | | I | P | H | H | H | Y | R | | | 2H6; 3H6 | 2 | | |
| 17 | | I | P | H | H | H | Y | I | | | 3A2 | 1 | | |
| 18 | | I | P | H | H | H | T | N | | | 3H7 | 1 | | |
| 19 | | I | P | H | H | H | Y | T | | | 4B3 | 1 | | |
| 20 | | I | P | A | H | H | Y | T | | | 3G7 | 1 | | |
| 21 | | I | P | D | H | H | Y | R | | | 1A4 | 1 | | |
| 22 | | I | P | D | H | H | Y | S | | | 3C2 | 1 | | |
| 23 | | I | P | D | H | H | F | S | | | 4E11 | 1 | | |
| 24 | | I | P | P | H | H | Y | S | | | 1A6 | 1 | | |
| 25 | | I | P | Q | H | H | Y | S | | | 4B3 | 1 | | |
| 26 | | I | P | T | H | H | Y | S | | | 1B4, 3G8 | 2 | | |
| 27 | | I | A | H | H | H | Y | S | | | 3D11 | 1 | | |
| 28 | | I | A | Q | H | H | F | S | | | 4E10 | 1 | | |
| 29 | | I | A | T | H | H | Y | S | | | 4G4 | 1 | | |
| 30 | | I | T | T | H | H | F | S | | | 2G12 | 1 | | |
| 31 | | I | T | T | H | H | Y | S | | | 4D8 | 1 | | |
| 32 | Group 4 (PTR) | I | P | T | R | H | Y | S | | | 1E1, 3G6 | 2 | 4.98E-10 | |
| 33 | | I | P | T | R | H | F | S | | | 2F4, 4D7 | 2 | | |
| 34 | | I | P | T | R | H | L | S | | | 4A11 | 1 | | |
| 35 | | I | P | T | R | H | Y | I | | | 2G7, 4B7 | 2 | | |
| 36 | | I | P | T | R | H | F | G | | | 5A10 | 1 | | |
| 37 | | I | T | T | R | H | F | S | | | 1B3; 2C2 | 2 | | |
| 38 | | I | T | T | R | H | Y | S | | | 1E5; 2B8 | 2 | | |
| 39 | | I | T | T | R | H | W | S | | | 3C10 | 1 | | |
| 40 | | I | P | T | R | H | F | I | | | PN04-90 | | 4.25E-10 | Yes |
| 41 | | I | T | T | R | H | F | I | | | V5 | | 2.35E-08 | |
| 42 | | I | P | H | R | H | F | I | | | V1 | | 1.08E-08 | Yes |
| 43 | | I | P | T | N | H | F | I | | | V2 | | 1.62E-06 | |
| 44 | | I | P | T | R | H | Y | I | | | V3 | | 2.11E-10 | |
| 45 | | I | P | T | R | H | F | S | | | V4 | | 2.75E-10 | |
| 46 | Group 5 (PVR) | I | P | V | R | H | Y | S | | | 1A1, 1F9, 1G8, 1H5, 2E11, 4C15, 3C7 | 7 | 1.69E-10 | |
| 47 | | I | P | V | R | H | F | S | | | 1A3, 1D6, 3C7, 3F2, 4F1, 3F5 | 6 | | |
| 48 | | I | P | V | R | H | Y | G | | | 1G2, 4G9 | 2 | | |
| 49 | | I | P | V | R | H | L | S | | | 1H4 | 1 | | |
| 50 | | I | P | V | R | H | F | R | | | 3A3 | 1 | | |
| 51 | | I | P | V | R | H | Y | R | | | 4A5, 4G6 | 2 | | |
| 52 | | I | P | V | R | H | Y | P | | | 4F10 | 1 | | |
| 53 | | I | A | V | R | H | T | N | | | 3C12 | 1 | | |
| 54 | | I | A | V | R | H | Y | I | | | 3F12 | 1 | | |
| 55 | | I | T | V | R | H | T | R | | | 1C4 | 1 | | |
| 56 | | I | T | V | R | H | Y | I | | | 1F4 | 1 | | |
| 57 | | I | T | V | R | H | T | S | | | 1G3 | 1 | | |
| 58 | | I | T | V | R | H | Y | V | | | 2B4 | 1 | | |
| 59 | | I | T | V | R | H | Y | S | | | 2C4, 3F2, 4A1 | 3 | | |
| 60 | | I | T | V | R | L | Y | S | | | 2B9 | 1 | | |
| 61 | | I | T | V | R | H | Y | R | | | 3E5, 3G9, 4E7, 4B6 | 4 | | |
| 62 | | I | P | I | R | H | F | S | | | 1E2 | 1 | | |
| 63 | | I | P | I | R | H | Y | S | | | 2H7 | 1 | | |

Figure 13A

| SN | GROUP | CH2 REGION | | CH3 REGION | | | | | ELISA ID IN EXPT #1 | ELISA ID IN EXPT #2 | ELISA ID IN EXPT #3 | No of clones in Expt#3 | KD (M) | mxOC maturation Assay |
|---|---|---|---|---|---|---|---|---|---|---|---|---|---|---|
| | | I253* | T256 | H433 | N434 | H435* | Y436 | S440 | | | | | | |
| 64 | | I | P | H | N | H | F | R | | | 1B5 | 1 | | |
| 65 | | I | P | H | N | H | F | T | | | 1B7 | 1 | | |
| 66 | | I | P | H | N | H | T | R | | | 1B9, 4A6 | 2 | | |
| 67 | | I | P | H | N | H | Y | S | | | 1B12, 1C7, 1F7, 1F10, 1G5, 1H6, 2B3, 2D1, 2D4, 2E12, 2F10, 2G2, 2G10, 2H3, 2H8, 3D10, 3E3, 3E9, 3F2, 3F4, 3H1, 3H6, 4C12, 4D2, 4D8, 4E8, 4E4 | 27 | | |
| 68 | | I | P | H | N | H | T | S | | | 1C3, 1D7, 4G12, 3B6 | 4 | | |
| 69 | | I | P | H | N | H | T | T | | | 1C5 | 1 | | |
| 70 | | I | P | H | N | H | Y | D | | | 1F6, 4A7 | 2 | | |
| 71 | | I | P | H | N | H | S | W | | | 3G1 | 1 | | |
| 72 | | I | P | H | N | H | T | M | | | 1G7 | 1 | | |
| 73 | | I | P | H | N | H | T | A | | | 1G12 | 1 | | |
| 74 | | I | P | H | N | H | T | D | | | 1H8 | 1 | | |
| 75 | Group 6 (P) | I | P | H | N | H | Y | R | | 3B6 | 3A1, 2C12, 3B7, 4G3, 4F2 | 5 | | |
| 76 | | I | P | H | N | H | Y | A | | | 2A8, 4E8 | 2 | | |
| 77 | | I | P | H | N | H | L | S | | | 3A10 | 1 | | |
| 78 | | I | P | H | N | H | F | S | | 2C12 | 2B6, 2F8 | 2 | | |
| 79 | | I | P | H | N | H | Y | T | | | 2D6, 2D7, 4E8, 3G2 | 4 | | |
| 80 | | I | P | H | N | H | F | I | | | 2F12 | 1 | | |
| 81 | | I | P | H | N | H | T | N | | | 3D1 | 1 | | |
| 82 | | I | P | H | N | H | Y | K | | | 3D8 | 1 | | |
| 83 | | I | P | H | N | H | S | S | | | 3H5 | 1 | | |
| 84 | | I | P | H | I | H | Y | S | | | 1F11 | 1 | | |
| 85 | | I | P | H | I | H | F | M | | | 3E11 | 1 | | |
| 86 | | I | P | H | L | M | T | S | | | 2H5, 4B11 | 2 | | |
| 87 | | I | P | H | L | H | Y | S | | | 4D12 | 1 | | |
| 88 | | I | P | H | M | H | T | R | | | 1D2 | 1 | | |
| 89 | | I | P | H | M | H | Y | S | | | 2D9 | 1 | | |
| 90 | | I | P | H | N | H | L | N | | 2G1 | | 0 | | |
| 91 | | I | P | H | N | H | T | Y | D11 | | | 0 | | |
| 92 | | I | A | H | N | H | F | M | D5 | 4D6, 2C6 | | 0 | 3.68E-09 | |
| 93 | | I | A | H | N | H | F | S | | | 1H2, 3D6, 2C9 | 3 | | |
| 94 | | I | A | H | N | H | T | S | | | 2A2, 1G4 | 2 | | |
| 95 | | I | A | H | N | H | T | F | | | 2A4 | 1 | | |
| 96 | Group 7 (A) | I | A | H | N | M | Y | S | | | 1B3, 4E2, 3A12 | 3 | | |
| 97 | | I | A | H | N | H | Y | I | | | 1F4 | 1 | | |
| 98 | | I | A | H | N | H | Y | G | | | 2B8 | 1 | | |
| 99 | | I | A | H | N | H | Y | D | | | 4A10 | 1 | | |
| 100 | | I | A | H | N | H | Y | N | | | 4B2 | 1 | | |
| 101 | | I | A | H | M | H | Y | S | | | 4F5 | 1 | | |
| 102 | | I | T | H | N | H | Y | A | | | 1C3 | 1 | | |
| 103 | | I | T | H | N | H | Y | I | | | 1D9, 4A9, 3F11 | 3 | | |
| 104 | | I | T | H | N | H | Y | T | | | 1E5, 3C8, 4H9, 4F11 | 4 | | |
| 105 | | L | T | H | N | M | Y | A | | | 1E7 | 1 | | |
| 106 | | I | T | H | N | H | Y | R | | | 2F5, 4C8 | 2 | | |
| 107 | | L | T | H | N | H | Y | S | | | 2F9 | 1 | | |
| 108 | | I | T | H | N | H | Y | E | | | 2D9 | 1 | | |
| 109 | | I | T | H | N | M | Y | C | | | 3F9 | 1 | | |
| 110 | | I | T | H | N | H | Y | Y | | | 4C1 | 1 | | |
| 111 | | I | T | H | N | H | Y | D | | | 4E5 | 1 | | |
| 112 | | I | T | H | N | H | F | S | | 4A3 | 1C12, 1F3, 1G9, 2C11, 2E6, 2F3, 3F11, 2G5, 3A6, 4E9, 3B2 | 11 | | |
| 113 | | I | T | H | N | H | F | C | | | 3C11 | 1 | | |
| 114 | | I | T | H | N | H | F | Y | | | 3D7 | 1 | | |
| 115 | | I | T | H | N | H | F | N | | | 3G3 | 1 | | |
| 116 | | I | T | H | N | H | F | R | | | 4B4 | 1 | | |
| 117 | | I | T | H | N | H | T | S | | 3H1 | 2D5 | 1 | | |
| 118 | Group 8 (others) | I | T | H | L | H | F | S | | 4B11 | 1B10, 2B1, 2B2, 4G7, 4D10 | 5 | | |
| 119 | | I | T | H | L | H | Y | S | | | 3A6, 2B9, 2B10, 2D6, 2F1, 2F7, 2G8, 3B9, 3B12, 4H5, 3E19 | 11 | | |
| 120 | | I | T | H | L | H | Y | P | | | 2B12, 4FA | 2 | | |
| 121 | | I | T | H | L | H | F | R | | | 2D2 | 1 | | |
| 122 | | I | T | H | L | L | Y | G | | | 2E10 | 1 | | |
| 123 | | I | T | H | L | H | Y | T | | | 3D12 | 1 | | |
| 124 | | I | T | H | L | H | Y | V | | | 4A8 | 1 | | |
| 125 | | I | T | H | M | H | Y | S | | | 1B2, 4C3, | 2 | | |
| 126 | | I | V | H | N | H | Y | R | | | 4A3 | 1 | | |
| 127 | | I | G | H | N | H | Y | M | | | 1H3 | 1 | | |
| 128 | | I | I | H | N | H | Y | N | | | 3F7 | 1 | | |
| 129 | | I | K | H | N | H | F | S | | | 1G4 | 1 | | |
| 130 | | I | N | H | N | H | T | N | | | 3B1 | 1 | | |
| 131 | | I | N | H | N | H | Y | S | | | 3E7, 4A4, 4H7, 4D4 | 4 | | |
| 132 | | I | N | H | N | H | Y | R | | | 4A12 | 1 | | |
| 133 | | I | S | H | N | H | Y | S | | | 1D4, 4E8, 1D11 | 3 | | |
| 134 | | I | S | H | N | H | S | S | | | 3E12 | 1 | | |
| 135 | | I | S | H | N | H | Y | A | | | 4F12 | 1 | | |

Figure 13B

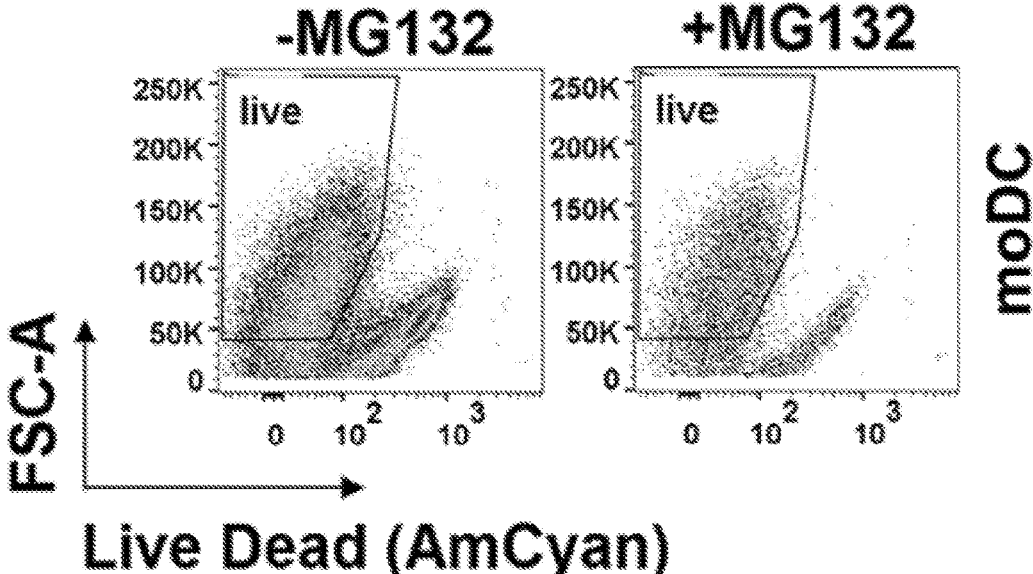
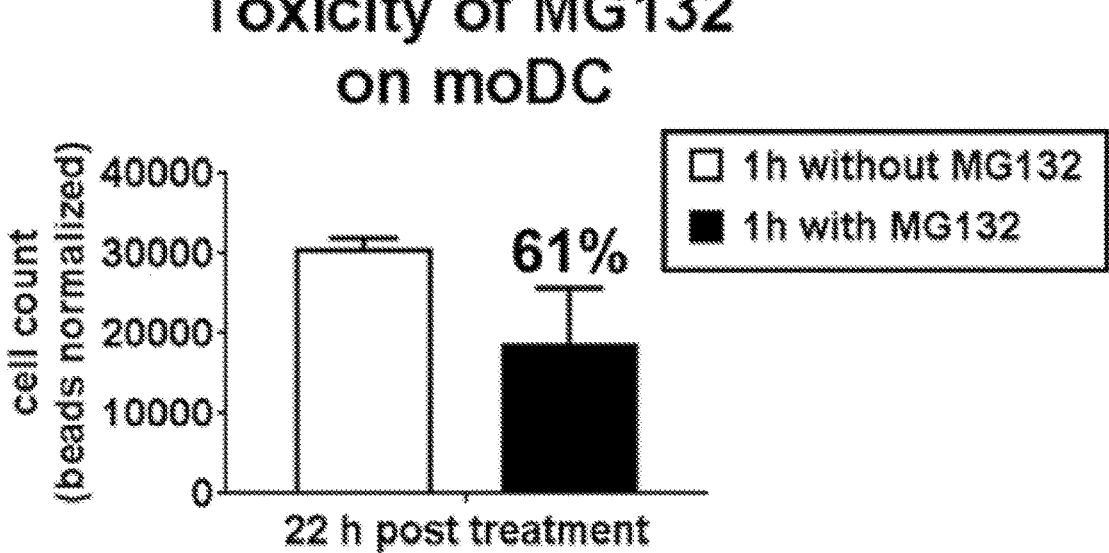
Figure 17C

SEQUENCE LISTING

<160> NUMBER OF SEQ ID NOS: 188

<210> SEQ ID NO 1
<211> LENGTH: 475
<212> TYPE: PRT
<213> ORGANISM: Homo sapiens
<220> FEATURE:
<223> OTHER INFORMATION: TRIM21 isoform 1 (UniProt: P19474-1, v1)

<400> SEQUENCE: 1

```
Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
            20                  25                  30

His Ser Phe Cys Gln Glu Cys Ile Ser Gln Val Gly Lys Gly Gly Gly
            35                  40                  45

Ser Val Cys Pro Val Cys Arg Gln Arg Phe Leu Leu Lys Asn Leu Arg
        50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
                85                  90                  95

Glu Arg Leu His Leu Phe Cys Glu Lys Asp Gly Lys Ala Leu Cys Trp
            100                 105                 110

Val Cys Ala Gln Ser Arg Lys His Arg Asp His Ala Met Val Pro Leu
            115                 120                 125

Glu Glu Ala Ala Gln Glu Tyr Gln Glu Lys Leu Gln Val Ala Leu Gly
        130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
            180                 185                 190

Glu Gln Arg Gln Leu Gln Glu Leu Glu Lys Asp Glu Arg Glu Gln Leu
            195                 200                 205

Arg Ile Leu Gly Glu Lys Glu Ala Lys Leu Ala Gln Gln Ser Gln Ala
        210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
            245                 250                 255

Trp Asn Leu Lys Asp Leu Asp Ile Thr Ser Pro Glu Leu Arg Ser Val
            260                 265                 270

Cys His Val Pro Gly Leu Lys Lys Met Leu Arg Thr Cys Ala Val His
            275                 280                 285

Ile Thr Leu Asp Pro Asp Thr Ala Asn Pro Trp Leu Ile Leu Ser Glu
        290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
                325                 330                 335

Phe His Ser Gly Lys His Tyr Trp Glu Val Asp Val Thr Gly Lys Glu
            340                 345                 350

Ala Trp Asp Leu Gly Val Cys Arg Asp Ser Val Arg Arg Lys Gly His
```

-continued

```
            355                 360                 365

Phe Leu Leu Ser Ser Lys Ser Gly Phe Trp Thr Ile Trp Leu Trp Asn
    370                 375                 380

Lys Gln Lys Tyr Glu Ala Gly Thr Tyr Pro Gln Thr Pro Leu His Leu
385                 390                 395                 400

Gln Val Pro Pro Cys Gln Val Gly Ile Phe Leu Asp Tyr Glu Ala Gly
                405                 410                 415

Met Val Ser Phe Tyr Asn Ile Thr Asp His Gly Ser Leu Ile Tyr Ser
                420                 425                 430

Phe Ser Glu Cys Ala Phe Thr Gly Pro Leu Arg Pro Phe Phe Ser Pro
                435                 440                 445

Gly Phe Asn Asp Gly Gly Lys Asn Thr Ala Pro Leu Thr Leu Cys Pro
                450                 455                 460

Leu Asn Ile Gly Ser Gln Gly Ser Thr Asp Tyr
465                 470                 475
```

<210> SEQ ID NO 2
<211> LENGTH: 398
<212> TYPE: PRT
<213> ORGANISM: Homo sapiens
<220> FEATURE:
<223> OTHER INFORMATION: TRIM21 isoform 2 (UniProt: P19474-2)

<400> SEQUENCE: 2

```
Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
                20                  25                  30

His Ser Phe Cys Gln Glu Cys Ile Ser Gln Val Gly Lys Gly Gly Gly
                35                  40                  45

Ser Val Cys Pro Val Cys Arg Gln Arg Phe Leu Leu Lys Asn Leu Arg
    50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
                85                  90                  95

Glu Arg Leu His Leu Phe Cys Glu Lys Asp Gly Lys Ala Leu Cys Trp
                100                 105                 110

Val Cys Ala Gln Ser Arg Lys His Arg Asp His Ala Met Val Pro Leu
                115                 120                 125

Glu Glu Ala Ala Gln Glu Tyr Gln Glu Lys Leu Gln Val Ala Leu Gly
    130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Glu Val Ile Ile Val Leu Glu Arg
                165                 170                 175

Ser Glu Ser Trp Asn Leu Lys Asp Leu Asp Ile Thr Ser Pro Glu Leu
                180                 185                 190

Arg Ser Val Cys His Val Pro Gly Leu Lys Lys Met Leu Arg Thr Cys
                195                 200                 205

Ala Val His Ile Thr Leu Asp Pro Asp Thr Ala Asn Pro Trp Leu Ile
    210                 215                 220

Leu Ser Glu Asp Arg Arg Gln Val Arg Leu Gly Asp Thr Gln Gln Ser
225                 230                 235                 240

Ile Pro Gly Asn Glu Glu Arg Phe Asp Ser Tyr Pro Met Val Leu Gly
```

-continued

```
                245                 250                 255

Ala Gln His Phe His Ser Gly Lys His Tyr Trp Glu Val Asp Val Thr
            260                 265                 270

Gly Lys Glu Ala Trp Asp Leu Gly Val Cys Arg Asp Ser Val Arg Arg
        275                 280                 285

Lys Gly His Phe Leu Leu Ser Ser Lys Ser Gly Phe Trp Thr Ile Trp
    290                 295                 300

Leu Trp Asn Lys Gln Lys Tyr Glu Ala Gly Thr Tyr Pro Gln Thr Pro
305                 310                 315                 320

Leu His Leu Gln Val Pro Pro Cys Gln Val Gly Ile Phe Leu Asp Tyr
                325                 330                 335

Glu Ala Gly Met Val Ser Phe Tyr Asn Ile Thr Asp His Gly Ser Leu
            340                 345                 350

Ile Tyr Ser Phe Ser Glu Cys Ala Phe Thr Gly Pro Leu Arg Pro Phe
        355                 360                 365

Phe Ser Pro Gly Phe Asn Asp Gly Gly Lys Asn Thr Ala Pro Leu Thr
    370                 375                 380

Leu Cys Pro Leu Asn Ile Gly Ser Gln Gly Ser Thr Asp Tyr
385                 390                 395
```

```
<210> SEQ ID NO 3
<211> LENGTH: 40
<212> TYPE: PRT
<213> ORGANISM: Artificial Sequence
<220> FEATURE:
<223> OTHER INFORMATION: TRIM21 RING domain (positions 16 to 55 of
      UniProt: P19474-1)

<400> SEQUENCE: 3

Cys Pro Ile Cys Leu Asp Pro Phe Val Glu Pro Val Ser Ile Glu Cys
1               5                   10                  15

Gly His Ser Phe Cys Gln Glu Cys Ile Ser Gln Val Gly Lys Gly Gly
                20                  25                  30

Gly Ser Val Cys Pro Val Cys Arg
        35                  40
```

```
<210> SEQ ID NO 4
<211> LENGTH: 32
<212> TYPE: PRT
<213> ORGANISM: Artificial Sequence
<220> FEATURE:
<223> OTHER INFORMATION: TRIM21 B-box (positions 92 to 123 of UniProt:
      P19474-1)

<400> SEQUENCE: 4

Cys Ala Val His Gly Glu Arg Leu His Leu Phe Cys Glu Lys Asp Gly
1               5                   10                  15

Lys Ala Leu Cys Trp Val Cys Ala Gln Ser Arg Lys His Arg Asp His
                20                  25                  30
```

```
<210> SEQ ID NO 5
<211> LENGTH: 111
<212> TYPE: PRT
<213> ORGANISM: Artificial Sequence
<220> FEATURE:
<223> OTHER INFORMATION: TRIM21 Coiled coil domain (positions 128 to 238
      of UniProt: P19474-1)

<400> SEQUENCE: 5

Leu Glu Glu Ala Ala Gln Glu Tyr Gln Glu Lys Leu Gln Val Ala Leu
1               5                   10                  15
```

Gly Glu Leu Arg Arg Lys Gln Glu Leu Ala Glu Lys Leu Glu Val Glu
            20                  25                  30

Ile Ala Ile Lys Arg Ala Asp Trp Lys Lys Thr Val Glu Thr Gln Lys
            35                  40                  45

Ser Arg Ile His Ala Glu Phe Val Gln Gln Lys Asn Phe Leu Val Glu
        50                  55                  60

Glu Glu Gln Arg Gln Leu Gln Glu Leu Glu Lys Asp Glu Arg Glu Gln
65                  70                  75                  80

Leu Arg Ile Leu Gly Glu Lys Glu Ala Lys Leu Ala Gln Gln Ser Gln
                85                  90                  95

Ala Leu Gln Glu Leu Ile Ser Glu Leu Asp Arg Arg Cys His Ser
            100                 105                 110

<210> SEQ ID NO 6
<211> LENGTH: 198
<212> TYPE: PRT
<213> ORGANISM: Artificial Sequence
<220> FEATURE:
<223> OTHER INFORMATION: TRIM21 PRYSPRY domain (positions 268 to 465 of
      UniProt: P19474-1)

<400> SEQUENCE: 6

Glu Leu Arg Ser Val Cys His Val Pro Gly Leu Lys Lys Met Leu Arg
1               5                   10                  15

Thr Cys Ala Val His Ile Thr Leu Asp Pro Asp Thr Ala Asn Pro Trp
            20                  25                  30

Leu Ile Leu Ser Glu Asp Arg Arg Gln Val Arg Leu Gly Asp Thr Gln
            35                  40                  45

Gln Ser Ile Pro Gly Asn Glu Glu Arg Phe Asp Ser Tyr Pro Met Val
        50                  55                  60

Leu Gly Ala Gln His Phe His Ser Gly Lys His Tyr Trp Glu Val Asp
65                  70                  75                  80

Val Thr Gly Lys Glu Ala Trp Asp Leu Gly Val Cys Arg Asp Ser Val
                85                  90                  95

Arg Arg Lys Gly His Phe Leu Leu Ser Ser Lys Ser Gly Phe Trp Thr
            100                 105                 110

Ile Trp Leu Trp Asn Lys Gln Lys Tyr Glu Ala Gly Thr Tyr Pro Gln
            115                 120                 125

Thr Pro Leu His Leu Gln Val Pro Pro Cys Gln Val Gly Ile Phe Leu
        130                 135                 140

Asp Tyr Glu Ala Gly Met Val Ser Phe Tyr Asn Ile Thr Asp His Gly
145                 150                 155                 160

Ser Leu Ile Tyr Ser Phe Ser Glu Cys Ala Phe Thr Gly Pro Leu Arg
                165                 170                 175

Pro Phe Phe Ser Pro Gly Phe Asn Asp Gly Gly Lys Asn Thr Ala Pro
            180                 185                 190

Leu Thr Leu Cys Pro Leu
            195

<210> SEQ ID NO 7
<211> LENGTH: 330
<212> TYPE: PRT
<213> ORGANISM: Homo sapiens
<220> FEATURE:
<223> OTHER INFORMATION: IgG1 constant region (IGHG1; UniProt:P01857-1,
      v1)

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 8
<211> LENGTH: 113
<212> TYPE: PRT
<213> ORGANISM: Artificial Sequence
<220> FEATURE:
<223> OTHER INFORMATION: CH2 IgG1 (positions 111-223 of P01857-1, v1)

<400> SEQUENCE: 8
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

```
Thr Cys Val Val Val Asp Val Ser His Glu Asp Pro Glu Val Lys Phe
    35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys
```

```
<210> SEQ ID NO 9
<211> LENGTH: 107
<212> TYPE: PRT
<213> ORGANISM: Artificial Sequence
<220> FEATURE:
<223> OTHER INFORMATION: CH3 IgG1 (positions 224-330 of P01857-1, v1)

<400> SEQUENCE: 9

Gly Gln Pro Arg Glu Pro Gln Val Tyr Thr Leu Pro Pro Ser Arg Asp
1                   5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

```
<210> SEQ ID NO 10
<211> LENGTH: 220
<212> TYPE: PRT
<213> ORGANISM: Artificial Sequence
<220> FEATURE:
<223> OTHER INFORMATION: CH2-CH3 IgG1 (positions 111-330 of P01857-1,
      v1)

<400> SEQUENCE: 10

Pro Cys Pro Ala Pro Glu Leu Leu Gly Gly Pro Ser Val Phe Leu Phe
1                   5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
```

-continued

```
              100                 105                 110

Lys Gly Gln Pro Arg Glu Pro Gln Val Tyr Thr Leu Pro Pro Ser Arg
          115                 120                 125

Asp Glu Leu Thr Lys Asn Gln Val Ser Leu Thr Cys Leu Val Lys Gly
      130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
              165                 170                 175

Phe Phe Leu Tyr Ser Lys Leu Thr Val Asp Lys Ser Arg Trp Gln Gln
              180                 185                 190

Gly Asn Val Phe Ser Cys Ser Val Met His Glu Ala Leu His Asn His
              195                 200                 205

Tyr Thr Gln Lys Ser Leu Ser Leu Ser Pro Gly Lys
      210                 215                 220

<210> SEQ ID NO 11
<211> LENGTH: 326
<212> TYPE: PRT
<213> ORGANISM: Homo sapiens
<220> FEATURE:
<223> OTHER INFORMATION: IgG2 constant region (IGHG2; UniProt:P01859-1,
      v2)

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
          35                  40                  45

Gly Val His Thr Phe Pro Ala Val Leu Gln Ser Ser Gly Leu Tyr Ser
      50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
              85                  90                  95

Thr Val Glu Arg Lys Cys Cys Val Glu Cys Pro Pro Cys Pro Ala Pro
              100                 105                 110

Pro Val Ala Gly Pro Ser Val Phe Leu Phe Pro Pro Lys Pro Lys Asp
              115                 120                 125

Thr Leu Met Ile Ser Arg Thr Pro Glu Val Thr Cys Val Val Val Asp
      130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
              165                 170                 175

Ser Thr Phe Arg Val Val Ser Val Leu Thr Val Val His Gln Asp Trp
              180                 185                 190

Leu Asn Gly Lys Glu Tyr Lys Cys Lys Val Ser Asn Lys Gly Leu Pro
              195                 200                 205

Ala Pro Ile Glu Lys Thr Ile Ser Lys Thr Lys Gly Gln Pro Arg Glu
      210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 12
<211> LENGTH: 109
<212> TYPE: PRT
<213> ORGANISM: Artificial Sequence
<220> FEATURE:
<223> OTHER INFORMATION: CH2 IgG2 (positions 111-219 of P01859-1, v2)

<400> SEQUENCE: 12

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: CH3 IgG2 (positions 220-326 of P01859-1, v2)

<400> SEQUENCE: 13

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ser Val Glu Trp Glu Ser Asn Gly Gln Pro Glu
            35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

-continued

<210> SEQ ID NO 14
<211> LENGTH: 216
<212> TYPE: PRT
<213> ORGANISM: Artificial Sequence
<220> FEATURE:
<223> OTHER INFORMATION: CH2-CH3 IgG2 (positions 111-326 of P01859-1,
     v2)

<400> SEQUENCE: 14

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
    210                 215

<210> SEQ ID NO 15
<211> LENGTH: 377
<212> TYPE: PRT
<213> ORGANISM: Homo sapiens
<220> FEATURE:
<223> OTHER INFORMATION: IgG3 constant region (IGHG3; UniProt:P01860-1,
     v2)

<400> SEQUENCE: 15

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375
```

```
<210> SEQ ID NO 16
<211> LENGTH: 110
<212> TYPE: PRT
<213> ORGANISM: Artificial Sequence
<220> FEATURE:
<223> OTHER INFORMATION: CH2 IgG3 (positions 161-270 of P01860-1, v2)

<400> SEQUENCE: 16

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
                35                  40                  45

Val Asp Gly Val Glu Val His Asn Ala Lys Thr Lys Pro Arg Glu Glu
        50                  55                  60
```

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 17
<211> LENGTH: 106
<212> TYPE: PRT
<213> ORGANISM: Artificial Sequence
<220> FEATURE:
<223> OTHER INFORMATION: CH3 IgG3 (positions 271-376 of P01860-1, v2)

<400> SEQUENCE: 17

Gly Gln Pro Arg Glu Pro Gln Val Tyr Thr Leu Pro Pro Ser Arg Glu
1                   5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly
            100                 105

<210> SEQ ID NO 18
<211> LENGTH: 216
<212> TYPE: PRT
<213> ORGANISM: Artificial Sequence
<220> FEATURE:
<223> OTHER INFORMATION: CH2-CH3 IgG3 (positions 161-376 of P01860-1,
      v2)

<400> SEQUENCE: 18

Ala Pro Glu Leu Leu Gly Gly Pro Ser Val Phe Leu Phe Pro Pro Lys
1                   5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

-continued

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly
    210                 215

<210> SEQ ID NO 19
<211> LENGTH: 327
<212> TYPE: PRT
<213> ORGANISM: Homo sapiens
<220> FEATURE:
<223> OTHER INFORMATION: IgG4 constant region (IGHG4; UniProt:P01861-1,
      v1)

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325
```

```
<210> SEQ ID NO 20
<211> LENGTH: 110
<212> TYPE: PRT
<213> ORGANISM: Artificial Sequence
<220> FEATURE:
<223> OTHER INFORMATION: CH2 IgG4 (positions 111-220 of P01861-1, v1)

<400> SEQUENCE: 20

Ala Pro Glu Phe Leu Gly Gly Pro Ser Val Phe Leu Phe Pro Pro Lys
1                 5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

```
<210> SEQ ID NO 21
<211> LENGTH: 107
<212> TYPE: PRT
<213> ORGANISM: Artificial Sequence
<220> FEATURE:
<223> OTHER INFORMATION: CH3 IgG4 (positions 221-327 of P01861-1, v1)

<400> SEQUENCE: 21

Gly Gln Pro Arg Glu Pro Gln Val Tyr Thr Leu Pro Pro Ser Gln Glu
1                 5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

```
<210> SEQ ID NO 22
<211> LENGTH: 217
<212> TYPE: PRT
<213> ORGANISM: Artificial Sequence
<220> FEATURE:
<223> OTHER INFORMATION: CH2-CH3 IgG4 (positions 111-327 of P01861-1,
```

-continued v1)

<400> SEQUENCE: 22

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
    210                 215

<210> SEQ ID NO 23
<211> LENGTH: 353
<212> TYPE: PRT
<213> ORGANISM: Homo sapiens
<220> FEATURE:
<223> OTHER INFORMATION: IgA1 constant region (IGHA1; UniProt:P01876-1,
      v2)

<400> SEQUENCE: 23

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser

-continued

```
            115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 24
<211> LENGTH: 340
<212> TYPE: PRT
<213> ORGANISM: Homo sapiens
<220> FEATURE:
<223> OTHER INFORMATION: IgA2 constant region (IGHA2; UniProt:P01877-1,
      v4)

<400> SEQUENCE: 24

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
```

-continued

```
            115                      120                      125

Glu Ala Asn Leu Thr Cys Thr Leu Thr Gly Leu Arg Asp Ala Ser Gly
    130                      135                      140

Ala Thr Phe Thr Trp Thr Pro Ser Ser Gly Lys Ser Ala Val Gln Gly
145                      150                      155                      160

Pro Pro Glu Arg Asp Leu Cys Gly Cys Tyr Ser Val Ser Ser Val Leu
                    165                      170                      175

Pro Gly Cys Ala Gln Pro Trp Asn His Gly Glu Thr Phe Thr Cys Thr
                180                      185                      190

Ala Ala His Pro Glu Leu Lys Thr Pro Leu Thr Ala Asn Ile Thr Lys
                    195                      200                      205

Ser Gly Asn Thr Phe Arg Pro Glu Val His Leu Leu Pro Pro Pro Ser
    210                      215                      220

Glu Glu Leu Ala Leu Asn Glu Leu Val Thr Leu Thr Cys Leu Ala Arg
225                      230                      235                      240

Gly Phe Ser Pro Lys Asp Val Leu Val Arg Trp Leu Gln Gly Ser Gln
                    245                      250                      255

Glu Leu Pro Arg Glu Lys Tyr Leu Thr Trp Ala Ser Arg Gln Glu Pro
                260                      265                      270

Ser Gln Gly Thr Thr Thr Tyr Ala Val Thr Ser Ile Leu Arg Val Ala
                275                      280                      285

Ala Glu Asp Trp Lys Lys Gly Glu Thr Phe Ser Cys Met Val Gly His
    290                      295                      300

Glu Ala Leu Pro Leu Ala Phe Thr Gln Lys Thr Ile Asp Arg Met Ala
305                      310                      315                      320

Gly Lys Pro Thr His Ile Asn Val Ser Val Val Met Ala Glu Ala Asp
                    325                      330                      335

Gly Thr Cys Tyr
                340

<210> SEQ ID NO 25
<211> LENGTH: 384
<212> TYPE: PRT
<213> ORGANISM: Homo sapiens
<220> FEATURE:
<223> OTHER INFORMATION: IgD constant region (IGHD; UniProt:P01880-1,
      v3)

<400> SEQUENCE: 25

Ala Pro Thr Lys Ala Pro Asp Val Phe Pro Ile Ile Ser Gly Cys Arg
1               5                        10                       15

His Pro Lys Asp Asn Ser Pro Val Val Leu Ala Cys Leu Ile Thr Gly
                20                       25                       30

Tyr His Pro Thr Ser Val Thr Val Thr Trp Tyr Met Gly Thr Gln Ser
            35                       40                       45

Gln Pro Gln Arg Thr Phe Pro Glu Ile Gln Arg Arg Asp Ser Tyr Tyr
        50                       55                       60

Met Thr Ser Ser Gln Leu Ser Thr Pro Leu Gln Gln Trp Arg Gln Gly
65                       70                       75                       80

Glu Tyr Lys Cys Val Val Gln His Thr Ala Ser Lys Ser Lys Lys Glu
                    85                       90                       95

Ile Phe Arg Trp Pro Glu Ser Pro Lys Ala Gln Ala Ser Ser Val Pro
                100                      105                      110

Thr Ala Gln Pro Gln Ala Glu Gly Ser Leu Ala Lys Ala Thr Thr Ala
            115                      120                      125
```

```
Pro Ala Thr Thr Arg Asn Thr Gly Arg Gly Gly Glu Glu Lys Lys Lys
130              135              140

Glu Lys Glu Lys Glu Glu Gln Glu Glu Arg Glu Thr Lys Thr Pro Glu
145              150              155              160

Cys Pro Ser His Thr Gln Pro Leu Gly Val Tyr Leu Leu Thr Pro Ala
              165              170              175

Val Gln Asp Leu Trp Leu Arg Asp Lys Ala Thr Phe Thr Cys Phe Val
              180              185              190

Val Gly Ser Asp Leu Lys Asp Ala His Leu Thr Trp Glu Val Ala Gly
              195              200              205

Lys Val Pro Thr Gly Gly Val Glu Glu Gly Leu Leu Glu Arg His Ser
       210              215              220

Asn Gly Ser Gln Ser Gln His Ser Arg Leu Thr Leu Pro Arg Ser Leu
225              230              235              240

Trp Asn Ala Gly Thr Ser Val Thr Cys Thr Leu Asn His Pro Ser Leu
              245              250              255

Pro Pro Gln Arg Leu Met Ala Leu Arg Glu Pro Ala Ala Gln Ala Pro
              260              265              270

Val Lys Leu Ser Leu Asn Leu Leu Ala Ser Ser Asp Pro Pro Glu Ala
       275              280              285

Ala Ser Trp Leu Leu Cys Glu Val Ser Gly Phe Ser Pro Pro Asn Ile
       290              295              300

Leu Leu Met Trp Leu Glu Asp Gln Arg Glu Val Asn Thr Ser Gly Phe
305              310              315              320

Ala Pro Ala Arg Pro Pro Gln Pro Arg Ser Thr Thr Phe Trp Ala
              325              330              335

Trp Ser Val Leu Arg Val Pro Ala Pro Pro Ser Pro Gln Pro Ala Thr
              340              345              350

Tyr Thr Cys Val Val Ser His Glu Asp Ser Arg Thr Leu Leu Asn Ala
       355              360              365

Ser Arg Ser Leu Glu Val Ser Tyr Val Thr Asp His Gly Pro Met Lys
       370              375              380
```

```
<210> SEQ ID NO 26
<211> LENGTH: 428
<212> TYPE: PRT
<213> ORGANISM: Homo sapiens
<220> FEATURE:
<223> OTHER INFORMATION: IgE constant region (IGHE; UniProt:P01854-1,
      v1)

<400> SEQUENCE: 26

Ala Ser Thr Gln Ser Pro Ser Val Phe Pro Leu Thr Arg Cys Cys Lys
1              5              10              15

Asn Ile Pro Ser Asn Ala Thr Ser Val Thr Leu Gly Cys Leu Ala Thr
              20              25              30

Gly Tyr Phe Pro Glu Pro Val Met Val Thr Trp Asp Thr Gly Ser Leu
       35              40              45

Asn Gly Thr Thr Met Thr Leu Pro Ala Thr Thr Leu Thr Leu Ser Gly
       50              55              60

His Tyr Ala Thr Ile Ser Leu Leu Thr Val Ser Gly Ala Trp Ala Lys
65              70              75              80

Gln Met Phe Thr Cys Arg Val Ala His Thr Pro Ser Ser Thr Asp Trp
              85              90              95

Val Asp Asn Lys Thr Phe Ser Val Cys Ser Arg Asp Phe Thr Pro Pro
              100              105              110
```

-continued

```
Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
        130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
                180                 185                 190

Cys Gln Val Thr Tyr Gln Gly His Thr Phe Glu Asp Ser Thr Lys Lys
                195                 200                 205

Cys Ala Asp Ser Asn Pro Arg Gly Val Ser Ala Tyr Leu Ser Arg Pro
        210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
                275                 280                 285

Arg Asp Trp Ile Glu Gly Glu Thr Tyr Gln Cys Arg Val Thr His Pro
        290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
                340                 345                 350

Glu Asp Ile Ser Val Gln Trp Leu His Asn Glu Val Gln Leu Pro Asp
                355                 360                 365

Ala Arg His Ser Thr Thr Gln Pro Arg Lys Thr Lys Gly Ser Gly Phe
        370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
                420                 425
```

```
<210> SEQ ID NO 27
<211> LENGTH: 453
<212> TYPE: PRT
<213> ORGANISM: Homo sapiens
<220> FEATURE:
<223> OTHER INFORMATION: IgM constant region (IGHM; UniProt:P01871-1,
      v4)

<400> SEQUENCE: 27
```

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
```

```
              35                    40                    45

Asp Ile Ser Ser Thr Arg Gly Phe Pro Ser Val Leu Arg Gly Gly Lys
    50                    55                    60

Tyr Ala Ala Thr Ser Gln Val Leu Leu Pro Ser Lys Asp Val Met Gln
65                    70                    75                    80

Gly Thr Asp Glu His Val Val Cys Lys Val Gln His Pro Asn Gly Asn
                85                    90                    95

Lys Glu Lys Asn Val Pro Leu Pro Val Ile Ala Glu Leu Pro Pro Lys
            100                   105                   110

Val Ser Val Phe Val Pro Pro Arg Asp Gly Phe Phe Gly Asn Pro Arg
            115                   120                   125

Lys Ser Lys Leu Ile Cys Gln Ala Thr Gly Phe Ser Pro Arg Gln Ile
    130                   135                   140

Gln Val Ser Trp Leu Arg Glu Gly Lys Gln Val Gly Ser Gly Val Thr
145                   150                   155                   160

Thr Asp Gln Val Gln Ala Glu Ala Lys Glu Ser Gly Pro Thr Thr Tyr
                165                   170                   175

Lys Val Thr Ser Thr Leu Thr Ile Lys Glu Ser Asp Trp Leu Gly Gln
                180                   185                   190

Ser Met Phe Thr Cys Arg Val Asp His Arg Gly Leu Thr Phe Gln Gln
                195                   200                   205

Asn Ala Ser Ser Met Cys Val Pro Asp Gln Asp Thr Ala Ile Arg Val
    210                   215                   220

Phe Ala Ile Pro Pro Ser Phe Ala Ser Ile Phe Leu Thr Lys Ser Thr
225                   230                   235                   240

Lys Leu Thr Cys Leu Val Thr Asp Leu Thr Thr Tyr Asp Ser Val Thr
                245                   250                   255

Ile Ser Trp Thr Arg Gln Asn Gly Glu Ala Val Lys Thr His Thr Asn
                260                   265                   270

Ile Ser Glu Ser His Pro Asn Ala Thr Phe Ser Ala Val Gly Glu Ala
                275                   280                   285

Ser Ile Cys Glu Asp Asp Trp Asn Ser Gly Glu Arg Phe Thr Cys Thr
    290                   295                   300

Val Thr His Thr Asp Leu Pro Ser Pro Leu Lys Gln Thr Ile Ser Arg
305                   310                   315                   320

Pro Lys Gly Val Ala Leu His Arg Pro Asp Val Tyr Leu Leu Pro Pro
                325                   330                   335

Ala Arg Glu Gln Leu Asn Leu Arg Glu Ser Ala Thr Ile Thr Cys Leu
                340                   345                   350

Val Thr Gly Phe Ser Pro Ala Asp Val Phe Val Gln Trp Met Gln Arg
                355                   360                   365

Gly Gln Pro Leu Ser Pro Glu Lys Tyr Val Thr Ser Ala Pro Met Pro
    370                   375                   380

Glu Pro Gln Ala Pro Gly Arg Tyr Phe Ala His Ser Ile Leu Thr Val
385                   390                   395                   400

Ser Glu Glu Glu Trp Asn Thr Gly Glu Thr Tyr Thr Cys Val Val Ala
                405                   410                   415

His Glu Ala Leu Pro Asn Arg Val Thr Glu Arg Thr Val Asp Lys Ser
                420                   425                   430

Thr Gly Lys Pro Thr Leu Tyr Asn Val Ser Leu Val Met Ser Asp Thr
            435                   440                   445

Ala Gly Thr Cys Tyr
    450
```

<210> SEQ ID NO 28
<211> LENGTH: 112
<212> TYPE: PRT
<213> ORGANISM: Artificial Sequence
<220> FEATURE:
<223> OTHER INFORMATION: CH2 IgM (positions 106-217 of P01871-1, v4)

<400> SEQUENCE: 28

Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
            20                  25                  30

Gly Phe Ser Pro Arg Gln Ile Gln Val Ser Trp Leu Arg Glu Gly Lys
        35                  40                  45

Gln Val Gly Ser Gly Val Thr Thr Asp Gln Val Gln Ala Glu Ala Lys
        50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
            85                  90                  95

Arg Gly Leu Thr Phe Gln Gln Asn Ala Ser Ser Met Cys Val Pro Asp
            100                 105                 110

<210> SEQ ID NO 29
<211> LENGTH: 106
<212> TYPE: PRT
<213> ORGANISM: Artificial Sequence
<220> FEATURE:
<223> OTHER INFORMATION: CH3 IgM (positions 218-323 of P01871-1, v4)

<400> SEQUENCE: 29

Gln Asp Thr Ala Ile Arg Val Phe Ala Ile Pro Pro Ser Phe Ala Ser
1               5                   10                  15

Ile Phe Leu Thr Lys Ser Thr Lys Leu Thr Cys Leu Val Thr Asp Leu
            20                  25                  30

Thr Thr Tyr Asp Ser Val Thr Ile Ser Trp Thr Arg Gln Asn Gly Glu
        35                  40                  45

Ala Val Lys Thr His Thr Asn Ile Ser Glu Ser His Pro Asn Ala Thr
        50                  55                  60

Phe Ser Ala Val Gly Glu Ala Ser Ile Cys Glu Asp Asp Trp Asn Ser
65                  70                  75                  80

Gly Glu Arg Phe Thr Cys Thr Val Thr His Thr Asp Leu Pro Ser Pro
            85                  90                  95

Leu Lys Gln Thr Ile Ser Arg Pro Lys Gly
            100                 105

<210> SEQ ID NO 30
<211> LENGTH: 129
<212> TYPE: PRT
<213> ORGANISM: Artificial Sequence
<220> FEATURE:
<223> OTHER INFORMATION: CH4 IgM (positions 324-452 of P01871-1, v4)

<400> SEQUENCE: 30

Val Ala Leu His Arg Pro Asp Val Tyr Leu Leu Pro Pro Ala Arg Glu
1               5                   10                  15

Gln Leu Asn Leu Arg Glu Ser Ala Thr Ile Thr Cys Leu Val Thr Gly
            20                  25                  30

-continued

Phe Ser Pro Ala Asp Val Phe Val Gln Trp Met Gln Arg Gly Gln Pro
        35                  40                  45

Leu Ser Pro Glu Lys Tyr Val Thr Ser Ala Pro Met Pro Glu Pro Gln
        50                  55                  60

Ala Pro Gly Arg Tyr Phe Ala His Ser Ile Leu Thr Val Ser Glu Glu
65                  70                  75                  80

Glu Trp Asn Thr Gly Glu Thr Tyr Thr Cys Val Val Ala His Glu Ala
                85                  90                  95

Leu Pro Asn Arg Val Thr Glu Arg Thr Val Asp Lys Ser Thr Gly Lys
                100                 105                 110

Pro Thr Leu Tyr Asn Val Ser Leu Val Met Ser Asp Thr Ala Gly Thr
        115                 120                 125

Cys

<210> SEQ ID NO 31
<211> LENGTH: 347
<212> TYPE: PRT
<213> ORGANISM: Artificial Sequence
<220> FEATURE:
<223> OTHER INFORMATION: CH2-CH3-CH4 IgM (positions 106-452 of P01871-1,
      v4)

<400> SEQUENCE: 31

Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
                20                  25                  30

Gly Phe Ser Pro Arg Gln Ile Gln Val Ser Trp Leu Arg Glu Gly Lys
        35                  40                  45

Gln Val Gly Ser Gly Val Thr Thr Asp Gln Val Gln Ala Glu Ala Lys
        50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
                85                  90                  95

Arg Gly Leu Thr Phe Gln Gln Asn Ala Ser Ser Met Cys Val Pro Asp
                100                 105                 110

Gln Asp Thr Ala Ile Arg Val Phe Ala Ile Pro Pro Ser Phe Ala Ser
        115                 120                 125

Ile Phe Leu Thr Lys Ser Thr Lys Leu Thr Cys Leu Val Thr Asp Leu
        130                 135                 140

Thr Thr Tyr Asp Ser Val Thr Ile Ser Trp Thr Arg Gln Asn Gly Glu
145                 150                 155                 160

Ala Val Lys Thr His Thr Asn Ile Ser Glu Ser His Pro Asn Ala Thr
                165                 170                 175

Phe Ser Ala Val Gly Glu Ala Ser Ile Cys Glu Asp Asp Trp Asn Ser
                180                 185                 190

Gly Glu Arg Phe Thr Cys Thr Val Thr His Thr Asp Leu Pro Ser Pro
                195                 200                 205

Leu Lys Gln Thr Ile Ser Arg Pro Lys Gly Val Ala Leu His Arg Pro
        210                 215                 220

Asp Val Tyr Leu Leu Pro Pro Ala Arg Glu Gln Leu Asn Leu Arg Glu
225                 230                 235                 240

Ser Ala Thr Ile Thr Cys Leu Val Thr Gly Phe Ser Pro Ala Asp Val
                245                 250                 255

```
Phe Val Gln Trp Met Gln Arg Gly Gln Pro Leu Ser Pro Glu Lys Tyr
            260             265             270

Val Thr Ser Ala Pro Met Pro Glu Pro Gln Ala Pro Gly Arg Tyr Phe
            275             280             285

Ala His Ser Ile Leu Thr Val Ser Glu Glu Glu Trp Asn Thr Gly Glu
    290             295             300

Thr Tyr Thr Cys Val Val Ala His Glu Ala Leu Pro Asn Arg Val Thr
305             310             315             320

Glu Arg Thr Val Asp Lys Ser Thr Gly Lys Pro Thr Leu Tyr Asn Val
            325             330             335

Ser Leu Val Met Ser Asp Thr Ala Gly Thr Cys
            340             345
```

<210> SEQ ID NO 32
<211> LENGTH: 220
<212> TYPE: PRT
<213> ORGANISM: Artificial Sequence
<220> FEATURE:
<223> OTHER INFORMATION: CH2-CH3 IgG1_256P/433S/434H/440G

<400> SEQUENCE: 32

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
            130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Ser His His
            195             200             205

Tyr Thr Gln Lys Gly Leu Ser Leu Ser Pro Gly Lys
            210             215             220
```

<210> SEQ ID NO 33
<211> LENGTH: 220
<212> TYPE: PRT
<213> ORGANISM: Artificial Sequence
<220> FEATURE:
<223> OTHER INFORMATION: CH2-CH3 IgG1_256P/433S/434H

<400> SEQUENCE: 33

-continued

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ser His His
            195                 200                 205

Tyr Thr Gln Lys Ser Leu Ser Leu Ser Pro Gly Lys
    210                 215                 220

<210> SEQ ID NO 34
<211> LENGTH: 220
<212> TYPE: PRT
<213> ORGANISM: Artificial Sequence
<220> FEATURE:
<223> OTHER INFORMATION: CH2-CH3 IgG1_256P/433S/434H/440I

<400> SEQUENCE: 34

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140
```

-continued

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ser His His
        195                 200                 205

Tyr Thr Gln Lys Ile Leu Ser Leu Ser Pro Gly Lys
    210                 215                 220
```

<210> SEQ ID NO 35
<211> LENGTH: 220
<212> TYPE: PRT
<213> ORGANISM: Artificial Sequence
<220> FEATURE:
<223> OTHER INFORMATION: CH2-CH3 IgG1_256P/433S/434H/440R

<400> SEQUENCE: 35

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ser His His
        195                 200                 205

Tyr Thr Gln Lys Arg Leu Ser Leu Ser Pro Gly Lys
    210                 215                 220
```

<210> SEQ ID NO 36
<211> LENGTH: 220
<212> TYPE: PRT
<213> ORGANISM: Artificial Sequence
<220> FEATURE:
<223> OTHER INFORMATION: CH2-CH3 IgG1_256P/433S/434H/435L/440Y

<400> SEQUENCE: 36

```
Pro Cys Pro Ala Pro Glu Leu Leu Gly Gly Pro Ser Val Phe Leu Phe
```

-continued

```
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ser His Leu
            195                 200                 205

Tyr Thr Gln Lys Tyr Leu Ser Leu Ser Pro Gly Lys
    210                 215                 220

<210> SEQ ID NO 37
<211> LENGTH: 220
<212> TYPE: PRT
<213> ORGANISM: Artificial Sequence
<220> FEATURE:
<223> OTHER INFORMATION: CH2-CH3 IgG1_256P/433S/434H/436F

<400> SEQUENCE: 37

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
```

-continued

```
145              150              155              160

Glu Asn Asn Tyr Lys Thr Thr Pro Pro Val Leu Asp Ser Asp Gly Ser
                165              170              175

Phe Phe Leu Tyr Ser Lys Leu Thr Val Asp Lys Ser Arg Trp Gln Gln
                180              185              190

Gly Asn Val Phe Ser Cys Ser Val Met His Glu Ala Leu Ser His His
                195              200              205

Phe Thr Gln Lys Ser Leu Ser Leu Ser Pro Gly Lys
    210              215              220
```

<210> SEQ ID NO 38
<211> LENGTH: 220
<212> TYPE: PRT
<213> ORGANISM: Artificial Sequence
<220> FEATURE:
<223> OTHER INFORMATION: CH2-CH3 IgG1_256A/433S/434H

<400> SEQUENCE: 38

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Ala Pro Glu Val
                20              25              30

Thr Cys Val Val Val Asp Val Ser His Glu Asp Pro Glu Val Lys Phe
                35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
                100             105             110

Lys Gly Gln Pro Arg Glu Pro Gln Val Tyr Thr Leu Pro Pro Ser Arg
                115             120             125

Asp Glu Leu Thr Lys Asn Gln Val Ser Leu Thr Cys Leu Val Lys Gly
                130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
                180             185             190

Gly Asn Val Phe Ser Cys Ser Val Met His Glu Ala Leu Ser His His
                195             200             205

Tyr Thr Gln Lys Ser Leu Ser Leu Ser Pro Gly Lys
    210             215             220
```

<210> SEQ ID NO 39
<211> LENGTH: 220
<212> TYPE: PRT
<213> ORGANISM: Artificial Sequence
<220> FEATURE:
<223> OTHER INFORMATION: CH2-CH3 IgG1_256S/433S/434H/440N

<400> SEQUENCE: 39

```
Pro Cys Pro Ala Pro Glu Leu Leu Gly Gly Pro Ser Val Phe Leu Phe
1               5               10              15
```

-continued

```
Pro Pro Lys Pro Lys Asp Thr Leu Met Ile Ser Arg Ser Pro Glu Val
        20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
        100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
        130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Ser His His
            195             200             205

Tyr Thr Gln Lys Asn Leu Ser Leu Ser Pro Gly Lys
    210             215             220
```

```
<210> SEQ ID NO 40
<211> LENGTH: 220
<212> TYPE: PRT
<213> ORGANISM: Artificial Sequence
<220> FEATURE:
<223> OTHER INFORMATION: CH2-CH3 IgG1_256P/433V/434H

<400> SEQUENCE: 40
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
        20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
        100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
        130             135             140

Phe Tyr Pro Ser Asp Ile Ala Val Glu Trp Glu Ser Asn Gly Gln Pro
145             150             155             160
```

```
Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val His His
            195                 200                 205

Tyr Thr Gln Lys Ser Leu Ser Leu Ser Pro Gly Lys
    210                 215                 220

<210> SEQ ID NO 41
<211> LENGTH: 220
<212> TYPE: PRT
<213> ORGANISM: Artificial Sequence
<220> FEATURE:
<223> OTHER INFORMATION: CH2-CH3 IgG1_256P/433V/434H/440R

<400> SEQUENCE: 41

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val His His
            195                 200                 205

Tyr Thr Gln Lys Arg Leu Ser Leu Ser Pro Gly Lys
    210                 215                 220

<210> SEQ ID NO 42
<211> LENGTH: 220
<212> TYPE: PRT
<213> ORGANISM: Artificial Sequence
<220> FEATURE:
<223> OTHER INFORMATION: CH2-CH3 IgG1_256P/433V/434H/436F

<400> SEQUENCE: 42

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30
```

-continued

```
Thr Cys Val Val Val Asp Val Ser His Glu Asp Pro Glu Val Lys Phe
    35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Val His His
            195             200             205

Phe Thr Gln Lys Ser Leu Ser Leu Ser Pro Gly Lys
    210             215             220
```

```
<210> SEQ ID NO 43
<211> LENGTH: 220
<212> TYPE: PRT
<213> ORGANISM: Artificial Sequence
<220> FEATURE:
<223> OTHER INFORMATION: CH2-CH3 IgG1_256P/433V/434H/440V

<400> SEQUENCE: 43
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
    35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175
```

-continued

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val His His
            195                 200                 205

Tyr Thr Gln Lys Val Leu Ser Leu Ser Pro Gly Lys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: CH2-CH3 IgG1_256A/433V/434H/440G

<400> SEQUENCE: 44

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
            50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val His His
            195                 200                 205

Tyr Thr Gln Lys Gly Leu Ser Leu Ser Pro Gly Lys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: CH2-CH3 IgG1_433V/434H/436F

<400> SEQUENCE: 45

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe

-continued

```
         35                    40                    45

Asn Trp Tyr Val Asp Gly Val Glu Val His Asn Ala Lys Thr Lys Pro
    50                    55                    60

Arg Glu Glu Gln Tyr Asn Ser Thr Tyr Arg Val Val Ser Val Leu Thr
65                    70                    75                    80

Val Leu His Gln Asp Trp Leu Asn Gly Lys Glu Tyr Lys Cys Lys Val
                85                    90                    95

Ser Asn Lys Ala Leu Pro Ala Pro Ile Glu Lys Thr Ile Ser Lys Ala
            100                   105                   110

Lys Gly Gln Pro Arg Glu Pro Gln Val Tyr Thr Leu Pro Pro Ser Arg
            115                   120                   125

Asp Glu Leu Thr Lys Asn Gln Val Ser Leu Thr Cys Leu Val Lys Gly
    130                   135                   140

Phe Tyr Pro Ser Asp Ile Ala Val Glu Trp Glu Ser Asn Gly Gln Pro
145                   150                   155                   160

Glu Asn Asn Tyr Lys Thr Thr Pro Pro Val Leu Asp Ser Asp Gly Ser
                165                   170                   175

Phe Phe Leu Tyr Ser Lys Leu Thr Val Asp Lys Ser Arg Trp Gln Gln
                180                   185                   190

Gly Asn Val Phe Ser Cys Ser Val Met His Glu Ala Leu Val His His
            195                   200                   205

Phe Thr Gln Lys Ser Leu Ser Leu Ser Pro Gly Lys
    210                   215                   220

<210> SEQ ID NO 46
<211> LENGTH: 220
<212> TYPE: PRT
<213> ORGANISM: Artificial Sequence
<220> FEATURE:
<223> OTHER INFORMATION: CH2-CH3 IgG1_256P/434H

<400> SEQUENCE: 46

Pro Cys Pro Ala Pro Glu Leu Leu Gly Gly Pro Ser Val Phe Leu Phe
1                   5                    10                    15

Pro Pro Lys Pro Lys Asp Thr Leu Met Ile Ser Arg Pro Pro Glu Val
            20                    25                    30

Thr Cys Val Val Val Asp Val Ser His Glu Asp Pro Glu Val Lys Phe
            35                    40                    45

Asn Trp Tyr Val Asp Gly Val Glu Val His Asn Ala Lys Thr Lys Pro
    50                    55                    60

Arg Glu Glu Gln Tyr Asn Ser Thr Tyr Arg Val Val Ser Val Leu Thr
65                    70                    75                    80

Val Leu His Gln Asp Trp Leu Asn Gly Lys Glu Tyr Lys Cys Lys Val
                85                    90                    95

Ser Asn Lys Ala Leu Pro Ala Pro Ile Glu Lys Thr Ile Ser Lys Ala
            100                   105                   110

Lys Gly Gln Pro Arg Glu Pro Gln Val Tyr Thr Leu Pro Pro Ser Arg
            115                   120                   125

Asp Glu Leu Thr Lys Asn Gln Val Ser Leu Thr Cys Leu Val Lys Gly
    130                   135                   140

Phe Tyr Pro Ser Asp Ile Ala Val Glu Trp Glu Ser Asn Gly Gln Pro
145                   150                   155                   160

Glu Asn Asn Tyr Lys Thr Thr Pro Pro Val Leu Asp Ser Asp Gly Ser
                165                   170                   175

Phe Phe Leu Tyr Ser Lys Leu Thr Val Asp Lys Ser Arg Trp Gln Gln
```

```
                180                 185                 190
Gly Asn Val Phe Ser Cys Ser Val Met His Glu Ala Leu His His His
        195                 200                 205

Tyr Thr Gln Lys Ser Leu Ser Leu Ser Pro Gly Lys
    210                 215                 220

<210> SEQ ID NO 47
<211> LENGTH: 220
<212> TYPE: PRT
<213> ORGANISM: Artificial Sequence
<220> FEATURE:
<223> OTHER INFORMATION: CH2-CH3 IgG1_256P/434H/440R

<400> SEQUENCE: 47

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His His His
        195                 200                 205

Tyr Thr Gln Lys Arg Leu Ser Leu Ser Pro Gly Lys
    210                 215                 220

<210> SEQ ID NO 48
<211> LENGTH: 220
<212> TYPE: PRT
<213> ORGANISM: Artificial Sequence
<220> FEATURE:
<223> OTHER INFORMATION: CH2-CH3 IgG1_256P/434H/440I

<400> SEQUENCE: 48

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45
```

```
Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His His His
            195                 200                 205

Tyr Thr Gln Lys Ile Leu Ser Leu Ser Pro Gly Lys
    210                 215                 220
```

```
<210> SEQ ID NO 49
<211> LENGTH: 220
<212> TYPE: PRT
<213> ORGANISM: Artificial Sequence
<220> FEATURE:
<223> OTHER INFORMATION: CH2-CH3 IgG1_256P/434H/436T/440N

<400> SEQUENCE: 49

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190
```

-continued

```
Gly Asn Val Phe Ser Cys Ser Val Met His Glu Ala Leu His His His
        195                 200                 205

Thr Thr Gln Lys Asn Leu Ser Leu Ser Pro Gly Lys
    210                 215                 220

<210> SEQ ID NO 50
<211> LENGTH: 220
<212> TYPE: PRT
<213> ORGANISM: Artificial Sequence
<220> FEATURE:
<223> OTHER INFORMATION: CH2-CH3 IgG1_256P/434H/440T

<400> SEQUENCE: 50

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His His His
        195                 200                 205

Tyr Thr Gln Lys Thr Leu Ser Leu Ser Pro Gly Lys
    210                 215                 220

<210> SEQ ID NO 51
<211> LENGTH: 220
<212> TYPE: PRT
<213> ORGANISM: Artificial Sequence
<220> FEATURE:
<223> OTHER INFORMATION: CH2-CH3 IgG1_256P/433A/434H/440T

<400> SEQUENCE: 51

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60
```

```
Arg Glu Glu Gln Tyr Asn Ser Thr Tyr Arg Val Val Ser Val Leu Thr
65              70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Ala His His
            195             200             205

Tyr Thr Gln Lys Thr Leu Ser Leu Ser Pro Gly Lys
    210             215             220
```

```
<210> SEQ ID NO 52
<211> LENGTH: 220
<212> TYPE: PRT
<213> ORGANISM: Artificial Sequence
<220> FEATURE:
<223> OTHER INFORMATION: CH2-CH3 IgG1_256P/433D/434H/440R

<400> SEQUENCE: 52
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65              70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Asp His His
            195             200             205
```

-continued

```
Tyr Thr Gln Lys Arg Leu Ser Leu Ser Pro Gly Lys
    210             215             220

<210> SEQ ID NO 53
<211> LENGTH: 220
<212> TYPE: PRT
<213> ORGANISM: Artificial Sequence
<220> FEATURE:
<223> OTHER INFORMATION: CH2-CH3 IgG1_256P/433D/434H

<400> SEQUENCE: 53

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Asp His His
            195             200             205

Tyr Thr Gln Lys Ser Leu Ser Leu Ser Pro Gly Lys
    210             215             220

<210> SEQ ID NO 54
<211> LENGTH: 220
<212> TYPE: PRT
<213> ORGANISM: Artificial Sequence
<220> FEATURE:
<223> OTHER INFORMATION: CH2-CH3 IgG1_256P/433D/434H/436F

<400> SEQUENCE: 54

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
```

```
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Asp His His
            195                 200                 205

Phe Thr Gln Lys Ser Leu Ser Leu Ser Pro Gly Lys
    210                 215                 220

<210> SEQ ID NO 55
<211> LENGTH: 220
<212> TYPE: PRT
<213> ORGANISM: Artificial Sequence
<220> FEATURE:
<223> OTHER INFORMATION: CH2-CH3 IgG1_256P/433P/434H

<400> SEQUENCE: 55

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Pro His His
            195                 200                 205

Tyr Thr Gln Lys Ser Leu Ser Leu Ser Pro Gly Lys
```

-continued

```
            210                 215                 220

<210> SEQ ID NO 56
<211> LENGTH: 220
<212> TYPE: PRT
<213> ORGANISM: Artificial Sequence
<220> FEATURE:
<223> OTHER INFORMATION: CH2-CH3 IgG1_256P/433Q/434H

<400> SEQUENCE: 56

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Gln His His
            195                 200                 205

Tyr Thr Gln Lys Ser Leu Ser Leu Ser Pro Gly Lys
    210                 215                 220

<210> SEQ ID NO 57
<211> LENGTH: 220
<212> TYPE: PRT
<213> ORGANISM: Artificial Sequence
<220> FEATURE:
<223> OTHER INFORMATION: CH2-CH3 IgG1_256P/433T/434H

<400> SEQUENCE: 57

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

```
Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr His His
            195                 200                 205

Tyr Thr Gln Lys Ser Leu Ser Leu Ser Pro Gly Lys
    210                 215                 220

<210> SEQ ID NO 58
<211> LENGTH: 220
<212> TYPE: PRT
<213> ORGANISM: Artificial Sequence
<220> FEATURE:
<223> OTHER INFORMATION: CH2-CH3 IgG1_256A/434H

<400> SEQUENCE: 58

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His His His
            195                 200                 205

Tyr Thr Gln Lys Ser Leu Ser Leu Ser Pro Gly Lys
    210                 215                 220
```

<210> SEQ ID NO 59
<211> LENGTH: 220
<212> TYPE: PRT
<213> ORGANISM: Artificial Sequence
<220> FEATURE:
<223> OTHER INFORMATION: CH2-CH3 IgG1_256A/433Q/434H/436F

<400> SEQUENCE: 59

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Gln His His
            195                 200                 205

Phe Thr Gln Lys Ser Leu Ser Leu Ser Pro Gly Lys
        210                 215                 220

<210> SEQ ID NO 60
<211> LENGTH: 220
<212> TYPE: PRT
<213> ORGANISM: Artificial Sequence
<220> FEATURE:
<223> OTHER INFORMATION: CH2-CH3 IgG1_256A/433T/434H

<400> SEQUENCE: 60

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

-continued

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr His His
            195                 200                 205

Tyr Thr Gln Lys Ser Leu Ser Leu Ser Pro Gly Lys
    210                 215                 220
```

<210> SEQ ID NO 61
<211> LENGTH: 220
<212> TYPE: PRT
<213> ORGANISM: Artificial Sequence
<220> FEATURE:
<223> OTHER INFORMATION: CH2-CH3 IgG1_433T/434H/436F

<400> SEQUENCE: 61

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr His His
            195                 200                 205

Phe Thr Gln Lys Ser Leu Ser Leu Ser Pro Gly Lys
    210                 215                 220
```

<210> SEQ ID NO 62

```
<211> LENGTH: 220
<212> TYPE: PRT
<213> ORGANISM: Artificial Sequence
<220> FEATURE:
<223> OTHER INFORMATION: CH2-CH3 IgG1_433T/434H

<400> SEQUENCE: 62

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr His His
            195                 200                 205

Tyr Thr Gln Lys Ser Leu Ser Leu Ser Pro Gly Lys
    210                 215                 220

<210> SEQ ID NO 63
<211> LENGTH: 220
<212> TYPE: PRT
<213> ORGANISM: Artificial Sequence
<220> FEATURE:
<223> OTHER INFORMATION: CH2-CH3 IgG1_256P/433T/434R

<400> SEQUENCE: 63

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
```

-continued

```
              100                 105                 110

Lys Gly Gln Pro Arg Glu Pro Gln Val Tyr Thr Leu Pro Pro Ser Arg
          115                 120                 125

Asp Glu Leu Thr Lys Asn Gln Val Ser Leu Thr Cys Leu Val Lys Gly
      130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
              165                 170                 175

Phe Phe Leu Tyr Ser Lys Leu Thr Val Asp Lys Ser Arg Trp Gln Gln
              180                 185                 190

Gly Asn Val Phe Ser Cys Ser Val Met His Glu Ala Leu Thr Arg His
          195                 200                 205

Tyr Thr Gln Lys Ser Leu Ser Leu Ser Pro Gly Lys
    210                 215                 220
```

<210> SEQ ID NO 64
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/436F

<400> SEQUENCE: 64

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
          20                  25                  30

Thr Cys Val Val Val Asp Val Ser His Glu Asp Pro Glu Val Lys Phe
          35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
          85                  90                  95

Ser Asn Lys Ala Leu Pro Ala Pro Ile Glu Lys Thr Ile Ser Lys Ala
          100                 105                 110

Lys Gly Gln Pro Arg Glu Pro Gln Val Tyr Thr Leu Pro Pro Ser Arg
          115                 120                 125

Asp Glu Leu Thr Lys Asn Gln Val Ser Leu Thr Cys Leu Val Lys Gly
      130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
              165                 170                 175

Phe Phe Leu Tyr Ser Lys Leu Thr Val Asp Lys Ser Arg Trp Gln Gln
              180                 185                 190

Gly Asn Val Phe Ser Cys Ser Val Met His Glu Ala Leu Thr Arg His
          195                 200                 205

Phe Thr Gln Lys Ser Leu Ser Leu Ser Pro Gly Lys
    210                 215                 220
```

<210> SEQ ID NO 65
<211> LENGTH: 220
<212> TYPE: PRT

<213> ORGANISM: Artificial Sequence
<220> FEATURE:
<223> OTHER INFORMATION: CH2-CH3 IgG1_256P/433T/434R/436L

<400> SEQUENCE: 65

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
            195                 200                 205

Leu Thr Gln Lys Ser Leu Ser Leu Ser Pro Gly Lys
    210                 215                 220

<210> SEQ ID NO 66
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/440I

<400> SEQUENCE: 66

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

-continued

```
Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
                195                 200                 205

Tyr Thr Gln Lys Ile Leu Ser Leu Ser Pro Gly Lys
        210                 215                 220

<210> SEQ ID NO 67
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/436F/440G

<400> SEQUENCE: 67

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
                195                 200                 205

Phe Thr Gln Lys Gly Leu Ser Leu Ser Pro Gly Lys
        210                 215                 220

<210> SEQ ID NO 68
<211> LENGTH: 220
<212> TYPE: PRT
<213> ORGANISM: Artificial Sequence
<220> FEATURE:
```

<223> OTHER INFORMATION: CH2-CH3 IgG1_433T/434R/436F

<400> SEQUENCE: 68

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
                195                 200                 205

Phe Thr Gln Lys Ser Leu Ser Leu Ser Pro Gly Lys
        210                 215                 220

<210> SEQ ID NO 69
<211> LENGTH: 220
<212> TYPE: PRT
<213> ORGANISM: Artificial Sequence
<220> FEATURE:
<223> OTHER INFORMATION: CH2-CH3 IgG1_433T/434R

<400> SEQUENCE: 69

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

```
Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Thr Arg His
        195             200             205

Tyr Thr Gln Lys Ser Leu Ser Leu Ser Pro Gly Lys
    210             215             220
```

<210> SEQ ID NO 70
<211> LENGTH: 220
<212> TYPE: PRT
<213> ORGANISM: Artificial Sequence
<220> FEATURE:
<223> OTHER INFORMATION: CH2-CH3 IgG1_433T/434R/436W

<400> SEQUENCE: 70

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Thr Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Thr Arg His
        195             200             205

Trp Thr Gln Lys Ser Leu Ser Leu Ser Pro Gly Lys
    210             215             220
```

<210> SEQ ID NO 71
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/436F/440I (also
      referred to herein as "PN04-90")

-continued

<400> SEQUENCE: 71

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr Arg His
            195                 200                 205

Phe Thr Gln Lys Ile Leu Ser Leu Ser Pro Gly Lys
        210                 215                 220
```

<210> SEQ ID NO 72
<211> LENGTH: 220
<212> TYPE: PRT
<213> ORGANISM: Artificial Sequence
<220> FEATURE:
<223> OTHER INFORMATION: CH2-CH3 IgG1_433T/434R/436F/440I (also referred
      to herein as "V5")

<400> SEQUENCE: 72

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125
```

```
Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
            195                 200                 205

Phe Thr Gln Lys Ile Leu Ser Leu Ser Pro Gly Lys
    210                 215                 220
```

<210> SEQ ID NO 73
<211> LENGTH: 220
<212> TYPE: PRT
<213> ORGANISM: Artificial Sequence
<220> FEATURE:
<223> OTHER INFORMATION: CH2-CH3 IgG1_256P/434R/436F/440I (also referred
      to herein as "V1")

<400> SEQUENCE: 73

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Arg His
            195                 200                 205

Phe Thr Gln Lys Ile Leu Ser Leu Ser Pro Gly Lys
    210                 215                 220
```

<210> SEQ ID NO 74
<211> LENGTH: 220
<212> TYPE: PRT
<213> ORGANISM: Artificial Sequence
<220> FEATURE:
<223> OTHER INFORMATION: CH2-CH3 IgG1_256P/433T/436F/440I (also referred to herein as "V2")

<400> SEQUENCE: 74

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Thr Asn His
            195                 200                 205

Phe Thr Gln Lys Ile Leu Ser Leu Ser Pro Gly Lys
    210                 215                 220
```

<210> SEQ ID NO 75
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/440I (also referred
     to herein as "V3")

<400> SEQUENCE: 75

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
```

```
               115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
                195                 200                 205

Tyr Thr Gln Lys Ile Leu Ser Leu Ser Pro Gly Lys
    210                 215                 220
```

<210> SEQ ID NO 76
<211> LENGTH: 220
<212> TYPE: PRT
<213> ORGANISM: Artificial Sequence
<220> FEATURE:
<223> OTHER INFORMATION: CH2-CH3 IgG1_256P/433T/434R/436F (also referred
      to herein as "V4")

<400> SEQUENCE: 76

```
Pro Cys Pro Ala Pro Glu Leu Leu Gly Gly Pro Ser Val Phe Leu Phe
1                 5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Thr Arg His
                195                 200                 205

Phe Thr Gln Lys Ser Leu Ser Leu Ser Pro Gly Lys
    210                 215                 220
```

<210> SEQ ID NO 77
<211> LENGTH: 220
<212> TYPE: PRT
<213> ORGANISM: Artificial Sequence
<220> FEATURE:

-continued

<223> OTHER INFORMATION: CH2-CH3 IgG1_256P/433V/434R

<400> SEQUENCE: 77

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg His
            195                 200                 205

Tyr Thr Gln Lys Ser Leu Ser Leu Ser Pro Gly Lys
    210                 215                 220

<210> SEQ ID NO 78
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/436F

<400> SEQUENCE: 78

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

-continued

```
Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
        180             185             190

Gly Asn Val Phe Ser Cys Ser Val Met His Glu Ala Leu Val Arg His
        195             200             205

Phe Thr Gln Lys Ser Leu Ser Leu Ser Pro Gly Lys
    210             215             220
```

<210> SEQ ID NO 79
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/440G

<400> SEQUENCE: 79

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
        20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
        180             185             190

Gly Asn Val Phe Ser Cys Ser Val Met His Glu Ala Leu Val Arg His
        195             200             205

Tyr Thr Gln Lys Gly Leu Ser Leu Ser Pro Gly Lys
    210             215             220
```

<210> SEQ ID NO 80
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/436L

<400> SEQUENCE: 80

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val Arg His
        195                 200                 205

Leu Thr Gln Lys Ser Leu Ser Leu Ser Pro Gly Lys
        210                 215                 220
```

<210> SEQ ID NO 81
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/436F/440R

<400> SEQUENCE: 81

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
```

-continued

```
            130              135              140

Phe Tyr Pro Ser Asp Ile Ala Val Glu Trp Glu Ser Asn Gly Gln Pro
145                 150              155                 160

Glu Asn Asn Tyr Lys Thr Thr Pro Pro Val Leu Asp Ser Asp Gly Ser
                165              170              175

Phe Phe Leu Tyr Ser Lys Leu Thr Val Asp Lys Ser Arg Trp Gln Gln
            180              185              190

Gly Asn Val Phe Ser Cys Ser Val Met His Glu Ala Leu Val Arg His
        195              200              205

Phe Thr Gln Lys Arg Leu Ser Leu Ser Pro Gly Lys
    210              215              220
```

<210> SEQ ID NO 82
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/440R

<400> SEQUENCE: 82

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65                  70              75                  80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
        130             135             140

Phe Tyr Pro Ser Asp Ile Ala Val Glu Trp Glu Ser Asn Gly Gln Pro
145                 150             155                 160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu Val Arg His
        195             200             205

Tyr Thr Gln Lys Arg Leu Ser Leu Ser Pro Gly Lys
    210             215             220
```

<210> SEQ ID NO 83
<211> LENGTH: 220
<212> TYPE: PRT
<213> ORGANISM: Artificial Sequence
<220> FEATURE:
<223> OTHER INFORMATION: CH2-CH3 IgG1_256P/433V/434R/440P

<400> SEQUENCE: 83

-continued

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg His
            195                 200                 205

Tyr Thr Gln Lys Pro Leu Ser Leu Ser Pro Gly Lys
    210                 215                 220
```

```
<210> SEQ ID NO 84
<211> LENGTH: 220
<212> TYPE: PRT
<213> ORGANISM: Artificial Sequence
<220> FEATURE:
<223> OTHER INFORMATION: CH2-CH3 IgG1_256A/433V/434R/436T/440N

<400> SEQUENCE: 84
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140
```

-continued

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val Arg His
                195                 200                 205

Thr Thr Gln Lys Asn Leu Ser Leu Ser Pro Gly Lys
        210                 215                 220

<210> SEQ ID NO 85
<211> LENGTH: 220
<212> TYPE: PRT
<213> ORGANISM: Artificial Sequence
<220> FEATURE:
<223> OTHER INFORMATION: CH2-CH3 IgG1_256A/433V/434R/440I

<400> SEQUENCE: 85

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val Arg His
                195                 200                 205

Tyr Thr Gln Lys Ile Leu Ser Leu Ser Pro Gly Lys
        210                 215                 220

<210> SEQ ID NO 86
<211> LENGTH: 220
<212> TYPE: PRT
<213> ORGANISM: Artificial Sequence
<220> FEATURE:
<223> OTHER INFORMATION: CH2-CH3 IgG1_433V/434R/436T/440R

<400> SEQUENCE: 86

Pro Cys Pro Ala Pro Glu Leu Leu Gly Gly Pro Ser Val Phe Leu Phe
1               5                   10                  15
```

-continued

```
Pro Pro Lys Pro Lys Asp Thr Leu Met Ile Ser Arg Thr Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val Arg His
            195                 200                 205

Thr Thr Gln Lys Arg Leu Ser Leu Ser Pro Gly Lys
        210                 215                 220

<210> SEQ ID NO 87
<211> LENGTH: 220
<212> TYPE: PRT
<213> ORGANISM: Artificial Sequence
<220> FEATURE:
<223> OTHER INFORMATION: CH2-CH3 IgG1_433V/434R/440I

<400> SEQUENCE: 87

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160
```

```
Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg His
            195                 200                 205

Tyr Thr Gln Lys Ile Leu Ser Leu Ser Pro Gly Lys
    210                 215                 220

<210> SEQ ID NO 88
<211> LENGTH: 220
<212> TYPE: PRT
<213> ORGANISM: Artificial Sequence
<220> FEATURE:
<223> OTHER INFORMATION: CH2-CH3 IgG1_433V/434R/436T

<400> SEQUENCE: 88

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg His
            195                 200                 205

Thr Thr Gln Lys Ser Leu Ser Leu Ser Pro Gly Lys
    210                 215                 220

<210> SEQ ID NO 89
<211> LENGTH: 220
<212> TYPE: PRT
<213> ORGANISM: Artificial Sequence
<220> FEATURE:
<223> OTHER INFORMATION: CH2-CH3 IgG1_433V/434R/440V

<400> SEQUENCE: 89

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
```

-continued

```
                20                  25                  30
Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Val Arg His
                195                 200                 205

Tyr Thr Gln Lys Val Leu Ser Leu Ser Pro Gly Lys
    210                 215                 220

<210> SEQ ID NO 90
<211> LENGTH: 220
<212> TYPE: PRT
<213> ORGANISM: Artificial Sequence
<220> FEATURE:
<223> OTHER INFORMATION: CH2-CH3 IgG1_433V/434R

<400> SEQUENCE: 90

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
```

-continued

```
                     165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg His
        195                 200                 205

Tyr Thr Gln Lys Ser Leu Ser Leu Ser Pro Gly Lys
    210                 215                 220

<210> SEQ ID NO 91
<211> LENGTH: 220
<212> TYPE: PRT
<213> ORGANISM: Artificial Sequence
<220> FEATURE:
<223> OTHER INFORMATION: CH2-CH3 IgG1_433V/434R/435L

<400> SEQUENCE: 91

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val Arg Leu
        195                 200                 205

Tyr Thr Gln Lys Ser Leu Ser Leu Ser Pro Gly Lys
    210                 215                 220

<210> SEQ ID NO 92
<211> LENGTH: 220
<212> TYPE: PRT
<213> ORGANISM: Artificial Sequence
<220> FEATURE:
<223> OTHER INFORMATION: CH2-CH3 IgG1_433V/434R/440R

<400> SEQUENCE: 92

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

```
Thr Cys Val Val Val Asp Val Ser His Glu Asp Pro Glu Val Lys Phe
    35              40              45
```

```
Asn Trp Tyr Val Asp Gly Val Glu Val His Asn Ala Lys Thr Lys Pro
    50              55              60
```

```
Arg Glu Glu Gln Tyr Asn Ser Thr Tyr Arg Val Val Ser Val Leu Thr
65              70              75              80
```

```
Val Leu His Gln Asp Trp Leu Asn Gly Lys Glu Tyr Lys Cys Lys Val
            85              90              95
```

```
Ser Asn Lys Ala Leu Pro Ala Pro Ile Glu Lys Thr Ile Ser Lys Ala
            100             105             110
```

```
Lys Gly Gln Pro Arg Glu Pro Gln Val Tyr Thr Leu Pro Pro Ser Arg
            115             120             125
```

```
Asp Glu Leu Thr Lys Asn Gln Val Ser Leu Thr Cys Leu Val Lys Gly
    130             135             140
```

```
Phe Tyr Pro Ser Asp Ile Ala Val Glu Trp Glu Ser Asn Gly Gln Pro
145             150             155             160
```

```
Glu Asn Asn Tyr Lys Thr Thr Pro Pro Val Leu Asp Ser Asp Gly Ser
            165             170             175
```

```
Phe Phe Leu Tyr Ser Lys Leu Thr Val Asp Lys Ser Arg Trp Gln Gln
            180             185             190
```

```
Gly Asn Val Phe Ser Cys Ser Val Met His Glu Ala Leu Val Arg His
            195             200             205
```

```
Tyr Thr Gln Lys Arg Leu Ser Leu Ser Pro Gly Lys
    210             215             220
```

```
<210> SEQ ID NO 93
<211> LENGTH: 220
<212> TYPE: PRT
<213> ORGANISM: Artificial Sequence
<220> FEATURE:
<223> OTHER INFORMATION: CH2-CH3 IgG1_256P/433I/434R/436F

<400> SEQUENCE: 93
```

```
Pro Cys Pro Ala Pro Glu Leu Leu Gly Gly Pro Ser Val Phe Leu Phe
1               5               10              15
```

```
Pro Pro Lys Pro Lys Asp Thr Leu Met Ile Ser Arg Pro Pro Glu Val
            20              25              30
```

```
Thr Cys Val Val Val Asp Val Ser His Glu Asp Pro Glu Val Lys Phe
    35              40              45
```

```
Asn Trp Tyr Val Asp Gly Val Glu Val His Asn Ala Lys Thr Lys Pro
    50              55              60
```

```
Arg Glu Glu Gln Tyr Asn Ser Thr Tyr Arg Val Val Ser Val Leu Thr
65              70              75              80
```

```
Val Leu His Gln Asp Trp Leu Asn Gly Lys Glu Tyr Lys Cys Lys Val
            85              90              95
```

```
Ser Asn Lys Ala Leu Pro Ala Pro Ile Glu Lys Thr Ile Ser Lys Ala
            100             105             110
```

```
Lys Gly Gln Pro Arg Glu Pro Gln Val Tyr Thr Leu Pro Pro Ser Arg
            115             120             125
```

```
Asp Glu Leu Thr Lys Asn Gln Val Ser Leu Thr Cys Leu Val Lys Gly
    130             135             140
```

```
Phe Tyr Pro Ser Asp Ile Ala Val Glu Trp Glu Ser Asn Gly Gln Pro
145             150             155             160
```

```
Glu Asn Asn Tyr Lys Thr Thr Pro Pro Val Leu Asp Ser Asp Gly Ser
            165             170             175
```

```
Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ile Arg His
        195                 200                 205

Phe Thr Gln Lys Ser Leu Ser Leu Ser Pro Gly Lys
    210                 215                 220

<210> SEQ ID NO 94
<211> LENGTH: 220
<212> TYPE: PRT
<213> ORGANISM: Artificial Sequence
<220> FEATURE:
<223> OTHER INFORMATION: CH2-CH3 IgG1_256P/433I/434R

<400> SEQUENCE: 94

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Ile Arg His
        195                 200                 205

Tyr Thr Gln Lys Ser Leu Ser Leu Ser Pro Gly Lys
    210                 215                 220

<210> SEQ ID NO 95
<211> LENGTH: 220
<212> TYPE: PRT
<213> ORGANISM: Artificial Sequence
<220> FEATURE:
<223> OTHER INFORMATION: CH2-CH3 IgG1_256P/436F/440R

<400> SEQUENCE: 95

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45
```

-continued

```
Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Phe Thr Gln Lys Arg Leu Ser Leu Ser Pro Gly Lys
    210                 215                 220
```

```
<210> SEQ ID NO 96
<211> LENGTH: 220
<212> TYPE: PRT
<213> ORGANISM: Artificial Sequence
<220> FEATURE:
<223> OTHER INFORMATION: CH2-CH3 IgG1_256P/436F/440T

<400> SEQUENCE: 96
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190
```

-continued

```
Gly Asn Val Phe Ser Cys Ser Val Met His Glu Ala Leu His Asn His
    195                 200                 205

Phe Thr Gln Lys Thr Leu Ser Leu Ser Pro Gly Lys
    210                 215                 220
```

<210> SEQ ID NO 97
<211> LENGTH: 220
<212> TYPE: PRT
<213> ORGANISM: Artificial Sequence
<220> FEATURE:
<223> OTHER INFORMATION: CH2-CH3 IgG1_256P/436T/440R

<400> SEQUENCE: 97

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
    195                 200                 205

Thr Thr Gln Lys Arg Leu Ser Leu Ser Pro Gly Lys
    210                 215                 220
```

<210> SEQ ID NO 98
<211> LENGTH: 220
<212> TYPE: PRT
<213> ORGANISM: Artificial Sequence
<220> FEATURE:
<223> OTHER INFORMATION: CH2-CH3 IgG1_256P

<400> SEQUENCE: 98

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
```

-continued

```
              50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
    210                 215                 220
```

```
<210> SEQ ID NO 99
<211> LENGTH: 220
<212> TYPE: PRT
<213> ORGANISM: Artificial Sequence
<220> FEATURE:
<223> OTHER INFORMATION: CH2-CH3 IgG1_256P/436T

<400> SEQUENCE: 99
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
```

-continued

```
          195                 200                 205

Thr Thr Gln Lys Ser Leu Ser Leu Ser Pro Gly Lys
    210                 215                 220

<210> SEQ ID NO 100
<211> LENGTH: 220
<212> TYPE: PRT
<213> ORGANISM: Artificial Sequence
<220> FEATURE:
<223> OTHER INFORMATION: CH2-CH3 IgG1_256P/436T/440T

<400> SEQUENCE: 100

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Thr Leu Ser Leu Ser Pro Gly Lys
    210                 215                 220

<210> SEQ ID NO 101
<211> LENGTH: 220
<212> TYPE: PRT
<213> ORGANISM: Artificial Sequence
<220> FEATURE:
<223> OTHER INFORMATION: CH2-CH3 IgG1_256P/440D

<400> SEQUENCE: 101

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60
```

```
Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Tyr Thr Gln Lys Asp Leu Ser Leu Ser Pro Gly Lys
    210             215             220
```

```
<210> SEQ ID NO 102
<211> LENGTH: 220
<212> TYPE: PRT
<213> ORGANISM: Artificial Sequence
<220> FEATURE:
<223> OTHER INFORMATION: CH2-CH3 IgG1_256P/436S/440W

<400> SEQUENCE: 102
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205
```

```
Ser Thr Gln Lys Trp Leu Ser Leu Ser Pro Gly Lys
    210                 215                 220

<210> SEQ ID NO 103
<211> LENGTH: 220
<212> TYPE: PRT
<213> ORGANISM: Artificial Sequence
<220> FEATURE:
<223> OTHER INFORMATION: CH2-CH3 IgG1_256P/436T/440M

<400> SEQUENCE: 103

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Met Leu Ser Leu Ser Pro Gly Lys
    210                 215                 220

<210> SEQ ID NO 104
<211> LENGTH: 220
<212> TYPE: PRT
<213> ORGANISM: Artificial Sequence
<220> FEATURE:
<223> OTHER INFORMATION: CH2-CH3 IgG1_256P/436T/440A

<400> SEQUENCE: 104

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

-continued

```
Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Ala Leu Ser Leu Ser Pro Gly Lys
    210                 215                 220

<210> SEQ ID NO 105
<211> LENGTH: 220
<212> TYPE: PRT
<213> ORGANISM: Artificial Sequence
<220> FEATURE:
<223> OTHER INFORMATION: CH2-CH3 IgG1_256P/436T/440D

<400> SEQUENCE: 105

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Asp Leu Ser Leu Ser Pro Gly Lys
    210                 215                 220
```

<210> SEQ ID NO 106
<211> LENGTH: 220
<212> TYPE: PRT
<213> ORGANISM: Artificial Sequence
<220> FEATURE:
<223> OTHER INFORMATION: CH2-CH3 IgG1_256P/440R

<400> SEQUENCE: 106

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Arg Leu Ser Leu Ser Pro Gly Lys
        210                 215                 220

<210> SEQ ID NO 107
<211> LENGTH: 220
<212> TYPE: PRT
<213> ORGANISM: Artificial Sequence
<220> FEATURE:
<223> OTHER INFORMATION: CH2-CH3 IgG1_256P/440A

<400> SEQUENCE: 107

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val

-continued

```
                    85                90                95

Ser Asn Lys Ala Leu Pro Ala Pro Ile Glu Lys Thr Ile Ser Lys Ala
            100                105                110

Lys Gly Gln Pro Arg Glu Pro Gln Val Tyr Thr Leu Pro Pro Ser Arg
            115                120                125

Asp Glu Leu Thr Lys Asn Gln Val Ser Leu Thr Cys Leu Val Lys Gly
        130                135                140

Phe Tyr Pro Ser Asp Ile Ala Val Glu Trp Glu Ser Asn Gly Gln Pro
145                150                155                160

Glu Asn Asn Tyr Lys Thr Thr Pro Pro Val Leu Asp Ser Asp Gly Ser
                165                170                175

Phe Phe Leu Tyr Ser Lys Leu Thr Val Asp Lys Ser Arg Trp Gln Gln
            180                185                190

Gly Asn Val Phe Ser Cys Ser Val Met His Glu Ala Leu His Asn His
            195                200                205

Tyr Thr Gln Lys Ala Leu Ser Leu Ser Pro Gly Lys
    210                215                220

<210> SEQ ID NO 108
<211> LENGTH: 220
<212> TYPE: PRT
<213> ORGANISM: Artificial Sequence
<220> FEATURE:
<223> OTHER INFORMATION: CH2-CH3 IgG1_256P/436L

<400> SEQUENCE: 108

Pro Cys Pro Ala Pro Glu Leu Leu Gly Gly Pro Ser Val Phe Leu Phe
1                5                10                15

Pro Pro Lys Pro Lys Asp Thr Leu Met Ile Ser Arg Pro Pro Glu Val
            20                25                30

Thr Cys Val Val Val Asp Val Ser His Glu Asp Pro Glu Val Lys Phe
            35                40                45

Asn Trp Tyr Val Asp Gly Val Glu Val His Asn Ala Lys Thr Lys Pro
    50                55                60

Arg Glu Glu Gln Tyr Asn Ser Thr Tyr Arg Val Val Ser Val Leu Thr
65                70                75                80

Val Leu His Gln Asp Trp Leu Asn Gly Lys Glu Tyr Lys Cys Lys Val
            85                90                95

Ser Asn Lys Ala Leu Pro Ala Pro Ile Glu Lys Thr Ile Ser Lys Ala
            100                105                110

Lys Gly Gln Pro Arg Glu Pro Gln Val Tyr Thr Leu Pro Pro Ser Arg
            115                120                125

Asp Glu Leu Thr Lys Asn Gln Val Ser Leu Thr Cys Leu Val Lys Gly
        130                135                140

Phe Tyr Pro Ser Asp Ile Ala Val Glu Trp Glu Ser Asn Gly Gln Pro
145                150                155                160

Glu Asn Asn Tyr Lys Thr Thr Pro Pro Val Leu Asp Ser Asp Gly Ser
                165                170                175

Phe Phe Leu Tyr Ser Lys Leu Thr Val Asp Lys Ser Arg Trp Gln Gln
            180                185                190

Gly Asn Val Phe Ser Cys Ser Val Met His Glu Ala Leu His Asn His
            195                200                205

Leu Thr Gln Lys Ser Leu Ser Leu Ser Pro Gly Lys
    210                215                220
```

```
<210> SEQ ID NO 109
<211> LENGTH: 220
<212> TYPE: PRT
<213> ORGANISM: Artificial Sequence
<220> FEATURE:
<223> OTHER INFORMATION: CH2-CH3 IgG1_256P/436F

<400> SEQUENCE: 109

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Phe Thr Gln Lys Ser Leu Ser Leu Ser Pro Gly Lys
    210                 215                 220

<210> SEQ ID NO 110
<211> LENGTH: 220
<212> TYPE: PRT
<213> ORGANISM: Artificial Sequence
<220> FEATURE:
<223> OTHER INFORMATION: CH2-CH3 IgG1_256P/440T

<400> SEQUENCE: 110

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95
```

-continued

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Thr Leu Ser Leu Ser Pro Gly Lys
    210                 215                 220
```

```
<210> SEQ ID NO 111
<211> LENGTH: 220
<212> TYPE: PRT
<213> ORGANISM: Artificial Sequence
<220> FEATURE:
<223> OTHER INFORMATION: CH2-CH3 IgG1_256P/436F/440I

<400> SEQUENCE: 111
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Phe Thr Gln Lys Ile Leu Ser Leu Ser Pro Gly Lys
    210                 215                 220
```

```
<210> SEQ ID NO 112
<211> LENGTH: 220
```

<212> TYPE: PRT
<213> ORGANISM: Artificial Sequence
<220> FEATURE:
<223> OTHER INFORMATION: CH2-CH3 IgG1_256P/436T/440N

<400> SEQUENCE: 112

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Asn Leu Ser Leu Ser Pro Gly Lys
        210                 215                 220
```

<210> SEQ ID NO 113
<211> LENGTH: 220
<212> TYPE: PRT
<213> ORGANISM: Artificial Sequence
<220> FEATURE:
<223> OTHER INFORMATION: CH2-CH3 IgG1_256P/440K

<400> SEQUENCE: 113

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

-continued

```
Lys Gly Gln Pro Arg Glu Pro Gln Val Tyr Thr Leu Pro Pro Ser Arg
    115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Lys Leu Ser Leu Ser Pro Gly Lys
    210                 215                 220
```

<210> SEQ ID NO 114
<211> LENGTH: 220
<212> TYPE: PRT
<213> ORGANISM: Artificial Sequence
<220> FEATURE:
<223> OTHER INFORMATION: CH2-CH3 IgG1_256P/436S

<400> SEQUENCE: 114

```
Pro Cys Pro Ala Pro Glu Leu Leu Gly Gly Pro Ser Val Phe Leu Phe
1                 5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
    115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Ser Thr Gln Lys Ser Leu Ser Leu Ser Pro Gly Lys
    210                 215                 220
```

<210> SEQ ID NO 115
<211> LENGTH: 220
<212> TYPE: PRT
<213> ORGANISM: Artificial Sequence
<220> FEATURE:
<223> OTHER INFORMATION: CH2-CH3 IgG1_256P/434I

<400> SEQUENCE: 115

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Ile His
            195                 200                 205

Tyr Thr Gln Lys Ser Leu Ser Leu Ser Pro Gly Lys
    210                 215                 220

<210> SEQ ID NO 116
<211> LENGTH: 220
<212> TYPE: PRT
<213> ORGANISM: Artificial Sequence
<220> FEATURE:
<223> OTHER INFORMATION: CH2-CH3 IgG1_256P/434I/436F/440M

<400> SEQUENCE: 116

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg

-continued

```
         115              120              125

Asp Glu Leu Thr Lys Asn Gln Val Ser Leu Thr Cys Leu Val Lys Gly
    130              135              140

Phe Tyr Pro Ser Asp Ile Ala Val Glu Trp Glu Ser Asn Gly Gln Pro
145              150              155              160

Glu Asn Asn Tyr Lys Thr Thr Pro Pro Val Leu Asp Ser Asp Gly Ser
                 165              170              175

Phe Phe Leu Tyr Ser Lys Leu Thr Val Asp Lys Ser Arg Trp Gln Gln
             180              185              190

Gly Asn Val Phe Ser Cys Ser Val Met His Glu Ala Leu His Ile His
             195              200              205

Phe Thr Gln Lys Met Leu Ser Leu Ser Pro Gly Lys
    210              215              220
```

```
<210> SEQ ID NO 117
<211> LENGTH: 220
<212> TYPE: PRT
<213> ORGANISM: Artificial Sequence
<220> FEATURE:
<223> OTHER INFORMATION: CH2-CH3 IgG1_256P/434L/436T

<400> SEQUENCE: 117
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Pro Pro Glu Val
             20              25              30

Thr Cys Val Val Val Asp Val Ser His Glu Asp Pro Glu Val Lys Phe
             35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
             85              90              95

Ser Asn Lys Ala Leu Pro Ala Pro Ile Glu Lys Thr Ile Ser Lys Ala
             100             105             110

Lys Gly Gln Pro Arg Glu Pro Gln Val Tyr Thr Leu Pro Pro Ser Arg
             115             120             125

Asp Glu Leu Thr Lys Asn Gln Val Ser Leu Thr Cys Leu Val Lys Gly
    130              135              140

Phe Tyr Pro Ser Asp Ile Ala Val Glu Trp Glu Ser Asn Gly Gln Pro
145              150              155              160

Glu Asn Asn Tyr Lys Thr Thr Pro Pro Val Leu Asp Ser Asp Gly Ser
                 165              170              175

Phe Phe Leu Tyr Ser Lys Leu Thr Val Asp Lys Ser Arg Trp Gln Gln
             180              185              190

Gly Asn Val Phe Ser Cys Ser Val Met His Glu Ala Leu His Leu His
             195              200              205

Thr Thr Gln Lys Ser Leu Ser Leu Ser Pro Gly Lys
    210              215              220
```

```
<210> SEQ ID NO 118
<211> LENGTH: 220
<212> TYPE: PRT
<213> ORGANISM: Artificial Sequence
<220> FEATURE:
<223> OTHER INFORMATION: CH2-CH3 IgG1_256P/434L
```

-continued

<400> SEQUENCE: 118

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu His
            195                 200                 205

Tyr Thr Gln Lys Ser Leu Ser Leu Ser Pro Gly Lys
    210                 215                 220
```

<210> SEQ ID NO 119
<211> LENGTH: 220
<212> TYPE: PRT
<213> ORGANISM: Artificial Sequence
<220> FEATURE:
<223> OTHER INFORMATION: CH2-CH3 IgG1_256P/434M/436T/440R

<400> SEQUENCE: 119

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125
```

```
Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Met His
                195                 200                 205

Thr Thr Gln Lys Arg Leu Ser Leu Ser Pro Gly Lys
    210                 215                 220
```

<210> SEQ ID NO 120
<211> LENGTH: 220
<212> TYPE: PRT
<213> ORGANISM: Artificial Sequence
<220> FEATURE:
<223> OTHER INFORMATION: CH2-CH3 IgG1_256P/434M

<400> SEQUENCE: 120

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Met His
                195                 200                 205

Tyr Thr Gln Lys Ser Leu Ser Leu Ser Pro Gly Lys
    210                 215                 220
```

<210> SEQ ID NO 121
<211> LENGTH: 220
<212> TYPE: PRT
<213> ORGANISM: Artificial Sequence
<220> FEATURE:
<223> OTHER INFORMATION: CH2-CH3 IgG1_256P/436L/440N

<400> SEQUENCE: 121

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Leu Thr Gln Lys Asn Leu Ser Leu Ser Pro Gly Lys
    210                 215                 220
```

<210> SEQ ID NO 122
<211> LENGTH: 220
<212> TYPE: PRT
<213> ORGANISM: Artificial Sequence
<220> FEATURE:
<223> OTHER INFORMATION: CH2-CH3 IgG1_256P/436T/440Y

<400> SEQUENCE: 122

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140
```

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Tyr Leu Ser Leu Ser Pro Gly Lys
    210                 215                 220
```

<210> SEQ ID NO 123
<211> LENGTH: 220
<212> TYPE: PRT
<213> ORGANISM: Artificial Sequence
<220> FEATURE:
<223> OTHER INFORMATION: CH2-CH3 IgG1_256A/436F/440M

<400> SEQUENCE: 123

```
Pro Cys Pro Ala Pro Glu Leu Leu Gly Gly Pro Ser Val Phe Leu Phe
1                 5                   10                  15

Pro Pro Lys Pro Lys Asp Thr Leu Met Ile Ser Arg Ala Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Phe Thr Gln Lys Met Leu Ser Leu Ser Pro Gly Lys
    210                 215                 220
```

<210> SEQ ID NO 124
<211> LENGTH: 220
<212> TYPE: PRT
<213> ORGANISM: Artificial Sequence
<220> FEATURE:
<223> OTHER INFORMATION: CH2-CH3 IgG1_256A/436F

<400> SEQUENCE: 124

```
Pro Cys Pro Ala Pro Glu Leu Leu Gly Gly Pro Ser Val Phe Leu Phe
```

```
1                5                    10                   15

Pro Pro Lys Pro Lys Asp Thr Leu Met Ile Ser Arg Ala Pro Glu Val
            20                   25                   30

Thr Cys Val Val Val Asp Val Ser His Glu Asp Pro Glu Val Lys Phe
            35                   40                   45

Asn Trp Tyr Val Asp Gly Val Glu Val His Asn Ala Lys Thr Lys Pro
        50                   55                   60

Arg Glu Glu Gln Tyr Asn Ser Thr Tyr Arg Val Val Ser Val Leu Thr
65                   70                   75                   80

Val Leu His Gln Asp Trp Leu Asn Gly Lys Glu Tyr Lys Cys Lys Val
                85                   90                   95

Ser Asn Lys Ala Leu Pro Ala Pro Ile Glu Lys Thr Ile Ser Lys Ala
            100                  105                  110

Lys Gly Gln Pro Arg Glu Pro Gln Val Tyr Thr Leu Pro Pro Ser Arg
            115                  120                  125

Asp Glu Leu Thr Lys Asn Gln Val Ser Leu Thr Cys Leu Val Lys Gly
        130                  135                  140

Phe Tyr Pro Ser Asp Ile Ala Val Glu Trp Glu Ser Asn Gly Gln Pro
145                  150                  155                  160

Glu Asn Asn Tyr Lys Thr Thr Pro Pro Val Leu Asp Ser Asp Gly Ser
                165                  170                  175

Phe Phe Leu Tyr Ser Lys Leu Thr Val Asp Lys Ser Arg Trp Gln Gln
            180                  185                  190

Gly Asn Val Phe Ser Cys Ser Val Met His Glu Ala Leu His Asn His
            195                  200                  205

Phe Thr Gln Lys Ser Leu Ser Leu Ser Pro Gly Lys
        210                  215                  220
```

<210> SEQ ID NO 125
<211> LENGTH: 220
<212> TYPE: PRT
<213> ORGANISM: Artificial Sequence
<220> FEATURE:
<223> OTHER INFORMATION: CH2-CH3 IgG1_256A/436T

<400> SEQUENCE: 125

```
Pro Cys Pro Ala Pro Glu Leu Leu Gly Gly Pro Ser Val Phe Leu Phe
1                5                    10                   15

Pro Pro Lys Pro Lys Asp Thr Leu Met Ile Ser Arg Ala Pro Glu Val
            20                   25                   30

Thr Cys Val Val Val Asp Val Ser His Glu Asp Pro Glu Val Lys Phe
            35                   40                   45

Asn Trp Tyr Val Asp Gly Val Glu Val His Asn Ala Lys Thr Lys Pro
        50                   55                   60

Arg Glu Glu Gln Tyr Asn Ser Thr Tyr Arg Val Val Ser Val Leu Thr
65                   70                   75                   80

Val Leu His Gln Asp Trp Leu Asn Gly Lys Glu Tyr Lys Cys Lys Val
                85                   90                   95

Ser Asn Lys Ala Leu Pro Ala Pro Ile Glu Lys Thr Ile Ser Lys Ala
            100                  105                  110

Lys Gly Gln Pro Arg Glu Pro Gln Val Tyr Thr Leu Pro Pro Ser Arg
            115                  120                  125

Asp Glu Leu Thr Lys Asn Gln Val Ser Leu Thr Cys Leu Val Lys Gly
        130                  135                  140

Phe Tyr Pro Ser Asp Ile Ala Val Glu Trp Glu Ser Asn Gly Gln Pro
```

-continued

```
145             150             155             160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
                180             185             190

Gly Asn Val Phe Ser Cys Ser Val Met His Glu Ala Leu His Asn His
                195             200             205

Thr Thr Gln Lys Ser Leu Ser Leu Ser Pro Gly Lys
    210             215             220
```

```
<210> SEQ ID NO 126
<211> LENGTH: 220
<212> TYPE: PRT
<213> ORGANISM: Artificial Sequence
<220> FEATURE:
<223> OTHER INFORMATION: CH2-CH3 IgG1_256A/436T/440F

<400> SEQUENCE: 126

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Ala Pro Glu Val
                20              25              30

Thr Cys Val Val Val Asp Val Ser His Glu Asp Pro Glu Val Lys Phe
                35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
                85              90              95

Ser Asn Lys Ala Leu Pro Ala Pro Ile Glu Lys Thr Ile Ser Lys Ala
                100             105             110

Lys Gly Gln Pro Arg Glu Pro Gln Val Tyr Thr Leu Pro Pro Ser Arg
                115             120             125

Asp Glu Leu Thr Lys Asn Gln Val Ser Leu Thr Cys Leu Val Lys Gly
                130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
                165             170             175

Phe Phe Leu Tyr Ser Lys Leu Thr Val Asp Lys Ser Arg Trp Gln Gln
                180             185             190

Gly Asn Val Phe Ser Cys Ser Val Met His Glu Ala Leu His Asn His
                195             200             205

Thr Thr Gln Lys Phe Leu Ser Leu Ser Pro Gly Lys
    210             215             220
```

```
<210> SEQ ID NO 127
<211> LENGTH: 220
<212> TYPE: PRT
<213> ORGANISM: Artificial Sequence
<220> FEATURE:
<223> OTHER INFORMATION: CH2-CH3 IgG1_256A

<400> SEQUENCE: 127

Pro Cys Pro Ala Pro Glu Leu Leu Gly Gly Pro Ser Val Phe Leu Phe
1               5               10              15
```

-continued

```
Pro Pro Lys Pro Lys Asp Thr Leu Met Ile Ser Arg Ala Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
            130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Tyr Thr Gln Lys Ser Leu Ser Leu Ser Pro Gly Lys
    210             215             220

<210> SEQ ID NO 128
<211> LENGTH: 220
<212> TYPE: PRT
<213> ORGANISM: Artificial Sequence
<220> FEATURE:
<223> OTHER INFORMATION: CH2-CH3 IgG1_256A/440I

<400> SEQUENCE: 128

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Ala Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
            130             135             140

Phe Tyr Pro Ser Asp Ile Ala Val Glu Trp Glu Ser Asn Gly Gln Pro
145             150             155             160
```

-continued

```
Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ile Leu Ser Leu Ser Pro Gly Lys
            210                 215                 220
```

<210> SEQ ID NO 129
<211> LENGTH: 220
<212> TYPE: PRT
<213> ORGANISM: Artificial Sequence
<220> FEATURE:
<223> OTHER INFORMATION: CH2-CH3 IgG1_256A/440G

<400> SEQUENCE: 129

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
            50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Gly Leu Ser Leu Ser Pro Gly Lys
            210                 215                 220
```

<210> SEQ ID NO 130
<211> LENGTH: 220
<212> TYPE: PRT
<213> ORGANISM: Artificial Sequence
<220> FEATURE:
<223> OTHER INFORMATION: CH2-CH3 IgG1_256A/440D

<400> SEQUENCE: 130

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ala Pro Glu Val
            20                  25                  30
```

```
Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Tyr Thr Gln Lys Asp Leu Ser Leu Ser Pro Gly Lys
    210             215             220

<210> SEQ ID NO 131
<211> LENGTH: 220
<212> TYPE: PRT
<213> ORGANISM: Artificial Sequence
<220> FEATURE:
<223> OTHER INFORMATION: CH2-CH3 IgG1_256A/440N

<400> SEQUENCE: 131

Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Ala Pro Glu Val
            20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175
```

Phe Phe Leu Tyr Ser Lys Leu Thr Val Asp Lys Ser Arg Trp Gln Gln
        180                 185                 190

Gly Asn Val Phe Ser Cys Ser Val Met His Glu Ala Leu His Asn His
        195                 200                 205

Tyr Thr Gln Lys Asn Leu Ser Leu Ser Pro Gly Lys
        210                 215                 220

<210> SEQ ID NO 132
<211> LENGTH: 220
<212> TYPE: PRT
<213> ORGANISM: Artificial Sequence
<220> FEATURE:
<223> OTHER INFORMATION: CH2-CH3 IgG1_256A/434M

<400> SEQUENCE: 132

Pro Cys Pro Ala Pro Glu Leu Leu Gly Gly Pro Ser Val Phe Leu Phe
1                   5                   10                  15

Pro Pro Lys Pro Lys Asp Thr Leu Met Ile Ser Arg Ala Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
        165                 170                 175

Phe Phe Leu Tyr Ser Lys Leu Thr Val Asp Lys Ser Arg Trp Gln Gln
        180                 185                 190

Gly Asn Val Phe Ser Cys Ser Val Met His Glu Ala Leu His Met His
        195                 200                 205

Tyr Thr Gln Lys Ser Leu Ser Leu Ser Pro Gly Lys
        210                 215                 220

<210> SEQ ID NO 133
<211> LENGTH: 220
<212> TYPE: PRT
<213> ORGANISM: Artificial Sequence
<220> FEATURE:
<223> OTHER INFORMATION: CH2-CH3 IgG1_440A

<400> SEQUENCE: 133

Pro Cys Pro Ala Pro Glu Leu Leu Gly Gly Pro Ser Val Phe Leu Phe
1                   5                   10                  15

Pro Pro Lys Pro Lys Asp Thr Leu Met Ile Ser Arg Thr Pro Glu Val
        20                  25                  30

Thr Cys Val Val Val Asp Val Ser His Glu Asp Pro Glu Val Lys Phe

-continued

```
          35                    40                    45
Asn Trp Tyr Val Asp Gly Val Glu Val His Asn Ala Lys Thr Lys Pro
    50                    55                    60
Arg Glu Glu Gln Tyr Asn Ser Thr Tyr Arg Val Val Ser Val Leu Thr
65                    70                    75                    80
Val Leu His Gln Asp Trp Leu Asn Gly Lys Glu Tyr Lys Cys Lys Val
                  85                    90                    95
Ser Asn Lys Ala Leu Pro Ala Pro Ile Glu Lys Thr Ile Ser Lys Ala
                  100                   105                   110
Lys Gly Gln Pro Arg Glu Pro Gln Val Tyr Thr Leu Pro Pro Ser Arg
                  115                   120                   125
Asp Glu Leu Thr Lys Asn Gln Val Ser Leu Thr Cys Leu Val Lys Gly
    130                   135                   140
Phe Tyr Pro Ser Asp Ile Ala Val Glu Trp Glu Ser Asn Gly Gln Pro
145                   150                   155                   160
Glu Asn Asn Tyr Lys Thr Thr Pro Pro Val Leu Asp Ser Asp Gly Ser
                  165                   170                   175
Phe Phe Leu Tyr Ser Lys Leu Thr Val Asp Lys Ser Arg Trp Gln Gln
                  180                   185                   190
Gly Asn Val Phe Ser Cys Ser Val Met His Glu Ala Leu His Asn His
                  195                   200                   205
Tyr Thr Gln Lys Ala Leu Ser Leu Ser Pro Gly Lys
    210                   215                   220

<210> SEQ ID NO 134
<211> LENGTH: 220
<212> TYPE: PRT
<213> ORGANISM: Artificial Sequence
<220> FEATURE:
<223> OTHER INFORMATION: CH2-CH3 IgG1_440I

<400> SEQUENCE: 134

Pro Cys Pro Ala Pro Glu Leu Leu Gly Gly Pro Ser Val Phe Leu Phe
1                   5                     10                    15
Pro Pro Lys Pro Lys Asp Thr Leu Met Ile Ser Arg Thr Pro Glu Val
                  20                    25                    30
Thr Cys Val Val Val Asp Val Ser His Glu Asp Pro Glu Val Lys Phe
                  35                    40                    45
Asn Trp Tyr Val Asp Gly Val Glu Val His Asn Ala Lys Thr Lys Pro
    50                    55                    60
Arg Glu Glu Gln Tyr Asn Ser Thr Tyr Arg Val Val Ser Val Leu Thr
65                    70                    75                    80
Val Leu His Gln Asp Trp Leu Asn Gly Lys Glu Tyr Lys Cys Lys Val
                  85                    90                    95
Ser Asn Lys Ala Leu Pro Ala Pro Ile Glu Lys Thr Ile Ser Lys Ala
                  100                   105                   110
Lys Gly Gln Pro Arg Glu Pro Gln Val Tyr Thr Leu Pro Pro Ser Arg
                  115                   120                   125
Asp Glu Leu Thr Lys Asn Gln Val Ser Leu Thr Cys Leu Val Lys Gly
    130                   135                   140
Phe Tyr Pro Ser Asp Ile Ala Val Glu Trp Glu Ser Asn Gly Gln Pro
145                   150                   155                   160
Glu Asn Asn Tyr Lys Thr Thr Pro Pro Val Leu Asp Ser Asp Gly Ser
                  165                   170                   175
Phe Phe Leu Tyr Ser Lys Leu Thr Val Asp Lys Ser Arg Trp Gln Gln
```

```
                180                    185                    190
Gly Asn Val Phe Ser Cys Ser Val Met His Glu Ala Leu His Asn His
        195                    200                    205
Tyr Thr Gln Lys Ile Leu Ser Leu Ser Pro Gly Lys
        210                    215                    220

<210> SEQ ID NO 135
<211> LENGTH: 220
<212> TYPE: PRT
<213> ORGANISM: Artificial Sequence
<220> FEATURE:
<223> OTHER INFORMATION: CH2-CH3 IgG1_440T

<400> SEQUENCE: 135

Pro Cys Pro Ala Pro Glu Leu Leu Gly Gly Pro Ser Val Phe Leu Phe
1               5                   10                  15
Pro Pro Lys Pro Lys Asp Thr Leu Met Ile Ser Arg Thr Pro Glu Val
            20                  25                  30
Thr Cys Val Val Val Asp Val Ser His Glu Asp Pro Glu Val Lys Phe
        35                  40                  45
Asn Trp Tyr Val Asp Gly Val Glu Val His Asn Ala Lys Thr Lys Pro
        50                  55                  60
Arg Glu Glu Gln Tyr Asn Ser Thr Tyr Arg Val Val Ser Val Leu Thr
65                  70                  75                  80
Val Leu His Gln Asp Trp Leu Asn Gly Lys Glu Tyr Lys Cys Lys Val
                85                  90                  95
Ser Asn Lys Ala Leu Pro Ala Pro Ile Glu Lys Thr Ile Ser Lys Ala
            100                 105                 110
Lys Gly Gln Pro Arg Glu Pro Gln Val Tyr Thr Leu Pro Pro Ser Arg
            115                 120                 125
Asp Glu Leu Thr Lys Asn Gln Val Ser Leu Thr Cys Leu Val Lys Gly
        130                 135                 140
Phe Tyr Pro Ser Asp Ile Ala Val Glu Trp Glu Ser Asn Gly Gln Pro
145                 150                 155                 160
Glu Asn Asn Tyr Lys Thr Thr Pro Pro Val Leu Asp Ser Asp Gly Ser
                165                 170                 175
Phe Phe Leu Tyr Ser Lys Leu Thr Val Asp Lys Ser Arg Trp Gln Gln
            180                 185                 190
Gly Asn Val Phe Ser Cys Ser Val Met His Glu Ala Leu His Asn His
        195                 200                 205
Tyr Thr Gln Lys Thr Leu Ser Leu Ser Pro Gly Lys
        210                 215                 220

<210> SEQ ID NO 136
<211> LENGTH: 220
<212> TYPE: PRT
<213> ORGANISM: Artificial Sequence
<220> FEATURE:
<223> OTHER INFORMATION: CH2-CH3 IgG1_253L/440A

<400> SEQUENCE: 136

Pro Cys Pro Ala Pro Glu Leu Leu Gly Gly Pro Ser Val Phe Leu Phe
1               5                   10                  15
Pro Pro Lys Pro Lys Asp Thr Leu Met Leu Ser Arg Thr Pro Glu Val
            20                  25                  30
Thr Cys Val Val Val Asp Val Ser His Glu Asp Pro Glu Val Lys Phe
        35                  40                  45
```

```
Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ala Leu Ser Leu Ser Pro Gly Lys
    210                 215                 220

<210> SEQ ID NO 137
<211> LENGTH: 220
<212> TYPE: PRT
<213> ORGANISM: Artificial Sequence
<220> FEATURE:
<223> OTHER INFORMATION: CH2-CH3 IgG1_440R

<400> SEQUENCE: 137

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190
```

```
Gly Asn Val Phe Ser Cys Ser Val Met His Glu Ala Leu His Asn His
        195                 200                 205

Tyr Thr Gln Lys Arg Leu Ser Leu Ser Pro Gly Lys
    210                 215                 220
```

```
<210> SEQ ID NO 138
<211> LENGTH: 220
<212> TYPE: PRT
<213> ORGANISM: Artificial Sequence
<220> FEATURE:
<223> OTHER INFORMATION: CH2-CH3 IgG1_253L

<400> SEQUENCE: 138
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Leu Ser Arg Thr Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
        100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
        180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220
```

```
<210> SEQ ID NO 139
<211> LENGTH: 220
<212> TYPE: PRT
<213> ORGANISM: Artificial Sequence
<220> FEATURE:
<223> OTHER INFORMATION: CH2-CH3 IgG1_440E

<400> SEQUENCE: 139
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
        20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60
```

```
Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
        130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Tyr Thr Gln Lys Glu Leu Ser Leu Ser Pro Gly Lys
    210             215             220
```

```
<210> SEQ ID NO 140
<211> LENGTH: 220
<212> TYPE: PRT
<213> ORGANISM: Artificial Sequence
<220> FEATURE:
<223> OTHER INFORMATION: CH2-CH3 IgG1_440C

<400> SEQUENCE: 140
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Thr Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
        130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205
```

```
Tyr Thr Gln Lys Cys Leu Ser Leu Ser Pro Gly Lys
    210             215             220

<210> SEQ ID NO 141
<211> LENGTH: 220
<212> TYPE: PRT
<213> ORGANISM: Artificial Sequence
<220> FEATURE:
<223> OTHER INFORMATION: CH2-CH3 IgG1_440Y

<400> SEQUENCE: 141

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Tyr Leu Ser Leu Ser Pro Gly Lys
    210             215             220

<210> SEQ ID NO 142
<211> LENGTH: 220
<212> TYPE: PRT
<213> ORGANISM: Artificial Sequence
<220> FEATURE:
<223> OTHER INFORMATION: CH2-CH3 IgG1_440D

<400> SEQUENCE: 142

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
```

-continued

```
65               70               75               80

Val Leu His Gln Asp Trp Leu Asn Gly Lys Glu Tyr Lys Cys Lys Val
                85               90               95

Ser Asn Lys Ala Leu Pro Ala Pro Ile Glu Lys Thr Ile Ser Lys Ala
            100              105              110

Lys Gly Gln Pro Arg Glu Pro Gln Val Tyr Thr Leu Pro Pro Ser Arg
            115              120              125

Asp Glu Leu Thr Lys Asn Gln Val Ser Leu Thr Cys Leu Val Lys Gly
        130              135              140

Phe Tyr Pro Ser Asp Ile Ala Val Glu Trp Glu Ser Asn Gly Gln Pro
145              150              155              160

Glu Asn Asn Tyr Lys Thr Thr Pro Pro Val Leu Asp Ser Asp Gly Ser
                165              170              175

Phe Phe Leu Tyr Ser Lys Leu Thr Val Asp Lys Ser Arg Trp Gln Gln
            180              185              190

Gly Asn Val Phe Ser Cys Ser Val Met His Glu Ala Leu His Asn His
            195              200              205

Tyr Thr Gln Lys Asp Leu Ser Leu Ser Pro Gly Lys
    210              215              220

<210> SEQ ID NO 143
<211> LENGTH: 220
<212> TYPE: PRT
<213> ORGANISM: Artificial Sequence
<220> FEATURE:
<223> OTHER INFORMATION: CH2-CH3 IgG1_436F

<400> SEQUENCE: 143

Pro Cys Pro Ala Pro Glu Leu Leu Gly Gly Pro Ser Val Phe Leu Phe
1               5               10               15

Pro Pro Lys Pro Lys Asp Thr Leu Met Ile Ser Arg Thr Pro Glu Val
            20               25               30

Thr Cys Val Val Val Asp Val Ser His Glu Asp Pro Glu Val Lys Phe
            35               40               45

Asn Trp Tyr Val Asp Gly Val Glu Val His Asn Ala Lys Thr Lys Pro
    50               55               60

Arg Glu Glu Gln Tyr Asn Ser Thr Tyr Arg Val Val Ser Val Leu Thr
65               70               75               80

Val Leu His Gln Asp Trp Leu Asn Gly Lys Glu Tyr Lys Cys Lys Val
                85               90               95

Ser Asn Lys Ala Leu Pro Ala Pro Ile Glu Lys Thr Ile Ser Lys Ala
            100              105              110

Lys Gly Gln Pro Arg Glu Pro Gln Val Tyr Thr Leu Pro Pro Ser Arg
            115              120              125

Asp Glu Leu Thr Lys Asn Gln Val Ser Leu Thr Cys Leu Val Lys Gly
        130              135              140

Phe Tyr Pro Ser Asp Ile Ala Val Glu Trp Glu Ser Asn Gly Gln Pro
145              150              155              160

Glu Asn Asn Tyr Lys Thr Thr Pro Pro Val Leu Asp Ser Asp Gly Ser
                165              170              175

Phe Phe Leu Tyr Ser Lys Leu Thr Val Asp Lys Ser Arg Trp Gln Gln
            180              185              190

Gly Asn Val Phe Ser Cys Ser Val Met His Glu Ala Leu His Asn His
            195              200              205

Phe Thr Gln Lys Ser Leu Ser Leu Ser Pro Gly Lys
```

```
     210              215              220
```

<210> SEQ ID NO 144
<211> LENGTH: 220
<212> TYPE: PRT
<213> ORGANISM: Artificial Sequence
<220> FEATURE:
<223> OTHER INFORMATION: CH2-CH3 IgG1_436F/440C

<400> SEQUENCE: 144

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Phe Thr Gln Lys Cys Leu Ser Leu Ser Pro Gly Lys
    210                 215                 220
```

<210> SEQ ID NO 145
<211> LENGTH: 220
<212> TYPE: PRT
<213> ORGANISM: Artificial Sequence
<220> FEATURE:
<223> OTHER INFORMATION: CH2-CH3 IgG1_436F/440Y

<400> SEQUENCE: 145

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80
```

```
Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Phe Thr Gln Lys Tyr Leu Ser Leu Ser Pro Gly Lys
    210                 215                 220

<210> SEQ ID NO 146
<211> LENGTH: 220
<212> TYPE: PRT
<213> ORGANISM: Artificial Sequence
<220> FEATURE:
<223> OTHER INFORMATION: CH2-CH3 IgG1_436F/440N

<400> SEQUENCE: 146

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Phe Thr Gln Lys Asn Leu Ser Leu Ser Pro Gly Lys
    210                 215                 220
```

-continued

<210> SEQ ID NO 147
<211> LENGTH: 220
<212> TYPE: PRT
<213> ORGANISM: Artificial Sequence
<220> FEATURE:
<223> OTHER INFORMATION: CH2-CH3 IgG1_436F/440R

<400> SEQUENCE: 147

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Phe Thr Gln Lys Arg Leu Ser Leu Ser Pro Gly Lys
    210                 215                 220

<210> SEQ ID NO 148
<211> LENGTH: 220
<212> TYPE: PRT
<213> ORGANISM: Artificial Sequence
<220> FEATURE:
<223> OTHER INFORMATION: CH2-CH3 IgG1_436T

<400> SEQUENCE: 148

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

```
Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Thr Thr Gln Lys Ser Leu Ser Leu Ser Pro Gly Lys
    210                 215                 220
```

<210> SEQ ID NO 149
<211> LENGTH: 220
<212> TYPE: PRT
<213> ORGANISM: Artificial Sequence
<220> FEATURE:
<223> OTHER INFORMATION: CH2-CH3 IgG1_434L/436F

<400> SEQUENCE: 149

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu His
            195                 200                 205

Phe Thr Gln Lys Ser Leu Ser Leu Ser Pro Gly Lys
    210                 215                 220
```

<210> SEQ ID NO 150

```
<211> LENGTH: 220
<212> TYPE: PRT
<213> ORGANISM: Artificial Sequence
<220> FEATURE:
<223> OTHER INFORMATION: CH2-CH3 IgG1_434L

<400> SEQUENCE: 150

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu His
            195                 200                 205

Tyr Thr Gln Lys Ser Leu Ser Leu Ser Pro Gly Lys
    210                 215                 220

<210> SEQ ID NO 151
<211> LENGTH: 220
<212> TYPE: PRT
<213> ORGANISM: Artificial Sequence
<220> FEATURE:
<223> OTHER INFORMATION: CH2-CH3 IgG1_434L/440R

<400> SEQUENCE: 151

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
```

-continued

```
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Leu His
            195                 200                 205

Tyr Thr Gln Lys Arg Leu Ser Leu Ser Pro Gly Lys
    210                 215                 220
```

<210> SEQ ID NO 152
<211> LENGTH: 220
<212> TYPE: PRT
<213> ORGANISM: Artificial Sequence
<220> FEATURE:
<223> OTHER INFORMATION: CH2-CH3 IgG1_434L/436F/440R

<400> SEQUENCE: 152

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Leu His
            195                 200                 205

Phe Thr Gln Lys Arg Leu Ser Leu Ser Pro Gly Lys
    210                 215                 220
```

<210> SEQ ID NO 153
<211> LENGTH: 220
<212> TYPE: PRT

```
<213> ORGANISM: Artificial Sequence
<220> FEATURE:
<223> OTHER INFORMATION: CH2-CH3 IgG1_434L/435L/440G

<400> SEQUENCE: 153

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu Leu
            195                 200                 205

Tyr Thr Gln Lys Gly Leu Ser Leu Ser Pro Gly Lys
    210                 215                 220

<210> SEQ ID NO 154
<211> LENGTH: 220
<212> TYPE: PRT
<213> ORGANISM: Artificial Sequence
<220> FEATURE:
<223> OTHER INFORMATION: CH2-CH3 IgG1_434L/440T

<400> SEQUENCE: 154

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110
```

-continued

```
Lys Gly Gln Pro Arg Glu Pro Gln Val Tyr Thr Leu Pro Pro Ser Arg
    115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu His
            195                 200                 205

Tyr Thr Gln Lys Thr Leu Ser Leu Ser Pro Gly Lys
    210                 215                 220
```

```
<210> SEQ ID NO 155
<211> LENGTH: 220
<212> TYPE: PRT
<213> ORGANISM: Artificial Sequence
<220> FEATURE:
<223> OTHER INFORMATION: CH2-CH3 IgG1_434L/440V

<400> SEQUENCE: 155
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
    115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Leu His
            195                 200                 205

Tyr Thr Gln Lys Val Leu Ser Leu Ser Pro Gly Lys
    210                 215                 220
```

```
<210> SEQ ID NO 156
<211> LENGTH: 220
<212> TYPE: PRT
<213> ORGANISM: Artificial Sequence
<220> FEATURE:
```

-continued

<223> OTHER INFORMATION: CH2-CH3 IgG1_434M

<400> SEQUENCE: 156

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Met His
            195                 200                 205

Tyr Thr Gln Lys Ser Leu Ser Leu Ser Pro Gly Lys
    210                 215                 220

<210> SEQ ID NO 157
<211> LENGTH: 220
<212> TYPE: PRT
<213> ORGANISM: Artificial Sequence
<220> FEATURE:
<223> OTHER INFORMATION: CH2-CH3 IgG1_256V/440R

<400> SEQUENCE: 157

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Val Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Arg Leu Ser Leu Ser Pro Gly Lys
    210                 215                 220

<210> SEQ ID NO 158
<211> LENGTH: 220
<212> TYPE: PRT
<213> ORGANISM: Artificial Sequence
<220> FEATURE:
<223> OTHER INFORMATION: CH2-CH3 IgG1_256G/440M

<400> SEQUENCE: 158

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Gly Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Tyr Thr Gln Lys Met Leu Ser Leu Ser Pro Gly Lys
    210                 215                 220

<210> SEQ ID NO 159
<211> LENGTH: 220
<212> TYPE: PRT
<213> ORGANISM: Artificial Sequence
<220> FEATURE:
<223> OTHER INFORMATION: CH2-CH3 IgG1_256I/440N

<400> SEQUENCE: 159

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Ile Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Asn Leu Ser Leu Ser Pro Gly Lys
    210                 215                 220
```

<210> SEQ ID NO 160
<211> LENGTH: 220
<212> TYPE: PRT
<213> ORGANISM: Artificial Sequence
<220> FEATURE:
<223> OTHER INFORMATION: CH2-CH3 IgG1_256K/436F

<400> SEQUENCE: 160

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Lys Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
```

```
            130             135             140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Phe Thr Gln Lys Ser Leu Ser Leu Ser Pro Gly Lys
    210                 215                 220

<210> SEQ ID NO 161
<211> LENGTH: 220
<212> TYPE: PRT
<213> ORGANISM: Artificial Sequence
<220> FEATURE:
<223> OTHER INFORMATION: CH2-CH3 IgG1_256N/436T/440N

<400> SEQUENCE: 161

Pro Cys Pro Ala Pro Glu Leu Leu Gly Gly Pro Ser Val Phe Leu Phe
1                 5                   10                  15

Pro Pro Lys Pro Lys Asp Thr Leu Met Ile Ser Arg Asn Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
            195                 200                 205

Thr Thr Gln Lys Asn Leu Ser Leu Ser Pro Gly Lys
    210                 215                 220

<210> SEQ ID NO 162
<211> LENGTH: 220
<212> TYPE: PRT
<213> ORGANISM: Artificial Sequence
<220> FEATURE:
<223> OTHER INFORMATION: CH2-CH3 IgG1_256N

<400> SEQUENCE: 162
```

-continued

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Asn Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
            195                 200                 205

Tyr Thr Gln Lys Ser Leu Ser Leu Ser Pro Gly Lys
    210                 215                 220

<210> SEQ ID NO 163
<211> LENGTH: 220
<212> TYPE: PRT
<213> ORGANISM: Artificial Sequence
<220> FEATURE:
<223> OTHER INFORMATION: CH2-CH3 IgG1_256N/440R

<400> SEQUENCE: 163

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Asn Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140
```

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Arg Leu Ser Leu Ser Pro Gly Lys
    210                 215                 220

<210> SEQ ID NO 164
<211> LENGTH: 220
<212> TYPE: PRT
<213> ORGANISM: Artificial Sequence
<220> FEATURE:
<223> OTHER INFORMATION: CH2-CH3 IgG1_256S

<400> SEQUENCE: 164

Pro Cys Pro Ala Pro Glu Leu Leu Gly Gly Pro Ser Val Phe Leu Phe
1                   5                   10                  15

Pro Pro Lys Pro Lys Asp Thr Leu Met Ile Ser Arg Ser Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
                195                 200                 205

Tyr Thr Gln Lys Ser Leu Ser Leu Ser Pro Gly Lys
    210                 215                 220

<210> SEQ ID NO 165
<211> LENGTH: 220
<212> TYPE: PRT
<213> ORGANISM: Artificial Sequence
<220> FEATURE:
<223> OTHER INFORMATION: CH2-CH3 IgG1_256S/436S

<400> SEQUENCE: 165

Pro Cys Pro Ala Pro Glu Leu Leu Gly Gly Pro Ser Val Phe Leu Phe
1                   5                   10                  15
```

-continued

```
Pro Pro Lys Pro Lys Asp Thr Leu Met Ile Ser Arg Ser Pro Glu Val
        20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
        100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160

Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Ser Thr Gln Lys Ser Leu Ser Leu Ser Pro Gly Lys
    210             215             220
```

```
<210> SEQ ID NO 166
<211> LENGTH: 220
<212> TYPE: PRT
<213> ORGANISM: Artificial Sequence
<220> FEATURE:
<223> OTHER INFORMATION: CH2-CH3 IgG1_256S/440A

<400> SEQUENCE: 166
```

```
Pro Cys Pro Ala Pro Glu Leu Leu Gly Gly Pro Ser Val Phe Leu Phe
1               5               10              15

Pro Pro Lys Pro Lys Asp Thr Leu Met Ile Ser Arg Ser Pro Glu Val
        20              25              30

Thr Cys Val Val Val Asp Val Ser His Glu Asp Pro Glu Val Lys Phe
        35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
        100             105             110

Lys Gly Gln Pro Arg Glu Pro Gln Val Tyr Thr Leu Pro Pro Ser Arg
        115             120             125

Asp Glu Leu Thr Lys Asn Gln Val Ser Leu Thr Cys Leu Val Lys Gly
    130             135             140

Phe Tyr Pro Ser Asp Ile Ala Val Glu Trp Glu Ser Asn Gly Gln Pro
145             150             155             160
```

-continued

```
Glu Asn Asn Tyr Lys Thr Thr Pro Pro Val Leu Asp Ser Asp Gly Ser
            165             170             175

Phe Phe Leu Tyr Ser Lys Leu Thr Val Asp Lys Ser Arg Trp Gln Gln
            180             185             190

Gly Asn Val Phe Ser Cys Ser Val Met His Glu Ala Leu His Asn His
            195             200             205

Tyr Thr Gln Lys Ala Leu Ser Leu Ser Pro Gly Lys
    210             215             220

<210> SEQ ID NO 167
<211> LENGTH: 220
<212> TYPE: PRT
<213> ORGANISM: Artificial Sequence
<220> FEATURE:
<223> OTHER INFORMATION: CH2-CH3 IgG1_1-8con
<220> FEATURE:
<221> NAME/KEY: MISC_FEATURE
<222> LOCATION: (26)..(26)
<223> OTHER INFORMATION: Xaa = I or L
<220> FEATURE:
<221> NAME/KEY: MISC_FEATURE
<222> LOCATION: (29)..(29)
<223> OTHER INFORMATION: Xaa = P, A, T, V, G, I, K, N or S
<220> FEATURE:
<221> NAME/KEY: MISC_FEATURE
<222> LOCATION: (206)..(206)
<223> OTHER INFORMATION: Xaa = S, V, H, A, D, P, Q, T or I
<220> FEATURE:
<221> NAME/KEY: MISC_FEATURE
<222> LOCATION: (207)..(207)
<223> OTHER INFORMATION: Xaa = H, R, N, I, L or M
<220> FEATURE:
<221> NAME/KEY: MISC_FEATURE
<222> LOCATION: (208)..(208)
<223> OTHER INFORMATION: Xaa = H or L
<220> FEATURE:
<221> NAME/KEY: MISC_FEATURE
<222> LOCATION: (209)..(209)
<223> OTHER INFORMATION: Xaa = Y, F, T, L, W or S
<220> FEATURE:
<221> NAME/KEY: MISC_FEATURE
<222> LOCATION: (213)..(213)
<223> OTHER INFORMATION: Xaa = S, G, I, R, Y, N, V, T, P, D, W, M, A, K,
      F, E or C

<400> SEQUENCE: 167

Pro Cys Pro Ala Pro Glu Leu Leu Gly Gly Pro Ser Val Phe Leu Phe
1               5               10              15

Pro Pro Lys Pro Lys Asp Thr Leu Met Xaa Ser Arg Xaa Pro Glu Val
            20              25              30

Thr Cys Val Val Val Asp Val Ser His Glu Asp Pro Glu Val Lys Phe
            35              40              45

Asn Trp Tyr Val Asp Gly Val Glu Val His Asn Ala Lys Thr Lys Pro
    50              55              60

Arg Glu Glu Gln Tyr Asn Ser Thr Tyr Arg Val Val Ser Val Leu Thr
65              70              75              80

Val Leu His Gln Asp Trp Leu Asn Gly Lys Glu Tyr Lys Cys Lys Val
            85              90              95

Ser Asn Lys Ala Leu Pro Ala Pro Ile Glu Lys Thr Ile Ser Lys Ala
            100             105             110

Lys Gly Gln Pro Arg Glu Pro Gln Val Tyr Thr Leu Pro Pro Ser Arg
            115             120             125

Asp Glu Leu Thr Lys Asn Gln Val Ser Leu Thr Cys Leu Val Lys Gly
    130             135             140
```

-continued

```
Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Xaa Xaa Xaa
                195                 200                 205

Xaa Thr Gln Lys Xaa Leu Ser Leu Ser Pro Gly Lys
    210                 215                 220
```

```
<210> SEQ ID NO 168
<211> LENGTH: 220
<212> TYPE: PRT
<213> ORGANISM: Artificial Sequence
<220> FEATURE:
<223> OTHER INFORMATION: CH2-CH3 IgG1_1con
<220> FEATURE:
<221> NAME/KEY: MISC_FEATURE
<222> LOCATION: (29)..(29)
<223> OTHER INFORMATION: Xaa = P, A or S
<220> FEATURE:
<221> NAME/KEY: MISC_FEATURE
<222> LOCATION: (208)..(208)
<223> OTHER INFORMATION: Xaa = H or L
<220> FEATURE:
<221> NAME/KEY: MISC_FEATURE
<222> LOCATION: (209)..(209)
<223> OTHER INFORMATION: Xaa = Y or F
<220> FEATURE:
<221> NAME/KEY: MISC_FEATURE
<222> LOCATION: (213)..(213)
<223> OTHER INFORMATION: Xaa = G, S, I, R, Y or N
```

```
<400> SEQUENCE: 168
```

```
Pro Cys Pro Ala Pro Glu Leu Leu Gly Gly Pro Ser Val Phe Leu Phe
1                   5                   10                  15

Pro Pro Lys Pro Lys Asp Thr Leu Met Ile Ser Arg Xaa Pro Glu Val
                20                  25                  30

Thr Cys Val Val Val Asp Val Ser His Glu Asp Pro Glu Val Lys Phe
                35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
                115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu Ser His Xaa
                195                 200                 205
```

```
Xaa Thr Gln Lys Xaa Leu Ser Leu Ser Pro Gly Lys
    210             215             220

<210> SEQ ID NO 169
<211> LENGTH: 220
<212> TYPE: PRT
<213> ORGANISM: Artificial Sequence
<220> FEATURE:
<223> OTHER INFORMATION: CH2-CH3 IgG1_2con
<220> FEATURE:
<221> NAME/KEY: MISC_FEATURE
<222> LOCATION: (29)..(29)
<223> OTHER INFORMATION: Xaa = P, A or T
<220> FEATURE:
<221> NAME/KEY: MISC_FEATURE
<222> LOCATION: (209)..(209)
<223> OTHER INFORMATION: Xaa = Y or F
<220> FEATURE:
<221> NAME/KEY: MISC_FEATURE
<222> LOCATION: (213)..(213)
<223> OTHER INFORMATION: Xaa = S, R, V or G

<400> SEQUENCE: 169

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Xaa Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Val His His
            195                 200                 205

Xaa Thr Gln Lys Xaa Leu Ser Leu Ser Pro Gly Lys
    210             215             220

<210> SEQ ID NO 170
<211> LENGTH: 220
<212> TYPE: PRT
<213> ORGANISM: Artificial Sequence
<220> FEATURE:
<223> OTHER INFORMATION: CH2-CH3 IgG1_3con
<220> FEATURE:
<221> NAME/KEY: MISC_FEATURE
<222> LOCATION: (29)..(29)
<223> OTHER INFORMATION: Xaa = P, A or T
```

```
<220> FEATURE:
<221> NAME/KEY: MISC_FEATURE
<222> LOCATION: (206)..(206)
<223> OTHER INFORMATION: Xaa = H, A, D, P, Q or T
<220> FEATURE:
<221> NAME/KEY: MISC_FEATURE
<222> LOCATION: (209)..(209)
<223> OTHER INFORMATION: Xaa = Y, T or F
<220> FEATURE:
<221> NAME/KEY: MISC_FEATURE
<222> LOCATION: (213)..(213)
<223> OTHER INFORMATION: Xaa = S, R, I, N or T

<400> SEQUENCE: 170

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Xaa Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Xaa His His
            195                 200                 205

Xaa Thr Gln Lys Xaa Leu Ser Leu Ser Pro Gly Lys
    210                 215                 220

<210> SEQ ID NO 171
<211> LENGTH: 220
<212> TYPE: PRT
<213> ORGANISM: Artificial Sequence
<220> FEATURE:
<223> OTHER INFORMATION: CH2-CH3 IgG1_4con
<220> FEATURE:
<221> NAME/KEY: MISC_FEATURE
<222> LOCATION: (29)..(29)
<223> OTHER INFORMATION: Xaa = P or T
<220> FEATURE:
<221> NAME/KEY: MISC_FEATURE
<222> LOCATION: (206)..(206)
<223> OTHER INFORMATION: Xaa =T or H
<220> FEATURE:
<221> NAME/KEY: MISC_FEATURE
<222> LOCATION: (207)..(207)
<223> OTHER INFORMATION: Xaa = R or N
<220> FEATURE:
<221> NAME/KEY: MISC_FEATURE
<222> LOCATION: (209)..(209)
```

```
<223> OTHER INFORMATION: Xaa = Y, F, L or W
<220> FEATURE:
<221> NAME/KEY: MISC_FEATURE
<222> LOCATION: (213)..(213)
<223> OTHER INFORMATION: Xaa = S, I or G

<400> SEQUENCE: 171

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Xaa Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Xaa Xaa His
            195                 200                 205

Xaa Thr Gln Lys Xaa Leu Ser Leu Ser Pro Gly Lys
    210                 215                 220

<210> SEQ ID NO 172
<211> LENGTH: 220
<212> TYPE: PRT
<213> ORGANISM: Artificial Sequence
<220> FEATURE:
<223> OTHER INFORMATION: CH2-CH3 IgG1_5con
<220> FEATURE:
<221> NAME/KEY: MISC_FEATURE
<222> LOCATION: (29)..(29)
<223> OTHER INFORMATION: Xaa = P, A or T
<220> FEATURE:
<221> NAME/KEY: MISC_FEATURE
<222> LOCATION: (206)..(206)
<223> OTHER INFORMATION: Xaa = V or I
<220> FEATURE:
<221> NAME/KEY: MISC_FEATURE
<222> LOCATION: (208)..(208)
<223> OTHER INFORMATION: Xaa = H or L
<220> FEATURE:
<221> NAME/KEY: MISC_FEATURE
<222> LOCATION: (209)..(209)
<223> OTHER INFORMATION: Xaa = Y, F, L or T
<220> FEATURE:
<221> NAME/KEY: MISC_FEATURE
<222> LOCATION: (213)..(213)
<223> OTHER INFORMATION: Xaa = S, G, R, P, N, I or V

<400> SEQUENCE: 172
```

-continued

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Xaa Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu Xaa Arg Xaa
            195                 200                 205

Xaa Thr Gln Lys Xaa Leu Ser Leu Ser Pro Gly Lys
    210                 215                 220
```

```
<210> SEQ ID NO 173
<211> LENGTH: 220
<212> TYPE: PRT
<213> ORGANISM: Artificial Sequence
<220> FEATURE:
<223> OTHER INFORMATION: CH2-CH3 IgG1_6con
<220> FEATURE:
<221> NAME/KEY: MISC_FEATURE
<222> LOCATION: (207)..(207)
<223> OTHER INFORMATION: Xaa = N, I, L or M
<220> FEATURE:
<221> NAME/KEY: MISC_FEATURE
<222> LOCATION: (209)..(209)
<223> OTHER INFORMATION: Xaa = F, T, Y, S or L
<220> FEATURE:
<221> NAME/KEY: MISC_FEATURE
<222> LOCATION: (213)..(213)
<223> OTHER INFORMATION: Xaa = R, T, S, D, W, M, A, K, N, Y or I

<400> SEQUENCE: 173
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Pro Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80
```

```
Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
               100                 105                 110

Lys Gly Gln Pro Arg Glu Pro Gln Val Tyr Thr Leu Pro Pro Ser Arg
               115                 120                 125

Asp Glu Leu Thr Lys Asn Gln Val Ser Leu Thr Cys Leu Val Lys Gly
       130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
               165                 170                 175

Phe Phe Leu Tyr Ser Lys Leu Thr Val Asp Lys Ser Arg Trp Gln Gln
               180                 185                 190

Gly Asn Val Phe Ser Cys Ser Val Met His Glu Ala Leu His Xaa His
               195                 200                 205

Xaa Thr Gln Lys Xaa Leu Ser Leu Ser Pro Gly Lys
       210                 215                 220
```

```
<210> SEQ ID NO 174
<211> LENGTH: 220
<212> TYPE: PRT
<213> ORGANISM: Artificial Sequence
<220> FEATURE:
<223> OTHER INFORMATION: CH2-CH3 IgG1_7con
<220> FEATURE:
<221> NAME/KEY: MISC_FEATURE
<222> LOCATION: (207)..(207)
<223> OTHER INFORMATION: Xaa = N or M
<220> FEATURE:
<221> NAME/KEY: MISC_FEATURE
<222> LOCATION: (209)..(209)
<223> OTHER INFORMATION: Xaa = F, T or Y
<220> FEATURE:
<221> NAME/KEY: MISC_FEATURE
<222> LOCATION: (213)..(213)
<223> OTHER INFORMATION: Xaa = M, S, F, I G, D or N

<400> SEQUENCE: 174
```

```
Pro Cys Pro Ala Pro Glu Leu Leu Gly Gly Pro Ser Val Phe Leu Phe
1               5                  10                  15

Pro Pro Lys Pro Lys Asp Thr Leu Met Ile Ser Arg Ala Pro Glu Val
               20                  25                  30

Thr Cys Val Val Val Asp Val Ser His Glu Asp Pro Glu Val Lys Phe
               35                  40                  45

Asn Trp Tyr Val Asp Gly Val Glu Val His Asn Ala Lys Thr Lys Pro
       50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
               100                 105                 110

Lys Gly Gln Pro Arg Glu Pro Gln Val Tyr Thr Leu Pro Pro Ser Arg
               115                 120                 125

Asp Glu Leu Thr Lys Asn Gln Val Ser Leu Thr Cys Leu Val Lys Gly
       130                 135                 140

Phe Tyr Pro Ser Asp Ile Ala Val Glu Trp Glu Ser Asn Gly Gln Pro
145                 150                 155                 160
```

```
Glu Asn Asn Tyr Lys Thr Thr Pro Pro Val Leu Asp Ser Asp Gly Ser
            165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Xaa His
            195                 200                 205

Xaa Thr Gln Lys Xaa Leu Ser Leu Ser Pro Gly Lys
    210                 215                 220
```

```
<210> SEQ ID NO 175
<211> LENGTH: 220
<212> TYPE: PRT
<213> ORGANISM: Artificial Sequence
<220> FEATURE:
<223> OTHER INFORMATION: CH2-CH3 IgG1_8con
<220> FEATURE:
<221> NAME/KEY: MISC_FEATURE
<222> LOCATION: (26)..(26)
<223> OTHER INFORMATION: Xaa = I or L
<220> FEATURE:
<221> NAME/KEY: MISC_FEATURE
<222> LOCATION: (29)..(29)
<223> OTHER INFORMATION: Xaa = T, V, G, I, K, N or S
<220> FEATURE:
<221> NAME/KEY: MISC_FEATURE
<222> LOCATION: (207)..(207)
<223> OTHER INFORMATION: Xaa = N, L or M
<220> FEATURE:
<221> NAME/KEY: MISC_FEATURE
<222> LOCATION: (208)..(208)
<223> OTHER INFORMATION: Xaa = H or L
<220> FEATURE:
<221> NAME/KEY: MISC_FEATURE
<222> LOCATION: (209)..(209)
<223> OTHER INFORMATION: Xaa = Y, F, T or S
<220> FEATURE:
<221> NAME/KEY: MISC_FEATURE
<222> LOCATION: (213)..(213)
<223> OTHER INFORMATION: Xaa = A, I, T, R, S, E, C, Y, D, N, G, V or M

<400> SEQUENCE: 175
```

```
Pro Cys Pro Ala Pro Glu Leu Leu Gly Gly Pro Ser Val Phe Leu Phe
1               5                   10                  15

Pro Pro Lys Pro Lys Asp Thr Leu Met Xaa Ser Arg Xaa Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
            130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
            165                 170                 175
```

```
Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Xaa Xaa
        195                 200                 205

Xaa Thr Gln Lys Xaa Leu Ser Leu Ser Pro Gly Lys
    210                 215                 220

<210> SEQ ID NO 176
<211> LENGTH: 9
<212> TYPE: PRT
<213> ORGANISM: Artificial Sequence
<220> FEATURE:
<223> OTHER INFORMATION: HLA-A*2401-Ad5 epitope

<400> SEQUENCE: 176

Thr Tyr Phe Ser Leu Asn Asn Lys Phe
1               5

<210> SEQ ID NO 177
<211> LENGTH: 10
<212> TYPE: PRT
<213> ORGANISM: Artificial Sequence
<220> FEATURE:
<223> OTHER INFORMATION: HLA-A*0201-Ad5 epitope

<400> SEQUENCE: 177

Tyr Val Leu Phe Glu Val Phe Asp Val Val
1               5                   10

<210> SEQ ID NO 178
<211> LENGTH: 10
<212> TYPE: PRT
<213> ORGANISM: Artificial Sequence
<220> FEATURE:
<223> OTHER INFORMATION: scrambled peptide

<400> SEQUENCE: 178

Leu Ala Val Phe Glu Asp Tyr Val Ala Phe
1               5                   10

<210> SEQ ID NO 179
<211> LENGTH: 9
<212> TYPE: PRT
<213> ORGANISM: Artificial Sequence
<220> FEATURE:
<223> OTHER INFORMATION: HLA-A2-HIV epitope

<400> SEQUENCE: 179

Ser Leu Tyr Asn Thr Val Ala Thr Leu
1               5

<210> SEQ ID NO 180
<211> LENGTH: 199
<212> TYPE: PRT
<213> ORGANISM: Artificial Sequence
<220> FEATURE:
<223> OTHER INFORMATION: CH2-CH3 IgA1

<400> SEQUENCE: 180

Pro Arg Leu Ser Leu His Arg Pro Ala Leu Glu Asp Leu Leu Leu Gly
1               5                   10                  15

Ser Glu Ala Asn Leu Thr Cys Thr Leu Thr Gly Leu Arg Asp Ala Ser
            20                  25                  30

Gly Val Thr Phe Thr Trp Thr Pro Ser Ser Gly Lys Ser Ala Val Gln
```

-continued

```
            35                    40                    45

Gly Pro Pro Glu Arg Asp Leu Cys Gly Cys Tyr Ser Val Ser Ser Val
    50                    55                    60

Leu Pro Gly Cys Ala Glu Pro Trp Asn His Gly Lys Thr Phe Thr Cys
65                    70                    75                    80

Thr Ala Ala Tyr Pro Glu Ser Lys Thr Pro Leu Thr Ala Thr Leu Ser
                85                    90                    95

Pro Glu Val His Leu Leu Pro Pro Ser Glu Glu Leu Ala Leu Asn
                100                   105                   110

Glu Leu Val Thr Leu Thr Cys Leu Ala Arg Gly Phe Ser Pro Lys Asp
                115                   120                   125

Val Leu Val Arg Trp Leu Gln Gly Ser Gln Glu Leu Pro Arg Glu Lys
    130                   135                   140

Tyr Leu Thr Trp Ala Ser Arg Gln Glu Pro Ser Gln Gly Thr Thr Thr
145                   150                   155                   160

Phe Ala Val Thr Ser Ile Leu Arg Val Ala Ala Glu Asp Trp Lys Lys
                165                   170                   175

Gly Asp Thr Phe Ser Cys Met Val Gly His Glu Ala Leu Pro Leu Ala
                180                   185                   190

Phe Thr Gln Lys Thr Ile Asp
        195

<210> SEQ ID NO 181
<211> LENGTH: 199
<212> TYPE: PRT
<213> ORGANISM: Artificial Sequence
<220> FEATURE:
<223> OTHER INFORMATION: CH2-CH3 IgA2

<400> SEQUENCE: 181

Pro Arg Leu Ser Leu His Arg Pro Ala Leu Glu Asp Leu Leu Leu Gly
1               5                     10                    15

Ser Glu Ala Asn Leu Thr Cys Thr Leu Thr Gly Leu Arg Asp Ala Ser
                20                    25                    30

Gly Ala Thr Phe Thr Trp Thr Pro Ser Ser Gly Lys Ser Ala Val Gln
        35                    40                    45

Gly Pro Pro Glu Arg Asp Leu Cys Gly Cys Tyr Ser Val Ser Ser Val
    50                    55                    60

Leu Pro Gly Cys Ala Gln Pro Trp Asn His Gly Glu Thr Phe Thr Cys
65                    70                    75                    80

Thr Ala Ala His Pro Glu Leu Lys Thr Pro Leu Thr Ala Asn Ile Thr
                85                    90                    95

Pro Glu Val His Leu Leu Pro Pro Ser Glu Glu Leu Ala Leu Asn
                100                   105                   110

Glu Leu Val Thr Leu Thr Cys Leu Ala Arg Gly Phe Ser Pro Lys Asp
                115                   120                   125

Val Leu Val Arg Trp Leu Gln Gly Ser Gln Glu Leu Pro Arg Glu Lys
    130                   135                   140

Tyr Leu Thr Trp Ala Ser Arg Gln Glu Pro Ser Gln Gly Thr Thr Thr
145                   150                   155                   160

Tyr Ala Val Thr Ser Ile Leu Arg Val Ala Ala Glu Asp Trp Lys Lys
                165                   170                   175

Gly Glu Thr Phe Ser Cys Met Val Gly His Glu Ala Leu Pro Leu Ala
                180                   185                   190

Phe Thr Gln Lys Thr Ile Asp
```

-continued

```
        195

<210> SEQ ID NO 182
<211> LENGTH: 199
<212> TYPE: PRT
<213> ORGANISM: Artificial Sequence
<220> FEATURE:
<223> OTHER INFORMATION: CH2-CH3 IgD

<400> SEQUENCE: 182

Pro Ala Val Gln Asp Leu Trp Leu Arg Asp Lys Ala Thr Phe Thr Cys
1               5                   10                  15

Phe Val Val Gly Ser Asp Leu Lys Asp Ala His Leu Thr Trp Glu Val
            20                  25                  30

Ala Gly Lys Val Pro Thr Gly Gly Val Glu Glu Gly Leu Leu Glu Arg
        35                  40                  45

His Ser Asn Gly Ser Gln Ser Gln His Ser Arg Leu Thr Leu Pro Arg
    50                  55                  60

Ser Leu Trp Asn Ala Gly Thr Ser Val Thr Cys Thr Leu Asn His Pro
65                  70                  75                  80

Ser Leu Pro Pro Gln Arg Leu Met Ala Leu Arg Glu Pro Ala Ala Gln
                85                  90                  95

Ala Pro Val Lys Leu Ser Leu Asn Leu Leu Ala Ser Ser Asp Pro Pro
            100                 105                 110

Glu Ala Ala Ser Trp Leu Leu Cys Glu Val Ser Gly Phe Ser Pro Pro
            115                 120                 125

Asn Ile Leu Leu Met Trp Leu Glu Asp Gln Arg Glu Val Asn Thr Ser
    130                 135                 140

Gly Phe Ala Pro Ala Arg Pro Pro Pro Gln Pro Arg Ser Thr Thr Phe
145                 150                 155                 160

Trp Ala Trp Ser Val Leu Arg Val Pro Ala Pro Pro Ser Pro Gln Pro
                165                 170                 175

Ala Thr Tyr Thr Cys Val Val Ser His Glu Asp Ser Arg Thr Leu Leu
            180                 185                 190

Asn Ala Ser Arg Ser Leu Glu
        195

<210> SEQ ID NO 183
<211> LENGTH: 312
<212> TYPE: PRT
<213> ORGANISM: Artificial Sequence
<220> FEATURE:
<223> OTHER INFORMATION: CH2-CH3-CH4 IgE

<400> SEQUENCE: 183

Pro Thr Val Lys Ile Leu Gln Ser Ser Cys Asp Gly Gly Gly His Phe
1               5                   10                  15

Pro Pro Thr Ile Gln Leu Leu Cys Leu Val Ser Gly Tyr Thr Pro Gly
            20                  25                  30

Thr Ile Asn Ile Thr Trp Leu Glu Asp Gly Gln Val Met Asp Val Asp
            35                  40                  45

Leu Ser Thr Ala Ser Thr Thr Gln Glu Gly Glu Leu Ala Ser Thr Gln
    50                  55                  60

Ser Glu Leu Thr Leu Ser Gln Lys His Trp Leu Ser Asp Arg Thr Tyr
65                  70                  75                  80

Thr Cys Gln Val Thr Tyr Gln Gly His Thr Phe Glu Asp Ser Thr Lys
                85                  90                  95
```

```
Lys Cys Ala Asp Ser Asn Pro Arg Gly Val Ser Ala Tyr Leu Ser Arg
            100                 105                 110

Pro Ser Pro Phe Asp Leu Phe Ile Arg Lys Ser Pro Thr Ile Thr Cys
            115                 120                 125

Leu Val Val Asp Leu Ala Pro Ser Lys Gly Thr Val Asn Leu Thr Trp
            130                 135                 140

Ser Arg Ala Ser Gly Lys Pro Val Asn His Ser Thr Arg Lys Glu Glu
145                 150                 155                 160

Lys Gln Arg Asn Gly Thr Leu Thr Val Thr Ser Thr Leu Pro Val Gly
                    165                 170                 175

Thr Arg Asp Trp Ile Glu Gly Glu Thr Tyr Gln Cys Arg Val Thr His
                    180                 185                 190

Pro His Leu Pro Arg Ala Leu Met Arg Ser Thr Thr Lys Thr Ser Gly
                    195                 200                 205

Pro Arg Ala Ala Pro Glu Val Tyr Ala Phe Ala Thr Pro Glu Trp Pro
            210                 215                 220

Gly Ser Arg Asp Lys Arg Thr Leu Ala Cys Leu Ile Gln Asn Phe Met
225                 230                 235                 240

Pro Glu Asp Ile Ser Val Gln Trp Leu His Asn Glu Val Gln Leu Pro
                    245                 250                 255

Asp Ala Arg His Ser Thr Thr Gln Pro Arg Lys Thr Lys Gly Ser Gly
                    260                 265                 270

Phe Phe Val Phe Ser Arg Leu Glu Val Thr Arg Ala Glu Trp Glu Gln
            275                 280                 285

Lys Asp Glu Phe Ile Cys Arg Ala Val His Glu Ala Ala Ser Pro Ser
            290                 295                 300

Gln Thr Val Gln Arg Ala Val Ser
305                 310
```

```
<210> SEQ ID NO 184
<211> LENGTH: 189
<212> TYPE: PRT
<213> ORGANISM: Artificial Sequence
<220> FEATURE:
<223> OTHER INFORMATION: TRIM21 PRYSPRY domain insert sequence

<400> SEQUENCE: 184
```

```
Val His Ile Thr Leu Asp Pro Asp Thr Ala Asn Pro Trp Leu Ile Leu
1               5                   10                  15

Ser Glu Asp Arg Arg Gln Val Arg Leu Gly Asp Thr Gln Gln Ser Ile
                20                  25                  30

Pro Gly Asn Glu Glu Arg Phe Asp Ser Tyr Pro Met Val Leu Gly Ala
            35                  40                  45

Gln His Phe His Ser Gly Lys His Tyr Trp Glu Val Asp Val Thr Gly
            50                  55                  60

Lys Glu Ala Trp Asp Leu Gly Val Cys Arg Asp Ser Val Arg Arg Lys
65                  70                  75                  80

Gly His Phe Leu Leu Ser Ser Lys Ser Gly Phe Trp Thr Ile Trp Leu
                    85                  90                  95

Trp Asn Lys Gln Lys Tyr Glu Ala Gly Thr Tyr Pro Gln Thr Pro Leu
            100                 105                 110

His Leu Gln Val Pro Pro Cys Gln Val Gly Ile Phe Leu Asp Tyr Glu
            115                 120                 125

Ala Gly Met Val Ser Phe Tyr Asn Ile Thr Asp His Gly Ser Leu Ile
            130                 135                 140
```

-continued

```
Tyr Ser Phe Ser Glu Cys Ala Phe Thr Gly Pro Leu Arg Pro Phe Phe
145             150             155             160

Ser Pro Gly Phe Asn Asp Gly Gly Lys Asn Thr Ala Pro Leu Thr Leu
            165             170             175

Cys Pro Leu Asn Ile Gly Ser Gln Gly Ser Thr Asp Tyr
        180             185
```

```
<210> SEQ ID NO 185
<211> LENGTH: 209
<212> TYPE: PRT
<213> ORGANISM: Artificial Sequence
<220> FEATURE:
<223> OTHER INFORMATION: hIgG1 G1m3 allotype CH2-CH3 region

<400> SEQUENCE: 185

Ser Val Phe Leu Phe Pro Pro Lys Pro Lys Asp Thr Leu Met Ile Ser
1               5               10              15

Arg Thr Pro Glu Val Thr Cys Val Val Val Asp Val Ser His Glu Asp
            20              25              30

Pro Glu Val Lys Phe Asn Trp Tyr Val Asp Gly Val Glu Val His Asn
        35              40              45

Ala Lys Thr Lys Pro Arg Glu Glu Gln Tyr Asn Ser Thr Tyr Arg Val
    50              55              60

Val Ser Val Leu Thr Val Leu His Gln Asp Trp Leu Asn Gly Lys Glu
65              70              75              80

Tyr Lys Cys Lys Val Ser Asn Lys Ala Leu Pro Ala Pro Ile Glu Lys
                85              90              95

Thr Ile Ser Lys Ala Lys Gly Gln Pro Arg Glu Pro Gln Val Tyr Thr
            100             105             110

Leu Pro Pro Ser Arg Glu Glu Met Thr Lys Asn Gln Val Ser Leu Thr
            115             120             125

Cys Leu Val Lys Gly Phe Tyr Pro Ser Asp Ile Ala Val Glu Trp Glu
        130             135             140

Ser Asn Gly Gln Pro Glu Asn Asn Tyr Lys Thr Thr Pro Pro Val Leu
145             150             155             160

Asp Ser Asp Gly Ser Phe Phe Leu Tyr Ser Lys Leu Thr Val Asp Lys
            165             170             175

Ser Arg Trp Gln Gln Gly Asn Val Phe Ser Cys Ser Val Met His Glu
            180             185             190

Ala Leu His Asn His Tyr Thr Gln Lys Ser Leu Ser Leu Ser Pro Gly
        195             200             205

Lys
```

```
<210> SEQ ID NO 186
<211> LENGTH: 8
<212> TYPE: PRT
<213> ORGANISM: Artificial Sequence
<220> FEATURE:
<223> OTHER INFORMATION: Misc_Feature Synethetic AA

<400> SEQUENCE: 186

His Asn His Tyr Thr Gln Gln Arg
1               5
```

```
<210> SEQ ID NO 187
<211> LENGTH: 8
<212> TYPE: PRT
<213> ORGANISM: Artificial Sequence
<220> FEATURE:
```

-continued

```
<223> OTHER INFORMATION: Misc_Feature Synethetic AA.

<400> SEQUENCE: 187

Thr Arg His Phe Thr Gln Lys Ile
1               5

<210> SEQ ID NO 188
<211> LENGTH: 8
<212> TYPE: PRT
<213> ORGANISM: Artificial Sequence
<220> FEATURE:
<223> OTHER INFORMATION: Misc_Feature Synethetic AA

<400> SEQUENCE: 188

His Asn His Tyr Thr Gln Lys Ser
1               5
```

MODIFIED FC REGION

This application claims priority from SG 10201810463Y filed 22 Nov. 2018, the contents and elements of which are herein incorporated by reference for all purposes.

SEQUENCE LISTING

In accordance with 37 CFR 1.52(e)(5), the present specification makes references to a Sequence Listing submitted electronically in the form of a text file (entitled "091404_744365_SL created October 28_2025", created on Oct. 28, 2025, and is 366,962 bytes in size), the entire contents of which are incorporated herein by reference in its entirety for all purposes.

FIELD OF THE INVENTION

The present invention relates to the fields of molecular biology, more specifically antibody technology. The present invention also relates to methods of medical treatment and prophylaxis.

BACKGROUND TO THE INVENTION

Tripartite motif-containing 21 (TRIM21) is a highly-conserved, ubiquitously-expressed cytosolic protein which defends against pathogenic agents that enter the cytosol as immune complexes. TRIM21 has been shown to bind to the Fc region of immune complexes of intracellular antibodies specific for adenoviruses. This leads to TRIM21 ubiquitination, which in turn targets the immune complexes for proteasomal degradation (Mallery et al., 2010). TRIM21-mediated pathogen degradation in non-immune cells has been shown for adenoviruses (Mallery et al., 2010), human rhinovirus (Watkinson et al., 2015), picornaviruses (Fan et al., 2016), *Salmonella* (Rakebrandt et al., 2014), and the Alzheimer's Disease pathogenic protein, Tau (McEwan et al., 2017), and is termed 'antibody-dependent intracellular neutralization' (ADIN) (McEwan et al., 2011). During proteasomal degradation, TRIM21 releases free ubiquitin chains that initiate pro-inflammatory signalling through NFκB, AP-1 and IRF signalling pathways (McEwan et al., 2013; Fletcher et al., 2015). Hence TRIM21 sets the cell into an anti-pathogen state by mediating pathogen degradation and triggering pro-inflammatory pathways.

Alongside ADIN, the generation of pathogen-derived peptides during proteasomal degradation can have important immune consequences. Mammalian cells routinely present proteasome-generated peptides on major histocompatibility complex I (MHC class I) for screening by CD8 T cells; when these T cells recognize the peptides, they kill the infected cell and thereby control infections. For this to occur, CD8 T cells must first be stimulated by recognition of their cognate peptide presented by MHC class I on an activated dendritic cell (DC) (Joffre et al., 2012). Accordingly, many pathogens have developed immune evasion strategies for this pathway, leading to chronic infection. For example, in Human Immunodeficiency Virus (HIV) and Hepatitis C Virus (HCV) infections, expression of T cell-stimulatory molecules by DCs is suppressed by viral products (Granelli-piperno et al., 2004; Zimmermann et al., 2008), and production of the anti-inflammatory cytokine IL-10 is increased (Saito et al., 2008), leading to reduced activation of CD8 T cells (Liu et al., 2009). Therapeutic vaccination to boost antigen-specific CD8 T cell responses is therefore a promising treatment for these chronic diseases. Induction of effective immunity following prophylactic vaccination also relies on efficient cross-presentation of exogenous vaccine antigen to stimulate optimal CD8 T cell responses. However, vaccines that can activate an effective CD8 T cell response remain challenging to design.

SUMMARY OF THE INVENTION

In a first aspect, the present invention provides an Fc region, optionally isolated, comprising modification to increase the affinity of association between the Fc region and TRIM21.

In some embodiments, the modification comprises one or more substitutions to the amino acid sequence of a polypeptide of the Fc region. In some embodiments, the polypeptide comprises substitution at one or more positions corresponding to the following positions of IGHG1: 252, 253, 254, 256, 309, 310, 311, 314, 315, 345, 428, 430, 431, 432, 433, 434, 435, 436, 437, 438, 439 or 440. In some embodiments, the polypeptide comprises substitution at one or more positions corresponding to the following positions of IGHG1: 253, 256, 433, 434, 435, 436 or 440. In some embodiments, the Fc region according to any one of claims 1 to 4, wherein the Fc region comprises a polypeptide comprising: I or L at the position corresponding to position 253; P, A, T, V, G, I, $K_D$, N or S at the position corresponding to position 256; S, V, H, A, D, P, Q, T or I at the position corresponding to position 433; H, R, N, I, L or M at the position corresponding to position 434; H or L at the position corresponding to position 435; Y, F, T, L, W or S at the position corresponding to position 436; and S, G, I, R, Y, N, V, T, P, D, W, M, A, K, F, E or C at the position corresponding to position 440.

Unless stated otherwise, positions in polypeptides of Fc regions herein are numbered according to the EU numbering system as described in Kabat et al., Sequences of Proteins of Immunological Interest, 5th Ed. Public Health Service, National Institutes of Health, Bethesda, MD, 1991 (hereby incorporated by reference in its entirety).

In some embodiments, the Fc region comprises a polypeptide comprising an amino acid sequence having at least 60% sequence identity to one of SEQ ID NOs:167 to 175. In some embodiments, the Fc region comprises a polypeptide comprising an amino acid sequence having at least 60% sequence identity to one of SEQ ID NOs:32 to 166. The present invention also provides a polypeptide, optionally isolated, comprising: an amino acid sequence having at least 60% sequence identity to SEQ ID NO:10, wherein the polypeptide comprises the following amino acid residues at the specified positions numbered relative to SEQ ID NO:10: I or L at the position corresponding to position 26; P, A, T, V, G, I, K, N or S at the position corresponding to position 29; S, V, H, A, D, P, Q, T or I at the position corresponding to position 206; H, R, N, I, L or M at the position corresponding to position 207; H or L at the position corresponding to position 208; Y, F, T, L, W or S at the position corresponding to position 209; and S, G, I, R, Y, N, V, T, P, D, W, M, A, K, F, E or C at the position corresponding to position 213; and wherein the amino acid sequence of the polypeptide is not identical to the amino acid sequence of a constituent polypeptide of the Fc region of a wildtype immunoglobulin.

In some embodiments the polypeptide comprises an amino acid sequence having at least 60% sequence identity to one of SEQ ID NOs:167 to 175. In some embodiments the polypeptide comprises an amino acid sequence having at least 60% sequence identity to one of SEQ ID NOs:32 to 166 The present invention also provides a polypeptide, optionally isolated, comprising the amino acid sequence of one of SEQ ID NOs:32 to 166.

The present invention also provides an Fc region, optionally isolated, comprising a polypeptide according to the present invention.

The present invention also provides a polypeptide complex, optionally isolated, comprising an Fc region according to the present invention, or a polypeptide according to the present invention.

The present invention also provides an antigen-binding molecule comprising an antigen-binding domain capable of specific binding to a target antigen and an Fc region according to the present invention, a polypeptide according to the present invention, or a polypeptide complex according to the present invention.

In some embodiments, the target antigen is an antigen of a pathogen, a cancer-associated antigen or an autoimmune disease-associated antigen. In some embodiments, the antigen-binding molecule comprises an antigen-binding domain capable of specific binding to an endocytosis receptor. In some embodiments, the antigen-binding molecule is a multispecific antigen-binding molecule. In some embodiments, the antigen-binding molecule further comprises an antigenic sequence of a target antigen.

The present invention also provides an immunogen comprising an antigenic sequence of a target antigen and an Fc region according to the invention, a polypeptide according to the invention, or a polypeptide complex according to the invention.

In some embodiments, the target antigen is an antigen of a pathogen, a cancer-associated antigen or an autoimmune disease-associated antigen. In some embodiments, the immunogen additionally comprises an antigen-presenting cell (APC)-targeting region. In some embodiments, the APC-targeting region comprises or consists of a moiety capable of specific binding to an endocytosis receptor. In some embodiments the immunogen further comprises an antigen-binding domain capable of specific binding to a target antigen.

The present invention also provides a nucleic acid, or a plurality of nucleic acids, optionally isolated, encoding an Fc region, a polypeptide, a polypeptide complex, an antigen-binding molecule or an immunogen according to the present invention.

The present invention also provides an expression vector, or a plurality of expression vectors, comprising a nucleic acid or a plurality of nucleic acids according to the present invention.

The present invention also provides a cell comprising an Fc region, a polypeptide, a polypeptide complex, an antigen-binding molecule, an immunogen, a nucleic acid or a plurality of nucleic acids or an expression vector or a plurality of expression vectors according to the present invention.

The present invention also provides a method comprising culturing a cell comprising a nucleic acid or a plurality of nucleic acids or an expression vector or a plurality of expression vectors according the invention under conditions suitable for expression of the Fc region, polypeptide, antigen-binding molecule or immunogen from the nucleic acid(s) or expression vector(s).

The present invention also provides a composition comprising an Fc region, a polypeptide, a polypeptide complex, an antigen-binding molecule, an immunogen, a nucleic acid or a plurality of nucleic acids, an expression vector or a plurality of expression vectors, or a cell according to the present invention.

The present invention also provides a polypeptide complex, optionally isolated, comprising an antigen-binding molecule or the immunogen according to the invention bound to the target antigen or a fragment thereof.

The present invention also provides a pharmaceutical composition comprising an antigen-binding molecule, an immunogen or a polypeptide complex according to the present invention, and a pharmaceutically acceptable carrier, diluent, excipient or adjuvant.

The present invention also provides an antigen-binding molecule, an immunogen, a polypeptide complex, or a pharmaceutical composition according to the present invention, for use in a method of medical treatment or prophylaxis.

The present invention also provides an antigen-binding molecule, an immunogen, a polypeptide complex, or a pharmaceutical composition according to the present invention for use in a method of medical treatment or prevention of an infectious disease, a cancer or an autoimmune disease.

The present invention also provides the use of an antigen-binding molecule, an immunogen, a polypeptide complex, or a pharmaceutical composition according to the present invention in the manufacture of a medicament for use in a method of treatment or prevention of an infectious disease, a cancer or an autoimmune disease.

The present invention also provides a method of treating or preventing an infectious disease, a cancer or an autoimmune disease, comprising administering to a subject a therapeutically or prophylactically effective amount of an antigen-binding molecule, an immunogen, a polypeptide complex, or a pharmaceutical composition according to the present invention.

The present invention also provides an immunogen or a polypeptide complex according to the present invention, for use in a method for inducing or enhancing an immune response to a target antigen in a subject.

The present invention also provides the use of an immunogen or a polypeptide complex according to the present invention in the manufacture of a medicament for use in a method for inducing or enhancing an immune response to a target antigen in a subject.

The present invention also provides a method for inducing or enhancing an immune response to a target antigen in a subject, comprising administering an immunogen or a polypeptide complex according to the present invention to the subject.

The present invention also provides a method comprising contacting a population of antigen-presenting cells with an immunogen or a polypeptide complex according to the present invention.

The present invention also provides a method for generating or expanding a population of immune cells specific for a target antigen, comprising contacting a population of immune cells with an antigen-presenting cell obtained by the method according to the invention.

DESCRIPTION

The present invention provides an Fc regions engineered for improved affinity to TRIM21, constituent polypeptides thereof, and larger molecules and complexes comprising the engineered Fc regions.

Improved affinity for TRIM21 is demonstrated to provide advantageous properties relevant to therapeutic and prophylactic applications of molecules and complexes comprising the modified Fc regions. In particular, antigen-presenting cells stimulated with molecules/complexes comprising Fc regions modified for increased affinity to TRIM21 are shown to be capable of stimulating an improved cell-mediated immune response to target antigen.

TRIM21

Human tripartite motif containing-21 (TRIM21; also known as RNF81, R052, SSA) is the protein identified by UniProt P19474. Alternative splicing of mRNA encoded by the human TRIM21 gene yields two isoforms: isoform 1 (UniProt: P19474-1, v1; SEQ ID NO:1) and isoform 2 (UniProt: P19474-2; SEQ ID NO:2), which lacks the amino acid sequence corresponding to positions 169 to 245 of SEQ ID NO:1.

The structure and function of TRIM21 is reviewed e.g. in Foss et al., Immunol Rev. (2015) 268(1):328-39, which is hereby incorporated by reference in its entirety. TRIM21 is a cytosolic Fc receptor that is structurally unrelated to all other classes of Fc receptors (James et al., Proc Natl Acad Sci USA. (2007) 104(15):6200-5). It is part of the TRIM family of proteins, which have cellular roles antiviral defence. Like other TRIM proteins, TRIM21 comprises an N-terminal RING domain (shown in SEQ ID NO:3) which has E3 ubiquitin ligase activity, a B-box (shown in SEQ ID NO:4), and a central coiled-coil domain (shown in SEQ ID NO:5). The C-terminal domain determines ligand specificity and function, and is referred to as the PRYSPRY domain (shown in SEQ ID NO:6). The PRYSPRY domain of TRIM21 contains the antibody binding site, and is a globular fold comprising a β-sandwich of two antiparallel β-sheets connected by flexible loops (James et al., Proc Natl Acad Sci USA. (2007) 104(15):6200-5). TRIM21 exists as a dimer in solution and forms stable 1:1 complexes with human IgG1; the two PRYSPRY domains of a dimeric TRIM21 molecule may bind simultaneously to one IgG Fc (Mallery et al., Proc Natl Acad Sci USA. (2010) 107(46):19985-90).

Antibody-mediated protection against intracellular pathogens such as viruses occurs through binding of neutralising antibody to epitopes of surface-exposed viral proteins. In recent years, it has become clear that the antiviral function of antibodies extends into the cytosolic compartment of cells, and is orchestrated by TRIM21. Engagement of TRIM21 results in rapid postentry elimination of antibody:virus complexes via recruitment of the proteasomal machinery (Mallery et al., Proc Natl Acad Sci USA. (2010) 107(46):19985-90), in a mechanism termed antibody-dependent cellular neutralization (ADIN). Inflammatory signalling is also induced (McEwan et al., Nat Immunol. 2013 April; 14(4):327-36). In this way, antibodies that have failed to block entry of a virus particle into the cell and which are not intercepted by other antibody-mediated effector functions (such as antibody-dependent cellular phagocytosis or antibody-dependent cellular cytotoxicity) may still be protective in the cytosolic compartment.

TRIM21 shows remarkably broad antibody specificity as it can activate its functions upon binding to IgG, IgM or IgA (Mallery et al., Proc Natl Acad Sci USA. (2010) 107(46): 19985-90 and Bidgood et al., Proc Natl Acad Sci USA. 2014 Sep. 16; 111(37):13463-8). TRIM21 is also expressed by cells of most linages (Reymond et al., EMBO J. (2001) 20(9):2140-51), suggesting that a susceptible pathogen may be targeted by TRIM21 independently of the site of infection and local distribution of antibody isotypes.

In this specification 'TRIM21' refers to TRIM21 from any species and includes TRIM21 isoforms, fragments, variants or homologues from any species.

As used herein, a 'fragment', 'variant' or 'homologue' of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments fragments, variants, isoforms and homologues of a reference protein may be characterised by ability to perform a function performed by the reference protein.

A 'fragment' generally refers to a fraction of the reference protein. A 'variant' generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An 'isoform' generally refers to a variant of the reference protein expressed by the same species as the species of the reference protein (e.g. TRIM21 isoforms 1 and 2 are isoforms of one another). A 'homologue' generally refers to a variant of the reference protein produced by a different species as compared to the species of the reference protein. For example, human TRIM21 isoform 1 (UniProt: P19474-1, v1; SEQ ID NO:1) and Rhesus macaque TRIM21 (UniProt: F7C1A0-1) are homologues of one another. Homologues include orthologues.

A 'fragment' of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of TRIM21 may have a minimum length of one of 10, 20, 30, 40, 50, 100, 150, 200, 250, 300, 350, 400, or 450 amino acids, and may have a maximum length of one of 20, 30, 40, 50, 100, 150, 200, 250, 300, 350, 400, or 450 amino acids.

In some embodiments, the TRIM21 is TRIM21 from a mammal (e.g. a primate (rhesus, cynomolgous, non-human primate or human) and/or a rodent (e.g. rat or murine) TRIM21). Isoforms, fragments, variants or homologues of TRIM21 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of a TRIM21 isoform from a given species, e.g. human.

Isoforms, fragments, variants or homologues may optionally be functional isoforms, fragments, variants or homologues, e.g. having a functional property/activity of the reference TRIM21 (e.g. human TRIM21 isoform 1), as determined by analysis by a suitable assay for the functional property/activity. For example, an isoform, fragment, variant or homologue of TRIM21 may display association with one or more of IgG, IgM or IgA, and/or may potentiate proteasomal degradation of antibody complexes.

In some embodiments, the TRIM21 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1 or 2.

Fc Region

Fc regions comprise two polypeptide regions comprising immunoglobulin heavy chain constant regions. The two polypeptide regions associate to form a dimer.

In some embodiments of the Fc region of the present invention, the two polypeptides regions are provided on separate polypeptide chains, which associate to form the Fc region. In some embodiments the two polypeptide regions are provided within the same polypeptide chain. In such embodiments the two polypeptide regions may be connected by a linker sequence, e.g. as described herein below. It will be appreciated that in such embodiments the linker sequence is of sufficient length and flexibility to allow association of the two polypeptide regions to form the Fc region.

Fc regions of IgG, IgA and IgD molecules comprise dimers of polypeptides comprising constant heavy chain domains 2 and 3 (i.e. CH2 and CH3). Fc regions of IgM and IgE molecules comprise dimers of polypeptides comprising CH2, CH3 and CH4 domains.

An Fc region according to the present disclosure may be derived from an Fc region of any wildtype immunoglobulin isotype, e.g. IgG (e.g. IgG1, IgG2, IgG3, IgG4), IgA (e.g. IgA1, IgA2), IgD, IgE or IgM. In some embodiments, an Fc region may be derived from an Fc region of a human IgG1 allotype (e.g. G1 m1, G1m2, G1m3 or G1m17).

As used herein, an Fc region which is 'derived from' a reference Fc region comprises a polypeptide having an amino acid sequence having at least 60%, sequence identity to the amino acid sequence of a polypeptide of the reference Fc region. For example, an Fc region which is derived from the Fc region of IgG1 comprises a polypeptide having at least 60% sequence identity to SEQ ID NO:10. It will be appreciated that because Fc regions are dimers, an Fc region which is 'derived from' a reference Fc region comprises two polypeptides each having at least 60% sequence identity to the amino acid sequence of a polypeptide of the reference Fc region.

The Fc region of human immunoglobulin G 1 (IGHG1; UniProt: P01857-1, v1; SEQ ID NO:7) comprises polypeptides comprising the CH2-CH3 region sequence shown in SEQ ID NO:10. The Fc region of human immunoglobulin G 2 constant (IGHG2; UniProt: P01859-1, v2; SEQ ID NO:11) comprises polypeptides comprising the CH2-CH3 region sequence shown in SEQ ID NO:14. The Fc region of human immunoglobulin G 3 constant (IGHG3; UniProt: P01860-1, v2; SEQ ID NO:15) comprises polypeptides comprising the CH2-CH3 region sequence shown in SEQ ID NO:18. The Fc region of human immunoglobulin G 4 constant (IGHG4; UniProt: P01861-1, v1; SEQ ID NO:19) comprises polypeptides comprising the CH2-CH3 region sequence shown in SEQ ID NO:22.

The Fc region of human immunoglobulin A 1 constant (IGHA1; UniProt: P01876-1, v2; SEQ ID NO:23) comprises polypeptides comprising the CH2-CH3 region sequence shown in SEQ ID NO:180. The Fc region of human immunoglobulin A 2 constant (IGHA1; UniProt: P01877-1, v4; SEQ ID NO:24) comprises polypeptides comprising the CH2-CH3 region sequence shown in SEQ ID NO:181.

The Fc region of human immunoglobulin D constant (IGHD; UniProt: P01880-1, v3; SEQ ID NO:25) comprises polypeptides comprising the CH2-CH3 region sequence shown in SEQ ID NO:182.

The Fc region of human immunoglobulin E constant (IGHE; UniProt: P01854-1, v1; SEQ ID NO:26) comprises polypeptides comprising the CH2-CH3-CH4 region sequence shown in SEQ ID NO:183.

The Fc region of human immunoglobulin M constant (IGHM; UniProt: P01871-1, v4; SEQ ID NO:27) comprises polypeptides comprising the CH2-CH3-CH4 region sequence shown in SEQ ID NO:31.

In some embodiments the Fc region of the present invention comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:10. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:14. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:18. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:22. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:180. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:181. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:182. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:183. In some embodiments the Fc region comprises one or more polypeptides comprising an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:31.

Modified Fc Regions

Aspects of the present invention relate to Fc regions comprising modification to increase the affinity of association with TRIM21.

Herein, a 'modified' Fc region refers to an Fc region comprising one or more polypeptides comprising a modification relative to the polypeptides of a reference Fc region not comprising the modification(s). A reference Fc region may be a wildtype Fc region, e.g. the Fc region of an IgG (e.g. IgG1, IgG2, IgG3, IgG4), IgA (e.g. IgA1, IgA2), IgD, IgE or IgM. Modification may e.g. be to one or both of the polypeptides of the reference Fc region. Modification may be to one or more amino acids of the polypeptides of the reference Fc region. Modification may introduce a moiety/ amino acid side chain/structural motif which increases/ stabilises interaction with TRIM21. Modification may remove a moiety/amino acid side chain/structural motif which decreases/destabilises interaction with TRIM21.

Modifications which increase the affinity of association between an Fc region and TRIM21 can be identified using a suitable assay, such as Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or Enzyme-linked immunosorbent assay. The affinity of association between two molecules can be analysed and quantified using such methods. Such assays may be performed e.g. using full-length recombinant TRIM21, or recombinant PRYSPRY domain of TRIM21.

In some embodiments the modification increases the affinity of association between the modified Fc region and TRIM21 to more than 1 times, e.g. 1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, 70 times, ≥80 times, ≥90 times, ≥100 times, ≥200 times, ≥300 times, ≥400 times, ≥500 times, ≥600 times, ≥700 times, ≥800 times, ≥900 times or 1000 times the affinity of association between TRIM21 and the equivalent Fc region lacking the modification (i.e. the reference, unmodified Fc region).

In some embodiments the modification comprises substitution of one or more amino acids of one or more of the polypeptides of the reference Fc region. In such embodiments the one or more amino acid substitutions result in increased affinity of association between the modified Fc region and TRIM21. By way of illustration, in the experimental examples of the present disclosure the inventors demonstrate that an Fc region comprising substitutions at positions 433, 434, 436, 440 and 256 numbered according to the EU numbering system (described in Kabat et al., Sequences of Proteins of Immunological Interest, 5th Ed. Public Health Service, National Institutes of Health, Bethesda, MD, 1991) has increased affinity for TRIM21.

In some embodiments the modified Fc region comprises modification to one or more positions of the Fc region polypeptides which are known or predicted to be important for interaction of the Fc region with TRIM21. Such positions may participate directly in the interaction with TRIM21, or may be involved in forming the three dimensional structure necessary for interaction with TRIM21. Such positions can be identified with reference e.g. to the crystal structure of the human IgG Fc-TRIM21 complex, described in James et al., Proc Natl Acad Sci USA. (2007) 104(15):6200-5, which is hereby incorporated by reference in its entirety. Positions may be predicted/known to contact TRIM21, or may be predicted/known to be present in a surface which is in close proximity to TRIM21.

The three-dimensional structure of an Fc region and/or an Fc region in complex with TRIM21 can be determined by analysis using methods known to the skilled person, described for example in Berg et al., Biochemistry, 5th Edn., Chapter 4, which is hereby incorporated by reference in its entirety. Such methods include X-ray crystallography, nuclear magnetic resonance (NMR) spectroscopy, etc. The structure of an Fc region and/or an Fc region in complex with TRIM21 can also be modelled or predicted using methods known to the skilled person, reviewed in Zhang, Curr Opin Struct Biol, 2008, 18(3) 342-348, which is hereby incorporated by reference in its entirety. Such methods include homology modelling, protein threading and fold recognition analysis. Homology modelling uses known three-dimensional structures of amino acid sequences having homology to an amino acid sequence of interest as the basis for predicting the three-dimensional structure of the amino acid sequence. Homology modelling can be performed, for example, using the methods described in Marti- Renom et al., Annu Rev Biophys Biomol Struct, 2000, 29: 291-325, which is hereby incorporated by reference in its entirety.

In some embodiments the modified Fc region comprises modification to one or more positions which are predicted in a resolved/predicted three-dimensional structure of the Fc region interacting with TRIM21 (e.g. the structure described in James et al., supra) to be: within 50 Å (e.g. within 40 Å, 30A, 20 Å, 10 Å or 5 Å) of TRIM21; present in a surface facing TRIM21; and/or orientated with their side chains facing towards TRIM21.

Positions which are important for interaction of an Fc region with TRIM21 can also be functional analysis. For example, candidate positions of Fc region polypeptides can be substituted, and the effect of the substitution on interaction between the Fc region and TRIM21 can be analysed, e.g. using a suitable assay, e.g. SPR or Bio-Layer Interferometry. A position which is important for interaction of an Fc region with TRIM21 is identified by determination of a change (i.e. a decrease or increase) in the level of interaction between the Fc region and TRIM21 associated with substitution at the relevant position.

In some embodiments the modified Fc region comprises one or more polypeptides comprising amino acid substitution(s) (relative to the reference, unmodified Fc region) at one or more positions. Substitution may be with any naturally- or non-naturally-occurring amino acid. Naturally-occurring amino acids include alanine (Ala/A), arginine (Arg/R), asparagine (Asn/N), aspartic acid (Asp/D), cysteine (Cys/C), glycine (Gly/G), glutamine (Gln/Q), glutamic acid (Glu/E), histidine (His/H), isoleucine (Ile/I), leucine (Leu/L), lysine (Lys/K), methionine (Met/M), phenylalanine (Phe/F), proline (Pro/P), serine (Ser/S), threonine (Thr/T), tryptophan (Trp/W), tyrosine (Tyr/Y) and valine (Val/V). Non-natural amino acids are described e.g. in Saladino et al., Mini-Reviews in Medicinal Chemistry (2012), 12(4) 227-300 (hereby incorporated by reference in its entirety), and include β-3 and β2 amino acids, homo-amino acids, proline and pyruvic acid derivatives, 3-substituted alanine derivatives, glycine derivatives, ring-substituted phenylalanine and tyrosine derivatives, linear core amino acids and N-methyl amino acids.

In some embodiments the modified Fc region comprises one or more polypeptides comprising amino acid substitution(s) (relative to the reference, unmodified Fc region) at one or more positions corresponding to the following positions of IGHG1 (numbered according to the EU numbering system): 252, 253, 254, 256, 309, 310, 311, 314, 315, 345, 428, 430, 431, 432, 433, 434, 435, 436, 437, 438, 439 or 440 (see e.g. Example 2.1). In some embodiments the modified Fc region comprises one or more polypeptides comprising amino acid substitution(s) (relative to the reference, unmodified Fc region) at one or more positions corresponding to the following positions of IGHG1 (numbered according to the EU numbering system): 252, 253, 254, 256, 309, 310, 311, 314, 315, 345, 428, 430, 431, 432, 433, 434, 435, 436, 437, 438, 439 or 440.

It will be appreciated that positions 252, 253, 254, 256, 309, 310, 311, 314, 315, 345, 428, 430, 431, 432, 433, 434, 435, 436, 437, 438, 439 or 440 numbered according to the EU numbering system correspond respectively to positions 135, 136, 137, 139, 192, 193, 194, 197, 198, 228, 311, 313, 314, 315, 316, 317, 318, 319, 320, 321, 322 and 323 of SEQ ID NO:7.

In some embodiments the modified Fc region comprises one or more polypeptides comprising amino acid substitution(s) (relative to the reference, unmodified Fc region) at one or more positions corresponding to the following positions of IGHG1 (numbered according to the EU numbering system): 253, 256, 433, 434, 435, 436, or 440.

The skilled person able to identify positions of a given amino acid sequence 'corresponding to' positions of a reference amino acid sequence e.g. by alignment of the amino acid sequence to the reference sequence, for example using publicly available computer software such as ClustalOmega (Soding, J. 2005, Bioinformatics 21, 951-960).

By way of example, an alignment of the amino acid sequences encoding IGHG1 (SEQ ID NO:7), IGHG2 (SEQ ID NO:11), IGHG3 (SEQ ID NO:15), IGHG4 (SEQ ID NO:19), IGHA1 (SEQ ID NO:23), IGHA2 (SEQ ID NO:24), IGHD (SEQ ID NO:25), IGHE (SEQ ID NO:26) and IGHM (SEQ ID NO:27) is shown in FIG. 9. It is clear from the alignment of FIG. 9 that e.g. position 312 of SEQ ID NO:11 (IGHG2) corresponds to position 316 of SEQ ID NO:7 (IGHG1) (which is position 433 according to EU numbering). The skilled person is also able to identify positions of a given amino acid sequence 'corresponding to' positions of a reference amino acid sequence e.g. by comparison of known/predicted three-dimensional structures for the amino acid sequences.

Where a heavy chain Fc region/polypeptide is described herein as comprising specified amino acid(s) at position(s) "corresponding to" reference position(s), or is described as comprising specified substitutions "corresponding to" reference substitution(s), equivalent position(s)/substitution(s) in homologous Fc regions/polypeptides are contemplated.

By way of illustration (with reference to FIG. 9), the substitution in IGHG3 which corresponds to Y436T in IGHG1 (EU numbering) is the substitution Phe>Thr at position 366 numbered according to SEQ ID NO:15.

Positions in IGHG2, IGHG3, IGHG4, IGHA1, IGHA2, IGHD, IGHE and IGHM corresponding to positions of particular interest in IGHG1, as determined from the alignment shown in FIG. 9, are shown below:

system): 256, 433, 434, 435, 436, 438, 439 or 440. In some embodiments the modified Fc region comprises one or more polypeptides comprising amino acid substitution(s) (relative to the reference, unmodified Fc region) at one or more positions corresponding to the following positions of IGHG1 (numbered according to the EU numbering system): 433, 434, 435, 436, 438, 439 or 440. In some embodiments the modified Fc region comprises one or more polypeptides comprising amino acid substitution(s) (relative to the reference, unmodified Fc region) at one or more positions corresponding to the following positions of IGHG1 (numbered according to the EU numbering system): 433, 434, 436, or 440. In some embodiments the modified Fc region comprises a polypeptide comprising amino acid substitution(s) (relative to the reference, unmodified Fc region) at one or more positions corresponding to the following positions of IGHG1 (numbered according to the EU numbering system): 256, 433, 434, 436, or 440. In some embodiments the modified Fc region comprises a polypeptide comprising amino acid substitution(s) (relative to the reference, unmodified Fc region) at one or more positions corresponding to the following positions of IGHG1 (numbered according to the EU numbering system): 256, 433 or 434.

In some embodiments the amino acid at the position corresponding to position 253 is I or L. In some embodiments the amino acid at the position corresponding to position 253 is 1.

In some embodiments the amino acid at the position corresponding to position 256 is P, A, T, V, G, I, K, N or S. In some embodiments the amino acid at the position corresponding to position 256 is P, A or S. In some embodiments the amino acid at the position corresponding to position 256 is P, A or T. In some embodiments the amino acid at the position corresponding to position 256 is P or T. In some embodiments the amino acid at the position corresponding to position 256 is P. In some embodiments the amino acid at the position corresponding to position 256 is A. In some

| IGHG1 (Eu numbering) | IGHG1 (SEQ ID NO: 7) | IGHG2 (SEQ ID NO: 11) | IGHG3 (SEQ ID NO: 15) | IGHG4 (SEQ ID NO: 19) | IGHA1 (SEQ ID NO: 23) | IGHA2 (SEQ ID NO: 24) | IGHD (SEQ ID NO: 25) | IGHE (SEQ ID NO: 26) | IGHM (SEQ ID NO: 27) |
|---|---|---|---|---|---|---|---|---|---|
| M252 | M135 | M131 | M182 | M132 | L138 | L125 | W181 | F230 | F235 |
| I253 | I136 | I132 | I183 | I133 | L139 | L126 | L182 | I231 | L236 |
| S254 | S137 | S133 | S184 | S134 | G140 | G127 | R183 | R232 | T237 |
| T256 | T139 | T135 | T186 | T136 | E142 | E129 | K185 | S234 | S239 |
| L309 | L192 | V188 | L239 | L189 | C192 | C179 | P237 | G287 | C291 |
| H310 | H193 | H189 | H240 | H190 | A193 | A180 | R238 | T288 | E292 |
| Q311 | Q194 | Q190 | Q241 | Q191 | E194 | Q181 | S239 | R289 | D293 |
| L314 | L197 | L193 | L244 | L194 | N197 | N184 | 1292 | 1292 | N296 |
| N315 | N198 | N194 | N245 | N195 | H198 | H185 | A243 | E293 | S297 |
| E345 | E228 | E224 | E275 | E225 | R227 | R214 | K274 | A323 | R328 |
| M428 | M311 | M307 | M358 | M308 | G316 | G303 | S358 | V408 | A416 |
| E430 | E313 | E309 | E360 | E310 | E318 | E305 | E360 | E410 | E418 |
| A431 | A314 | A310 | A361 | A311 | A319 | A306 | D361 | A411 | A419 |
| L432 | L315 | L311 | L362 | L312 | L320 | L307 | S362 | A412 | L420 |
| H433 | H316 | H312 | H363 | H313 | P321 | P308 | R363 | S413 | P421 |
| N434 | N317 | N313 | N364 | N314 | L322 | L309 | T364 | P414 | N422 |
| H435 | H318 | H314 | R365 | H315 | A323 | A310 | L366 | Q416 | R423 |
| Y436 | Y319 | Y315 | F366 | Y316 | F324 | F311 | N367 | T417 | V424 |
| T437 | T320 | T316 | T367 | T317 | T325 | T312 | A368 | V418 | T425 |
| Q438 | Q321 | Q317 | Q368 | Q318 | Q326 | Q313 | S369 | Q419 | E426 |
| K439 | K322 | K318 | K369 | K319 | K327 | K314 | R370 | R420 | R427 |
| S440 | S323 | S319 | S370 | S319 | T328 | T315 | S371 | A421 | T428 |

In some embodiments the modified Fc region comprises one or more polypeptides comprising amino acid substitution(s) (relative to the reference, unmodified Fc region) at one or more positions corresponding to the following positions of IGHG1 (numbered according to the EU numbering embodiments the amino acid at the position corresponding to position 256 is T, V, G, I, K, N or S.

In some embodiments the amino acid at the position corresponding to position 433 is S, V, H, A, D, P, Q, T or I. In some embodiments the amino acid at the position corresponding to position 433 is S. In some embodiments the amino acid at the position corresponding to position 433 is V. In some embodiments the amino acid at the position corresponding to position 433 is H, A, D, P, Q or T. In some embodiments the amino acid at the position corresponding to position 433 is T or H. In some embodiments the amino acid at the position corresponding to position 433 is V or I. In some embodiments the amino acid at the position corresponding to position 433 is H.

In some embodiments the amino acid at the position corresponding to position 434 is H, R, N, I, L or M. In some embodiments the amino acid at the position corresponding to position 434 is H. In some embodiments the amino acid at the position corresponding to position 434 is R or N. In some embodiments the amino acid at the position corresponding to position 434 is R. In some embodiments the amino acid at the position corresponding to position 434 is N, I, L or M. In some embodiments the amino acid at the position corresponding to position 434 is N or M. In some embodiments the amino acid at the position corresponding to position 434 is N, L or M.

In some embodiments the amino acid at the position corresponding to position 435 is H or L. In some embodiments the amino acid at the position corresponding to position 435 is H.

In some embodiments the amino acid at the position corresponding to position 436 is Y, F, T, L, W or S. In some embodiments the amino acid at the position corresponding to position 436 is Y or F. In some embodiments the amino acid at the position corresponding to position 436 is Y, T or F. In some embodiments the amino acid at the position corresponding to position 436 is Y, F, L or W. In some embodiments the amino acid at the position corresponding to position 436 is Y, F, L or T. In some embodiments the amino acid at the position corresponding to position 436 is F, T, Y, S or L. In some embodiments the amino acid at the position corresponding to position 436 is F, T or Y. In some embodiments the amino acid at the position corresponding to position 436 is Y, F, T or S.

In some embodiments the amino acid at the position corresponding to position 440 is S, G, I, R, Y, N, V, T, P, D, W, M, A, K, F, E or C. In some embodiments the amino acid at the position corresponding to position 440 is G, S, I, R, Y or N. In some embodiments the amino acid at the position corresponding to position 440 is S, R, V or G. In some embodiments the amino acid at the position corresponding to position 440 is S, R, I, N or T. In some embodiments the amino acid at the position corresponding to position 440 is S, I or G. In some embodiments the amino acid at the position corresponding to position 440 is S, G, R, P, N, I or V. In some embodiments the amino acid at the position corresponding to position 440 is R, T, S, D, W, M, A, K, N, Y or I. In some embodiments the amino acid at the position corresponding to position 440 is M, S, F, I G, D or N. In some embodiments the amino acid at the position corresponding to position 440 is A, I, T, R, S, E, C, Y, D, N, G, V or M.

In some embodiments the Fc region of the invention comprises one or more polypeptides comprising, or consisting of, the amino acid sequence of one of SEQ ID NO:167 to 175, or an amino acid sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of one of SEQ ID NOs:167 to 175.

In some embodiments the Fc region of the invention comprises one or more polypeptides comprising, or consisting of, the amino acid sequence of one of SEQ ID NOs:32 to 166, or an amino acid sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of one of SEQ ID NOs:32 to 166.

Fc regions provide for interaction with Fc receptors and other molecules of the immune system to bring about functional effects. IgG Fc-mediated effector functions are reviewed e.g. in Jefferis et al., Immunol Rev 1998 163:59-76 (hereby incorporated by reference in its entirety), and are brought about through Fc-mediated recruitment and activation of immune cells (e.g. macrophages, dendritic cells, NK cells and T cells) through interaction between the Fc region and Fc receptors expressed by the immune cells, recruitment of complement pathway components through binding of the Fc region to complement protein Clq, and consequent activation of the complement cascade. Fc-mediated functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation.

Modifications to antibody Fc regions that influence Fc-mediated functions are known in the art, such as those described e.g. in Wang et al., Protein Cell (2018) 9(1):63-73, which is hereby incorporated by reference in its entirety. In particular, exemplary Fc region modifications known to influence antibody effector function are summarised in Table 1 of Wang et al., Protein Cell (2018) 9(1):63-73. In some embodiments the polypeptide comprises any one of the following amino acid substitutions/combinations of amino acid substitutions (or corresponding substitutions): F243L/R292P/Y300L/V3051/P396L; S239D/1332E; S239D/1332E/A330L; S298A/E333A/K334A; L234Y/L235Q/G236W/S239M/H268D/D270E/S298A; D270E/K326D/A330M/K334E; G236A/S239D/1332E; K326W/E333S; S267E/H268F/S324T; E345R/E430G/S440Y; M252Y/S254T/T256E; and M428L/N434S.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety.

In some embodiments the Fc region comprises one or more paired substitutions for stabilising association between the constituent polypeptides. In some embodiments the Fc region comprises polypeptides comprising paired substitutions at positions corresponding to those indicated in Table 1 of Ha et al., Front. Immnol (2016) 7:394 (hereby incorporated by reference in its entirety), for the following formats: $KiH_{s-s}$, $KiH_{s-s}$, HA-TF, ZW1, 7.8.60, DD-KK, EW-RVT$_{s-s}$, EW-RVT$_{s-s}$, SEED or A107.

It will be appreciated that the present invention relates to modified, i.e. non-wildtype Fc regions. Accordingly, in some embodiments the Fc region of the invention does not consist of polypeptides having amino acid sequences which are identical to those of wildtype IgG (e.g. IgG1, IgG2, IgG3, IgG4), IgA (e.g. IgA1, IgA2), IgD, IgE or IgM.

In some embodiments the Fc region lacks a polypeptide comprising an amino acid sequence which is identical to the amino acid sequence of the CH2-CH3 region of a wildtype IgG (e.g. IgG1, IgG2, IgG3, IgG4), IgA (e.g. IgA1, IgA2) or IgD. In some embodiments the Fc region lacks a polypeptide comprising an amino acid sequence which is identical to the amino acid sequence of the CH2-CH3-CH4 region of a wildtype IgE or IgM.

In some embodiments the Fc region of the present invention does not comprise a polypeptide comprising an the amino acid sequence of SEQ ID NO:10. In some embodiments the Fc region does not comprise a polypeptide comprising an the amino acid sequence of SEQ ID NO:14. In some embodiments the Fc region does not comprise a polypeptide comprising an the amino acid sequence of SEQ ID NO:18. In some embodiments the Fc region does not comprise a polypeptide comprising an the amino acid sequence of SEQ ID NO:22. In some embodiments the Fc region does not comprise a polypeptide comprising an the amino acid sequence of SEQ ID NO:180. In some embodiments the Fc region does not comprise a polypeptide comprising an the amino acid sequence of SEQ ID NO:181. In some embodiments the Fc region does not comprise a polypeptide comprising an the amino acid sequence of SEQ ID NO:182. In some embodiments the Fc region does not comprise a polypeptide comprising an the amino acid sequence of SEQ ID NO:183. In some embodiments the Fc region does not comprise a polypeptide comprising an the amino acid sequence of SEQ ID NO:31.

It will also be appreciated that an Fc region according to the present can be a component of a larger molecule, e.g. an antigen-binding molecule or an immunogen as described herein. The Fc region may be covalently or non-covalently associated with the other components of the larger molecule.

Polypeptides

The present invention also provides constituent polypeptides of Fc regions according to the invention. The polypeptides may be provided in isolated or substantially purified form. The Fc region of the invention may be, or may comprise, a complex (e.g. a non-covalent complex) of the polypeptides according to the invention.

As used herein, a 'peptide' is a chain of two or more amino acid monomers linked by peptide bonds. A peptide typically has a length in the region of about 2 to 50 amino acids. A 'polypeptide' is a polymer chain of two or more peptides. Polypeptides typically have a length greater than about 50 amino acids.

The present invention provides a polypeptide comprising immunoglobulin heavy chain constant regions capable of forming an Fc region. In some embodiments the polypeptide comprises heavy chain constant regions derived from CH2 and CH3 of IgG (e.g. IgG1, IgG2, IgG3 or IgG4). In some embodiments the polypeptide comprises heavy chain constant regions derived from CH2 and CH3 of IgA (e.g. IgA1 or IgA2). In some embodiments the polypeptide comprises heavy chain constant regions derived from CH2 and CH3 of IgD. In some embodiments the polypeptide comprises heavy chain constant regions derived from CH2, CH3 and CH4 of IgM. In some embodiments the polypeptide comprises heavy chain constant regions derived from CH2, CH3 and CH4 of IgE. As used herein a heavy chain constant region which is 'derived from' a reference heavy chain constant region has an amino acid sequence having at least 60%, e.g.

one of at least 65%, 70%, 75%, 80%, 85%, 90%, 91%, 92%, 93%, 94%, 95%, 96%, 97%, 98%, 99% or 100% sequence identity to the amino acid sequence of the reference heavy chain constant region.

In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:10. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:14. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:18. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:22. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:180. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:181. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:182. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:183. In some embodiments the polypeptide comprises, or consists of, an amino acid sequence having at least 60%, e.g. one of at least 65%, 70%, 75%, 80%, 85%, 90%, 91%, 92%, 93%, 94%, 95%, 96%, 97%, 98% or 99% sequence identity to the amino acid sequence of SEQ ID NO:31.

In some embodiments the polypeptide comprises amino acid substitution(s) at one or more positions corresponding to the following positions of IGHG1 (numbered according to the EU numbering system): 252, 253, 254, 309, 310, 311, 314, 315, 345, 428, 430, 431, 432, 433, 434, 435, 436, 437, 438, 439 or 440 (see e.g. Example 2.1). In some embodiments the polypeptide comprises amino acid substitution(s) at one or more positions corresponding to the following positions of IGHG1 (numbered according to the EU numbering system): 252, 253, 254, 256, 309, 310, 311, 314, 315, 345, 428, 430, 431, 432, 433, 434, 435, 436, 437, 438, 439 or 440.

In some embodiments the polypeptide comprises amino acid substitution(s) at one or more positions corresponding to the following positions of IGHG1 (numbered according to the EU numbering system): 253, 256, 433, 434, 435, 436 or 440.

In some embodiments the polypeptide comprises an amino acid sequence having at least 60% sequence identity to SEQ ID NO:10, wherein the polypeptide comprises amino acid substitution(s) at one or more positions corresponding to the following positions numbered relative to SEQ ID NO:10: 26, 29, 206, 207, 208, 209 and 213.

In some embodiments the amino acid at the position corresponding to position 26 of SEQ ID NO:10 is I or L. In some embodiments the amino acid at the position corresponding to position 26 of SEQ ID NO:10 is 1.

In some embodiments the amino acid at the position corresponding to position 29 of SEQ ID NO:10 is P, A, T, V, G, I, K, N or S. In some embodiments the amino acid at the position corresponding to position 29 of SEQ ID NO:10 is P, A or S. In some embodiments the amino acid at the position corresponding to position 29 of SEQ ID NO:10 is P, A or T. In some embodiments the amino acid at the position corresponding to position 29 of SEQ ID NO:10 is P or T. In some embodiments the amino acid at the position corresponding to position 29 of SEQ ID NO:10 is P. In some embodiments the amino acid at the position corresponding to position 29 of SEQ ID NO:10 is A. In some embodiments the amino acid at the position corresponding to position 29 of SEQ ID NO:10 is T, V, G, I, K, N or S.

In some embodiments the amino acid at the position corresponding to position 206 of SEQ ID NO:10 is S, V, H, A, D, P, Q, T or I. In some embodiments the amino acid at the position corresponding to position 206 of SEQ ID NO:10 is S. In some embodiments the amino acid at the position corresponding to position 206 of SEQ ID NO:10 is V. In some embodiments the amino acid at the position corresponding to position 206 of SEQ ID NO:10 is H, A, D, P, Q or T. In some embodiments the amino acid at the position corresponding to position 206 of SEQ ID NO:10 is T or H. In some embodiments the amino acid at the position corresponding to position 206 of SEQ ID NO:10 is V or I. In some embodiments the amino acid at the position corresponding to position 206 of SEQ ID NO:10 is H.

In some embodiments the amino acid at the position corresponding to position 207 of SEQ ID NO:10 is H, R, N, I, L or M. In some embodiments the amino acid at the position corresponding to position 207 of SEQ ID NO:10 is H. In some embodiments the amino acid at the position corresponding to position 207 of SEQ ID NO:10 is R or N. In some embodiments the amino acid at the position corresponding to position 207 of SEQ ID NO:10 is R. In some embodiments the amino acid at the position corresponding to position 207 of SEQ ID NO:10 is N, I, L or M. In some embodiments the amino acid at the position corresponding to position 207 of SEQ ID NO:10 is N or M. In some embodiments the amino acid at the position corresponding to position 207 of SEQ ID NO:10 is N, L or M.

In some embodiments the amino acid at the position corresponding to position 208 of SEQ ID NO:10 is H or L. In some embodiments the amino acid at the position corresponding to position 208 of SEQ ID NO:10 is H.

In some embodiments the amino acid at the position corresponding to position 209 of SEQ ID NO:10 is Y, F, T, L, W or S. In some embodiments the amino acid at the position corresponding to position 209 of SEQ ID NO:10 is Y or F. In some embodiments the amino acid at the position corresponding to position 209 of SEQ ID NO:10 is Y, T or F. In some embodiments the amino acid at the position corresponding to position 209 of SEQ ID NO:10 is Y, F, L or W. In some embodiments the amino acid at the position corresponding to position 209 of SEQ ID NO:10 is Y, F, L or T. In some embodiments the amino acid at the position corresponding to position 209 of SEQ ID NO:10 is F, T, Y, S or L. In some embodiments the amino acid at the position corresponding to position 209 of SEQ ID NO:10 is F, T or Y. In some embodiments the amino acid at the position corresponding to position 209 of SEQ ID NO:10 is Y, F, T or S.

In some embodiments the amino acid at the position corresponding to position 213 of SEQ ID NO:10 is S, G, I, R, Y, N, V, T, P, D, W, M, A, K, F, E or C. In some embodiments the amino acid at the position corresponding to position 213 of SEQ ID NO:10 is G, S, I, R, Y or N. In some embodiments the amino acid at the position corresponding to position 213 of SEQ ID NO:10 is S, R, V or G. In some embodiments the amino acid at the position corresponding to position 213 of SEQ ID NO:10 is S, R, I, N or T. In some embodiments the amino acid at the position corresponding to position 213 of SEQ ID NO:10 is S, I or G. In some embodiments the amino acid at the position corresponding to position 213 of SEQ ID NO:10 is S, G, R, P, N, I or V. In some embodiments the amino acid at the position corresponding to position 213 of SEQ ID NO:10 is R, T, S, D, W, M, A, K, N, Y or I. In some embodiments the amino acid at the position corresponding to position 213 of SEQ ID NO:10 is M, S, F, I G, D or N. In some embodiments the amino acid at the position corresponding to position 213 of SEQ ID NO:10 is A, I, T, R, S, E, C, Y, D, N, G, V or M.

In some embodiments a polypeptide comprises, or consists of, the amino acid sequence of one of SEQ ID NOs:167 to 175, or an amino acid sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of one of SEQ ID NOs:167 to 175.

In some embodiments a polypeptide comprises, or consists of, the amino acid sequence of one of SEQ ID NOs:32 to 166, or an amino acid sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of one of SEQ ID NOs:32 to 166.

In some embodiments polypeptide comprises any one of the following amino acid substitutions/combinations of amino acid substitutions (shown e.g. in Table 1 of Ha et al., Front. Immnol (2016) 7:394, incorporated by reference hereinabove; numbered according to the EU numbering system): T366W; T366S, L368A and Y407V; T366W and S354C; T366S, L368A, Y407V and Y349C; S364H and F405A; Y349T and T394F; T350V, L351Y, F405A and Y407V; T350V, T366L, K392L and T394W; K360D, D399M and Y407A; E345R, Q347R, T366V and K409V; K409D and K392D; D399K and E356K; K360E and K409W; Q347R, D399V and F405T; K360E, K409W and Y349C; Q347R, D399V, F405T and S354C; K370E and K409W; and E357N, D399V and F405T.

Modifications to antibody Fc regions that influence Fc-mediated functions are known in the art, such as those described e.g. in Wang et al., Protein Cell (2018) 9(1):63-73, which is hereby incorporated by reference in its entirety. Exemplary Fc region modifications known to influence antibody effector function are summarised in Table 1 of Wang et al., Protein Cell (2018) 9(1):63-73. In some embodiments the polypeptide comprises any one of the following amino acid substitutions/combinations of amino acid substitutions (or corresponding substitutions): F243L/R292P/Y300L/V3051/P396L; S239D/1332E; S239D/1332E/A330L; S298A/E333A/K334A; L234Y/L235Q/G236W/S239M/H268D/D270E/S298A; D270E/K326D/

A330M/K334E; G236A/S239D/I332E; K326W/E333S; S267E/H268F/S324T; E345R/E430G/S440Y; M252Y/S254T/T256E; and M428L/N434S.

In some embodiments the amino acid sequence of the polypeptide of the present invention is not identical to the amino acid sequence of a constituent polypeptide of the Fc region of a wildtype immunoglobulin (e.g. IgG (e.g. IgG1, IgG2, IgG3, IgG4), IgA (e.g. IgA1, IgA2), IgD, IgE or IgM).

In some embodiments the polypeptide does not comprise an amino acid sequence which is identical to the amino acid sequence of the CH2-CH3 region of a wildtype IgG (e.g. IgG1, IgG2, IgG3, IgG4), IgA (e.g. IgA1, IgA2) or IgD. In some embodiments the polypeptide does not comprise an amino acid sequence which is identical to the amino acid sequence of the CH2-CH3-CH4 region of a wildtype IgE or IgM.

In some embodiments the polypeptide of the invention does not comprise the amino acid sequence of SEQ ID NO:10. In some embodiments the polypeptide does not comprise the amino acid sequence of SEQ ID NO:14. In some embodiments the polypeptide does not comprise the amino acid sequence of SEQ ID NO:18. In some embodiments the polypeptide does not comprise the amino acid sequence of SEQ ID NO:22. In some embodiments the polypeptide does not comprise the amino acid sequence of SEQ ID NO:180. In some embodiments the polypeptide does not comprise the amino acid sequence of SEQ ID NO:181. In some embodiments the polypeptide does not comprise the amino acid sequence of SEQ ID NO:182. In some embodiments the polypeptide does not comprise the amino acid sequence of SEQ ID NO:183. In some embodiments the polypeptide does not comprise the amino acid sequence of SEQ ID NO:31.

In some embodiments the polypeptide additionally comprises amino acid sequence encoding one or more further functional regions. For example, in some embodiments the polypeptide additionally comprises an amino acid sequence forming an antigen-binding domain according to the present disclosure (e.g. scFv specific for a target antigen, or a peptide aptamer specific for a target antigen). In some embodiments the polypeptide additionally comprises an amino acid sequence forming part of an antigen-binding domain according to the present disclosure (e.g. VL or VH of an antigen-binding moiety specific for a target antigen). In some embodiments the polypeptide additionally comprises an amino acid sequence forming all or part of an antigenic sequence according to the present disclosure.

Polypeptide Complexes

The present invention also provides polypeptide complexes comprising the Fc regions and/or the polypeptides of the invention.

As used herein, a 'polypeptide complex' refers to a complex comprising a polypeptide associated with another molecule. The association may involve covalent interaction (e.g. disulfide bonding) and/or non-covalent interaction (e.g. electrostatic interaction (e.g. ionic bonding, hydrogen bonding), Van der Waals forces) between the polypeptide and another molecule.

In some embodiments, a polypeptide complex may comprise, or consist of, a complex of more than one polypeptide (e.g. 2, 3, 4, 6, or 8 polypeptides). For example, polypeptide complexes include IgG-like antigen-binding molecules, which comprise heavy and light chain polypeptides associated into a polypeptide complex.

Polypeptide complexes include e.g. antigen-binding molecules as described herein, immunogens described herein and complexes of antigen-binding molecules/immunogens with cognate target antigen.

Antigen-Binding Molecules

The present invention also provides antigen-binding molecules comprising the Fc regions and/or the polypeptides of the invention.

An 'antigen-binding molecule' refers to a molecule which is capable of binding to a target antigen, and encompasses monoclonal antibodies, polyclonal antibodies, monospecific and multispecific antibodies (e.g., bispecific antibodies, trispecific antibodies, etc.).

The antigen-binding molecule of the present invention comprises an antigen-binding domain. The antigen-binding domain may comprise, or consist of, a moiety capable of specific binding to a target antigen. In some embodiments, the moiety capable of binding to a target antigen comprises an antibody heavy chain variable region (VH) and an antibody light chain variable region (VL) of an antibody capable of specific binding to the target antigen. An antigen-binding domain formed by a VH and a VL may also be referred to as an Fv region. In some embodiments the antigen-binding domain comprises, or consists of, an antibody fragment of an antibody capable of specific binding to the target antigen (e.g. Fv, scFv, Fab$_2$, scFab, F(ab')$_2$, Fab$_2$, diabody, triabody, scFv-Fc, minibody, single domain antibody (e.g. VhH), etc.). In some embodiments the antigen-binding molecule is a human, humanised or chimeric (e.g. mouse/human chimeric) antigen-binding molecule.

In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202, which is hereby incorporated by reference in its entirety). 'Nucleic acid' refers to deoxyribonucleotides or ribonucleotides and polymers thereof in either single-, double- or multiple-stranded form, or complements thereof. The term 'polynucleotide' refers to a linear sequence of nucleotides. The term 'nucleotide' typically refers to a single unit of a polynucleotide, i.e., a monomer. Nucleotides can be ribonucleotides, deoxyribonucleotides, or modified versions thereof.

In some embodiments, the moiety capable of binding to a target antigen comprises or consists of an antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

An antigen-binding molecule preferably displays specific binding to a target antigen. As used herein, 'specific binding' refers to binding which is selective for the target antigen, and which can be discriminated from non-specific binding to non-target antigen. An antigen-binding molecule that specifically binds to a target antigen preferably binds the target with greater affinity, and/or with greater duration than it binds to other, non-target antigen. The ability of a given antigen-binding molecule to bind specifically to a target can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given target can be detected and quantified.

Antigen-binding molecule valency refers to the number of binding sites provided, and specificity refers to the number of different target antigens for which the antigen-binding molecule comprises an antigen-binding domain.

The antigen-binding molecule of the present invention comprises at least one antigen-binding domain. In some embodiments the antigen-binding molecules comprise e.g. 1, 2, 3, 4, 5, 6, 7, 8, 9, or 10 antigen-binding domains. In embodiments where the antigen-binding molecule of the present invention comprises more than one antigen-binding domain, the antigen-binding domains may be the same or different. Where the antigen-binding molecule comprises two or more different (i.e. non-identical) antigen-binding domains, the antigen-binding molecule is multispecific. The non-identical antigen-binding domains of a multispecific antigen-binding molecule may preferably be specific for non-identical target antigens. In some embodiments the antigen-binding molecule of the present invention is mono-specific. In some embodiments the antigen-binding molecule is multispecific (e.g. bispecific, trispecific, etc.).

The antigen-binding molecule of the present invention is at least monovalent. In some embodiments the antigen-binding molecule of the present invention is multivalent (e.g. bivalent, trivalent, tetravalent, etc.).

An antigen-binding molecule may be, or may comprise, an antigen-binding polypeptide, or an antigen-binding poly-peptide complex. An antigen-binding molecule may comprise more than one polypeptide which together form an antigen-binding domain. The polypeptides may associate covalently or non-covalently. An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding domain of the antigen-binding mol-ecule of the present invention may be specific for any target antigen(s) of interest. In some embodiments the antigen-binding domain is specific for an antigen which is an antigen of a pathogen, a cancer-associated antigen or an autoimmune disease-associated antigen.

In some embodiments the target antigen is an antigen of a pathogen. In some embodiments the pathogen may be prokaryotic (bacteria), eukaryotic (e.g. protozoan, helminth, fungus), virus or prion. In some embodiments, the pathogen is an intracellular pathogen. In some embodiments, the pathogen is a parasite.

In some embodiments the pathogen is a virus. A virus may be a dsDNA virus (e.g. adenovirus, herpesvirus, poxvirus), ssRNA virus (e.g. parvovirus), dsRNA virus (e.g. reovirus), (+)ssRNA virus (e.g. picornavirus, togavirus), (−)ssRNA virus (e.g. orthomyxovirus, rhabdovirus), ssRNA-RT virus (e.g. retrovirus) or dsDNA-RT virus (e.g. hepadnavirus). In particular, the present disclosure contemplates viruses of the families adenoviridae, herpesviridae, papillomaviridae, polyomaviridae, poxviridae, hepadnaviridae, parvoviridae, astroviridae, caliciviridae, picornaviridae, coronaviridae, flaviviridae, togaviridae, hepeviridae, retroviridae, orthom-yxoviridae, arenaviridae, bunyaviridae, filoviridae, paramyxoviridae, rhabdoviridae and reoviridae. In some embodiments the virus is selected from adenovirus, Herpes simplex type 1 virus, Herpes simplex type 2 virus, Varicella-zoster virus, Epstein-barr virus, Human cytomegalovirus, Human herpesvirus type 8, Human papillomavirus, BK virus, JC virus, Smallpox, Hepatitis B virus, Parvovirus B19, Human Astrovirus, Norwalk virus, coxsackievirus, hepatitis A virus, poliovirus, rhinovirus, severe acute respi-ratory syndrome virus, Hepatitis C virus, yellow fever virus, dengue virus, West Nile virus, TBE virus, Rubella virus, Hepatitis E virus, Human immunodeficiency virus, influenza virus, lassa virus, Crimean-Congo hemorrhagic fever virus, Hantaan virus, ebola virus, Marburg virus, measles virus, mumps virus, parainfluenza virus, picornavirus, respiratory syncytial virus, rabies virus, hepatitis D virus, rotavirus, orbivirus, coltivirus, and banna virus.

In some embodiments the pathogen is a bacterium. The bacterium may be gram positive or gram negative. In particular, the present disclosure contemplates bacteria of the genera *Bacillus, Bartonella, Bordetella, Borrelia, Bru-cella, Campylobacter, Chlamydia*, and, *Chlamydophila, Clostridium, Corynebacterium, Enterococcus, Escherichia, Francisella, Haemophilus, Helicobacter, Legionella, Lep-tospira, Listeria, Mycobacterium, Mycoplasma, Neisseria, Pseudomonas, Rickettsia, Salmonella, Shigella, Staphylo-coccus, Streptococcus, Treponema, Ureaplasma, Vibrio* and *Yersinia*.

In some embodiments the pathogen is protozoan. In particular, the present disclosure contemplates protozoa of the genera *Entamoeba, Plasmodium, Giardia, Trypano-soma, Leishmania, Besnoitia* and *Toxoplasma*.

In some embodiments the pathogen is a fungus. In par-ticular, the present disclosure contemplates fungi of the genera *Candida, Aspergillus, Blastomyces, Coccidioides, Sporothrix, Cryptococcus, Histoplasma, Pneumocystis, Stachybotrys, Rhizopus, Mucor, Cunninghamella, Apophy-somyces, Trichophyton, Microsporum, Epidermophyton, Fusarium*, and Lichtheimia.

In some embodiments the target antigen is a cancer-associated antigen. In some embodiments the cancer-asso-ciated antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer-associated antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type).

In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor sup-pressor gene. In some embodiments, the cancer-associated antigen may be the product of an overexpressed cellular protein, a cancer antigen produced by an oncogenic virus, an oncofetal antigen, or a cell surface glycolipid or glycopro-tein. GPC3 is an exemplary cancer-associated antigen.

Cancer-associated antigens are reviewed by Zarour H M, DeLeo A, Finn O J, et al. Categories of Tumor Antigens. In: Kufe D W, Pollock R E, Weichselbaum R R, et al., editors. Holland-Frei Cancer Medicine. 6th edition. Hamilton (ON): BC Decker; 2003. Cancer-associated antigens include oncofetal antigens: CEA, Immature laminin receptor, TAG-72; oncoviral antigens such as HPV E6 and E7; overex-pressed proteins: BING-4, calcium-activated chloride chan-nel 2, cyclin-B1, 9D7, Ep-CAM, EphA3, Her2/neu, telomerase, mesothelin, SAP-1, surviving; cancer-testis antigens: BAGE, CAGE, GAGE, MAGE, SAGE, XAGE, CT9, CT10, NY-ESO-1, PRAME, SSX-2; lineage restricted antigens: MART1, Gp100, tyrosinase, TRP-1/2, MC1R, prostate specific antigen; mutated antigens: β-catenin, BRCA1/2, CDK4, CML66, Fibronectin, MART-2, p53, Ras, TGF-βR11; post-translationally altered antigens: MUC1, idiotypic antigens: Ig, TCR. Other cancer-associated antigens include heat-shock protein 70 (HSP70), heat-shock protein 90 (HSP90), glucose-regulated protein 78 (GRP78), vimentin, nucleolin, feto-acinar pancreatic protein (FAPP), alkaline phosphatase placental-like 2 (ALPPL-2), siglec-5, stress-induced phosphoprotein 1 (STIP1), protein tyrosine kinase 7 (PTK7), and cyclophilin B.

In some embodiments the target antigen is an antigen of an adenovirus, e.g. adenovirus 5. In some embodiments the target antigen adenovirus 5 hexon.

In some embodiments the antigen-binding molecule of the present invention comprises the CDRs and/or the VH and VL domains of an adenovirus 5 hexon-binding antibody, e.g. 9C12 (described in Varghese et al., 2004a).

In some embodiments the antigen-binding molecule of the present invention comprises an antigen-binding domain capable of specific binding to an endocytosis receptor. As used herein, an 'endocytosis receptor' refers to receptor expressed at the cell surface which is capable of internalisation by the cell expressing the receptor, e.g. following binding of a molecule to the receptor. In this way the endocytosis receptor facilitates cellular uptake of molecules which bind to the receptor. Endocytosis is described e.g. in Alberts B, Johnson A, Lewis J, et al. Molecular Biology of the Cell, 4$^{th}$ Edn. (New York: Garland Science; 2002) at chapter 13, subsection entitled 'Transport into the Cell from the Plasma Membrane: Endocytosis', which is hereby incorporated by reference in its entirety. Briefly, endocytosis refers to uptake of extracellular material by cells through binding of the material to receptors expressed at the cell surface, and subsequent invagination of the plasma membrane and internalization of the material in a membrane-bound vesicle. Endocytosis receptors include e.g. DEC-205, CD11c/CD18, DC-SIGN, Toll-like receptors (TLRs) and phagocytosis receptors. Phagocytosis receptors are expressed at the cell surface of phagocytic cells and include e.g. FcγRlla, FcγRllb, CR3, SRAI, MARCO, CD36, Dectin-1, MICL, CD206 and CD169. Phagocytosis is described e.g. in Alberts B, Johnson A, Lewis J, et al. Molecular Biology of the Cell, 4$^{th}$ Edn. (New York: Garland Science; 2002) at Chapter 25, which is hereby incorporated by reference in its entirety.

In some embodiments the antigen-binding molecule comprises an antigen-binding domain capable of specific binding to an endocytosis receptor expressed by an antigen presenting cell (APC). APCs according to the present disclosure may be professional APCs. Professional APCs are specialised for presenting antigen to T cells; they are efficient at processing and presenting MHC-peptide complexes at the cell surface, and express high levels of costimulatory molecules. Professional APCs include dendritic cells (DCs), macrophages, and B cells. Non-professional APCs are other cells capable of presenting MHC-peptide complexes to T cells, in particular MHC Class I-peptide complexes to CD8+ T cells.

In some embodiments the APC is an APC capable of cross-presentation on MHC class I of antigen internalised by the APC (e.g. taken-up by endocytosis/phagocytosis). Cross-presentation on MHC class I of internalized antigens to CD8+ T cells is described e.g. in Alloatti et al., Immunological Reviews (2016), 272(1): 97-108 and Gros and Amigorena, Frontiers in Immunology (2019) 10:41, both of which are hereby incorporated by reference in their entirety. APCs capable of cross-presentation include e.g. dendritic cells (DCs), macrophages, B cells and sinusoidal endothelial cells. In some embodiments the antigen-binding molecule is specific for an endocytosis receptor expressed by a dendritic cell (DC).

In some embodiments the antigen-binding molecule of the present invention comprises an antigen-binding domain capable of specific binding to protein expressed at the cell surface of a dendritic cell, e.g. DEC-205 or CLEC9A. In some embodiments the antigen-binding molecule of the present invention comprises an antigen-binding domain capable of specific binding to DEC-205. In some embodiments the antigen-binding molecule of the present invention comprises the CDRs and/or the VH and VL domains of a DEC-205-binding antibody, e.g. 3G9-2D2 (described in Cheong et al., 2010).

In some embodiments the antigen-binding molecule of the present invention comprises (i) an antigen-binding domain specific for an antigen of a pathogen, a cancer-associated antigen or an autoimmune disease-associated antigen, (ii) an antigen-binding domain capable of specific binding to an endocytosis receptor, and (iii) an Fc region or polypeptide according to the invention. The skilled person is able to design and prepare such multispecific antigen-binding molecules with reference e.g. to Brinkmann and Kontermann MAbs (2017) 9(2): 182-212, which is hereby incorporated by reference in its entirety. Suitable formats include those formats comprising an Fc region which are shown in FIG. 2 of Brinkmann and Kontermann MAbs (2017) 9(2): 182-212.

In some embodiments, the antigen-binding molecule of the present invention further comprises an antigenic sequence of a target antigen, e.g. according to an embodiment described herein.

It will be appreciated that the antigenic sequence of a target antigen is comprised in a peptide or polypeptide. The peptide/polypeptide comprising the antigenic sequence of a target antigen may be covalently or non-covalently associated with the antigen-binding molecule.

In some embodiments the peptide/polypeptide comprising the antigenic sequence of a target antigen is joined to the antigen-binding molecule via a linker sequence (e.g. a linker sequence as described herein). In some embodiments the peptide/polypeptide comprising the antigenic sequence of a target antigen is joined to the antigen-binding molecule via chemical conjugation, e.g. via click chemistry or via maleimide-thiol conjugation chemistry. Click chemistry and its use to produce conjugates of biomolecules is described in Nwe and Brechbiel Cancer Biother Radiopharm. (2009) 24(3):289-302, which is hereby incorporated by reference in its entirety.

The peptide/polypeptide comprising the antigenic sequence of a target antigen may be associated to any suitable part of the antigen-binding molecule.

In some embodiments, the peptide/polypeptide comprising the antigenic sequence of a target antigen is joined via a peptide bond or a peptide linker to N- or C-terminus of a constituent polypeptide of the antigen-binding molecule. In some embodiments, the peptide/polypeptide comprising the antigenic sequence of a target antigen is joined via chemical conjugation to the N- or C-terminus of a constituent polypeptide of the antigen-binding molecule. In some embodiments, the peptide/polypeptide comprising the antigenic sequence of a target antigen is joined via chemical conjugation to the hinge region sequence or a cysteine residue of a constituent polypeptide of the antigen-binding molecule.

The present invention also provides a polypeptide complex comprising an antigen-binding molecule of the present invention and the target antigen or a fragment thereof. The target antigen is the target antigen for which the antigen-binding molecule comprises a specific antigen-binding domain. The polypeptide complex is preferably a non-covalent complex. The complex is preferably formed by interaction between the CDRs of the antigen-binding molecule and the epitope of the target antigen. In some embodiments the polypeptide complex may be provided in isolated or substantially purified form.

Where the polypeptide complex of the invention comprises a fragment of the target antigen, it will be appreciated that the fragment comprises the epitope for the antigen-binding domain of the antigen-binding molecule.

Immunogens

The present invention also provides immunogens comprising the Fc regions and/or the polypeptides of the invention.

In the present disclosure, an 'immunogen' is a molecule capable of stimulating an adaptive immune response, e.g. a B cell or T cell response. In some embodiments an immunogen is a molecule comprising an antigenic sequence. As used herein, an 'antigenic sequence' refers to an amino acid sequence which is capable of being specifically recognised by an antibody or, capable of being specifically recognised by an immune cell receptor (e.g. a T cell receptor), e.g. when presented by an appropriate MHC molecule.

An immunogen may be, or may comprise, a polypeptide complex. An immunogen may comprise more than one polypeptide which together form the immunogen. The polypeptides may associate covalently or non-covalently. An immunogen may refer to a non-covalent or covalent complex of more than one polypeptide (e.g. 2, 3, 4, 6, or 8 polypeptides).

The 'antigenic sequence' may be, or may be derived from, an amino acid sequence of an antigen, e.g. an antigen described herein (e.g. an antigen of a pathogen, a cancer-associated antigen or an autoimmune disease-associated antigen). An antigenic sequence which is 'derived from' an amino acid sequence of a reference antigen has an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the amino acid sequence of the reference antigen.

In some embodiments the antigenic sequence comprises, or consists of, 5 to 500, 5 to 400, 5 to 300, 5 to 200, 5 to 100, 5 to 90, 5 to 80, 5 to 70, 5 to 60, 5 to 50, 5 to 40, 5 to 35, 5 to 30, 5 to 25, 5 to 20, 5 to 19, 5 to 18, 5 to 17, 5 to 16, 5 to 15, 5 to 14, 5 to 13, 5 to 12, 5 to 11, or 5 to 10 contiguous amino acids of the amino acid sequence of the antigen. In some embodiments the antigenic sequence comprises, or consist of, the entire amino acid sequence of the antigen.

The immunogen of the present invention accordingly comprises at least an antigenic sequence and an Fc region and/or polypeptide according to the present invention.

In some embodiments the immunogen additionally comprises an APC-targeting region. An 'APC-targeting region' is capable of facilitating localisation to and/or uptake of the immunogen by an APC. The APC may be a professional or non-professional APC. In some embodiments the APC-targeting region is a DC-targeting region, a macrophage-targeting region or a B cell-targeting region.

In some embodiments the APC-targeting region comprises or consists of a moiety capable of binding to a receptor expressed on the surface of an APC, e.g. a moiety for capable of binding to an endocytosis receptor (e.g. an endocytosis receptor described herein). In some embodiments a moiety capable of specific binding to a receptor comprises the VH and VL of an antibody capable of specific binding to the receptor, a nucleic acid aptamer capable of binding to the receptor, or a receptor-binding peptide/polypeptide. In some embodiments the APC-targeting region comprises or consists of a ligand for the receptor.

In some embodiments the APC-targeting region comprises or consists of a moiety capable of binding to DEC-205.

In some embodiments the immunogen additionally comprises one or more carrier sequences. A carrier sequence may comprise, or consist of, the amino acid sequence of a carrier protein, e.g. selected from Keyhole Limpet Hemocyanin (KLH), Concholepas Concholepas Hemocyanin (CCH), Bovine Serum Albumin (BSA), or Ovalbumin (OVA).

In some embodiments, the immunogen of the present invention further comprises an antigen-binding domain capable of specific binding to a target antigen, e.g. according to an embodiment described herein. The antigen-binding domain may be covalently or non-covalently associated with the immunogen.

In some embodiments the antigen-binding domain is joined to the immunogen via a linker sequence (e.g. a linker sequence as described herein). In some embodiments the antigen-binding domain is joined to the immunogen via chemical conjugation, e.g. via click chemistry or maleimide-thiol conjugation chemistry.

The antigen-binding domain may be associated to any suitable part of the immunogen.

In some embodiments, the antigen-binding domain is joined via a peptide bond or a peptide linker to N- or C-terminus of a constituent polypeptide of the immunogen. In some embodiments, the antigen-binding domain is joined via chemical conjugation to the N- or C-terminus or to the side chains of a constituent polypeptide of the immunogen.

It will be appreciated that an immunogen of the present invention is useful in methods for generating and/or enhancing an immune response to the antigenic sequence (and thus also to the antigen). By way of illustration, Dhodapkar et al., Sci. Transl. Med. (2014) 6:232ra51 (hereby incorporated by reference in entirety) describes the production and characterisation of an antibody-antigen fusion protein comprising an antigen-binding molecule specific for human DEC-205 fused to the tumor antigen NY-ESO-1. The authors demonstrated that this molecule was capable of inducing humoral and cellular immunity to NY-ESO-1. Similarly, Bozzacco et al., Proc Natl Acad Sci USA. (2007) 104:1289-1294 (hereby incorporated by reference in entirety) describes the production and characterisation of an antibody-antigen fusion protein comprising an antigen-binding molecule specific for human DEC-205 fused to HIV p24 gag protein. The authors demonstrated that this molecule was capable of stimulating proliferation and IFN-gamma production by CD8+ T cells isolated from the blood of HIV-infected donors.

Accordingly the present invention provides the immunogen of the present invention for use in prophylactic and therapeutic applications, and also in methods for generating/expanding populations of immune cells specific for an antigen.

Particular exemplary molecules contemplated
  (1) An antigen-binding molecule comprising: (i) an Fc region according to the present invention, (ii) an antigen-binding domain specific for an endocytosis receptor expressed by a dendritic cell (e.g. DEC-205), and (iii) a peptide/polypeptide comprising an antigenic sequence of a disease-associated antigen.

(2) An antigen-binding molecule comprising: (i) an Fc region according to the present invention, (ii) an antigen-binding domain specific for an endocytosis receptor expressed by a dendritic cell (e.g. DEC-205), and (iii) a peptide/polypeptide comprising an antigenic sequence of a disease-associated antigen;

wherein the peptide/polypeptide comprising an antigenic sequence of a disease-associated antigen is joined via a peptide bond, peptide linker or chemical conjugation to the C-terminus of one or more of the CH3 domains of the Fc region.

(3) An antigen-binding molecule comprising: (i) an Fc region according to the present invention, (ii) an antigen-binding domain specific for an endocytosis receptor expressed by a dendritic cell (e.g. DEC-205), and (iii) a peptide/polypeptide comprising an antigenic sequence of a disease-associated antigen;

wherein the peptide/polypeptide comprising an antigenic sequence of a disease-associated antigen is joined via a peptide bond, peptide linker or chemical conjugation N-terminal to one or more of the CH2 domains of the Fc region.

(4) An antigen-binding molecule comprising an Fc region according to the present invention, and an antigen-binding domain specific for a disease-associated target antigen, (e.g. GPC3, or an antigen of a parasite).

(5) An antigen-binding molecule comprising: (i) an Fc region according to the present invention, (ii) an antigen-binding domain specific for a disease-associated target antigen, (e.g. GPC3, or an antigen of a parasite), and (iii) an antigen-binding domain specific for an endocytosis receptor expressed by a dendritic cell (e.g. DEC-205).

(6) An immunogen comprising an Fc region according to the present invention, and a peptide/polypeptide comprising an antigenic sequence of a disease-associated antigen (e.g. GPC3).

(7) An immunogen comprising: (i) an Fc region according to the present invention, (ii) a peptide/polypeptide comprising an antigenic sequence of a disease-associated antigen (e.g. GPC3), and (iii) an antigen-binding domain specific for an endocytosis receptor expressed by a dendritic cell (e.g. DEC-205).

Additional Sequences

The antigen-binding molecules, immunogens and polypeptides according to the present invention may additionally comprise further amino acids or sequences of amino acids.

For example, the antigen-binding molecules may comprise one or more linker sequences between the antigen-binding domain and the Fc region. The linker sequence(s) may be provided in one or more of the polypeptides of the antigen-binding molecule. Similarly, the immunogens may comprise one or more linker sequences between the antigenic sequence and the Fc region.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues. In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules, immunogens and polypeptides of the invention may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6XHis), Myc, GST, MBP, FLAG, HA, E, or Biotin tag, optionally at the N- or C- terminus of the antigen-binding molecule/immunogen/polypeptide. In some embodiments the antigen-binding molecule/polypeptide comprises a detectable moiety, e.g. a fluorescent, lunminescent, immuno-detectable, radio, chemical, nucleic acid or enzymatic label.

The antigen-binding molecules, immunogens and polypeptides of the present invention may additionally comprise a signal peptide (also known as a leader sequence or signal sequence). Signal peptides normally consist of a sequence of 5-30 hydrophobic amino acids, which form a single alpha helix.

Secreted proteins and proteins expressed at the cell surface often comprise signal peptides. A signal peptide may be present at the N-terminus of the antigen-binding molecule/polypeptide, and may be present in the newly synthesised antigen-binding molecule/polypeptide. The signal peptide provides for efficient trafficking and/or secretion of the antigen-binding molecule/polypeptide. Signal peptides are often removed by cleavage, and thus are not comprised in the mature antigen-binding molecule/polypeptide. Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Functional Properties

The antigen-binding molecules, polypeptide complexes and immunogens of the present invention may be defined by reference to certain functional properties.

In some embodiments, a molecule comprising a modified Fc region according to the present invention may display increased affinity for TRIM21 and/or increased binding to TRIM21 as compared to an equivalent molecule comprising an unmodified Fc region. The molecule comprising a modified Fc region may e.g. be an antigen-binding molecule or a polypeptide complex of an antigen-binding molecule and target antigen/fragment thereof. An equivalent molecule comprises all of the same features as the test molecule, the only difference being the modification(s) to the Fc region.

A "modified Fc region" may be any embodiment of an Fc region according to the present invention. An "unmodified Fc region" may be the wildtype Fc region of an IgG (e.g. IgG1, IgG2, IgG3, IgG4), IgA (e.g. IgA1, IgA2), IgD, IgE or IgM. In some embodiments, an unmodified Fc region is comprised of CH2-CH3 having the amino acid sequence of SEQ ID NO:10, 14, 18, 22, 180, 181 or 182. In some embodiments, an unmodified Fc region is comprised of CH2-CH3-CH4 having the amino acid sequence of SEQ ID NO:31 or 183. In particular embodiments, an unmodified Fc region is comprised of CH2-CH3 having the amino acid sequence of SEQ ID NO:10.

The affinity of association between a molecule comprising an Fc region and TRIM21 can be identified using a suitable assay, such as Surface Plasmon Resonance (SPR; see e.g.

Hearty et al., Methods Mol Biol (2012) 907:411-442), Bio-Layer Interferometry (see e.g. Lad et al., (2015) J Biomol Screen 20(4): 498-507), flow cytometry, or Enzyme-linked immunosorbent assay. The affinity of association between two molecules can be analysed and quantified using such methods. The affinity of association between a molecule comprising an Fc region and TRIM21 can be analysed as described in Example 1.10.

In some embodiments the molecule comprising a modified Fc region binds to TRIM21 with an affinity which is more than 1 times, e.g. 1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥22 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times, ≥100 times, ≥200 times, ≥300 times, ≥400 times, ≥500 times, ≥600 times, ≥700 times, 800 times, ≥900 times or 1000 times the affinity of association between TRIM21 and the equivalent molecule comprising an unmodified Fc region.

In some embodiments, an antigen-binding molecule comprising a modified Fc region according to the present invention displays one or more of the following properties as compared to an equivalent antigen-binding molecule comprising an unmodified Fc region:

Increased affinity for TRIM21; and

Similar level of antibody-dependent intracellular neutralization (ADIN).

An equivalent antigen-binding molecule comprises all of the same features as the test antigen-binding molecule, the only difference being the modification(s) to the Fc region.

Analysis of ADIN can be performed using a suitable assay, e.g. as described in Example 1.11 herein, or in Watkinson et al., J. Virol. (2013) 87(13) 7309-7313, which is hereby incorporated by reference in its entirety. It will be appreciated that the assay employs a suitable target and antigen-binding domain, e.g. a target and an antigen-binding domain of an antibody known to participate in ADIN.

A similar level of ADIN may be a level of ADIN which is ≥0.75 times and 1.25 times, e.g. ≥0.8 times and ≤1.2 times, ≥0.85 times and ≤1.15 times, ≥0.9 times and 1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≥0.98 times and ≤1.02 times, or ≥0.99 times and ≤1.01 times the level of ADIN displayed by an equivalent antigen-binding molecule comprising an unmodified Fc region.

In some embodiments, a polypeptide complex comprising an antigen-binding molecule according to the present invention and target antigen/fragment thereof is useful to stimulate dendritic cells (e.g. monocyte-derived dendritic cells) displaying one or more of the following properties as compared to dendritic cells stimulated with a polypeptide complex comprising an equivalent antigen-binding molecule having an unmodified Fc region and the target antigen/fragment thereof:

Increased expression of one or more markers of APC maturation;

Increased expression of one or more costimulatory molecules;

Increased expression of one or more Th1-associated factors;

Increased ability to expand T cells (e.g. CD8+ T cells, e.g. antigen-specific CD8+ T cells);

Increased ability to expand IFNγ-expressing T cells (e.g. IFNγ-expressing, CD8+ T cells, e.g.

IFNγ-expressing, antigen-specific CD8+ T cells); and

Increased cross-presentation of a peptide of the target antigen.

As used herein, 'expression' may be gene expression or protein expression. Gene expression can be determined e.g. by detection of mRNA encoding the marker, for example by quantitative real-time PCR (qRT-PCR), or by reporter-based methods. Protein expression can be determined e.g. by detection of the protein, for example by antibody-based methods which are well known to the skilled person, such as western blot, immunohistochemistry, immunocytochemistry, flow cytometry, and ELISA. Protein expression can be determined by reporter-based methods, e.g. assays for a function of the protein.

Assays for analysing expression of one or more factors by dendritic cells in response to stimulation with polypeptide complexes can be performed e.g. as described in Example 1.12. It will be appreciated that the assays employ a suitable target antigen/fragment and antigen-binding molecule combination, e.g. a combination known to induce maturation of dendritic cells and/or expression of Th1 factors by dendritic cells.

In some embodiments the one or more markers of APC maturation may be one or more markers of monocyte-derived dendritic cell (moDC) maturation. In some embodiments the one or more markers may be selected from CD80, CD83, CD86 and HLA-DR.

In some embodiments the one or more costimulatory molecules may be selected from CD80, CD83 and CD86.

Th1-associated factors are factors which promote differentiation of CD4+ helper T cells (i.e. Th cells) to a Th1 phenotype. In some embodiments the one or more Th1-associated factors are selected from CCL3 (MIP1-α), CCL4 (MIP-1β), CCL5 (RANTES), TRAIL, IFN-γ, IL-6 and TNF-α.

Increased expression may be a level of expression which is more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times, ≥100 times the level of expression of the relevant factor(s) by dendritic cells stimulated with a polypeptide complex comprising an equivalent antigen-binding molecule having an unmodified Fc region and the target antigen/fragment thereof.

Expansion of a cell type can be analysed by monitoring cell number/proportion or cell division over a period of time. Cell numbers and proportions can be determined e.g. by flow cytometry analysis using antibodies allowing detection of various cell types. Cell division can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

The ability of dendritic cells to stimulate expansion of a cell type of interest can be determined by analysis by flow cytometry following co-culture of a population of immune cells comprising the cell type of interest (e.g. PBMCs) in the presence of dendritic cells which have been stimulated with the polypeptide complex. Expansion of T cells may be analysed e.g. in an assay as described herein in Example 1.13. Expansion of antigen-specific T cells may be analysed e.g. in an assay as described herein in Example 1.14.

Increased ability to expand T cells may be determined by detection of an increased number/proportion of T cells following co-culture of a population of immune cells (e.g. PBMCs) with dendritic cells stimulated with a polypeptide complex according to the invention as compared to the number/proportion of T cells obtained following co-culture of a population of immune cells (e.g. PBMCs) with dendritic cells stimulated with a polypeptide complex comprising an equivalent antigen-binding molecule having an unmodified Fc region and the target antigen/fragment thereof. In some embodiments the increased number/proportion is more than 1 times, e.g. $\geq 1.01$ times, $\geq 1.02$ times, $\geq 1.03$ times, $\geq 1.04$ times, $\geq 1.05$ times, $\geq 1.06$ times, $\geq 1.07$ times, $\geq 1.08$ times, $\geq 1.09$ times, $\geq 1.1$ times, $\geq 1.2$ times, $\geq 1.3$ times, $\geq 1.4$ times, $\geq 1.5$ times, $\geq 1.6$ times, $\geq 1.7$ times, $\geq 1.8$ times, $\geq 1.9$ times, $\geq 2$ times, $\geq 3$ times, $\geq 4$ times, $\geq 5$ times, $\geq 6$ times, $\geq 7$ times, $\geq 8$ times, $\geq 9$ times, $\geq 10$ times, $\geq 20$ times, $\geq 30$ times, $\geq 40$ times, $\geq 50$ times, $\geq 60$ times, $\geq 70$ times, $\geq 80$ times, $\geq 90$ times, $\geq 100$ times the number/proportion of T cells obtained following co-culture of a population of immune cells (e.g. PBMCs) with dendritic cells stimulated with a polypeptide complex comprising an equivalent antigen-binding molecule having an unmodified Fc region and the target antigen/fragment thereof.

Increased ability to expand IFN-γ-expressing T cells (e.g. IFN-γ-expressing, CD8+ T cells, e.g. IFN-γ-expressing, antigen-specific CD8+ T cells) may be determined by detection of an increased number/proportion of IFN-γ-expressing T cells following co-culture of a population of immune cells (e.g. PBMCs) with dendritic cells stimulated with a polypeptide complex according to the invention as compared to the number/proportion of IFN-γ-expressing T cells obtained following co-culture of a population of immune cells (e.g. PBMCs) with dendritic cells stimulated with a polypeptide complex comprising an equivalent antigen-binding molecule having an unmodified Fc region and the target antigen/fragment thereof. In some embodiments the increased number/proportion is more than 1 times, e.g. $\geq 1.01$ times, $\geq 1.02$ times, $\geq 1.03$ times, $\geq 1.04$ times, $\geq 1.05$ times, $\geq 1.06$ times, $\geq 1.07$ times, $\geq 1.08$ times, $\geq 1.09$ times, $\geq 1.1$ times, $\geq 1.2$ times, $\geq 1.3$ times, $\geq 1.4$ times, $\geq 1.5$ times, $\geq 1.6$ times, $\geq 1.7$ times, $>1.8$ times, $\geq 1.9$ times, $\geq 2$ times, $\geq 3$ times, $\geq 4$ times, $\geq 5$ times, $\geq 6$ times, $\geq 7$ times, $\geq 8$ times, $\geq 9$ times, $\geq 10$ times, $\geq 20$ times, $\geq 30$ times, $\geq 40$ times, $\geq 50$ times, $\geq 60$ times, $\geq 70$ times, $\geq 80$ times, $\geq 90$ times, $\geq 100$ times the number/proportion of IFN-γ-expressing T cells obtained following co-culture of a population of immune cells (e.g. PBMCs) with dendritic cells stimulated with a polypeptide complex comprising an equivalent antigen-binding molecule having an unmodified Fc region and the target antigen/fragment thereof.

Cross-presentation refers to presentation of a peptide of the target antigen on an MHC class I molecule following internalisation and processing of the complex by the antigen-presenting cells (e.g. dendritic cells). Cross-presentation can be detected and quantified using methods capable of detecting MHC class I:target antigen peptide complexes expressed on the surface of the dendritic cells following incubation of the dendritic cells with polypeptide complexes of the antigen-binding molecule and the target antigen/fragment thereof.

Increased cross-presentation may be cross-presentation which is more than 1 times, e.g. $\geq 1.01$ times, $\geq 1.02$ times, $\geq 1.03$ times, $\geq 1.04$ times, $\geq 1.05$ times, $\geq 1.06$ times, $\geq 1.07$ times, $\geq 1.08$ times, $\geq 1.09$ times, $1.1$ times, $\geq 1.2$ times, $\geq 1.3$ times, $\geq 1.4$ times, $\geq 1.5$ times, $\geq 1.6$ times, $\geq 1.7$ times, $\geq 1.8$ times, $\geq 1.9$ times, $\geq 2$ times, $\geq 3$ times, $\geq 4$ times, $\geq 5$ times, $\geq 6$ times, $\geq 7$ times, $\geq 8$ times, $\geq 9$ times, $\geq 10$ times, $\geq 20$ times, $\geq 30$ times, $\geq 40$ times, $\geq 50$ times, $\geq 60$ times, $\geq 70$ times, $\geq 80$ times, $\geq 90$ times, $\geq 100$ times the level of cross-presentation by dendritic cells contacted with a polypeptide complex comprising an equivalent antigen-binding molecule having an unmodified Fc region and the target antigen/fragment thereof.

In some embodiments, an immunogen according to the present invention is useful to stimulate dendritic cells (e.g. monocyte-derived dendritic cells) displaying one or more of the following properties as compared to dendritic cells stimulated with a control immunogen comprising an unmodified Fc region:

Increased expression of one or more markers of maturation;

Increased expression of one or more Th1-associated factors;

Increased ability to stimulate T cell proliferation (e.g. CD8+ T cell proliferation, e.g. antigen-specific CD8+ T cell proliferation);

Increased ability to stimulate IFN-γ-expressing T cells (e.g. IFN-γ-expressing, CD8+ T cells, e.g. IFN-γ-expressing, antigen-specific CD8+ T cells); and Increased cross-presentation of a peptide of the target antigen.

Increased expression may be a level of expression which is more than 1 times, e.g. $\geq 1.01$ times, $\geq 1.02$ times, $\geq 1.03$ times, $\geq 1.04$ times, $\geq 1.05$ times, $\geq 1.06$ times, $\geq 1.07$ times, $\geq 1.08$ times, $\geq 1.09$ times, $\geq 1.1$ times, $\geq 1.2$ times, $\geq 1.3$ times, $\geq 1.4$ times, $\geq 1.5$ times, $\geq 1.6$ times, $\geq 1.7$ times, $\geq 1.8$ times, $\geq 1.9$ times, $\geq 2$ times, $\geq 3$ times, $\geq 4$ times, $\geq 5$ times, $\geq 6$ times, $\geq 7$ times, $\geq 8$ times, $\geq 9$ times, $\geq 10$ times, $\geq 20$ times, $\geq 30$ times, $\geq 40$ times, $\geq 50$ times, $\geq 60$ times, $\geq 70$ times, $\geq 80$ times, $\geq 90$ times, $\geq 100$ times the level of expression of the relevant factor(s) by dendritic cells stimulated with an equivalent immunogen having an unmodified Fc region.

Increased ability to expand T cells may be determined by detection of an increased number/proportion of T cells following co-culture of a population of immune cells (e.g. PBMCs) with dendritic cells stimulated with an immunogen according to the invention as compared to the number/proportion of T cells obtained following co-culture of a population of immune cells (e.g. PBMCs) with dendritic cells stimulated with a polypeptide complex comprising an equivalent immunogen having an unmodified Fc region. In some embodiments the increased number/proportion is more than 1 times, e.g. $1.01$ times, $\geq 1.02$ times, $\geq 1.03$ times, $\geq 1.04$ times, $\geq 1.05$ times, $\geq 1.06$ times, $\geq 1.07$ times, $\geq 1.08$ times, $\geq 1.09$ times, $\geq 1.1$ times, $\geq 1.2$ times, $\geq 1.3$ times, $\geq 1.4$ times, $\geq 1.5$ times, $\geq 1.6$ times, $\geq 1.7$ times, $\geq 1.8$ times, $\geq 1.9$ times, $\geq 2$ times, $\geq 3$ times, $\geq 4$ times, $\geq 5$ times, $\geq 6$ times, $\geq 7$ times, $\geq 8$ times, $\geq 9$ times, $\geq 10$ times, $\geq 20$ times, $\geq 30$ times, $\geq 40$ times, $\geq 50$ times, $\geq 60$ times, $\geq 70$ times, $\geq 80$ times, $\geq 90$ times, $\geq 100$ times the number/proportion of T cells obtained following co-culture of a population of immune cells (e.g. PBMCs) with dendritic cells stimulated with an equivalent immunogen having an unmodified Fc region.

Increased ability to expand IFN-γ-expressing T cells (e.g. IFN-γ-expressing, CD8+ T cells, e.g. IFN-γ-expressing, antigen-specific CD8+ T cells) may be determined by detection of an increased number/proportion of IFN-γ-expressing T cells following co-culture of a population of immune cells (e.g. PBMCs) with dendritic cells stimulated with an immunogen according to the invention as compared to the number/proportion of IFN-γ-expressing T cells obtained following co-culture of a population of immune cells (e.g. PBMCs) with dendritic cells stimulated with an equivalent immunogen having an unmodified Fc region. In some embodiments the increased number/proportion is more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times, ≥100 times the number/proportion of IFN-γ-expressing T cells obtained following co-culture of a population of immune cells (e.g. PBMCs) with dendritic cells stimulated with an equivalent immunogen having an unmodified Fc region.

Increased cross-presentation may be cross-presentation which is more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times, ≥100 times the level of cross-presentation by dendritic cells contacted with an equivalent immunogen having an unmodified Fc region.

Methods Using the Antigen-Binding Molecules, Immunogens and Polypeptide Complexes The antigen-binding molecules, immunogens and polypeptide complexes according to the present invention are useful in methods for producing antigen-presenting cells (e.g. dendritic cells) having desirable properties. The antigen-binding molecules, immunogens and polypeptide complexes according to the present invention are useful in methods for generating/expanding populations of immune cells of interest. The antigen-binding molecules, immunogens and polypeptide complexes according to the present invention are useful in methods for inducing or enhancing an immune response to a target antigen in a subject.

Antigen-presenting cells (e.g. dendritic cells) which are contacted/treated/stimulated with (and which subsequently internalise) the immunogens and polypeptide complexes according to the present invention are provided with desirable properties relevant to their use in methods for expanding populations of cells of interest (e.g. T cells, e.g. CD8+ T cells, e.g. antigen-specific CD8+ T cells), e.g. in vivo, ex vivo or in vitro.

Accordingly, the present invention provides a method comprising contacting a population of antigen-presenting cells (e.g. dendritic cells) with an immunogen according to the present invention or a polypeptide complex according to the invention (i.e. comprising an antigen-binding molecule according to the present invention and a target antigen/fragment thereof). The present invention also provides a population of antigen-presenting cells (e.g. dendritic cells) produced according to the method. Also provided is a method for generating or expanding a population of immune cells (e.g. T cells, e.g. CD8+ T cells) specific for a target antigen, comprising contacting a population of immune cells with an antigen-presenting cell produced according to the method.

Aspects of the present invention contemplate the use of the antigen-binding molecules, immunogens and polypeptide complexes of the present invention in methods for generating/stimulating/boosting/increasing an immune response (in particular a cell mediated-immune response, and in particular a T cell-mediated immune response (e.g. a CD8+ T cell-mediated immune response)) to a target antigen.

The antigen-presenting cells may be contacted/treated/stimulated with the immunogens/polypeptide complexes in vitro or in vivo. In some embodiments the polypeptide complexes may be formed in vivo following administration of an antigen-binding molecule to a subject infected with the relevant pathogen or expressing the relevant target antigen. In some embodiments the polypeptide complexes may be formed in vitro by contacting the antigen-binding molecule with the relevant target antigen/fragment thereof.

Culture of cells in accordance with the methods of the invention is performed using suitable medium and under suitable environmental conditions (e.g. temperature, pH, humidity, atmospheric conditions, agitation etc.) for the in vitro and/or ex vivo culture of immune cells, which are well known to the person skilled in the art of cell culture. Conveniently, cultures of cells may be maintained at 37° C. in a humidified atmosphere containing 5% $CO_2$. Cultures can be performed in any vessel suitable for the volume of the culture, e.g. in wells of a cell culture plate, cell culture flasks, a bioreactor, etc. The cell cultures can be established and/or maintained at any suitable density, as can readily be determined by the skilled person. For example, cultures may be established at an initial density of ~0.5×10$^6$ to ~5×10$^6$ cells/ml of the culture (e.g. ~1×10$^6$ cells/ml). Cells may be cultured in any suitable cell culture vessel. In some embodiments of the methods according to the various aspects of the present invention, cells are cultured in a bioreactor.

Populations of cells of interest (e.g. T cells, e.g. CD8+ T cells, e.g. antigen-specific CD8+ T cells) may be generated/expanded according to the present invention from within a population of immune cells. It will be appreciated that the population of immune cells comprises the cell type of interest, e.g. at low frequency. The population of immune cells from which the cells of interest are generated/expanded according to the methods of the present invention comprise at least one cell of interest.

In some embodiments, populations of cells of interest may be generated/expanded from within a population of immune cells, e.g. peripheral blood mononuclear cells (PBMCs). For example, a population of T cells (e.g. CD8+ T cells, e.g. antigen-specific CD8+ T cells) may be generated/expanded from within a population of immune cells (e.g. PBMCs), by culture of the immune cells in the presence of antigen-presenting cells (APCs; e.g. dendritic cells) which have been contacted with an immunogen or polypeptide complex according to the present invention. In embodiments of the methods disclosed herein, the antigen-presenting cells may be obtained/derived from a population of PBMCs. In some embodiments the antigen-presenting cells and the population of immune cells are autologous (i.e. are derived/obtained from the same subject).

Nucleic Acids and Vectors

The present invention provides a nucleic acid, or a plurality of nucleic acids, encoding an antigen-binding molecule, immunogen or polypeptide according to the present invention.

In some embodiments, the nucleic acid is purified or isolated, e.g. from other nucleic acid, or naturally-occurring biological material. In some embodiments the nucleic acid(s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A 'vector' as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term 'operably linked' may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule/Fc region/immunogen according to the present invention may be encoded by different nucleic acids of the plurality of nucleic acids, or by different vectors of the plurality of vectors.

Cells Comprising/Expressing the Antigen-Binding Molecules, Immunogens and Polypeptides The present invention also provides a cell comprising or expressing an antigen-binding molecule, immunogen or polypeptide according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) or vector(s) according to the invention into a cell comprises transformation, transfection, electroporation or transduction (e.g. retroviral transduction).

The present invention also provides a method for producing a cell expressing/comprising an antigen-binding molecule, immunogen or polypeptide according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides a method for producing an antigen-binding molecule, immunogen or polypeptide according to the present invention, comprising introducing a nucleic acid, a plurality of nucleic acids, a vector or a plurality of vectors according to the present invention in a cell and culturing the cell under conditions suitable for expression of the nucleic acid(s) or vector(s) by the cell. In some embodiments, the methods additionally comprise isolating/purifying the expressed antigen-binding molecule(s)/immunogen(s)/polypeptide(s). In some embodiments, the methods are performed in vitro.

The present invention also provides cells obtained or obtainable by the methods according to the present invention.

Producing the Antigen-Binding Molecules, Immunogens and Polypeptides

Antigen-binding molecules, immunogens and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules, immunogens and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases the antigen-binding molecules of the present invention are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition, incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/immunogen/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, immunogens, polypeptides, nucleic acids, expression vectors and cells described herein.

The antigen-binding molecules, immunogens, polypeptides, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule or immunogen in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In accordance with the invention described herein methods are also provided for the production of pharmaceutically useful compositions, such methods of production may comprise one or more steps selected from: producing an antigen-binding molecule, immunogen, polypeptide, nucleic acid (or plurality thereof), expression vector (or plurality thereof) or cell described herein, isolating an antigen-binding molecule, immunogen, polypeptide, nucleic acid (or plurality thereof), expression vector (or plurality thereof) or cell described herein; and/or mixing antigen-binding molecule, immunogen, polypeptide, nucleic acid (or plurality thereof), expression vector (or plurality thereof) or cell described herein with a pharmaceutically acceptable carrier, adjuvant, excipient or diluent.

For example, a further aspect the invention described herein relates to a method of formulating or producing a medicament or pharmaceutical composition for use in the treatment of a disease/condition, the method comprising formulating a pharmaceutical composition or medicament by mixing an antigen-binding molecule, immunogen, polypeptide, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptide complexes, immunogens, polypeptides and pharmaceutical compositions described herein find use in therapeutic and prophylactic applications.

The present invention provides an antigen-binding molecule, immunogen, polypeptide complex, nucleic acid (or plurality thereof), expression vector (or plurality thereof), cell or composition described herein for use in a method of medical treatment or prophylaxis. Also provided is the use of an antigen-binding molecule, immunogen, polypeptide complex, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, immunogen, polypeptide complex, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis).

It will be appreciated that the antigen-binding molecules and polypeptide complexes of the present invention may be used for the treatment/prevention of any disease/condition that would derive therapeutic or prophylactic benefit from a reduction in the number and/or activity of cells comprising/expressing the target antigen for which the antigen-binding molecule is specific.

Similarly, it will be appreciated that the immunogens of the present invention may be used for the treatment/prevention of any disease/condition that would derive therapeutic or prophylactic benefit from a reduction in the number and/or activity of cells comprising/expressing the target antigen corresponding to the antigenic sequence of the immunogen.

For example, the disease/condition may be a disease/condition in which cells expressing the target antigen are pathologically implicated, e.g. a disease/condition in which an increased number/proportion of cells expressing the target antigen is positively associated with the onset, development or progression of the disease/condition, and/or severity of one or more symptoms of the disease/condition, or for which an increased number/proportion of cells expressing the target antigen, is a risk factor for the onset, development or progression of the disease/condition.

In some embodiments, the disease/condition to be treated/prevented in accordance with the present invention is a disease/condition characterised by an increase in the number/proportion/activity of cells expressing the target antigen, e.g. as compared to the number/proportion/activity of cells expressing the target antigen in the absence of the disease/condition.

The treatment/prevention may be aimed at one or more of: delaying/preventing the onset/progression of symptoms of disease/condition, reducing the severity of symptoms of the disease/condition, reducing the survival/growth/activity/number of effectors of the disease/condition, and/or increasing survival of the subject.

In some embodiments the target antigen is an antigen of a pathogen (e.g. as described hereinabove), and the disease/condition to be treated/prevented is a disease/condition which is caused or exacerbated by infection with the pathogen, a disease for which infection with the pathogen is a risk factor and/or a disease for which infection with the pathogen is positively associated with disease onset, development, progression and/or severity. A subject may be determined to be infected with the pathogen or to have the have the disease/condition by analysis of a sample obtained from the subject.

In some embodiments the target antigen is a cancer-associated antigen (e.g. as described hereinabove), and the disease/condition to be treated/prevented is a cancer. The cancer may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells. Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma. The treatment/prevention may be aimed at one or more of: delaying/preventing the onset/progression of symptoms of the cancer, reducing the severity of symptoms of the cancer, reducing the survival/growth/invasion/metastasis of cells of the cancer, reducing the number of cells of the cancer and/or increasing survival of the subject.

In some embodiments, the cancer to be treated/prevented comprises cells expressing or overexpressing the target antigen. Overexpression can be determined by detection of a level of expression (gene/protein expression) of the target antigen which is greater than the level of expression by equivalent, non-cancerous cells/non-tumor tissue. A subject may be determined to have a cancer expressing or overexpressing the target antigen by analysis of a sample obtained from the subject.

Administration of the articles of the present invention is preferably in a "therapeutically effective" or "prophylactically effective" amount, this being sufficient to show therapeutic or prophylactic benefit to the subject. The actual amount administered, and rate and time-course of administration, will depend on the nature and severity of the disease/condition and the particular article administered. Prescription of treatment, e.g. decisions on dosage etc., is within the responsibility of general practitioners and other medical doctors, and typically takes account of the disease/ disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Administration may be alone or in combination with other treatments, either simultaneously or sequentially dependent upon the condition to be treated. The antigen-binding molecule or composition described herein and a therapeutic agent may be administered simultaneously or sequentially.

In some embodiments, the methods comprise additional therapeutic or prophylactic intervention, e.g. where the methods is for the treatment/prevention of a cancer. In some embodiments, the additional therapeutic or prophylactic intervention is selected from chemotherapy, immunotherapy, radiotherapy, surgery, vaccination and/or hormone therapy.

Multiple doses of the antigen-binding molecule, immunogen, polypeptide, polypeptide complex, nucleic acid (or plurality thereof), expression vector (or plurality thereof), cell or composition according to the invention may be provided. One or more, or each, of the doses may be accompanied by simultaneous or sequential administration of another therapeutic/prophylactic agent. Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

The immunogens and polypeptide complexes according to the present invention are useful as vaccines. The immunogens and polypeptide complexes can be used to generate immunity to a disease/condition in which the target antigen is implicated. Accordingly, the present invention provides a vaccine comprising, methods for vaccination using, and the use as a vaccine of, an immunogen or a polypeptide complex in accordance with any embodiment as described herein.

In some embodiments multiple, different immunogens/ polypeptide complexes may be used in a vaccine or vaccination according to the present invention. Such vaccines/ vaccination may therefore be useful to vaccinate against multiple diseases/conditions. The skilled person is readily able to determine suitable formulations for vaccines and schedules for vaccination in accordance with the present invention, e.g. by reference to Vaccines (6th Edn.) Plotkin et al. 2012, Elsevier Saunders, which is hereby incorporated by reference in its entirety.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present invention the subject is preferably a human subject. In some embodiments, the subject to be treated according to a therapeutic or prophylactic method of the invention herein is a subject having, or at risk of developing, a disease/condition. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, immunogen, polypeptide, polypeptide complex, nucleic acid (or plurality thereof), expression vector (or plurality thereof), cell or composition described herein.

In some embodiments, the kit may comprise materials for producing an antigen-binding molecule, immunogen, polypeptide, polypeptide complex, nucleic acid (or plurality thereof), expression vector (or plurality thereof), cell or composition described herein. In some embodiment the kit additionally comprises instructions for administration to a patient in order to treat or prevent a specified disease/ condition.

Sequence Identity

As used herein, 'sequence identity' refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Soding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human TRIM21 isoform 1 (UniProt: P19474-1, v1) | MASAARLTMMWEEVTCPICLDPFVEPVSIECGHSFCQECISQVGKGGGSVCPVCRQRFLLK NLRPNRQLANMVNNLKEISQEAREGTQGERCAVHGERLHLFCEKDGKALCWVCAQSRKHR DHAMVPLEEAAQEYQEKLQVALGELRRKQELAEKLEVEIAIKRADWKKTVETQKSRIHAEFV QQKNFLVEEEQRQLQELEKDEREQLRILGEKEAKLAQQSQALQELISELDRRCHSSALELLQ EVIIVLERSESWNLKDLDITSPELRSVCHVPGLKKMLRTCAVHITLDPDTANPWLILSEDRRQ VRLGDTQQSIPGNEERFDSYPMVLGAQHFHSGKHYWEVDVTGKEAWDLGVCRDSVRRKG HFLLSSKSGFWTIWLWNKQKYEAGTYPQTPLHLQVPPCQVGIFLDYEAGMVSFYNITDHGS LIYSFSECAFTGPLRPFFSPGFNDGGKNTAPLTLCPLNIGSQGSTDY |

-continued

| SEQ ID NO: | DESCRIPTION | SEQUENCE |
|---|---|---|
| 2 | Human TRIM21 isoform 2 (UniProt: P19474-2) | MASAARLTMMWEEVTCPICLDPFVEPVSIECGHSFCQECISQVGKGGGSVCPVCRQRFLLK NLRPNRQLANMVNNLKEISQEAREGTQGERCAVHGERLHLFCEKDGKALCWVCAQSRKHR DHAMVPLEEAAQEYQEKLQVALGELRRKQELAEKLEVEIAIKRADWKEVIIVLERSESWNLK DLDITSPELRSVCHVPGLKKMLRTCAVHITLDPDTANPWLILSEDRRQVRLGDTQQSIPGNE ERFDSYPMVLGAQHFHSGKHYWEVDVTGKEAWDLGVCRDSVRRKGHFLLSSKSGFWTIW LWNKQKYEAGTYPQTPLHLQVPPCQVGIFLDYEAGMVSFYNITDHGSLIYSFSECAFTGPLR PFFSPGFNDGGKNTAPLTLCPLNIGSQGSTDY |
| 3 | TRIM21 RING domain (positions 16 to 55 of UniProt: P19474-1) | CPICLDPFVEPVSIECGHSFCQECISQVGKGGGSVCPVCR |
| 4 | TRIM21 B-box (positions 92 to 123 of UniProt: P19474-1) | CAVHGERLHLFCEKDGKALCWVCAQSRKHRDH |
| 5 | TRIM21 Coiled coil domain (positions 128 to 238 of UniProt: P19474-1) | LEEAAQEYQEKLQVALGELRRKQELAEKLEVEIAIKRADWKKTVETQKSRIHAEFVQQKNFL VEEEQRQLQELEKDEREQLRILGEKEAKLAQQSQALQELISELDRRCHS |
| 6 | TRIM21 PRYSPRY domain (positions 268 to 465 of UniProt: P19474-1) | ELRSVCHVPGLKKMLRTCAVHITLDPDTANPWLILSEDRRQVRLGDTQQSIPGNEERFDSYP MVLGAQHFHSGKHYWEVDVTGKEAWDLGVCRDSVRRKGHFLLSSKSGFWTIWLWNKQKY EAGTYPQTPLHLQVPPCQVGIFLDYEAGMVSFYNITDHGSLIYSFSECAFTGPLRPFFSPGF NDGGKNTAPLTLCPL |
| 7 | Human IgG1 constant region (IGHG1; UniProt:P01857-1, v1) | ASTKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGPSV FLEPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTVDKSRWQQGNVFS CSVMHEALHNHYTQKSLSLSPGK |
| 8 | CH2 IgG1 (positions 111-223 of P01857-1, v1) | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAK |
| 9 | CH3 IgG1 (positions 224-330 of P01857-1, v1) | GQPREPQVYTLPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 10 | CH2-CH3 IgG1 (positions 111-330 of P01857-1, v1) | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 11 | Human IgG2 constant region (IGHG2; UniProt:P01859-1, v2) | ASTKGPSVFPLAPCSRSTSESTAALGCLVKDYFPEPVTVSWNSGALTSGVHTFPAVLQSSG LYSLSSVVTVPSSNFGTQTYTCNVDHKPSNTKVDKTVERKCCVECPPCPAPPVAGPSVFLF PPKPKDTLMISRTPEVTCVVVDVSHEDPEVQFNWYVDGVEVHNAKTKPREEQFNSTFRVVS VLTVVHQDWLNGKEYKCKVSNKGLPAPIEKTISKTKGQPREPQVYTLPPSREEMTKNQVSL TCLVKGFYPSDISVEWESNGQPENNYKTTPPMLDSDGSFFLYSKLTVDKSRWQQGNVFSC SVMHEALHNHYTQKSLSLSPGK |
| 12 | CH2 IgG2 (positions 111-219 of P01859-1, v2) | APPVAGPSVFLFPPKPKDTLMISRTPEVTCVVVDVSHEDPEVQFNWYVDGVEVHNAKTKPR EEQFNSTFRVVSVLTVVHQDWLNGKEYKCKVSNKGLPAPIEKTISKTK |
| 13 | CH3 IgG2 (positions 220-326 of P01859-1, v2) | GQPREPQVYTLPPSREEMTKNQVSLTCLVKGFYPSDISVEWESNGQPENNYKTTPPMLDS DGSFFLYSKLTVDKSRWQQGNVFSCSVMHEALHNHYTQKSLSLSPGK |
| 14 | CH2-CH3 IgG2 (positions 111-326 of P01859-1, v2) | APPVAGPSVFLFPPKPKDTLMISRTPEVTCVVVDVSHEDPEVQFNWYVDGVEVHNAKTKPR EEQFNSTFRVVSVLTVVHQDWLNGKEYKCKVSNKGLPAPIEKTISKTKGQPREPQVYTLPPS REEMTKNQVSLTCLVKGFYPSDISVEWESNGQPENNYKTTPPMLDSDGSFFLYSKLTVDKS RWQQGNVFSCSVMHEALHNHYTQKSLSLSPGK |
| 15 | Human IgG3 constant region (IGHG3; UniProt: P01860-1, v2) | ASTKGPSVFPLAPCSRSTSGGTAALGCLVKDYFPEPVTVSWNSGALTSGVHTFPAVLQSSG LYSLSSVVTVPSSSLGTQTYTCNVNHKPSNTKVDKRVELKTPLGDTTHTCPRCPEPKSCDT PPPCPRCPEPKSCDTPPPCPRCPEPKSCDTPPPCPRCPAPELLGGPSVFLFPPKPKDTLMI SRTPEVTCVVVDVSHEDPEVQFKWYVDGVEVHNAKTKPREEQYNSTFRVVSVLTVLHQDW LNGKEYKCKVSNKALPAPIEKTISKTKGQPREPQVYTLPPSREEMTKNQVSLTCLVKGFYPS DIAVEWESSGQPENNYNTTPPMLDSDGSFFLYSKLTVDKSRWQQGNIFSCSVMHEALHNR FTQKSLSLSPGK |
| 16 | CH2 IgG3 (positions 161-270 of P01860-1, v2) | APELLGGPSVFLFPPKPKDTLMISRTPEVTCVVVDVSHEDPEVQFKWYVDGVEVHNAKTKP REEQYNSTFRVVSVLTVLHQDWLNGKEYKCKVSNKALPAPIEKTISKTK |

-continued

| | | Sequences |
|---|---|---|

| SEQ ID NO: | DESCRIPTION | SEQUENCE |
|---|---|---|
| 17 | CH3 IgG3 (positions 271-376 of P01860-1, v2) | GQPREPQVYTLPPSREEMTKNQVSLTCLVKGFYPSDIAVEWESSGQPENNYNTTPPMLDS DGSFFLYSKLTVDKSRWQQGNIFSCSVMHEALHNRFTQKSLSLSPG |
| 18 | CH2-CH3 IgG3 (positions 161-376 of P01860-1, v2) | APELLGGPSVFLFPPKPKDTLMISRTPEVTCVVVDVSHEDPEVQFKWYVDGVEVHNAKTKP REEQYNSTFRVVSVLTVLHQDWLNGKEYKCKVSNKALPAPIEKTISKTKGQPREPQVYTLPP SREEMTKNQVSLTCLVKGFYPSDIAVEWESSGQPENNYNTTPPMLDSDGSFFLYSKLTVDK SRWQQGNIFSCSVMHEALHNRFTQKSLSLSPG |
| 19 | Human IgG4 constant region (IGHG4; UniProt:P01861-1, v1) | ASTKGPSVFPLAPCSRSTSESTAALGCLVKDYFPEPVTVSWNSGALTSGVHTFPAVLQSSG LYSLSSVVTVPSSSLGTKTYTCNVDHKPSNTKVDKRVESKYGPPCPSCPAPEFLGGPSVFLF PPKPKDTLMISRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQEGNVFSC SVMHEALHNHYTQKSLSLSLGK |
| 20 | CH2 IgG4 (positions 111-220 of P01861-1, v1) | APEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAK |
| 21 | CH3 IgG4 (positions 221-327 of P01861-1, v1) | GQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 22 | CH2-CH3 IgG4 (positions 111-327 of P01861-1, v1) | APEFLGGPSVFLFPPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKAKGQPREPQVYTLPP SQEEMTKNQVSLTCLVKGFYPSDIAVEWESNGQPENNYKTTPPVLDSDGSFFLYSRLTVDK SRWQEGNVFSCSVMHEALHNHYTQKSLSLSLGK |
| 23 | Human IgA1 constant region (IGHA1; UniProt:P01876-1, v2) | ASPTSPKVFPLSLCSTQPDGNVVIACLVQGFFPQEPLSVTWSESGQGVTARNFPPSQDASG DLYTTSSQLTLPATQCLAGKSVTCHVKHYTNPSVTVPCPVPSTPPTPSPSTPPTPSPSCC HPRLSLHRPALEDLLLGSEANLTCTLTGLRDASGVTFTWTPSSGKSAVQGPPERDLCGCYS VSSVLPGCAEPWNHGKTFTCTAAYPESKTPLTATLSKSGNTFRPEVHLLPPPSEELALNELV TLTCLARGFSPKDVLVRWLQGSQELPREKYLTWASRQEPSQGTTTFAVTSILRVAAEDWKK GDTFSCMVGHEALPLAFTQKTIDRLAGKPTHVNVSVVMAEVDGTCY |
| 24 | Human IgA2 constant region (IGHA2; UniProt: P01877-1, v4) | ASPTSPKVFPLSLDSTPQDGNVVVACLVQGFFPQEPLSVTWSESGQNVTARNFPPSQDAS GDLYTTSSQLTLPATQCPDGKSVTCHVKHYTNSSQDVTVPCRVPPPPPCCHPRLSLHRPAL EDLLLGSEANLTCTLTGLRDASGATFTWTPSSGKSAVQGPPERDLCGCYSVSSVLPGCAQP WNHGETFTCTAAHPELKTPLTANITKSGNTFRPEVHLLPPPSEELALNELVTLTCLARGFSPK DVLVRWLQGSQELPREKYLTWASRQEPSQGTTTYAVTSILRVAAEDWKKGETFSCMVGHE ALPLAFTQKTIDRMAGKPTHINVSVVMAEADGTCY |
| 25 | Human IgD constant region (IGHD; UniProt:P01880-1, v3) | APTKAPDVFPIISGCRHPKDNSPVVLACLITGYHPTSVTVTWYMGTQSQPQRTFPEIQRRDS YYMTSSQLSTPLQQWRQGEYKCVVQHTASKSKKEIFRWPESPKAQASSVPTAQPQAEGSL AKATTAPATTRNTGRGGEEKKKEKEKEEQEERETKTPECPSHTQPLGVYLLTPAVQDLWLR DKATFTCFVVGSDLKDAHLTWEVAGKVPTGGVEEGLLERHSNGSQSQHSRLTLPRSLWNA GTSVTCTLNHPSLPPQRLMALREPAAQAPVKLSLNLLASSDPPEAASWLLCEVSGFSPPNIL LMWLEDQREVNTSGFAPARPPPQPRSTTFWAWSVLRVPAPPSPQPATYTCVVSHEDSRTL LNASRSLEVSYVTDHGPMK |
| 26 | Human IgE constant region (IGHE; UniProt:P01854-1, v1) | ASTQSPSVFPLTRCCKNIPSNATSVTLGCLATGYFPEPVMVTWDTGSLNGTTMTLPATTLTL SGHYATISLLTVSGAWAKQMFTCRVAHTPSSTDWVDNKTFSVCSRDFTPPTVKILQSSCDG GGHFPPTIQLLCLVSGYTPGTINITWLEDGQVMDVDLSTASTTQEGELASTQSELTLSQKHW LSDRTYTCQVTYQGHTFEDSTKKCADSNPRGVSAYLSRPSPFDLFIRKSPTITCLVVDLAPS KGTVNLTWSRASGKPVNHSTRKEEKQRNGTLTVTSTLPVGTRDWIEGETYQCRVTHPHLP RALMRSTTKTSGPRAAPEVYAFATPEWPGSRDKRTLACLIQNFMPEDISVQWLHNEVQLPD ARHSTTQPRKTKGSGFFVFSRLEVTRAEWEQKDEFICRAVHEAASPSQTVQRAVSVNPGK |
| 27 | Human IgM constant region (IGHM; UniProt:P01871-1, v4) | GSASAPTLFPLVSCENSPSDTSSVAVGCLAQDFLPDSITFSWKYKNNSDISSTRGFPSVLRG GKYAATSQVLLPSKDVMQGTDEHVVCKVQHPNGNKEKNVPLPVIAELPPKVSVFVPPRDGF FGNPRKSKLICQATGFSPRQIQVSWLREGKQVGSGVTTDQVQAEAKESGPTTYKVTSTLTIK ESDWLGQSMFTCRVDHRGLTFQQNASSMCVPDQDTAIRVFAIPPSFASIFLTKSTKLTCLVT DLTTYDSVTISWTRQNGEAVKTHTNISESHPNATFSAVGEASICEDDWNSGERFTCTVTHTD LPSPLKQTISRPKGVALHRPDVYLLPPAREQLNLRESATITCLVTGFSPADVFVQWMQRGQP LSPEKYVTSAPMPEPQAPGRYFAHSILTVSEEEWNTGETYTCVVAHEALPNRVTERTVDKS TGKPTLYNVSLVMSDTAGTCY |
| 28 | CH2 IgM (positions 106-217 of P01871-1, v4) | IAELPPKVSVFVPPRDGFFGNPRKSKLICQATGFSPRQIQVSWLREGKQVGSGVTTDQVQA EAKESGPTTYKVTSTLTIKESDWLGQSMFTCRVDHRGLTFQQNASSMCVPD |
| 29 | CH3 IgM (positions 218-323 of P01871-1, v4) | QDTAIRVFAIPPSFASIFLTKSTKLTCLVTDLTTYDSVTISWTRQNGEAVKTHTNISESHPNATF SAVGEASICEDDWNSGERFTCTVTHTDLPSPLKQTISRPKG |

-continued

| SEQ ID NO: | DESCRIPTION | SEQUENCE |
|---|---|---|
| 30 | CH4 IgM (positions 324-452 of P01871-1, v4) | VALHRPDVYLLPPAREQLNLRESATITCLVTGFSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTC |
| 31 | CH2-CH3-CH4 IgM (positions 106-452 of P01871-1, v4) | IAELPPKVSVFVPPRDGFFGNPRKSKLICQATGFSPRQIQVSWLREGKQVGSGVTTDQVQAEAKESGPTTYKVTSTLTIKESDWLGQSMFTCRVDHRGLTFQQNASSMCVPDQDTAIRVFAIPPSFASIFLTKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGFSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTC |
| 32 | CH2-CH3 IgG1_256P/433S/434H/440G | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKGLSLSPGK |
| 33 | CH2-CH3 IgG1_256P/433S/434H | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKSLSLSPGK |
| 34 | CH2-CH3 IgG1_256P/433S/434H/440I | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKILSLSPGK |
| 35 | CH2-CH3 IgG1_256P/433S/434H/440R | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKRLSLSPGK |
| 36 | CH2-CH3 IgG1_256P/433S/434H/435L/440Y | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHLYTQKYLSLSPGK |
| 37 | CH2-CH3 IgG1_256P/433S/434H/436F | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHFTQKSLSLSPGK |
| 38 | CH2-CH3 IgG1_256A/433S/434H | PCPAPELLGGPSVFLFPPKPKDTLMISRAPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKSLSLSPGK |
| 39 | CH2-CH3 IgG1_256S/433S/434H/440N | PCPAPELLGGPSVFLFPPKPKDTLMISRSPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALSHHYTQKNLSLSPGK |
| 40 | CH2-CH3 IgG1_256P/433V/434H | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALVHHYTQKSLSLSPGK |
| 41 | CH2-CH3 IgG1_256P/433V/434H/440R | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALVHHYTQKRLSLSPGK |
| 42 | CH2-CH3 IgG1_256P/433V/434H/436F | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALVHHFTQKSLSLSPGK |
| 43 | CH2-CH3 IgG1_256P/433V/434H/440V | PCPAPELLGGPSVFLFPPKPKDTLMISRPPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALVHHYTQKVLSLSPGK |

-continued

| | | Sequences |
|---|---|---|

| SEQ ID NO: | DESCRIPTION | SEQUENCE |
|---|---|---|
| 44 | CH2-CH3 IgG1_256A/433V/434H/440G | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVHHYTQKGLSLSPGK |
| 45 | CH2-CH3 IgG1_433V/434H/436F | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVHHFTQKSLSLSPGK |
| 46 | CH2-CH3 IgG1_256P/434H | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHYTQKSLSLSPGK |
| 47 | CH2-CH3 IgG1_256P/434H/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHYTQKRLSLSPGK |
| 48 | CH2-CH3 IgG1_256P/434H/440I | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHYTQKILSLSPGK |
| 49 | CH2-CH3 IgG1_256P/434H/436T/440N | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHTTQKNLSLSPGK |
| 50 | CH2-CH3 IgG1_256P/434H/440T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHYTQKTLSLSPGK |
| 51 | CH2-CH3 IgG1_256P/433A/434H/440T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALAHHYTQKTLSLSPGK |
| 52 | CH2-CH3 IgG1_256P/433D/434H/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALDHHYTQKRLSLSPGK |
| 53 | CH2-CH3 IgG1_256P/433D/434H | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALDHHYTQKSLSLSPGK |
| 54 | CH2-CH3 IgG1_256P/433D/434H/436F | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALDHHFTQKSLSLSPGK |
| 55 | CH2-CH3 IgG1_256P/433P/434H | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALPHHYTQKSLSLSPGK |
| 56 | CH2-CH3 IgG1_256P/433Q/434H | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALQHHYTQKSLSLSPGK |
| 57 | CH2-CH3 IgG1_256P/433T/434H | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTHHYTQKSLSLSPGK |

-continued

| SEQ ID NO: | DESCRIPTION | SEQUENCE |
|---|---|---|
| 58 | CH2-CH3 IgG1_256A/434H | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHHHYTQKSLSLSPGK |
| 59 | CH2-CH3 IgG1_256A/433Q/434H/43 6F | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALQHHFTQKSLSLSPGK |
| 60 | CH2-CH3 IgG1_256A/433T/434H | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTHHYTQKSLSLSPGK |
| 61 | CH2-CH3 IgG1_433T/434H/436F | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTHHFTQKSLSLSPGK |
| 62 | CH2-CH3 IgG1_433T/434H | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTHHYTQKSLSLSPGK |
| 63 | CH2-CH3 IgG1_256P/433T/434R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHYTQKSLSLSPGK |
| 64 | CH2-CH3 IgG1_256P/433T/434R/43 6F | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKSLSLSPGK |
| 65 | CH2-CH3 IgG1_256P/433T/434R/43 6L | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHLTQKSLSLSPGK |
| 66 | CH2-CH3 IgG1_256P/433T/434R/44 | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHYTQKILSLSPGK |
| 67 | CH2-CH3 IgG1_256P/433T/434R/43 6F/440G | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKGLSLSPGK |
| 68 | CH2-CH3 IgG1_433T/434R/436F | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKSLSLSPGK |
| 69 | CH2-CH3 IgG1_433T/434R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHYTQKSLSLSPGK |
| 70 | CH2-CH3 IgG1_433T/434R/436W | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHWTQKSLSLSPGK |
| 71 | CH2-CH3 IgG1_256P/433T/434R/43 6F/440I (also referred to herein as "PN04-90") | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKILSLSPGK |

| SEQ ID NO: | DESCRIPTION | SEQUENCE |
|---|---|---|
| | | Sequences |
| 72 | CH2-CH3 IgG1_433T/434R/436F/440 I (also referred to herein as "V5") | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKILSLSPGK |
| 73 | CH2-CH3 IgG1_256P/434R/436F/44 0I (also referred to herein as "V1") | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHRHFTQKILSLSPGK |
| 74 | CH2-CH3 IgG1_256P/433T/436F/440 I (also referred to herein as "V2") | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTNHFTQKILSLSPGK |
| 75 | CH2-CH3 IgG1_256P/433T/434R/44 0I (also referred to herein as "V3") | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHYTQKILSLSPGK |
| 76 | CH2-CH3 IgG1_256P/433T/434R/43 6F (also referred to herein as "V4") | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALTRHFTQKSLSLSPGK |
| 77 | CH2-CH3 IgG1_256P/433V/434R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKSLSLSPGK |
| 78 | CH2-CH3 IgG1_256P/433V/434R/43 6F | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHFTQKSLSLSPGK |
| 79 | CH2-CH3 IgG1_256P/433V/434R/44 0G | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKGLSLSPGK |
| 80 | CH2-CH3 IgG1_256P/433V/434R/43 6L | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHLTQKSLSLSPGK |
| 81 | CH2-CH3 IgG1_256P/433V/434R/43 6F/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHFTQKRLSLSPGK |
| 82 | CH2-CH3 IgG1_256P/433V/434R/44 0R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKRLSLSPGK |
| 83 | CH2-CH3 IgG1_256P/433V/434R/44 0P | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKPLSLSPGK |
| 84 | CH2-CH3 IgG1_256A/433V/434R/43 6T/440N | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHTTQKNLSLSPGK |
| 85 | CH2-CH3 IgG1_256A/433V/434R/44 | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKILSLSPGK |

-continued

| | | Sequences |
|---|---|---|
| SEQ ID NO: | DESCRIPTION | SEQUENCE |
| 86 | CH2-CH3 IgG1_433V/434R/436T/440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHTTQKRLSLSPGK |
| 87 | CH2-CH3 IgG1_433V/434R/440I | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKILSLSPGK |
| 88 | CH2-CH3 IgG1_433V/434R/436T | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHTTQKSLSLSPGK |
| 89 | CH2-CH3 IgG1_433V/434R/440V | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKVLSLSPGK |
| 90 | CH2-CH3 IgG1_433V/434R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKSLSLSPGK |
| 91 | CH2-CH3 IgG1_433V/434R/435L | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRLYTQKSLSLSPGK |
| 92 | CH2-CH3 IgG1_433V/434R/440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALVRHYTQKRLSLSPGK |
| 93 | CH2-CH3 IgG1_256P/433I/434R/436F | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALIRHFTQKSLSLSPGK |
| 94 | CH2-CH3 IgG1_256P/433I/434R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALIRHYTQKSLSLSPGK |
| 95 | CH2-CH3 IgG1_256P/436F/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKRLSLSPGK |
| 96 | CH2-CH3 IgG1_256P/436F/440T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKTLSLSPGK |
| 97 | CH2-CH3 IgG1_256P/436T/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKRLSLSPGK |
| 98 | CH2-CH3 IgG1_256P | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 99 | CH2-CH3 IgG1_256P/436T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKSLSLSPGK |

-continued

| Sequences | | |
| --- | --- | --- |

| SEQ ID NO: | DESCRIPTION | SEQUENCE |
| --- | --- | --- |
| 100 | CH2-CH3 IgG1_256P/436T/440T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKTLSLSPGK |
| 101 | CH2-CH3 IgG1_256P/440D | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKDLSLSPGK |
| 102 | CH2-CH3 IgG1_256P/436S/440W | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHSTQKWLSLSPGK |
| 103 | CH2-CH3 IgG1_256P/436T/440M | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKMLSLSPGK |
| 104 | CH2-CH3 IgG1_256P/436T/440A | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKALSLSPGK |
| 105 | CH2-CH3 IgG1_256P/436T/440D | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKDLSLSPGK |
| 106 | CH2-CH3 IgG1_256P/440R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKRLSLSPGK |
| 107 | CH2-CH3 IgG1_256P/440A | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKALSLSPGK |
| 108 | CH2-CH3 IgG1_256P/436L | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHLTQKSLSLSPGK |
| 109 | CH2-CH3 IgG1_256P/436F | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKSLSLSPGK |
| 110 | CH2-CH3 IgG1_256P/440T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKTLSLSPGK |
| 111 | CH2-CH3 IgG1_256P/436F/440I | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKILSLSPGK |
| 112 | CH2-CH3 IgG1_256P/436T/440N | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKNLSLSPGK |
| 113 | CH2-CH3 IgG1_256P/440K | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKKLSLSPGK |

-continued

| Sequences | | |
|---|---|---|
| SEQ ID NO: | DESCRIPTION | SEQUENCE |
| 114 | CH2-CH3 IgG1_256P/436S | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHSTQKSLSLSPGK |
| 115 | CH2-CH3 IgG1_256P/434I | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHIHYTQKSLSLSPGK |
| 116 | CH2-CH3 IgG1_256P/4341/436F/440 M | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHIHFTQKMLSLSPGK |
| 117 | CH2-CH3 IgG1_256P/434L/436T | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHTTQKSLSLSPGK |
| 118 | CH2-CH3 IgG1_256P/434L | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHYTQKSLSLSPGK |
| 119 | CH2-CH3 IgG1_256P/434M/436T/44 0R | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHMHTTQKRLSLSPGK |
| 120 | CH2-CH3 IgG1_256P/434M | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHMHYTQKSLSLSPGK |
| 121 | CH2-CH3 IgG1_256P/436L/440N | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHLTQKNLSLSPGK |
| 122 | CH2-CH3 IgG1_256P/436T/440Y | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKYLSLSPGK |
| 123 | CH2-CH3 IgG1_256A/436F/440M | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKMLSLSPGK |
| 124 | CH2-CH3 IgG1_256A/436F | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKSLSLSPGK |
| 125 | CH2-CH3 IgG1_256A/436T | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKSLSLSPGK |
| 126 | CH2-CH3 IgG1_256A/436T/440F | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKFLSLSPGK |
| 127 | CH2-CH3 IgG1_256A | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |

-continued

| | | Sequences | |
|---|---|---|---|

| SEQ ID NO: | DESCRIPTION | SEQUENCE |
|---|---|---|
| 128 | CH2-CH3 IgG1_256A/440I | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKILSLSPGK |
| 129 | CH2-CH3 IgG1_256A/440G | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKGLSLSPGK |
| 130 | CH2-CH3 IgG1_256A/440D | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKDLSLSPGK |
| 131 | CH2-CH3 IgG1_256A/440N | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKNLSLSPGK |
| 132 | CH2-CH3 IgG1_256A/434M | PCPAPELLGGPSVFLFPPKPKDTLMISRAPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHMHYTQKSLSLSPGK |
| 133 | CH2-CH3 IgG1_440A | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKALSLSPGK |
| 134 | CH2-CH3 IgG1_440I | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKILSLSPGK |
| 135 | CH2-CH3 IgG1_440T | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKTLSLSPGK |
| 136 | CH2-CH3 IgG1_253L/440A | PCPAPELLGGPSVFLFPPKPKDTLMLSRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKALSLSPGK |
| 137 | CH2-CH3 IgG1_440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKRLSLSPGK |
| 138 | CH2-CH3 IgG1_253L | PCPAPELLGGPSVFLFPPKPKDTLMLSRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 139 | CH2-CH3 IgG1_440E | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKELSLSPGK |
| 140 | CH2-CH3 IgG1_440C | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKCLSLSPGK |
| 141 | CH2-CH3 IgG1_440Y | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKYLSLSPGK |

-continued

| | Sequences | |
|---|---|---|
| SEQ ID NO: | DESCRIPTION | SEQUENCE |
| 142 | CH2-CH3 IgG1_440D | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHYTQKDLSLSPGK |
| 143 | CH2-CH3 IgG1_436F | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKSLSLSPGK |
| 144 | CH2-CH3 IgG1_436F/440C | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKCLSLSPGK |
| 145 | CH2-CH3 IgG1_436F/440Y | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKYLSLSPGK |
| 146 | CH2-CH3 IgG1_436F/440N | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKNLSLSPGK |
| 147 | CH2-CH3 IgG1_436F/440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHFTQKRLSLSPGK |
| 148 | CH2-CH3 IgG1_436T | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHNHTTQKSLSLSPGK |
| 149 | CH2-CH3 IgG1_434L/436F | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHFTQKSLSLSPGK |
| 150 | CH2-CH3 IgG1_434L | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHYTQKSLSLSPGK |
| 151 | CH2-CH3 IgG1_434L/440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHYTQKRLSLSPGK |
| 152 | CH2-CH3 IgG1_434L/436F/440R | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHFTQKRLSLSPGK |
| 153 | CH2-CH3 IgG1_434L/435L/440G | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLLYTQKGLSLSPGK |
| 154 | CH2-CH3 IgG1_434L/440T | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHYTQKTLSLSPGK |
| 155 | CH2-CH3 IgG1_434L/440V | PCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHLHYTQKVLSLSPGK |

-continued

| Sequences | | |
|---|---|---|

| SEQ ID NO: | DESCRIPTION | SEQUENCE |
|---|---|---|
| 156 | CH2-CH3 IgG1_434M | PCPAPELLGGPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHMHYTQKSLSLSPGK |
| 157 | CH2-CH3<br>IgG1_256V/440R | PCPAPELLGGPSVFLFPPKPKDTLMISRVPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKRLSLSPGK |
| 158 | CH2-CH3<br>IgG1 256G/440M | PCPAPELLGGPSVFLFPPKPKDTLMISRGPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKMLSLSPGK |
| 159 | CH2-CH3 IgG1_256I/440N | PCPAPELLGGPSVFLFPPKPKDTLMISRIPEVTCVVVDVSHEDPEVKFNWYVDGVEVHNAKT<br>KPREEQYNSTYRVVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSDGSFFLYSKLTVD<br>KSRWQQGNVFSCSVMHEALHNHYTQKNLSLSPGK |
| 160 | CH2-CH3<br>IgG1_256K/436F | PCPAPELLGGPSVFLFPPKPKDTLMISRKPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHFTQKSLSLSPGK |
| 161 | CH2-CH3<br>IgG1_256N/436T/440N | PCPAPELLGGPSVFLFPPKPKDTLMISRNPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHTTQKNLSLSPGK |
| 162 | CH2-CH3 IgG1_256N | PCPAPELLGGPSVFLFPPKPKDTLMISRNPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 163 | CH2-CH3<br>IgG1_256N/440R | PCPAPELLGGPSVFLFPPKPKDTLMISRNPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKRLSLSPGK |
| 164 | CH2-CH3 IgG1_256S | PCPAPELLGGPSVFLFPPKPKDTLMISRSPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK |
| 165 | CH2-CH3<br>IgG1_256S/436S | PCPAPELLGGPSVFLFPPKPKDTLMISRSPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHSTQKSLSLSPGK |
| 166 | CH2-CH3<br>IgG1_256S/440A | PCPAPELLGGPSVFLFPPKPKDTLMISRSPEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALHNHYTQKALSLSPGK |
| 167 | CH2-CH3 IgG1_1-8con | PCPAPELLGGPSVFLFPPKPKDTLMX$_1$SRX$_2$PEVTCVVVDVSHEDPEVKFNWYVDGVEVHN<br>AKTKPREEQYNSTYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPVLDSDGSFFLYSK<br>LTVDKSRWQQGNVFSCSVMHEALX$_3$X$_4$X$_5$X$_6$TQKX$_7$LSLSPGK<br>wherein X$_1$ = I or L; X$_2$ = P, A, T, V, G, I, K, N or S; X$_3$ = S,<br>V, H, A, D, P, Q, T or I; X$_4$ = H, R, N, I, L or M; X$_5$ = H or L;<br>X$_6$ = Y, F, T, L, W or S; and X$_7$ = S, G, I, R, Y, N, V, T, P, D,<br>W, M, A, K, F, E or C. |
| 168 | CH2-CH3 IgG1_1con | PCPAPELLGGPSVFLFPPKPKDTLMISRX$_8$PEVTCVVVDVSHEDPEVKFNWYVDGVEVHNAK<br>TKPREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKLTV<br>DKSRWQQGNVFSCSVMHEALSHX$_9$X$_{10}$TQKX$_{11}$LSLSPGK<br>wherein X$_8$ = P, A or S; X$_9$ = H or L; X$_{10}$ = Y or F; and X$_{11}$ = G,<br>S, I, R, Y or N. |

-continued

| | | Sequences |
|---|---|---|

| SEQ ID NO: | DESCRIPTION | SEQUENCE |
|---|---|---|
| 169 | CH2-CH3 IgG1_2con | PCPAPELLGGPSVFLFPPKPKDTLMISRX$_{12}$PEVTCVVVDVSHEDPEVKFNWYVDGVEVHNA KTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKL TVDKSRWQQGNVFSCSVMHEALVHHX$_{13}$TQKX$_{14}$LSLSPGK<br>wherein X$_{12}$ = P, A or T; X$_{13}$ = Y or F; and X$_{14}$ = S, R, V or G. |
| 170 | CH2-CH3 IgG1_3con | PCPAPELLGGPSVFLFPPKPKDTLMISRX$_{15}$PEVTCVVVDVSHEDPEVKFNWYVDGVEVHNA KTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKL TVDKSRWQQGNVFSCSVMHEALX$_{16}$HHX$_{17}$TQKX$_{18}$LSLSPGK<br>wherein X$_{15}$ = P, A or T; X$_{16}$ = H, A, D, P, Q or T; X$_{17}$ = Y, T or F; and X$_{18}$ = S, R, I, N or T. |
| 171 | CH2-CH3 IgG1_4con | PCPAPELLGGPSVFLFPPKPKDTLMISRX$_{19}$PEVTCVVVDVSHEDPEVKFNWYVDGVEVHNA KTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKL TVDKSRWQQGNVFSCSVMHEALX$_{20}$X$_{21}$HX$_{22}$TQKX$_{23}$LSLSPGK<br>wherein X$_{19}$ = P or T; X$_{20}$ = T or H; X$_{21}$ = R or N; X$_{22}$ = Y, F, L or W; and X$_{23}$ = S, I or G. |
| 172 | CH2-CH3 IgG1_5con | PCPAPELLGGPSVFLFPPKPKDTLMISRX$_{24}$PEVTCVVVDVSHEDPEVKFNWYVDGVEVHNA KTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKL TVDKSRWQQGNVFSCSVMHEALX$_{25}$RX$_{26}$X$_{27}$TQKX$_{28}$LSLSPGK<br>wherein X$_{24}$ = P, A or T; X$_{25}$ = V or I; X$_{26}$ = H or L; X$_{27}$ = Y, F, L or T; and X$_{28}$ = S, G, R, P, N, I or V. |
| 173 | CH2-CH3 IgG1_6con | PCPAPELLGGPSVFLFPPKPKDTLMISRPPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHX$_{29}$HX$_{30}$TQKX$_{31}$LSLSPGK<br>wherein X$_{29}$ = N, I, L or M; X$_{30}$ = F, T, Y, S or L; and X$_{31}$ = R, T, S, D, W, M, A, K, N, Y or I. |
| 174 | CH2-CH3 IgG1_7con | PCPAPELLGGPSVFLFPPKPKDTLMISRAPEVTCVVVDVSHEDPEVKFNWYVDGVEVHNAK TKPREEQYNSTYRVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTV DKSRWQQGNVFSCSVMHEALHX$_{32}$HX$_{33}$TQKX$_{34}$LSLSPGK<br>wherein X$_{32}$ = N or M; X$_{33}$ = F, T or Y; and X$_{34}$ = M, S, F, I G, D or N. |
| 175 | CH2-CH3 IgG1_8con | PCPAPELLGGPSVFLFPPKPKDTLMX$_{35}$SRX$_{36}$PEVTCVVVDVSHEDPEVKFNWYVDGVEVH NAKTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFFLY SKLTVDKSRWQQGNVFSCSVMHEALHX$_{37}$X$_{38}$X$_{39}$TQKX$_{40}$LSLSPGK<br>wherein X$_{35}$ = I or L; X$_{36}$ = T, V, G, I, K, N or S; X$_{37}$ = N, L or M; X$_{38}$ = H or L; X$_{39}$ = Y, F, T or S; and X$_{40}$ = A, I, T, R, S, E, C, Y, D, N, G, V or M. |
| 176 | HLA-A*2401-Ad5 epitope | TYFSLNNKF |
| 177 | HLA-A*0201-Ad5 epitope | YVLFEVFDVV |
| 178 | scrambled peptide | LAVFEDYVAF |
| 179 | HLA-A2-HIV epitope | SLYNTVATL |
| 180 | CH2-CH3 IgA1 | PRLSLHRPALEDLLLGSEANLTCTLTGLRDASGVTFTWTPSSGKSAVQGPPERDLCGCYSV SSVLPGCAEPWNHGKTFTCTAAYPESKTPLTATLSPEVHLPPPSEELALNELVTLTCLARG FSPKDVLVRWLQGSQELPREKYLTWASRQEPSQGTTTFAVTSILRVAAEDWKKGDTFSCM VGHEALPLAFTQKTID |
| 181 | CH2-CH3 IgA2 | PRLSLHRPALEDLLLGSEANLTCTLTGLRDASGATFTWTPSSGKSAVQGPPERDLCGCYSV SSVLPGCAQPWNHGETFTCTAAHPELKTPLTANITPEVHLPPPSEELALNELVTLTCLARGF SPKDVLVRWLQGSQELPREKYLTWASRQEPSQGTTTYAVTSILRVAAEDWKKGETFSCMV GHEALPLAFTQKTID |
| 182 | CH2-CH3 IgD | PAVQDLWLRDKATFTCFVVGSDLKDAHLTWEVAGKVPTGGVEEGLLERHSNGSQSQHSRL TLPRSLWNAGTSVTCTLNHPSLPPQRLMALREPAAQAPVKLSLNLLASSDPPEASWLLCE VSGFSPPNILLMWLEDQREVNTSGFAPARPPPQPRSTTFWAWSVLRVPAPPSPQPATYTC VVSHEDSRTLLNASRSLE |

-continued

| | Sequences | |
|---|---|---|
| SEQ ID NO: | DESCRIPTION | SEQUENCE |
| 183 | CH2-CH3-CH4 IgE | PTVKILQSSCDGGGHFPPTIQLLCLVSGYTPGTINITWLEDGQVMDVDLSTASTTQEGELAST QSELTLSQKHWLSDRTYTCQVTYQGHTFEDSTKKCADSNPRGVSAYLSRPSPFDLFIRKSP TITCLVVDLAPSKGTVNLTWSRASGKPVNHSTRKEEKQRNGTLTVTSTLPVGTRDWIEGETY QCRVTHPHLPRALMRSTTKTSGPRAAPEVYAFATPEWPGSRDKRTLACLIQNFMPEDISVQ WLHNEVQLPDARHSTTQPRKTKGSGFFVFSRLEVTRAEWEQKDEFICRAVHEAASPSQTV QRAVS |
| 184 | TRIM21 PRYSPRY domain insert sequence | VHITLDPDTANPWLILSEDRRQVRLGDTQQSIPGNEERFDSYPMVLGAQHFHSGKHYWEVD VTGKEAWDLGVCRDSVRRKGHFLLSSKSGFWTIWLWNKQKYEAGTYPQTPLHLQVPPCQV GIFLDYEAGMVSFYNITDHGSLIYSFSECAFTGPLRPFFSPGFNDGGKNTAPLTLCPLNIGSQ GSTDY |
| 185 | hIgG1 G1m3 allotype CH2-CH3 region | SVFLFPPKPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKLTVDKSRWQQGN VFSCSVMHEALHNHYTQKSLSLSPGK |

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word 'comprise,' and variations such as 'comprises' and 'comprising,' will be understood to imply the inclusion of a stated integer or step or group of integers or steps but not the exclusion of any other integer or step or group of integers or steps.

It must be noted that, as used in the specification and the appended claims, the singular forms 'a,' 'an,' and 'the' include plural referents unless the context clearly dictates otherwise. Ranges may be expressed herein as from 'about' one particular value, and/or to 'about' another particular value. When such a range is expressed, another embodiment includes from the one particular value and/or to the other particular value. Similarly, when values are expressed as approximations, by the use of the antecedent 'about,' it will be understood that the particular value forms another embodiment.

Where a nucleic acid sequence is disclosed herein, the reverse complement thereof is also expressly contemplated.

Methods described herein may preferably performed in vitro. The term 'in vitro' is intended to encompass procedures performed with cells in culture whereas the term 'in vivo' is intended to encompass procedures with/on intact multi-cellular organisms.

BRIEF DESCRIPTION OF THE FIGURES

Embodiments and experiments illustrating the principles of the invention will now be discussed with reference to the accompanying figures.

FIGS. 2A to 2C. Histograms, graphs and image showing the results of analysis of the effect of Fc modification on ADIN. (2A) Flow cytometry histograms showing the percentage of GFP+ HeLa cells and moDCs 48 h after treatment with no virus, virus alone or virus with antibodies. For HeLa cells an MOI of 1.2 was used and an antibody concentration of 1.25 µM was used. For moDCs, an MOI of 400 was used and an antibody concentration of 55 nM was used. (2B) Graphs showing infection of HeLa cells and moDCs with adenovirus (MOI 1.2 and 400 respectively) in the presence of different concentrations of antibodies. The graphs shows the mean relative infection and the SEM of three different donors. (2C) Image of western blot detection for human Fab (hFab), TRIM21, and GAPDH in the lysate (L), unbound (U), or eluate (E) fractions of untreated or immune complex-treated moDC (from Donor C103) following coimmunoprecipitation with beads conjugated with anti-human Fab₂. The result shown is representative of three independent experiments.

FIG. 5A to 5E. Scatterplots and graphs showing the results of analysis of the effect of Fc modification on ability of moDCs to stimulate T cell expansion. (5A) Results of flow cytometry analysis of CD4+ and CD8+ cells in moDC: CD14–co-cultures at 13 days post infection of moDC with virus alone, immune complexes or controls. Cells were gated by singlets/live/CD3+CD56–. The numbers in the plots show the percentages of CD4 T cells and CD8 T cells in the total T cell population. (5B) Actual numbers of CD4 and CD8 T cells at 13 days post infection. Each point is a replicate of the experiment. Results show the mean and SEM of replicates for one donor (Donor 33). (5C) Fold change in T cell count relative to the PBS treatment for CD4 T cells and CD8 T cells. Each point represents one donor and the line represents the mean of 7 donors. (5D) Two groups of donors respond differently to the treatments. Type 1 donors are strong responders. Type 2 donors are poor responders to virus-alone treatment but they show a significant increase in CD8 T cell count when treated with modified Fc-immune complexes. Numbers in brackets indicate the mean fold change relative to treatment with PBS. Each point represents one donor. Statistical analyses were performed using ordinary one-way ANOVA. LPS and TransACT were omitted from statistical analysis. (5E) Fold change in CD4 T cell count and CD8 T cell count relative to treatment with PBS, unmodified Ab, or Fc-modified Ab, respectively. Each dot represents one donor. Friedman with Dunn correction was performed on the fold change of cell count. Statistical analyses were performed for treatments with lines. For all statistical results, ** represents p<0.0001, * represents p<0.001 ** represents p<0.01 and * represents p<0.05 and ns is not significant with p>0.05.

FIGS. 9A and 9B. Alignment of the amino acid sequences for IGHG1 (SEQ ID NO:7), IGHG2 (SEQ ID NO:11), IGHG3 (SEQ ID NO:15), IGHG4 (SEQ ID NO:19), IGHA1 (SEQ ID NO:23), IGHA2 (SEQ ID NO:24), IGHD (SEQ ID NO:25), IGHE (SEQ ID NO:26) and IGHM (SEQ ID NO:27) performed using ClustalOmega software (Soding, J. 2005, Bioinformatics 21, 951-960).

FIGS. 13A and 13B. Table summarising the sequence information for Fc molecules produced by clones identified as binding to TRIM21 PRYSPRY domain with greater affinity than wildtype IgG1 Fc. The affinity of binding to TRIM21 PRYSPRY domain as determined by Surface Plasmon Resonance analysis for certain of the Fc molecules is also shown.

FIGS. 17A to 17C. Scatterplots, histograms and bar charts relating to CD4 and CD8 T cell responses. (17A) CFSE dilution in T cells following coculture with moDC (Donor PAT35). TransACT is a positive control that stimulates T cells proliferation non-specifically. Results show CFSE dilution for T cells that are co-culture with moDC that were pretreated with virus and Fc-modified antibodies. Re-stimulation of the T cells for 16 h did not lead to further cell division. (17B) Viability of CD14−PBMCs after 16 h of Brefeldin A exposure. CD14–PBMCs from Donor PAT43 were cultured either in the presence or absence of TransACT for 2 days to generate activated or non-activated cells respectively. Thereafter, the cells were treated with or without Brefeldin A (BFA) for 16 h and were analysed using Live/Dead stain on flow cytometry. The graph shows the mean number of live cells from triplicate wells. Error bars show the SEM. The numbers of live cells in BFA-treatments are also expressed as a percentage of the no-BFA treatments. (17C) Viability of moDCs one day after MG132 treatment. The cells were incubated with or without MG132 for 1 h. After incubation, the cells were washed and resuspended in fresh medium without MG132 and cultured for one day before analysis using Live/Dead stain on flow cytometry. The graph shows the mean number of live cells from triplicate wells. Error bars show the SEM. The number of live cells in MG132-treatment is also expressed as a percentage of the no-MG132 treatment.

EXAMPLES

Figures 1A, 1B:
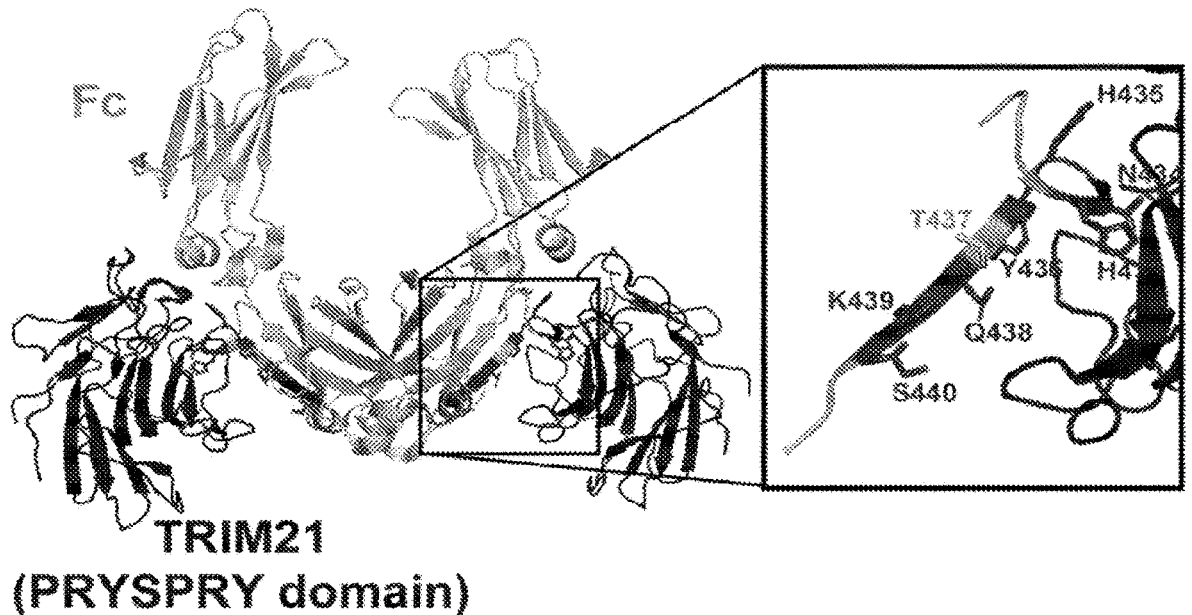
FIG. 1A to 1I. Images, schematics, tables and schematics relating to analysis of the effect of Fc modifications on Fc affinity for TRIM21. (1A) Crystal structure of TRIM21 PRYSPRY domain in complex with Fc region; the position of the amino acids selected for randomization is indicated. (1 B) shows the amino acid sequence of the CH2-CH3 region (SEQ ID NO: 185); amino acids selected for randomization are underlined. (1C) Frequencies of the different clones, Clone #1 (SEQ ID NO: 187) and Clone #2 (SEQ ID NO: 186) identified after Round 2 and Round 3 of biopanning and Wild type (SEQ ID NO: 188). (1D) Schematic representation of the two sets of antibodies: anti-DEC205 human IgG1 and anti-Ad5 chimeric IgG1, with modification (squares) or without modification to the Fc region. Figures (1 E-11) show the binding and dissociation of TRIM21 to Fc-modified human IgG1 (1E), Fc-modified chimeric IgG1 (1F), Fc-unmodified human IgG1 (1G), Fc-unmodified chimeric IgG1 (1H), and reverse mutant (11) which is the Fc-modified chimeric IgG1 but with the spurious mutation T256P corrected back to threonine. Raw data and curve fittings using Langmuir 1:1 stoichiometry are shown.

In the following Examples, the inventors describe the engineering of Immunoglobulin Fc to increase its affinity for TRIM21, and analysis of the effect of this improved affinity for TRIM21-mediated functions.

The entire contents of Ng et al., J Immunol. (2019) 202(8):2307-2319 is specifically incorporated by reference in its entirety.

Example 1: Materials and Methods 1.1 PBMCs

Peripheral blood mononuclear cells (PBMCs) were isolated from apheresis blood of healthy donors using Ficoll-Paque Premium (GE Healthcare).

1.2 MoDCs

Monocytes were isolated from PBMCs using CD14 Microbeads (Miltenyi). Monocytes were differentiated into moDC by culture in the presence of 100 ng/ml GM-CSF (premium grade, Miltenyi) and 100 ng/ml IL-4 (premium grade, Miltenyi) in RPMI-1640 with 25 mM HEPES and L-Glutamine (Hyclone) further supplemented with 10% FBS (South American origin, Gibco) and antibiotics comprising 100 U/ml Penicillin and 100ug/ml Streptomycin (Gibco). On the fourth day of the culture, one third of the culture medium was replaced with fresh culture medium with the same supplements. After 7 days, moDC (floating cells) from the cell culture were harvested for use in experiments.

1.3 Cell Lines

HEK293T cells and HeLa cells were maintained in 1 g/L glucose DMEM (Hyclone) supplemented with 10% FBS (South American origin, Gibco) and antibiotics (100 U/ml Penicillin, 100ug/ml Streptomycin, Gibco).

1.4 Viruses

Purified E1- and E3-deleted replication-deficient adenovirus type 5 with the eGFP reporter gene (VQAdCMV eGFP, ViraQuest) was used for the antibody-dependent intracellular neutralization (ADIN) assays. The same strain of adenovirus with no eGFP gene (VQAd EMPTY, ViraQuest) was used for all other assays. To titer the virus, HEK293T cells were seeded onto 0.01% poly-L-lysine (Sigma) coated 24-well plates at a cell density of $2.5 \times 10^5$ cells/ml. Once the cells had adhered, 10-fold serial dilutions of virus were added to the cell culture and incubated for 2 days. Viral titer was calculated from the number of infected cells as detected by the Adeno-X Rapid Titer Kit (Clontech).

1.5 Human TRIM21 (PRYSPRY Domain) Protein.

The human recombinant TRIM21 PRYSPRY domain sequence shown in SEQ ID NO:184 was cloned into the 3'-end of a His-tag in the pQE-2 bacteria expression vector, and expressed in *E. coli* BL21 (DE3). A 20 ml overnight culture was inoculated into 380 ml fresh growth medium and grown at 37° C. until the $OD_{600}$ reached 1.0. Protein expression was induced with 1 mM IPTG for 4.5 hours at room temperature. The expressed protein was then purified from cell lysates using Ni-NTA resin (Qiagen), followed by gel filtration in PBS using a Superdex 75 chromatography column (GE Healthcare).

1.6 Antibodies

The variable domains of the chimeric anti-adenovirus antibody were cloned from hybridoma 9C12 (TC31-9C12.C9)(Varghese et al., 2004b), obtained from the Developmental Studies Hybridoma bank (NICHD/University of Iowa). The variable domains of the human anti-DEC205 antibody were synthesized based on the published sequence of clone 3G9-2D2 (U.S. Pat. No. 8,236,318 B2). The variable domains were cloned into the N-terminal of the constant domains of the human IgG1 in the pTT5 vector. For the Fc-modified antibodies, the 5 amino acid modifications in the constant regions were modified using the Quikchange Lightning Multi Site-Directed Mutagenesis Kit (Agilent Technologies). Antibodies were expressed in HEK293-6E cells or in CHO cells, and purified from their supernatants using Protein G beads. The purified antibodies were buffer-exchanged into 20 mM His, 150 mM NaCl, pH 6.0, then filtered and assayed for endotoxin content using the Limulus Amoebocyte Lysate-QCL1000 (Lonza). Only antibody preparations with an endotoxin content of <1 EU/μg were used for cell-based assays.

1.7 Peptides

Peptides were synthesized according to the following sequences: TYFSLNNKF (SEQ ID NO:176; HLA-A*2401-Ad5 epitope), YVLFEVFDVV (SEQ ID NO:177; HLA-A*0201-Ad5 epitope), LAVFEDYVAF (SEQ ID NO:178; scrambled peptide) and SLYNTVATL (SEQ ID NO:179; HLA-A2-HIV epitope).

1.8 Phage Display Library Construction

The PN04-44AD phagemid has the human IgG1 Fc gene encoding amino acid positions 239 to 447 (EU numbering) fused to an amber stop (TAG) followed by a truncated gIII. PN04-44AD was used as the template for making the phage display library using a Kunkel reaction-based site-directed mutagenesis strategy previously described (Tonikian et al., 2007): briefly, a single-stranded template was used for annealing of oligonucleotides carrying the library sequences; double-stranded DNA was then produced and electroporated into *E. coli* TG-1 cells that were pre-infected with helper phage. The electroporated TG-1 cells were enumerated by plating dilutions of an aliquot onto 2YT plates with ampicillin and kanamycin. The remaining electroporated TG-1 were cultured at 37° C., overnight, in 2YT medium with ampicillin and kanamycin for the production of bacteriophages. The next day, bacteriophages were harvested from the cell culture supernatant and stored in PBS with 20% glycerol until use.

1.9 Biopanning of the Phage Display Library

Recombinant human TRIM21 PRYSPRY domain was biotinylated and then used as bait for biopanning. In the first round of biopanning, $2 \times 10^{12}$ bacteriophages were incubated with 5 nM of bait protein for 1 hour to allow for interaction. The bait was then captured using DynaBeads M-280 Streptavidin (Invitrogen). The beads were then washed five times with casein, incubated for 30 min with 1 μM of soluble Fc and eluted using trypsin. In the second round of biopanning, the eluted bacteriophages were amplified and incubated first with empty streptavidin beads, and followed by incubation with 0.5 nM of bait protein. The bait was then captured using streptavidin beads. The beads were then washed ten times with casein and incubated with 1 μM soluble Fc for two rounds of 30 mins, before elution using trypsin. In the third round of biopanning, the eluted phages were amplified, incubated with empty streptavidin beads, and then incubated with 0.05 nM of bait protein. The bait was then captured using streptavidin beads. The beads were washed ten times, then incubated for 5 hours with 1 μM of soluble Fc, before elution using trypsin. 50 clones from each of rounds two and three were sequenced.

1.10 Surface Plasmon Resonance (SPR) Analysis

The affinity constants were measured using ProteON XPR36 (Bio-Rad). Antibodies were immobilized onto a GLC sensor chip via amine coupling, and PBS with 0.05% Tween-20 was used as the running buffer. Curves were fitted with the ProteON Manager software using five concentrations of TRIM21 and based on a Langmuir 1:1 model.

1.11 Antibody-Dependent Intracellular Neutralization (ADIN) Assays

For ADIN assays, $1.25 \times 10^5$ HeLa cells were seeded into 24-well plates and $1 \times 10^5$ moDC were seeded into 96-well plates for infection with immune complexes, virus alone, antibodies alone or medium alone for 48 h. As HeLa cells are highly permissive to adenovirus infection (Fechner et al., 2000), an MOI of 1.2 was used, while for moDCs, an MOI of 400 was used. Infected cells were detected by analysis of expression of eGFP by flow cytometry. For HeLa cells, immune complexes were pre-formed by incubation of virus with antibodies at concentrations ranging from 0.3 μM to 35 nM for 1 h at room temperature prior to use. Thereafter, the incubation mixture was diluted 55-fold into the HeLa cell culture to give a final concentration ranging from 0.006 μM to 627 μM. For moDCs, immune complexes were pre-formed by incubation of virus with antibodies at concentrations ranging from 0.17 nM to 690 nM for 1 h at room temperature prior to use. Thereafter, the incubation mixture was diluted by 12.5-fold into the moDC culture to give a final concentration ranging from 0.01 nM to 55 nM.

Coimmunoprecipitation: Ad5 was preincubated with Abs for 1 h at room temperature in PBS to form immune complexes. Immature moDC were then treated with the immune complexes in RPMI 1640 supplemented with 10% FBS at an MOI of 200 and incubated at 37° C. with 5% $CO_2$ for 4 h. Cells were lysed on ice with RIPA buffer containing 1% Nonidet P-40 substitute (Sigma-Aldrich), 50 mM Tris-Cl (pH 7.6), 150 mM NaCl, 1 mM EDTA, 1% Phosphatase Inhibitor Cocktail 3 (Sigma-Aldrich), and 10% glycerol, supplemented with Protease Inhibitor Mini Tablets (Thermo Fisher Scientific), 1 mM PMSF (Roche), 10 mM MG132 (Sigma-Aldrich), and 20 mM N-ethylmaleimide (Sigma-Aldrich). Goat Fab anti-human Fab (Jackson ImmunoResearch) was coupled onto M-270 Epoxy Dynabeads (Thermo Fisher Scientific), following the manufacturer's instructions, in a Dynabeads Antibody Coupling Kit. Immunoprecipitations were performed by incubating cell lysates from 1.5 million cells with 1 mg of Dynabeads (prebound with anti-human Fab) overnight at 4° C. Beads were then washed with RIPA buffer, and immunoprecipitates were eluted with 0.1 M Glycine buffer (pH 2.7).

Western blot: Cell extracts and immunoprecipitates were resolved by SDS-PAGE and transferred to a polyvinylidene difluoride membrane using Trans-Blot SD semi-dry transfer cell (Bio-Rad Laboratories), according to the manufacturer's protocols. After incubation with 5% nonfat milk in TBST (25 mM Tris [pH 7.2], 140 mM NaCl, and 3 mM KCl, 0.2% Tween 20) for 1 h, the membrane was incubated with Abs against IgG Fab (1:5000; Jackson ImmunoResearch), Ro52/TRIM21 (1:500, D-12; Santa Cruz Biotechnology), and GAPDH (1:10000, VPA00187; Bio-Rad Laboratories) overnight at 4° C. Membranes were washed with TBST four times, then incubated with HRP-conjugated anti-mouse (1:10000; Dako) or anti-rabbit (1:20000; Thermo Fisher Scientific) Abs for 1 h. Blots were washed with TBST four times and developed with ECL Plus Western Blotting Substrate (Thermo Fisher Scientific) according to the manufacturer's protocols. Blot images were acquired using the ChemiDoc imaging system (Bio-Rad Laboratories).

1.12 MoDC maturation Assay $1 \times 10^5$ moDCs were incubated in 200 μl of cell culture medium in 96-well plates with either PBS, $4 \times 10^7$ Ad5 virus, 1.6 μg antibodies or immune complexes made from $4 \times 10^7$ Ad5 virus and 1.6 μg antibodies that were pre-incubated for 1 h at room temperature. All treatments were administered to the cell culture in a volume of between 8-80 μl, and medium was added accordingly to make the final cell culture volume up to 200 μl. For a positive control, 1 μg/ml LPS was used. The cells were analyzed by FACS after 24 h.

1.13 MoDC: Autologous CD14-PBMC Co-Culture Assay

MoDCs were prepared and treated in the same way as in the moDC maturation for 4 h.

Treatment of moDC with MG132 is done by incubating moDC in a six-well plate with 10 μM of MG132 (Sigma-Aldrich) in medium for 1 h at 37° C., 5% $CO_2$. After 1 h, the cells were centrifuged to remove MG132. MG132-treated or -untreated moDC were resuspended in fresh medium and treated in the same way as in the moDC maturation for 4 h.

After 4 h, the cells were co-cultured in fresh medium with $5 \times 10^5$ autologous CD14-PBMCs that had been labeled with 10 μM CFSE using the Vybrant™ CFDA SE Cell Tracer kit (Life technologies): briefly, 100 million cells were labeled in 1 ml of 10 μM CFSE in FBS-supplemented medium for 5 mins at 20° C. Excess dye was then removed by centrifugation at 10,000×g for 1 min and the cells were washed three times with fresh medium. The co-culture was maintained for up to 13 days with replacement of one third of old medium with fresh medium on days 4 and 7. For positive controls, either 1 μg/ml LPS was added to the moDCs, or 2 μl T Cell TransACT™ (Miltenyi) was used.

1.14 Peptide Re-Stimulation Assays

To prepare moDCs for pulsing of peptides, autologous moDCs were generated using the same method as above from frozen monocyte stock. After 6 days, moDCs were pulsed for a day with either 10 μg/ml of sterile-filtered peptides, or 200 μg peptide libraries (Miltenyi, PepTivator AdV5 Hexon or PepTivator NY-ESO-1) in medium containing 100 ng/ml GM-CSF (Miltenyi), 100 ng/ml IL-4 (Miltenyi) and 50 ng/ml TNF-α (Miltenyi). Thereafter, $1 \times 10^5$ peptide-pulsed moDCs were used to re-stimulate autologous 11 day old moDC:CD14-PBMC co-culture, at a ratio of 1:5 peptide-pulsed moDCs to 11 day old co-culture. This was done by harvesting the 11-d coculture, resuspending the cells to a concentration of $5 \times 10^6$ cells/ml in fresh medium (with or without brefeldin A), and adding 100 μl of cells (i.e., $5 \times 10^5$ cells) to the peptide-pulsed moDC in the 96-well, round-bottom plate. For donor LCYO2, cells were re-stimulated for 16 hours and the supernatant of the re-stimulated cells was harvested for analysis by ELISA. The cells were then treated with fresh medium containing 1 μg/ml Brefeldin A. After 5 h, cells were harvested and labelled for analysis by flow cytometry. For donors LCY10, PAT35 and LCY25 cells were re-stimulated for 16 hours in the presence of 1.5 µg/ml Brefeldin A and then harvested for analysis by flow cytometry. For the 11 day old moDC:CD14–PBMC co-cultures, replacement of one third old medium with fresh medium was performed at days 4 and 7 for LCY02, PAT35 and LCY25; and for LCY10, feeding was performed on day 4 followed by dilution of the co-culture into an equal volume of fresh medium containing 10 ng/mL IL-7 and IL-15 on days 7 and day 10.

1.15 Flow Cytometry

In all assays, LIVE/DEAD™ Fixable Aqua Dead Cell Stain Kit (Invitrogen) was used to exclude dead cells. In the moDC maturation assay, cells were incubated with anti-FcR-blocking antibody (eBioscience, San Diego, CA, USA) and then labelled using combinations of the following antibodies: Pacific-Blue-anti-CD14 (M5E2), APC-anti-CD11c (S-HCL-3), Alexa Fluor700-anti-CD80 (L307.4), FITC-anti-CD83 (HB15e), PE-Cy7-anti-CD86 (FUN-1), APC-Cy7-anti-HLA-DR (L243), BV650-anti-CCR7 (G043H7) and PE-anti-CD206 (19.2). In the co-culture assay, cells were incubated with human FcR blocking reagent (Miltenyi) and then labelled using the following antibodies: Alexa Fluor647-anti-CD3 (SK1), PE-Cy7-anti-CD4 (OKT4), Pacific Blue-anti-CD8 (SK7), and PE-anti-CD56 (AF12-7H3). In the haplotyping of donors, the dyes used were Alexa Fluor 647-anti-HLA-A24 (17A10) and PE-anti-HLA-A2 (BB7.2). For haplotype controls, a HLA-A24+ cell line HT29 and HLA-A2+ cell line MDA-MB-231 were also labelled and included in the analysis. In the re-stimulation assays, the dyes used were Alexa Fluor647-anti-CD3 (SK7), PE-Cy7-anti-IFN-γ (4S.B3), Pacific Blue-anti-CD8 (SK1), and PE-anti-CD56 (AF12-7H3). After the surface markers are labelled, cells were fixed and permeabilized using BD Cytofix/Cytoperm solution followed by PE-Cy7-anti-IFN-γ. For absolute cell counts 10 µl of Count-Bright™ Absolute Counting Beads were added to cells. Samples were acquired using BD FACSDiva software on the LSRFortessa cell analyzer and FACSCanto II (BD Biosciences). Data were analyzed using FlowJo software (Tree Star, Ash-land, OR, USA).

1.16 Cytokine and Chemokine Analysis

Supernatants from the moDC maturation assays were analyzed by a multiplex analysis using human cytokine/chemokine bead panel 1 and 2, which measure a total of 64 targets (Milliplex MAP kits, Millipore) on a Flexmap 3D system (Luminex Corp, Texas, USA). Supernatants from the co-culture assays were analyzed by ELISA for the level of IFN-γ using Human IFN-γ ELISA MAX™ Standard (Biolegend).

1.17 Statistical Analysis

Statistical analyses were performed using GraphPad Prism 7.01 software using repeated measure ANOVA with Dunnett's multiple comparison testing, or Friedman with Dunn's multiple comparison testing. The adjusted p-values are indicated in the Figures by asterisks.

Example 2: Results 2.1 a Modified Fc Exhibits Increased Affinity for TRIM21

The inventors first identified the amino acids in Fc region that are in contact with TRIM21, based on the crystal structure of the human IgG Fc-TRIM21 complex (FIG. 1A) (James et al., 2007). Both the CH2 and CH3 regions of the Fc interact with TRIM21. Using a cut-off distance of 5 Å, 21 potentially-interacting amino acids were identified:

| Amino acid (EU numbering) | CH Domain | Secondary Structure |
|---|---|---|
| 252(MET) | CH2 | Loop |
| 253(ILE) | | Loop |
| 254(SER) | | Loop |
| 309(LEU) | | Helix |
| 310(HIS) | | Helix |
| 311(GLN) | | Helix |
| 314(LEU) | | Helix |
| 315(ASN) | | Helix |
| 345(GLU) | CH3 | Loop |
| 428(MET) | | Sheet |
| 430(GLU) | | Loop |
| 431(ALA) | | Loop |
| 432(LEU) | | Loop |
| 433(HIS) | | Loop |
| 434(ASN) | | Loop |
| 435(HIS) | | Loop |
| 436(TYR) | | Sheet |
| 437(THR) | | Sheet |
| 438(GLN) | | Sheet |
| 439(LYS) | | Sheet |
| 440(SER) | | Sheet |

The majority of the amino acids interacting with TRIM21 in the CH2 domain were in the α-helix, and the inventors reasoned that this region could be destabilised by modification. The inventors therefore instead focused on modification of the amino acids in the CH3 domain, and selected 7 amino acids whose side groups were proximal to and facing towards TRIM21 for modification (see FIG. 1B).

Figures 1C, 1D:
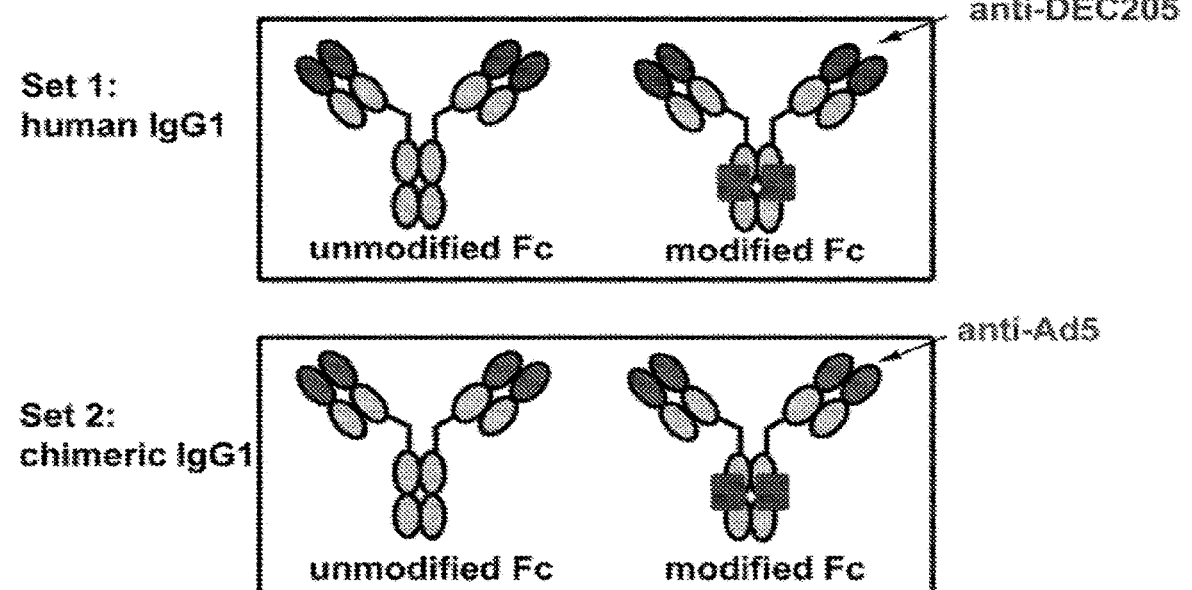

A phage library of 2 billion bacteriophages displaying the human IgG1 Fc was generated with randomly-substituted amino acids in the selected 7 positions. Recombinant human TRIM21 PRYSPRY domain was used as bait for biopanning. After three sequential rounds of biopanning, approximately 50 clones from the output of Rounds 2 and 3 were sequenced. One sequence was found in ~10% of the clones analysed in Round 2; and in 94% of the clones analysed in Round 3 (FIG. 1C, Clone #1). This variant (designated PN04-90) possessed five amino acid modifications relative to wildtype human IgG1: H433T, N434R, Y436F, S4401 and T256P, the last of which is a mutation in the CH2 domain. The amino acid sequence of the CH2-CH3 region for PN04-90 is shown in SEQ ID NO:71. While the crystal structure of IgG1 Fc with TRIM21 places T256 out of direct contact with TRIM21, it is in close proximity to three of the contact points (M252, I253 and S254) (James et al., 2007), and is therefore likely to improve Fc binding by bringing the contact points closer to TRIM21.

The inventors next investigated whether antibodies bearing the modified Fc bound to TRIM21 with higher affinity than antibodies comprising unmodified Fc. Two sets of antibodies were constructed: the first set comprises the variable domains of human antibody, 3G9-2D2 (Cheong et al., 2010) which recognizes human DEC-205, joined to human IgG1 constant regions that have the modified or unmodified Fc; the second set comprises variable domains of the mouse antibody, 9C12 (Varghese et al., 2004a) which recognizes the Adenovirus Type 5 (Ad5) hexon, joined to human IgG1 constant regions that have the modified or unmodified Fc. The first set was designated 'human IgG1', and the second set was designated 'chimeric IgG1' (FIG. 1D). This approach enabled the inventors to investigate whether the modified Fc could be applied to antibodies with different variable domains, and from different species.

Figure 1E:
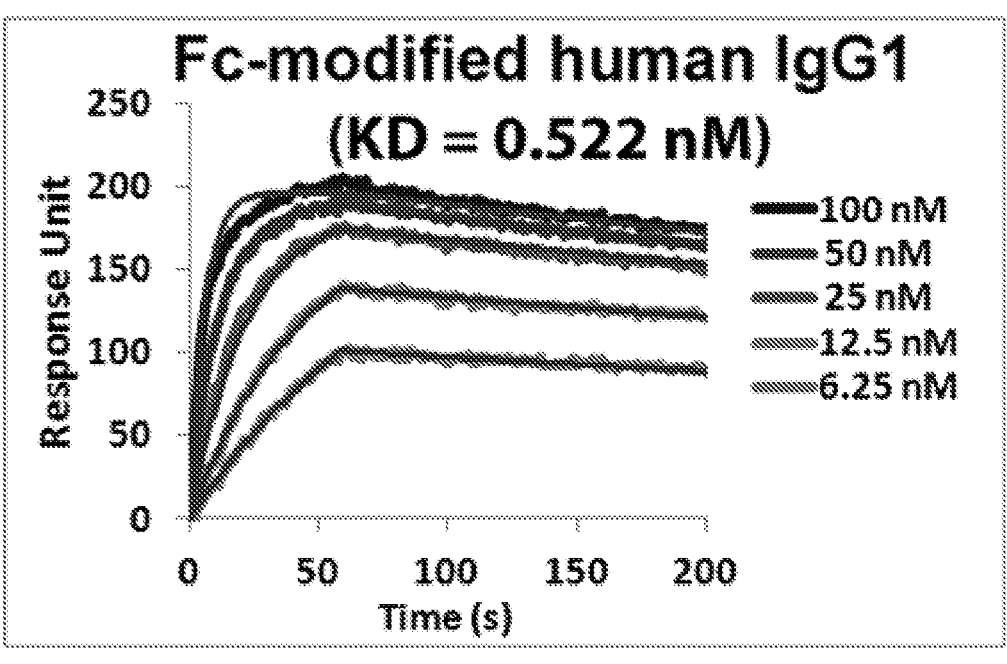
Figure 1F:
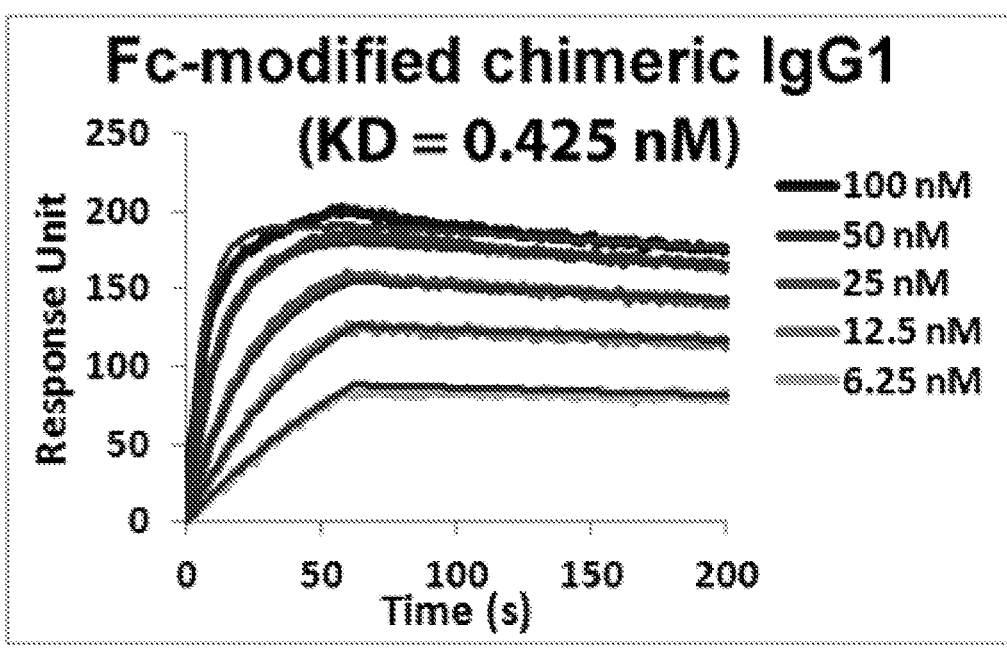
Figure 1G:
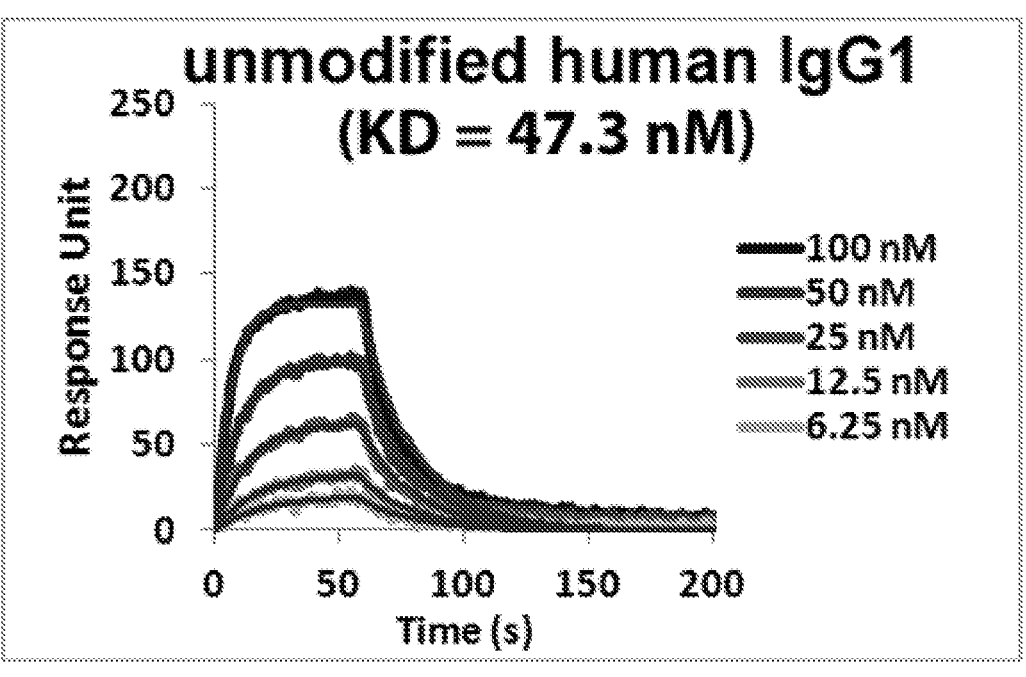
Figure 1H:
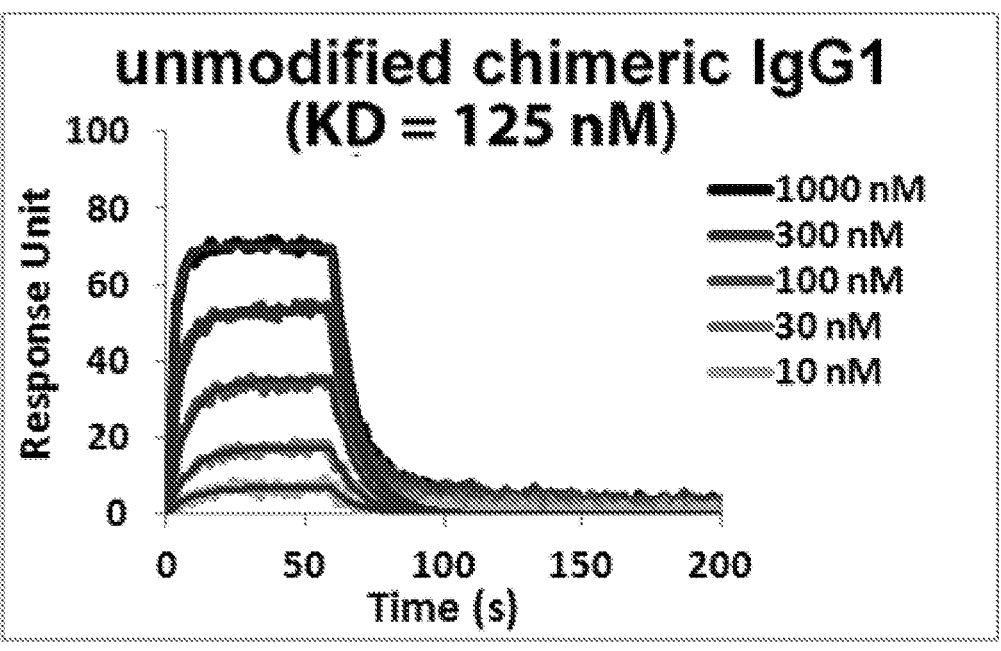
Figure 1I:
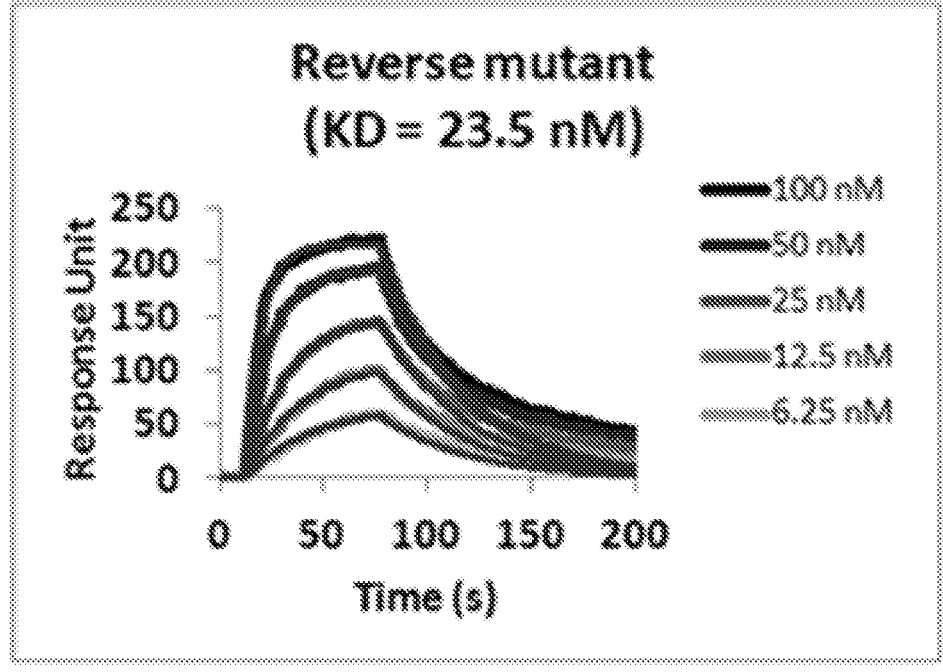

The affinity of the unmodified and Fc-modified antibodies for TRIM21 was measured by surface plasmon resonance analysis. Modifying the Fc region of human IgG1 increased its affinity for the PRYSPRY domain of TRIM21 by at least 100 fold: the affinity constants ($K_D$) were 0.522 nM for the Fc-modified human IgG1 (FIG. 1E) and 0.425 nM for the Fc-modified chimeric IgG1 (FIG. 1F); while unmodified human (FIG. 1G) and chimeric (FIG. 1H) IgG1 bound with lower affinity (47.3 nM and 125 nM, respectively). The T256P substitution in the CH2 domain was found to contribute towards improved affinity of the modified Fc antibodies, because a variant Fc comprising substitutions H433T, N434R, Y436F and S4401 but having Thr at position 256 (designated V5) was found to have reduced affinity for TRIM21 as compared to the PN04-90 variant ($K_D$=23.5 nM see FIG. 11). Therefore all five amino acid substitutions were incorporated into the chimeric, Ad5-specific Fc-modified antibodies that were used in subsequent functional characterization studies.

To assess the involvement of each single mutation in the affinity increase for TRIM21, 5 mutants with reversion to wild-type amino-acid in 1 single position were derived from Fc-modified chimeric IgG1 and their affinity for TRIM21 domain PRYSPRY was measured (Table 1). Reversion of mutations in positions 256, 433 and 434 resulted in lower affinity for TRIM21, suggesting that modifications T256P, H433T and N434R are important for improved binding.

TABLE 1

Affinity of Fc-modified and unmodified chimeric IgG1 for TRIM21.

| | Amino-acid position in IgG1 (EU numbering system) | | | | | Affinity $K_D$ |
|---|---|---|---|---|---|---|
| | 256 | 433 | 434 | 436 | 440 | (M) |
| Wildtype chimeric IgG1 | T | H | N | Y | S | 125 |
| PN04-90 | P | T | R | F | I | $4.25 \times 10^{-1}$ |
| V1 | P | H | R | F | I | $1.08 \times 10^{-8}$ |
| V2 | P | T | N | F | I | $1.62 \times 10^{-6}$ |
| V3 | P | T | R | Y | I | $2.11 \times 10^{-10}$ |
| V4 | P | T | R | F | S | $2.76 \times 10^{-10}$ |
| V5 | T | T | R | F | I | $2.35 \times 10^{-8}$ |

2.2 Increasing Fc Affinity for TRIM21 Preserves ADIN

Antibody-dependent intracellular neutralization (ADIN) was first demonstrated in HeLa cells infected with adenoviruses (Mallery et al., 2010). The hexon protein of adenovirus is recognized by the monoclonal antibody 9C12 (Varghese et al., 2004a), which was used in construction of the chimeric antibodies. 9C12 does not block viral entry, but mediates post-entry neutralization (Varghese et al., 2004b), in a TRIM21-dependent fashion (Mallery et al., 2010). While reducing the affinity of antibody for TRIM21 does not affect ADIN of adenovirus in HeLa cells (Foss et al., 2016), the effects of increasing affinity for TRIM21 have not been investigated. The inventors investigated how increasing Fc affinity for TRIM21 influences ADIN in both HeLa cells (non-immune cells) and monocyte-derived DCs (immune cells).

Different concentrations of Fc-modified antibodies comprising PN04-90 Fc and unmodified antibodies comprising wildtype human IgG1 Fc were incubated with replication-defective Ad5 which carries the eGFP (enhanced green fluorescent protein) reporter gene to form immune complexes, which were then added to HeLa cells or monocyte-derived DCs (moDCs). The frequency of infection was monitored after 48 h via analysis of eGFP expression (FIG. 2A). In HeLa cells, antibodies bearing PN04-90 Fc or unmodified Fc regions mediated ADIN of Ad5 infection equally well (FIG. 2B) with an IC50 of 0.9 μM for a viral MOI of 1.2; similarly in moDCs, the IC50 of unmodified Fc and the PN04-90 Fc were very similar (3.0 nM versus 4.5 nM; see FIG. 2B) at a viral MOI of 400. Increasing the affinity of Fc for TRIM21 was found not to disrupt ADIN in both non-immune and immune cells.

To verify that the Fc-modified Abs interact with TRIM21 in moDC, the treated moDC were lysed and beads conjugated with Fab anti-human Fab were used to immunoprecipitate the Fc-modified Abs. Western blot analysis showed that TRIM21 coimmunoprecipitated with modified Ab, suggesting that it binds to the internalized Fc-modified immune complexes (FIG. 2C).

Figure 15A:
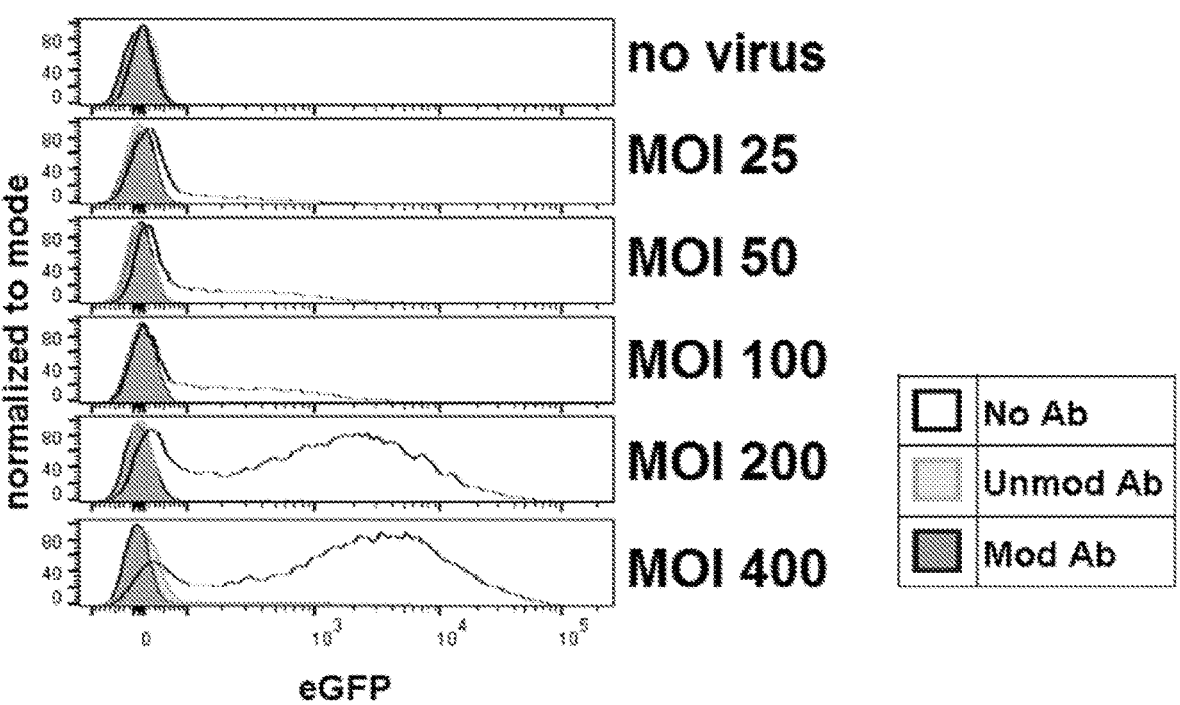
FIGS. 15A and 15B. Histograms and graph showing the results of analysis of antibody-dependent intracellular neutralization mediated by unmodified and Fc-modified antibody, as determined by flow cytometry. (15A) Expression of eGFP by moDCs in the absence of replication-defective Ad5 carrying eGFP reporter, following infection with the virus at different MOI (multiplicity of infection), or following treatment with immune complexes comprising 9C12-wildtpye hIgG1 Fc+virus (Unmod Ab) or 9C12-PN04-90 Fc+virus (Mod A)b at different MOI, for Donor C03. (15B) Percentage of eGFP-positive moDCs 48 h after infection with adenovirus alone, or with the immune complexes at different MOI. The MOI is based on the number of infectious units when the virus is added to HEK293T cells. Graph shows the mean percentage and SD for three independent donors (Donors C01, C02 and C03).
Figure 15B:
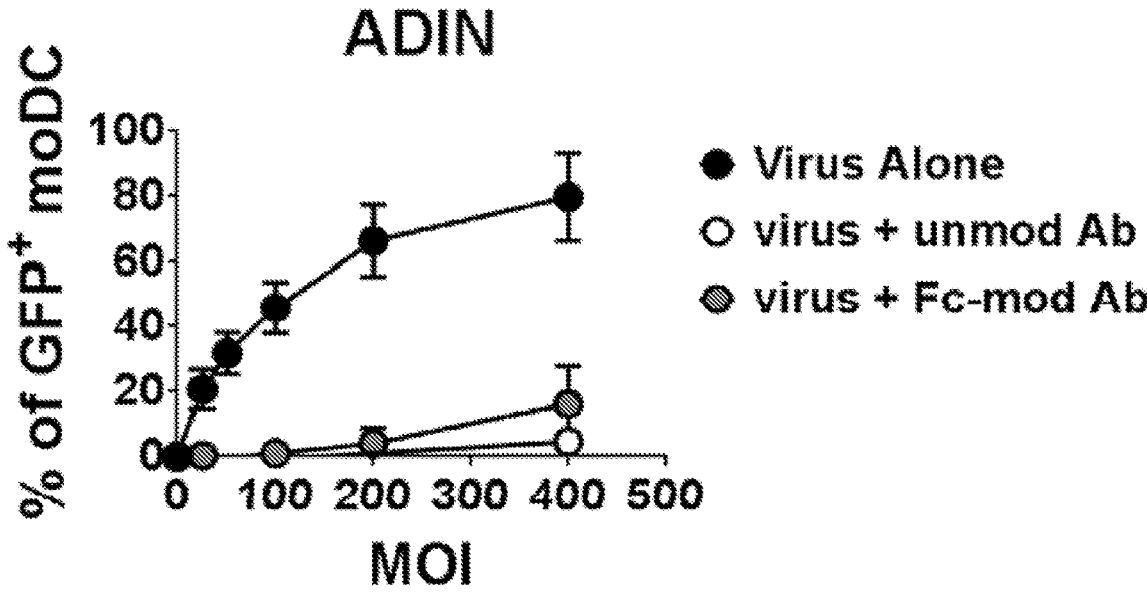

FIGS. 15A and 15B show the results obtained with moDCs when a range of different MOIs were used. An MOI of 100 gave ~46% infected moDC, and an MOI of 400 gave ~80% infected moDC (FIG. 15B).

ADIN mediated by the unmodified Fc and modified Fc remained the same when tested at lower viral MOI (i.e. less than 400).

2.3 Increasing Fc Affinity for TRIM21 Promotes moDC Maturation

Reducing the affinity of antibodies for TRIM21 has previously been shown to impair pro-inflammatory signalling in HEK293T cells (Foss et al., 2016). For moDCs, stimulation of a T cell response requires the simultaneous presentation of cognate antigen, and the provision of activating signals in the form of pro-inflammatory cytokines and co-stimulatory molecules on the DC surface. This process is often subverted by viruses, including adenoviruses (Newton et al., 2008). The inventors therefore investigated whether increasing Fc affinity for TRIM21 promoted moDC expression of co-stimulatory molecules and pro-inflammatory cytokines.

Figure 3A:
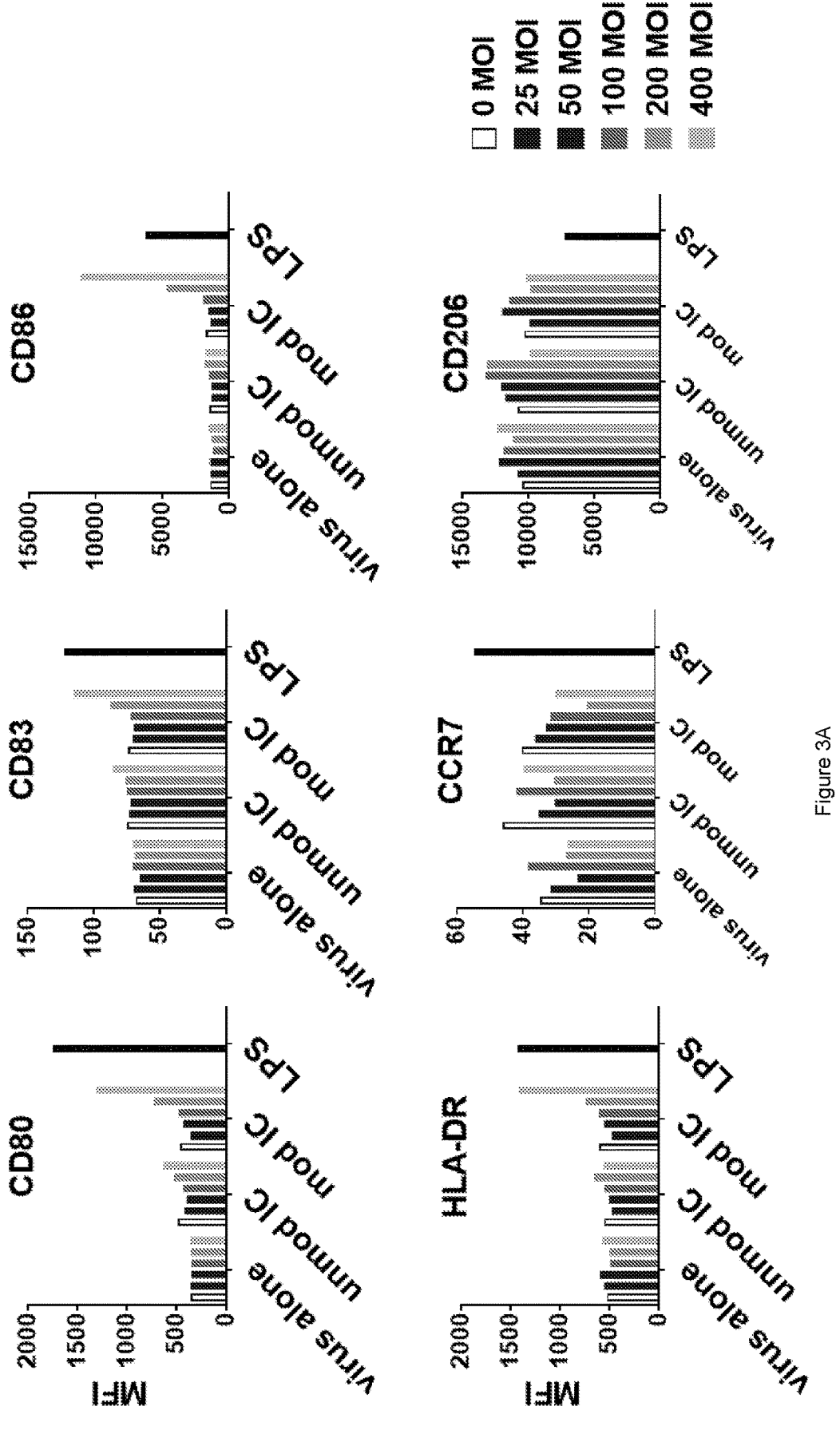
FIG. 3A to 3D. Bar charts and histograms showing the results of analysis of the effect of Fc modification on moDC maturation. moDCs were treated with Ad5 alone (virus alone), Fc-unmodified immune complexes (unmod IC) or Fc-modified immune complexes (mod IC) at an MOI of 0, 25, 50, 100, 200 and 400 and analysed 24 h after treatment for expression of maturation markers. Immune complexes were formed by pre-incubating the virus and antibody at $5 \times 10^8$ virus and 20 µg antibody per ml. Thereafter the amount of immune complex was added based on the MOI of the virus. LPS (1ug/ml) was used as a positive control. (3A) Bar charts showing the Median Fluorescent Intensities (MFIs) of the different maturation markers for one representative donor (Donor 22). (3B) Histograms showing the Median Fluorescent Intensity MFIs of the different maturation markers when moDCs were treated at the highest dose of 400 MOI virus alone, 55 nM antibody alone or immune complexes of the corresponding dosages for one donor (Donor 21) representative of five donors that responded to the Fc-modified immune complex, and Donor PAT37 that did not respond to the Fc-modified immune complex. (3C) Bar charts showing fold increase in MFI relative to treatment with virus alone for moDCs derived from 3 different donors. Each donor is represented by a circle. Error bar shows the SEM. Statistical analyses were performed using an ordinary one-way ANOVA. The adjusted P values are represented by * for p<0.05,  for p<0.01 and * for p<0.001. (3D) Bar charts showing MFIs of various different maturation markers from 6 different donors. Each donor is represented by a circle. Statistical analyses (repeated measure of ANOVA with Dunnett correction on log of MFI) were performed for treatments indicated with lines. The adjusted P values are represented by * for p<0.05,  for p<0.01 and * for p<0.001.
Figure 3B:
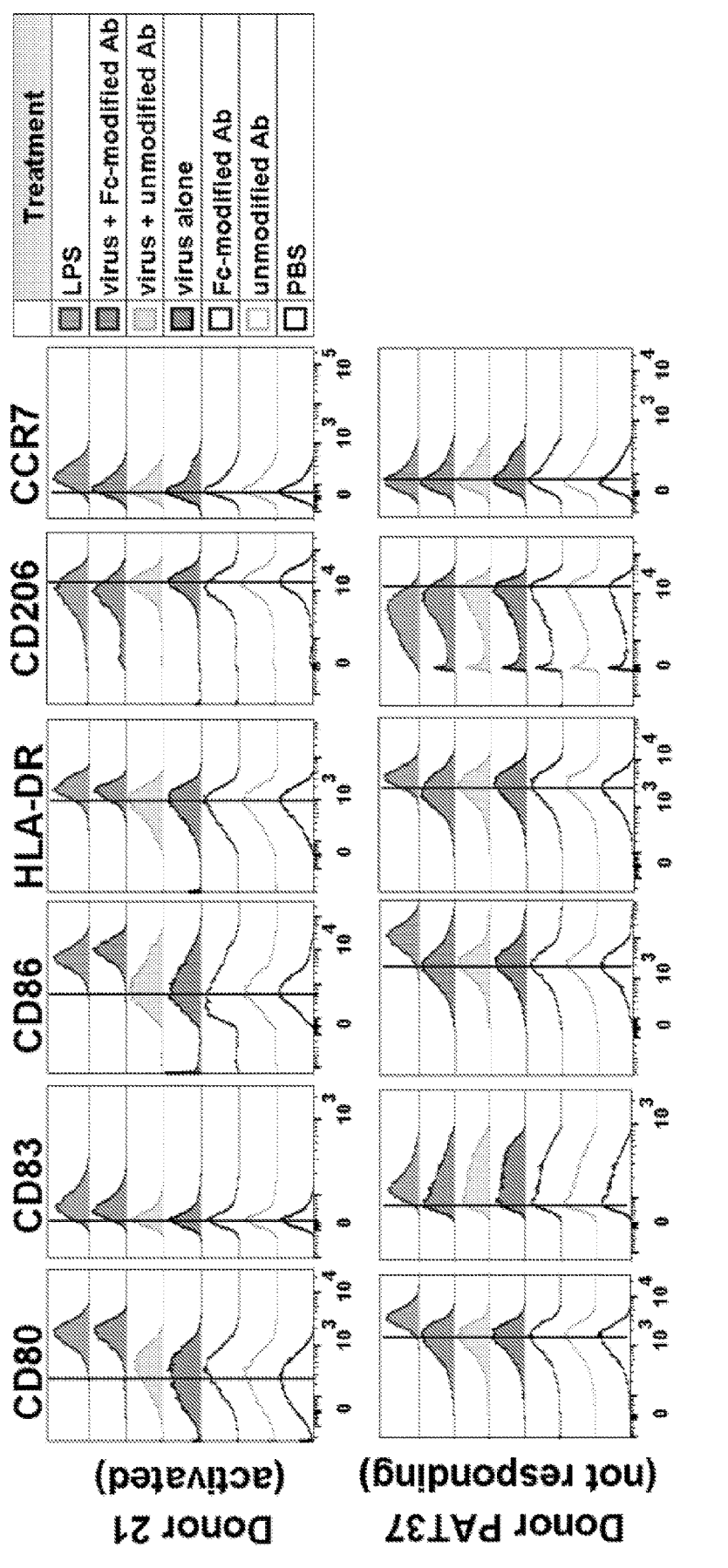
Figure 3C:
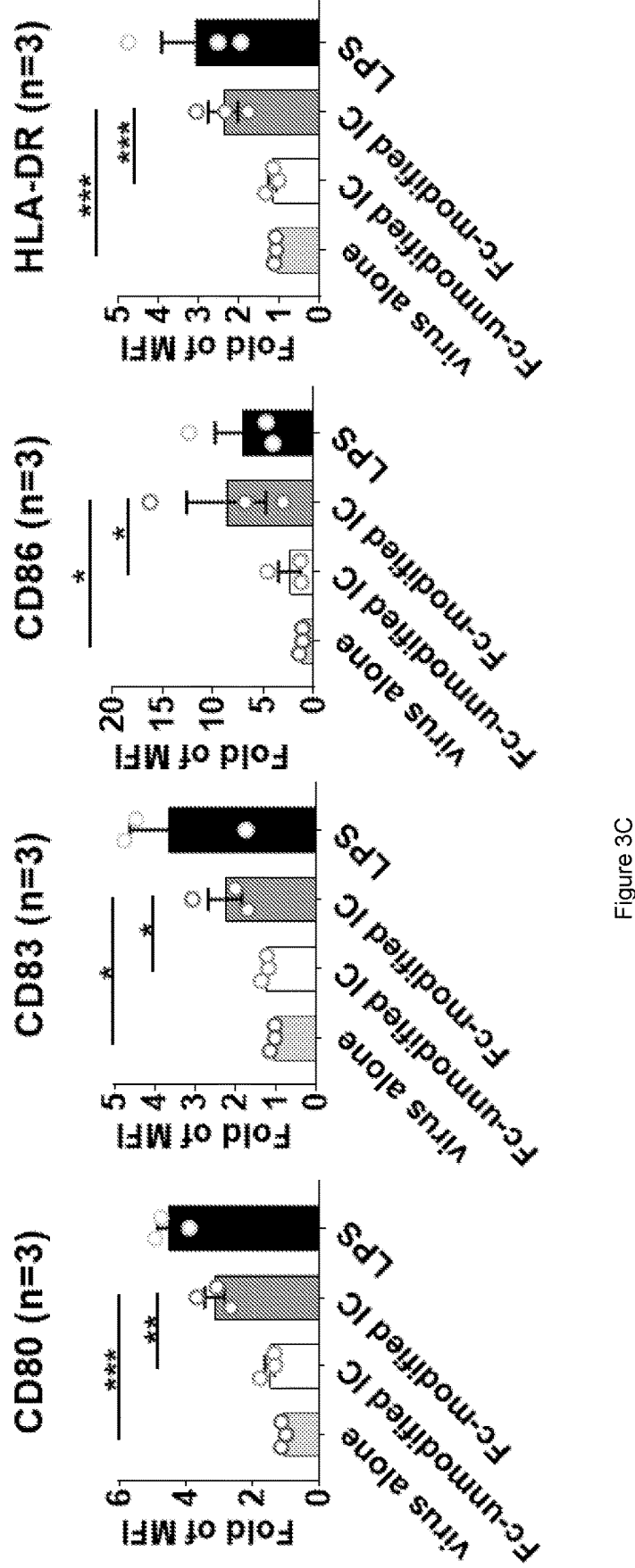
Figure 3D:
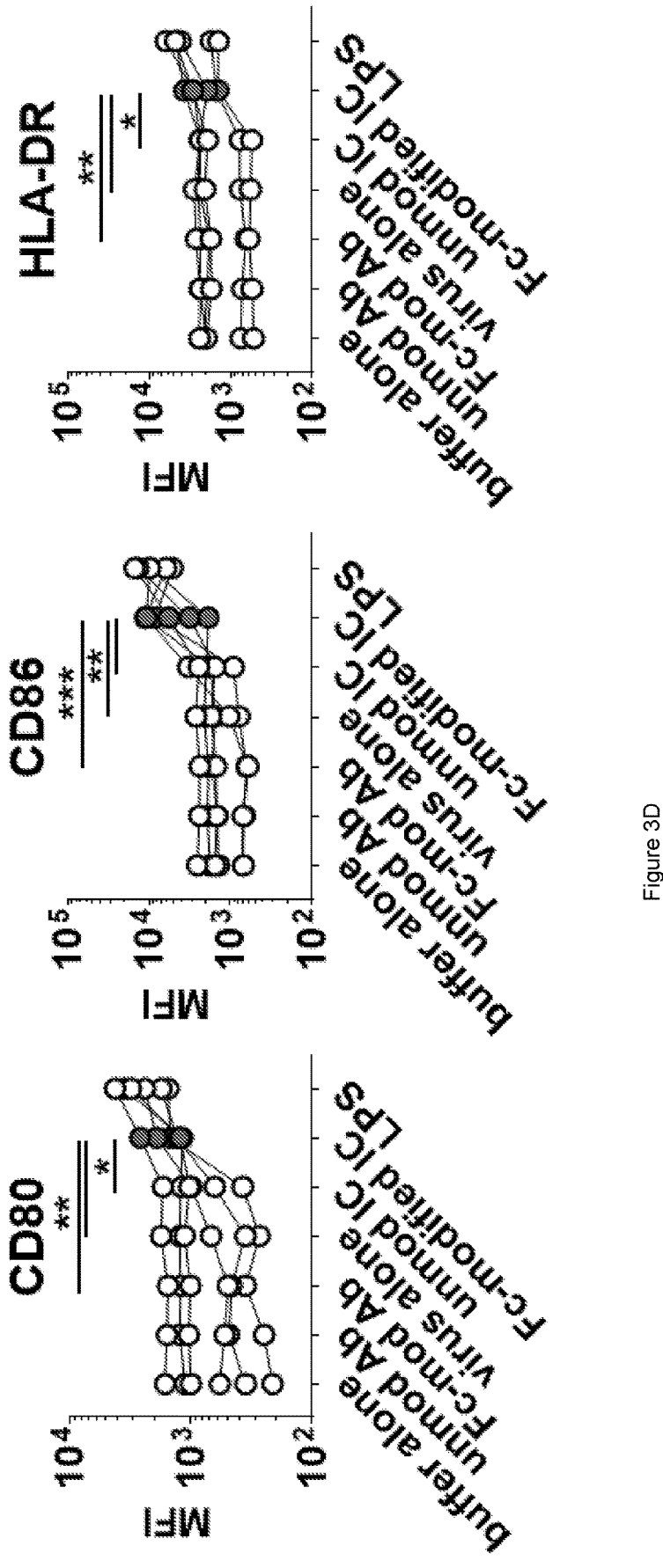
Figure 16A:
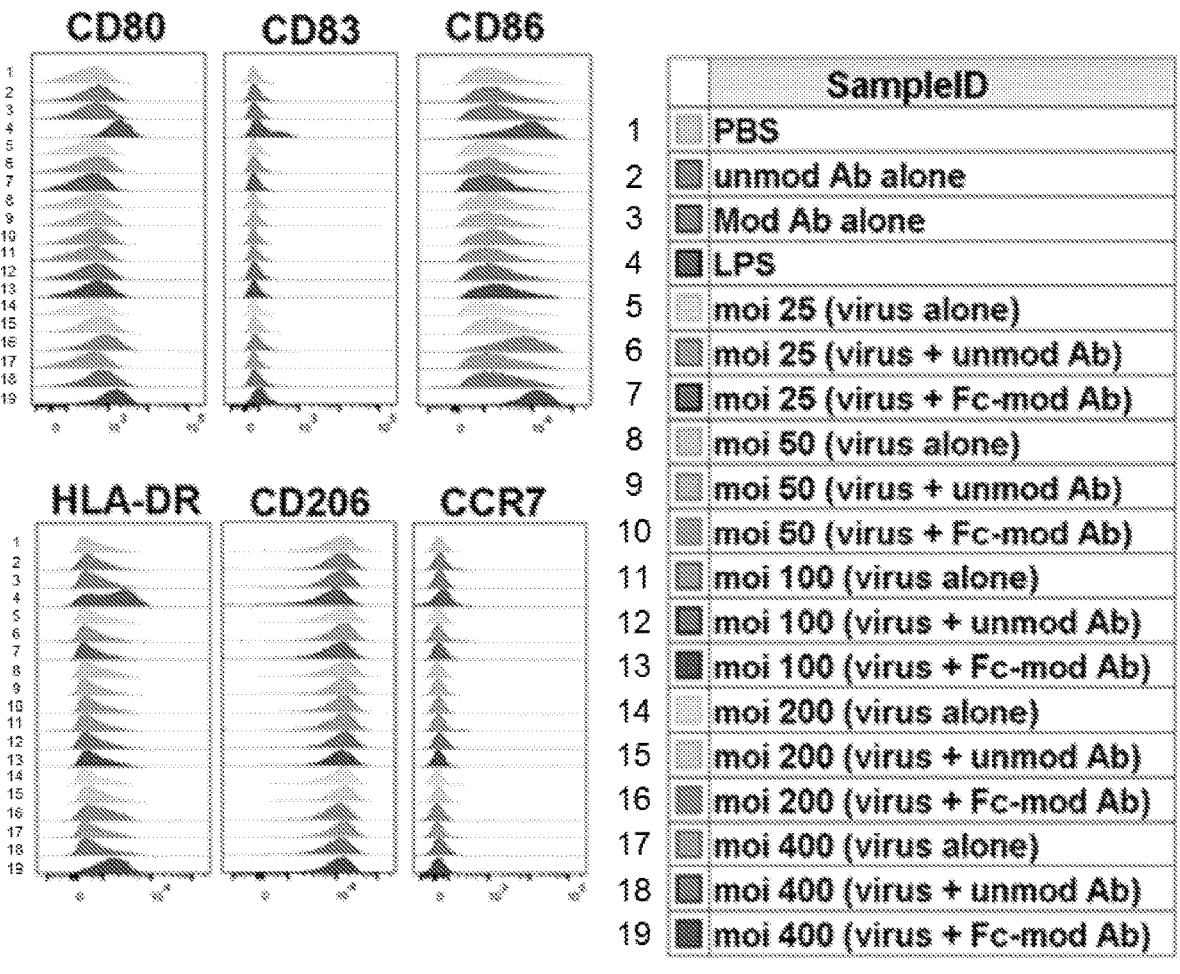
FIGS. 16A to 16C. Histograms, graphs and intensity plots relating to analysis of the effect of different dosages of Fc-modified immune complexes on moDC phenotype. (16A) Median Fluorescent Intensity (MFI) of CD80, CD83, CD86, HLA-DR, CD206 and CCR7 on moDC was analysed using flow cytometry. MoDC were treated for 24 h with different dosages immune complexes with Fc-unmodified or Fc-modified antibodies, or with virus alone. Treatment with PBS or antibodies alone are used as negative controls, and treatment with LPS are used as positive controls. Results from one representative donor (Donor 22) are shown. (16B) Differences between surface expression of CD83, CD206 and CCR7 by moDCs subjected to different treatments were not statistically significant. Repeated measure ANOVA with Dunnett correction was performed on the log of the MFI. Statistical analyses were performed only for treatments indicated with lines, n.s. means not significant (p>0.05). (16C) Cell purity of CD14+ cells after purification. PBMCs from three donors were subjected to CD14+ isolation. Cells before and after purification were stained for Live/Dead and CD14 and analysed by flow cytometry. Cells were gated for singlets/live/CD14+. The percentage of CD14+ cells in the sample before and after purification is shown in the box.
Figure 16B:
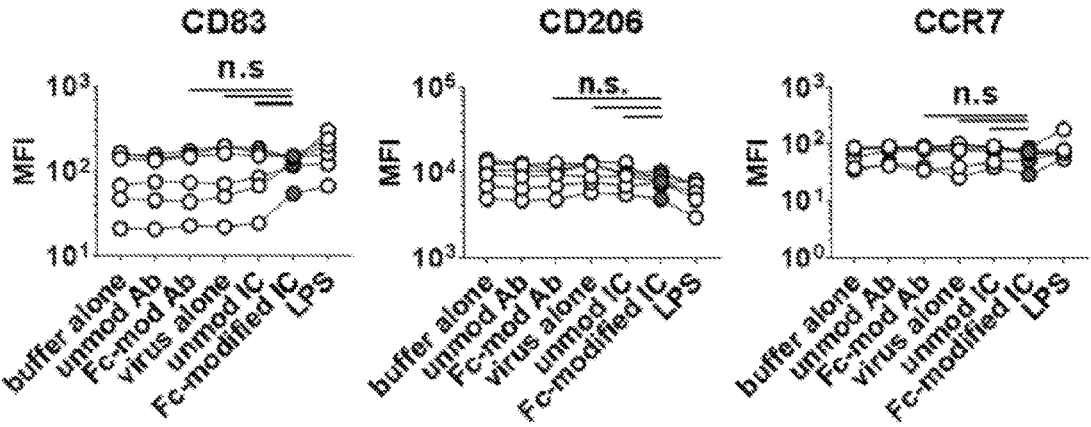

Incubating moDCs with Ad5 alone for 24 h did not increase expression of maturation markers, even at the highest dose of 400 MOI (FIGS. 3A and 3B), which resulted in an average of 69% of the moDCs being infected (FIG. 2A, moDC panel). This is in agreement with previous reports that at 50 MOI or higher, E1– and E3– deleted adenoviruses do not upregulate moDC co-stimulatory molecules, and instead suppress responses to LPS or PHA stimulation (Newton et al., 2008). Accordingly, incubating moDCs with wildtype IgG1 Fc (Fc-unmodified) Ad5 immune complexes also did not significantly increase the level of surface expression of CD80, CD83, CD86 or HLA-DR (FIGS. 3A and 3B, FIG. 16A), even though at the highest dose (400 MOI and 55 nM) the same concentration of antibodies were highly functional when it comes to ADIN (FIG. 2B, moDC panel). Only moDCs treated with PN04-90 Fc (Fc-modified) immune complexes significantly increased surface expression of CD80, CD83, CD86 and HLA-DR (FIG. 3C, FIG. 16A), and this trend was dose-dependent (FIG. 3A) and reproducible between different donors (FIG. 3C, 3D).

2.4 Increasing Fc Affinity for TRIM21 Promotes moDC Production of Th1-Associated Chemokines.

Figure 4A:
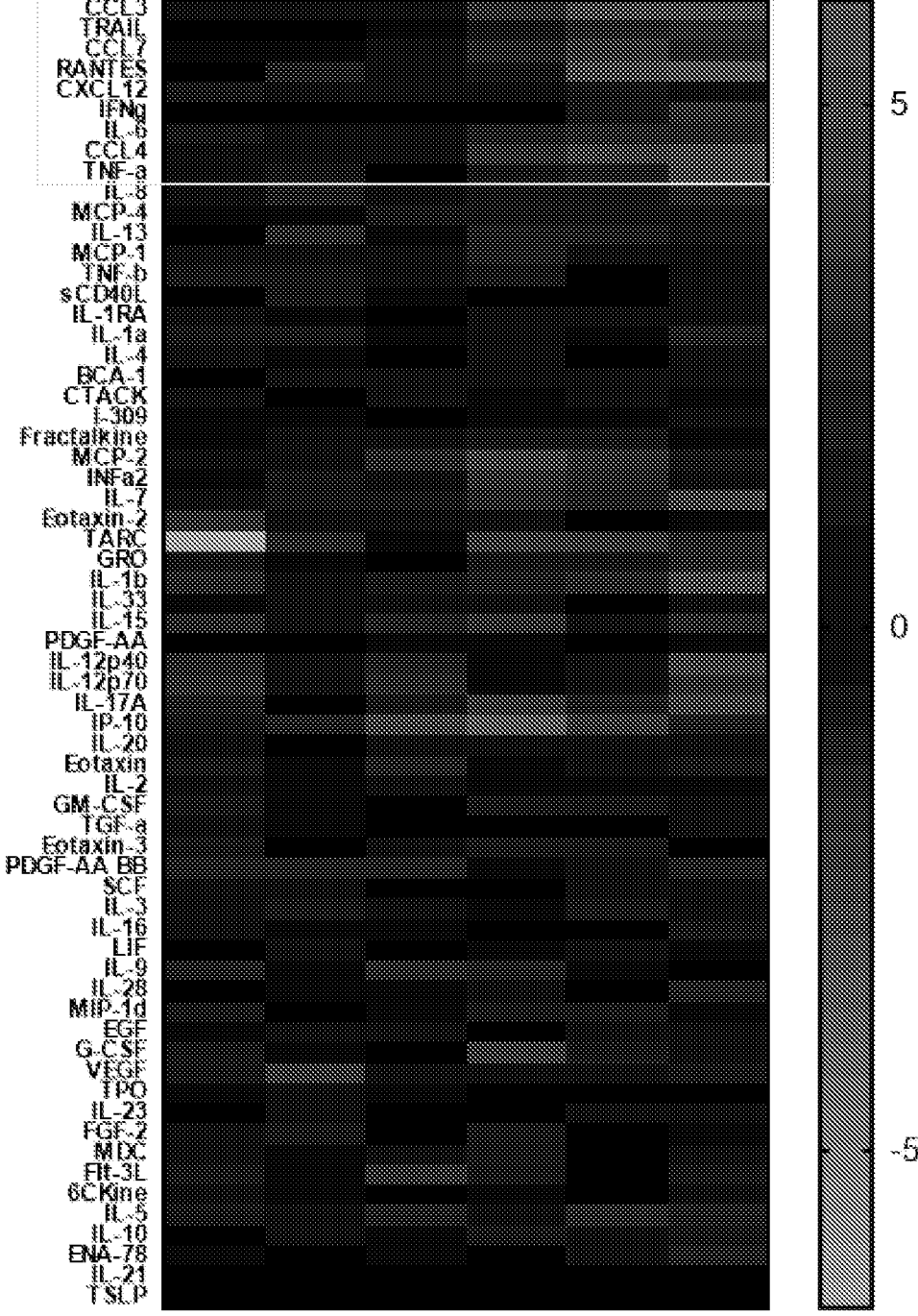
FIG. 4A to 4D. Heatmap and graphs showing the results of analysis of the effect of Fc modification on expression of soluble factors by moDCs. (4A) Fold change in cytokine and chemokine concentration is shown relative to treatment with unmodified immune complex detected in the culture supernatant. The heat map shows the cytokines and chemokines assayed using human Milliplex MAP kits immunology panel 1 and 2, which includes a total of 64 targets. The cytokines and chemokines are ranked by the Spearman rho correlation (for fold change versus dosages). The top nine factors (1,e, CCL3 to TNF-α) show a Spearman rho of >0.3 at p<0.05. (4B and 4C) Concentrations of the chemokines and cytokines CCL3, CCL4, CCL5, TRAIL, IFN-γ, IL-6, TNF-α, SDF-1a+b and MCP-3 are shown. Each donor is represented by a circle. IC: immune complexes. Graphs shows mean and SEM of three donors. Statistical analyses were performed using ordinary one-way ANOVA. For statistical analysis, the adjusted p-values are represented by ** for p<0.0001, * for p<0.001 ** for p<0.01 and * for p<0.05. (4D) Concentration of the seven chemokines and cytokines (CCL3, CCL4, CCL5, CCL7, IL-6, TNF-α, and IFN-g) for 6 donors. Each donor is represented by a circle. Repeated measure of ANOVA with Dunnett correction was performed on the logarithm of the cytokine/chemokine concentrations. Statistical analyses were performed for treatments with lines, and the adjusted P values are represented by * for p<0.05,  for p<0.01, * for p<0.001 and **** for p<0.0001.
Figure 4B:
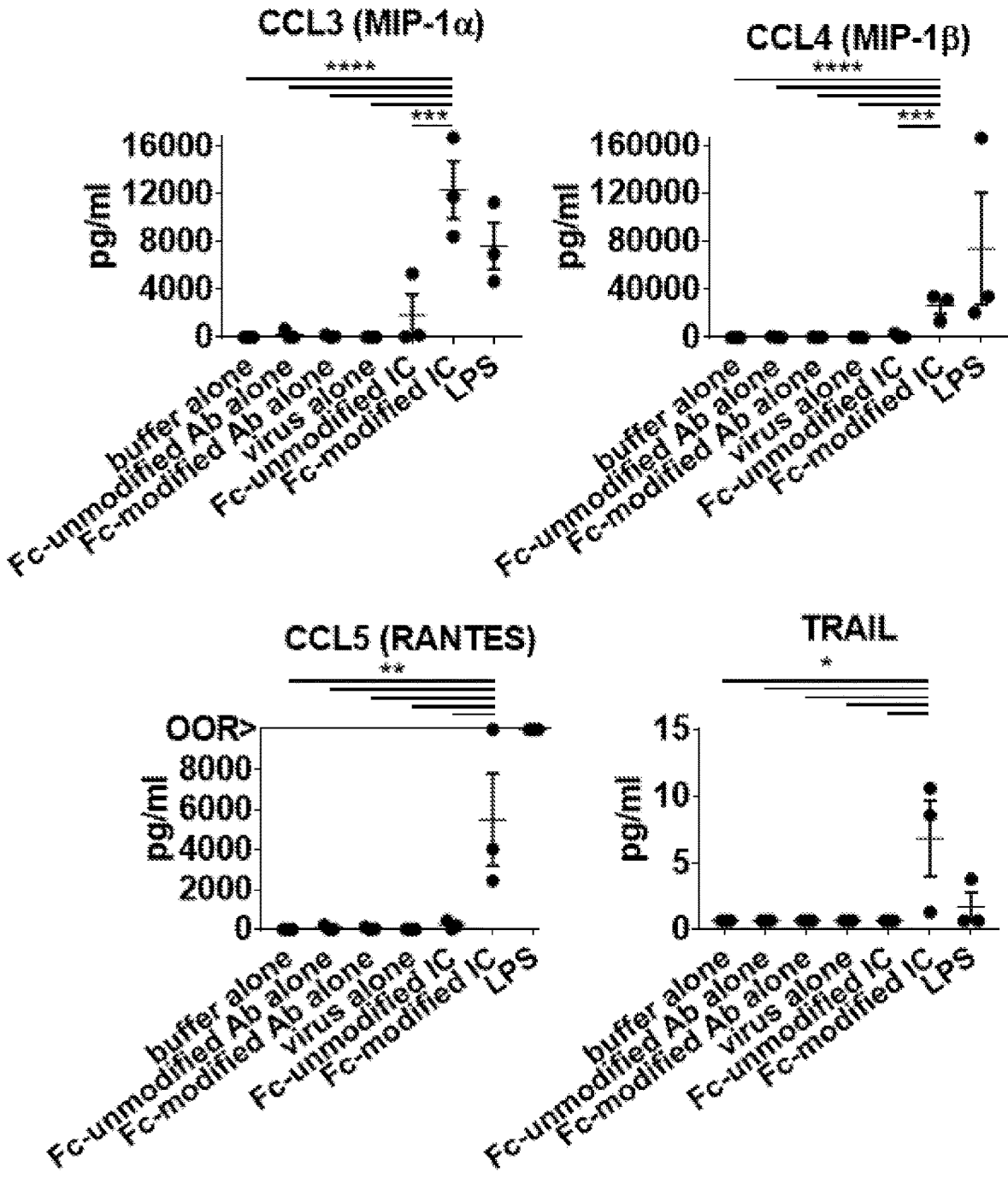
Figure 4C:
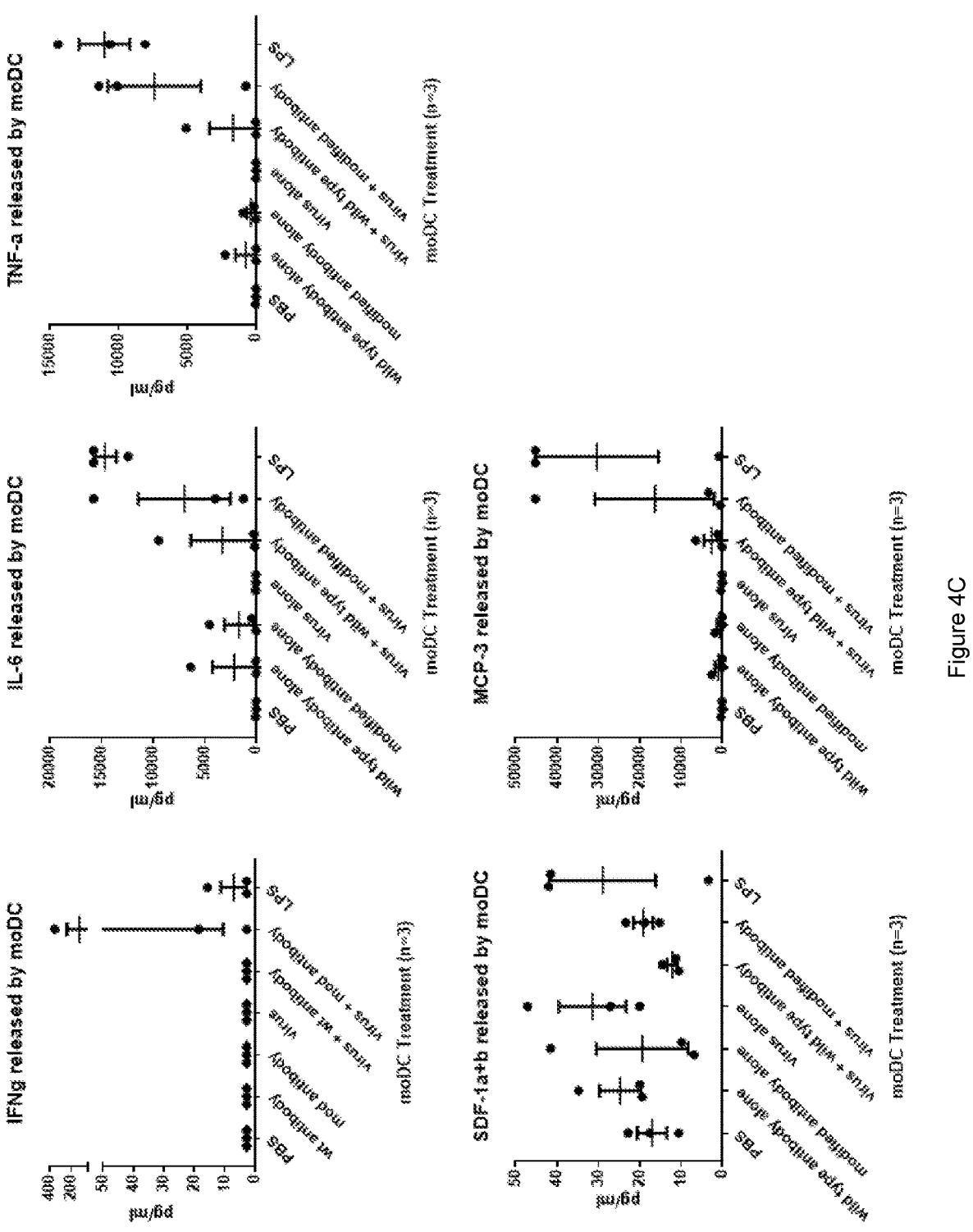
Figure 4D:
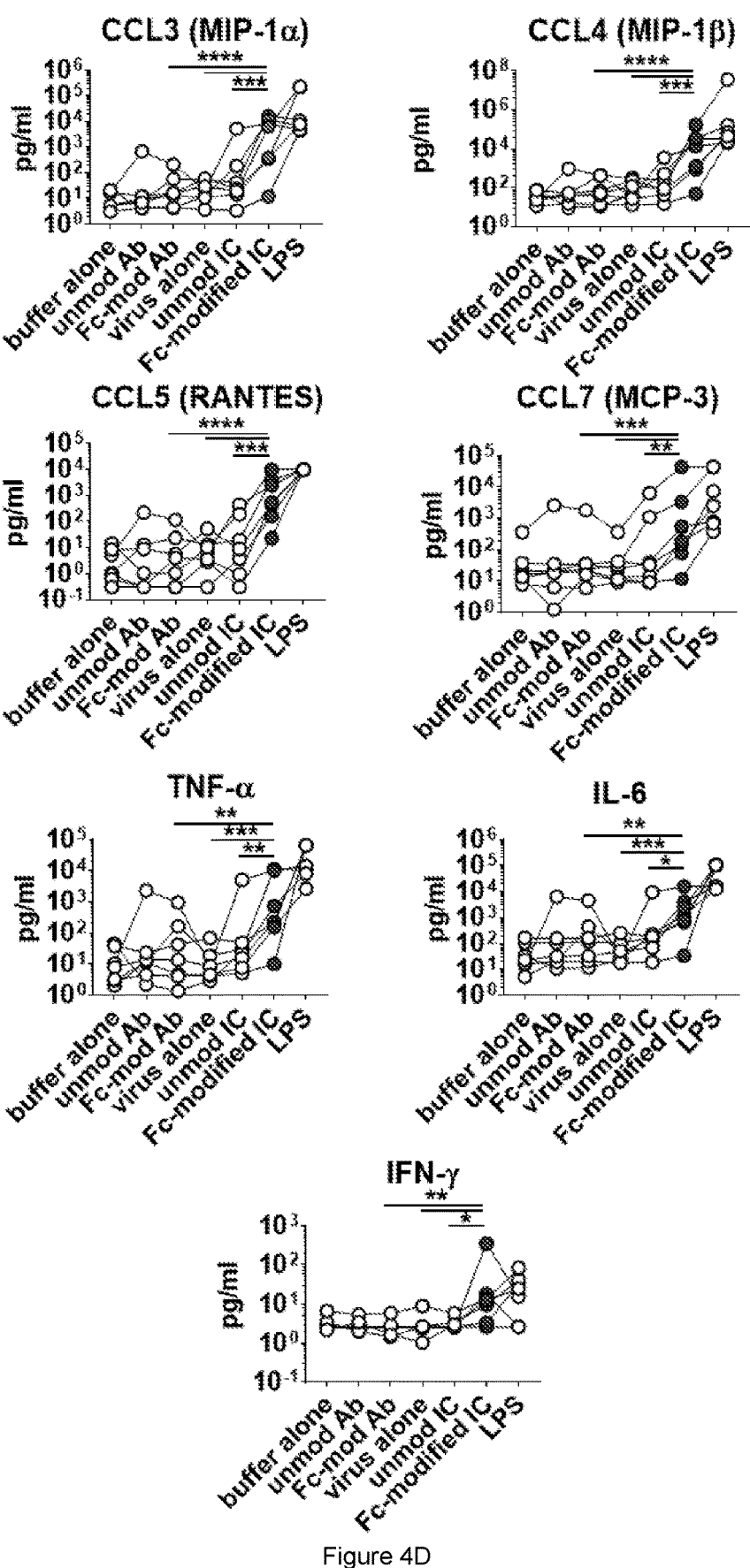

The inventors next investigated whether increasing Fc affinity for TRIM21 promoted expression of pro-inflammatory cytokines by moDCs. Using a multiplex bead-based assay, the inventors measured the secretion of 64 cytokines and chemokines by moDCs after 24 h of incubation with immune complexes comprising the Fc-modified or unmodified antibodies. For each cytokine/chemokine, fold change in expression level between treatments with PN04-90 Fc (Fc-modified) and wildtype IgG1 Fc (unmodified) immune complexes was calculated and correlated to their dosages (FIG. 4A). Nine proteins (CCL-3,-4,-5,-7, CXCL12, TRAIL, IL-6, TNF-α and IFN-γ) were determined to have a fold-change to dosage correlation higher than spearman rho 0.3 with p<0.05. Comparison of the concentrations of the molecules under different moDC treatment conditions by ANOVA revealed that CCL3 (MIP1-α), CCL4 (MIP-1β3), CCL5 (RANTES), CCL7, TNF-α and IL-6 production was significantly higher following moDC incubation with Fc-modified immune complexes as compared to other treatments (FIG. 4B, 4C, 4D).

Figure 16C:
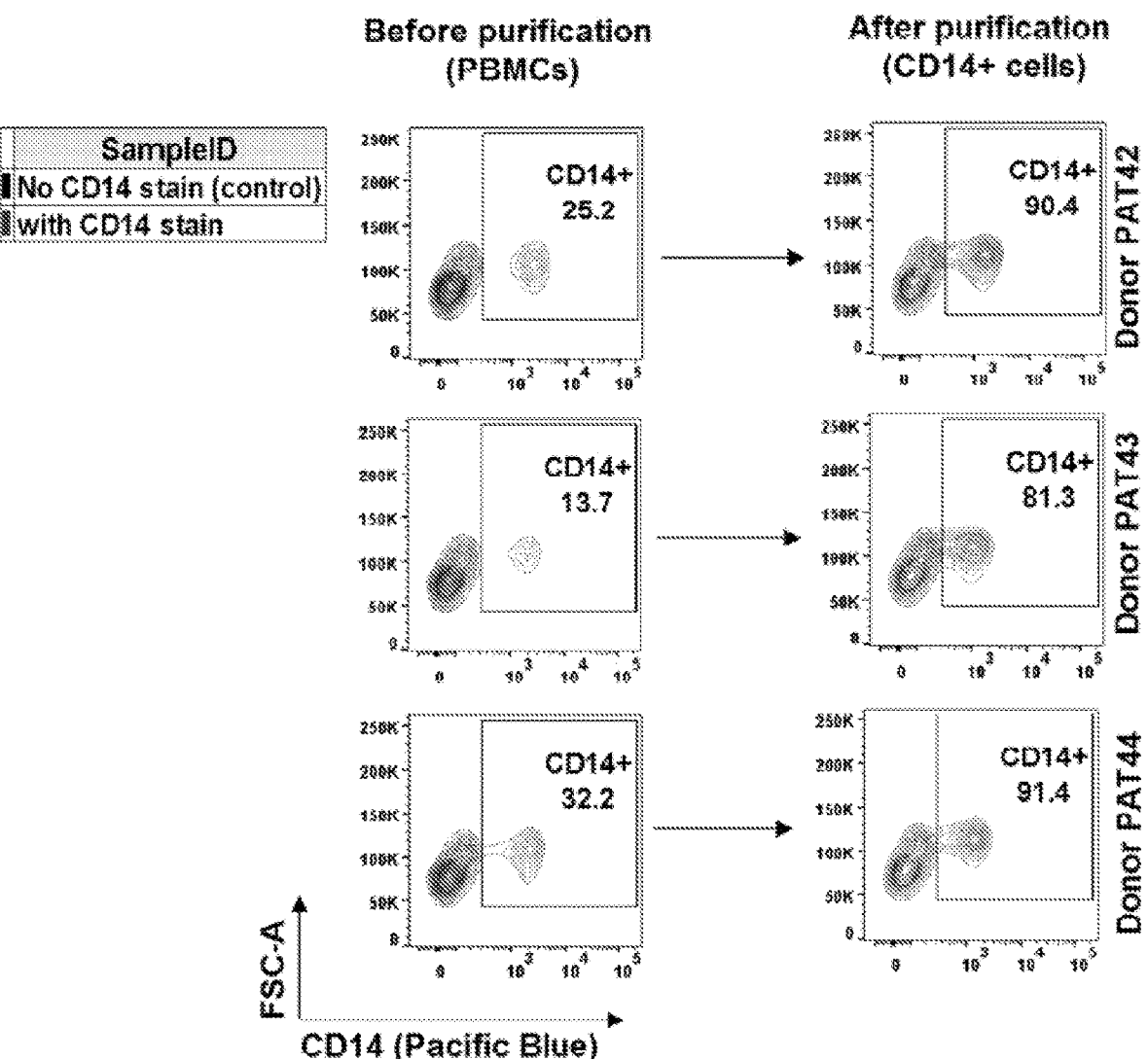

As IFN-γ is not a typical cytokine produced by moDCs, the slight increase in the levels of this cytokine most probably came from T cells and/or innate lymphoid cells that could be present in the CD14+ preparations, which had cell purity ranging from 81 to 91% (FIG. 16C).

In vivo, early-maturing DCs in peripheral tissues are the main producers of CCL3, CCL4 and CCL5 (Sallusto et al., 1999, 2000), which attract immature DC and T cells that promote a T helper type 1 (Th1) response (Lebre et al., 2005). Taken together, these data show that exposure of moDCs to Ad5 immune complexes comprising antibodies with Fc modified for increased affinity to TRIM21 induced increased co-stimulatory marker expression and greater production of Th1-associated pro-inflammatory cytokines compared to either virus alone, or Fc-unmodified immune complexes.

2.5 Increasing Fc Affinity for TRIM21 Increases T Cell Expansion by moDC

The inventors next assessed how Fc-modified immune complexes influenced CD8 T cell responses in PBMCs. moDCs were incubated either Ad5 alone, or with PN04-90 Fc (Fc-modified) or wildtype IgG1 Fc (unmodified) antibody-Ad5 immune complexes, and then co-cultured with autologous CD14–PBMCs for 13 days. LPS and TransACT (a CD3/CD28 agonist) were used as positive controls to non-specifically activate DCs and T cells respectively.

Figure 5A:
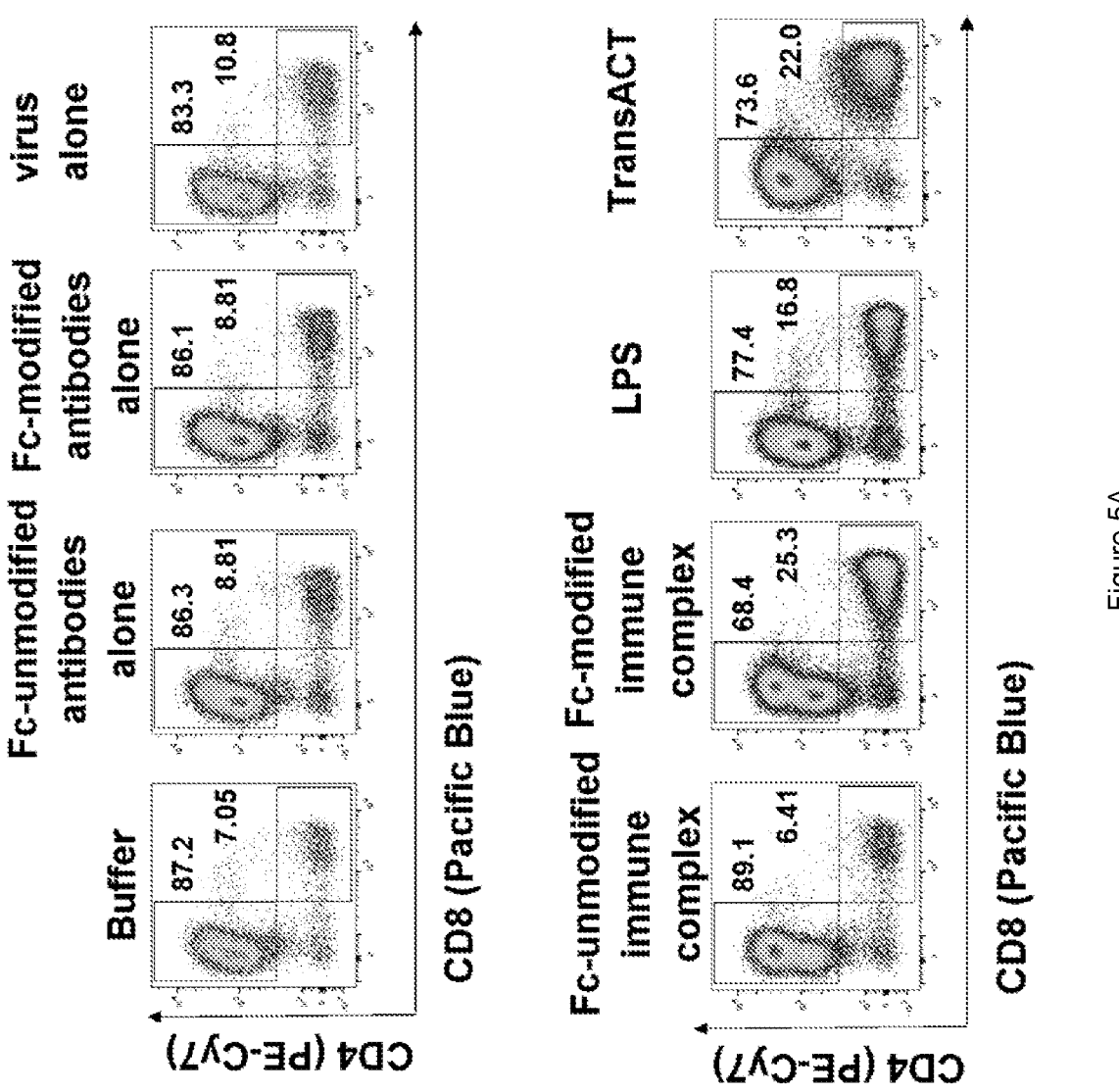
Figure 5B:
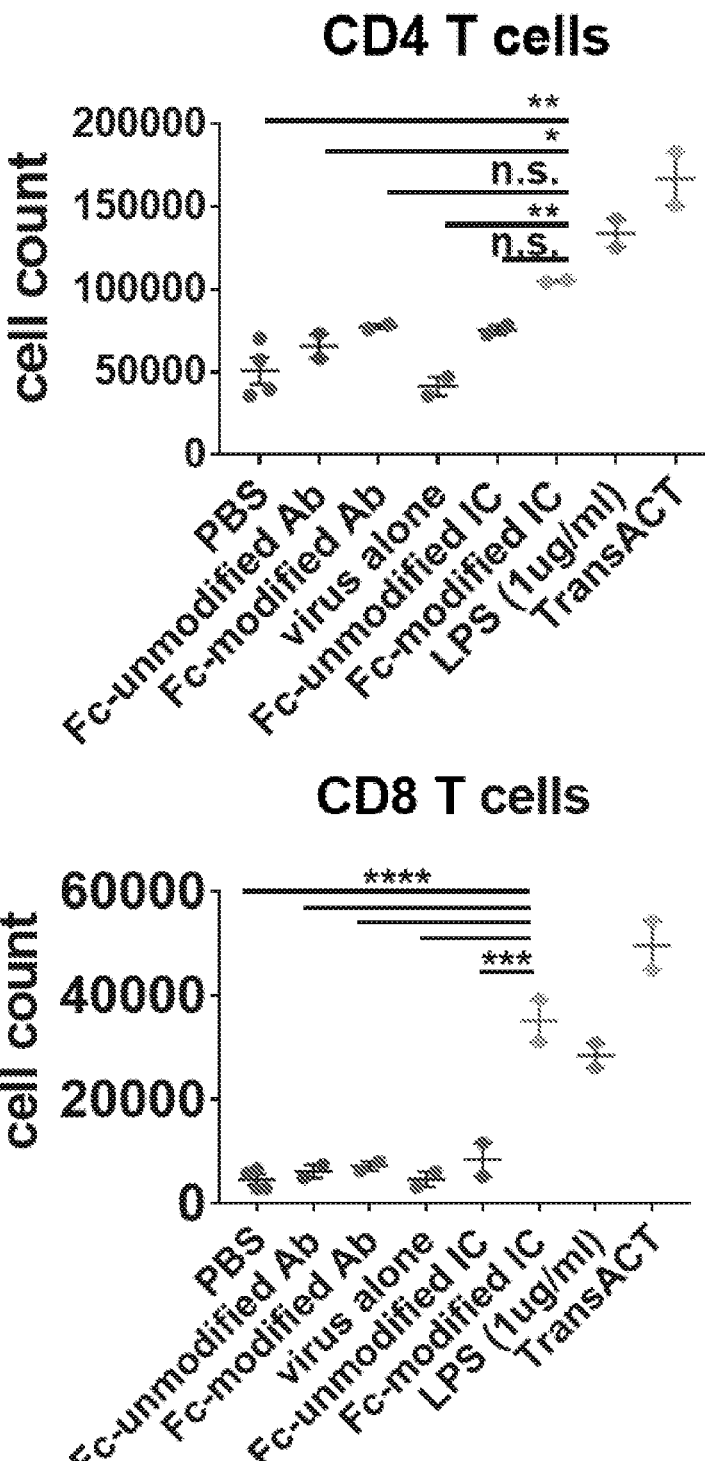

After 13 days of co-culture, the relative proportions of CD4 and CD8 T cells were determined by flow cytometry. Cells were gated for singlets/live/CD3+CD56– cells to include T cells and exclude NKT cells. CD8 T cells were found to be markedly enriched in co-cultures where moDC were treated with PN04-90 Fc (Fc-modified) immune complexes (FIG. 5A). Furthermore, this relative enrichment was not due to CD4 T cell death, as the absolute number of CD4 T cells was not lower (FIG. 5B); moreover, the absolute number of CD8 T cells was significantly higher in treatments with the modified Fc immune complexes compared to the other treatments (FIG. 5B).

Analyzing results from 7 different donors, the inventors observed that treatment of moDCs with Fc-modified immune complexes significantly increased CD8 T cell counts but not CD4 T cell counts in co-culture experiments, as compared to treatment with Fc-unmodified Ad5 immune complexes (FIG. 5C); Interestingly, heterogeneity in the capacity of cells from different donors to respond to Ad5 was observed and this could be separated into two groups: the first group (Type 1 donors) exhibited strong CD8 proliferation to virus alone (above 2-fold relative to no virus control) but a smaller increase in CD8 proliferation when moDCs were treated with the modified-Fc immune complexes; while donors that responded poorly to virus alone (below 2-fold relative to no virus control; Type 2 donors) showed a marked and significant increase of 5-fold when moDCs were treated with the modified-Fc immune complexes (FIG. 5D).

Treatment with Fc-modified immune complexes, compared with treatment with unmodified immune complex, resulted in an increase in cell count that was statistically significant for CD8 T cells but not CD4 T cells (FIG. 5E).

However, when compared with virus alone, the increase in CD8 T cell count was not statistically significant. This was believed to be due to donor variation. Three donors (LCYO4, LCY06, LCY08) who responded very well to virus alone (>3-fold increase compared with buffer treatment) responded poorly to the immune complexes comprising unmodified Fc or modified Fc.

Figure 6A:
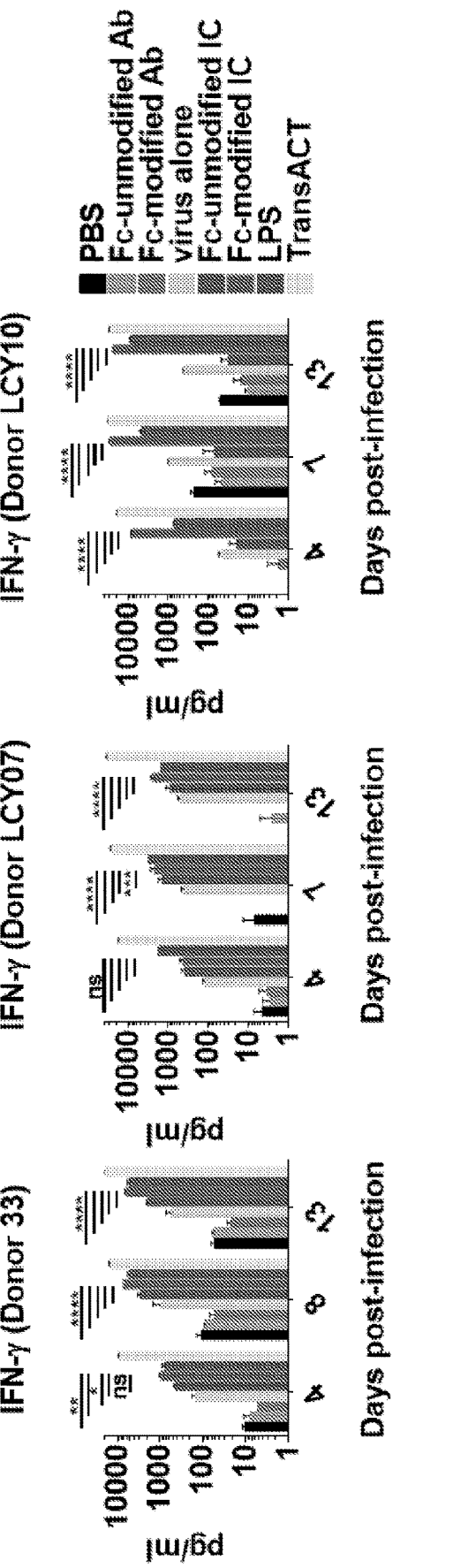
FIGS. 6A and 6B. Bar charts and graphs showing the results of analysis of the effect of Fc modification on ability of moDCs to stimulate IFN-γ production in a moDC:CD14– PBMC co-culture. (6A) Results of an ELISA analysis at 4, 7 and 13 days post infection by virus, immune complexes or controls. Each graph shows the mean and SEM of triplicates for a responding donor. Bars for PBS to TransACT are shown from left to right, for each period. Statistical analyses were performed using an ANOVA. LPS and TransACT are omitted from all statistical analysis. (6B) Levels of IFN-γ for the 7 donors at 7 days post infection for Type 1 donors (showing 3-fold or more increase in CD8 count when treated with virus alone) and Type 2 donors (showing a better response to Fc-modified immune complex than to virus alone), and donor LCY05, displaying high IFN-γ even in response to PBS treatment, and no expansion in CD8 count to all treatments. Each dot represents one donor and the line represents the mean of 7 donors. Repeated measure of ANOVA with Dunnett correction was performed on the logarithm of the IFN-γ concentrations. Statistical analyses were performed for treatments with lines. For all statistical results, ** represents p<0.0001, * represents p<0.001 ** represents p<0.01 and * represents p<0.05 and ns is not significant with p>0.05.

During T cell expansion, IFN-γ is produced and so the inventors measured secretion of IFN-γ at 4, 7 and 13 days of co-culture for each donor. As in the CD8 T cell response, treating moDCs with Fc-modified immune complexes induced significantly higher IFN-γ production in the moDCs:CD14–PBMC co-culture than did either virus alone or Fc-unmodified immune complexes at 4, 7 and 13 days post infection, as determined by ELISA of the donors that responded to the modified-Fc immune complexes (FIG. 6A).

Figure 6B:
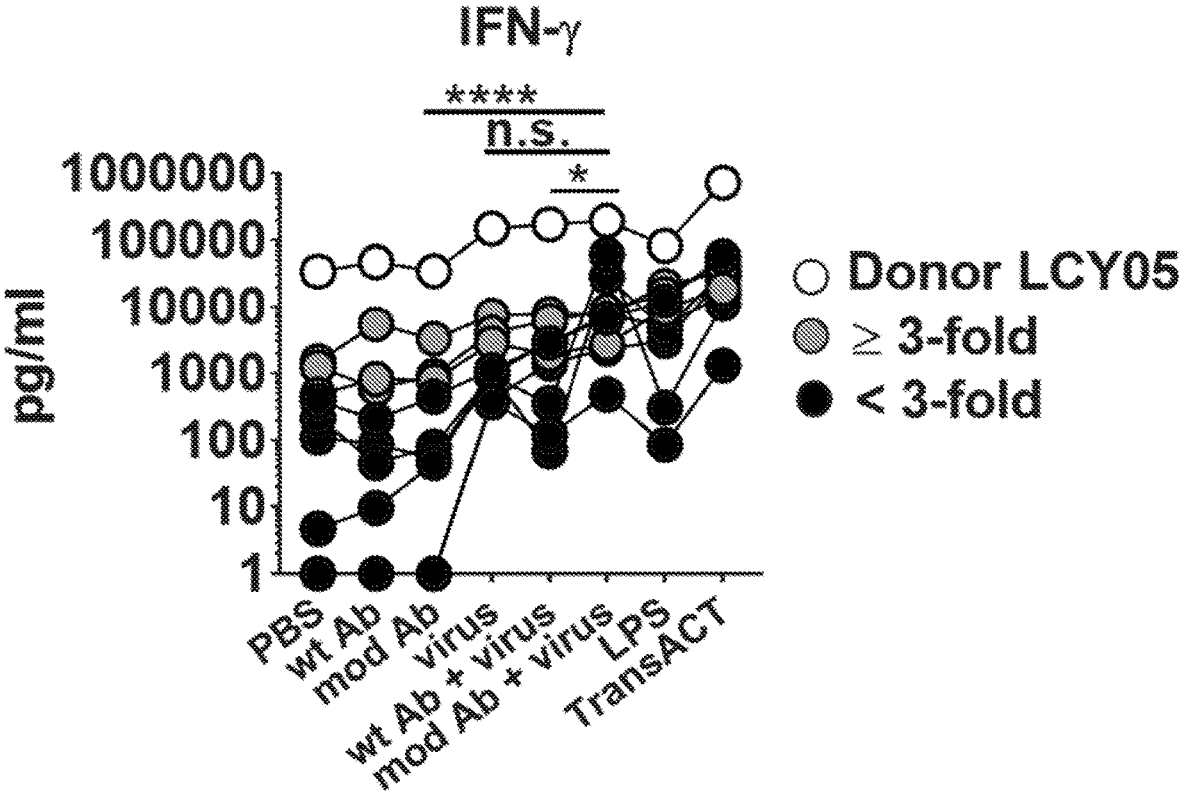

Analyzing the IFN-γ results from the same 7 donors again revealed a heterogeneity in response that could be grouped into the Type 1 and Type 2 donors (FIG. 6B). Type 1 donors displayed higher IFN-γ in control treatments and did not increase much more upon treatment with Fc-modified immune complexes. Type 2 donors displayed much lower IFN-γ levels in control treatments, and an increase upon treatment with Fc-modified immune complexes.

Taken together, the data show that through modifying Fc for improved affinity to TRIM21, immune complexes can be generated which increase the ability of moDC to stimulate IFN-γ production by PBMCs, and to stimulate CD4 and CD8 T cell expansion. In the case of CD8 T cell count, this effect is particularly marked in the Type 2 subset of donors that do not respond well to virus alone.

Figure 7:
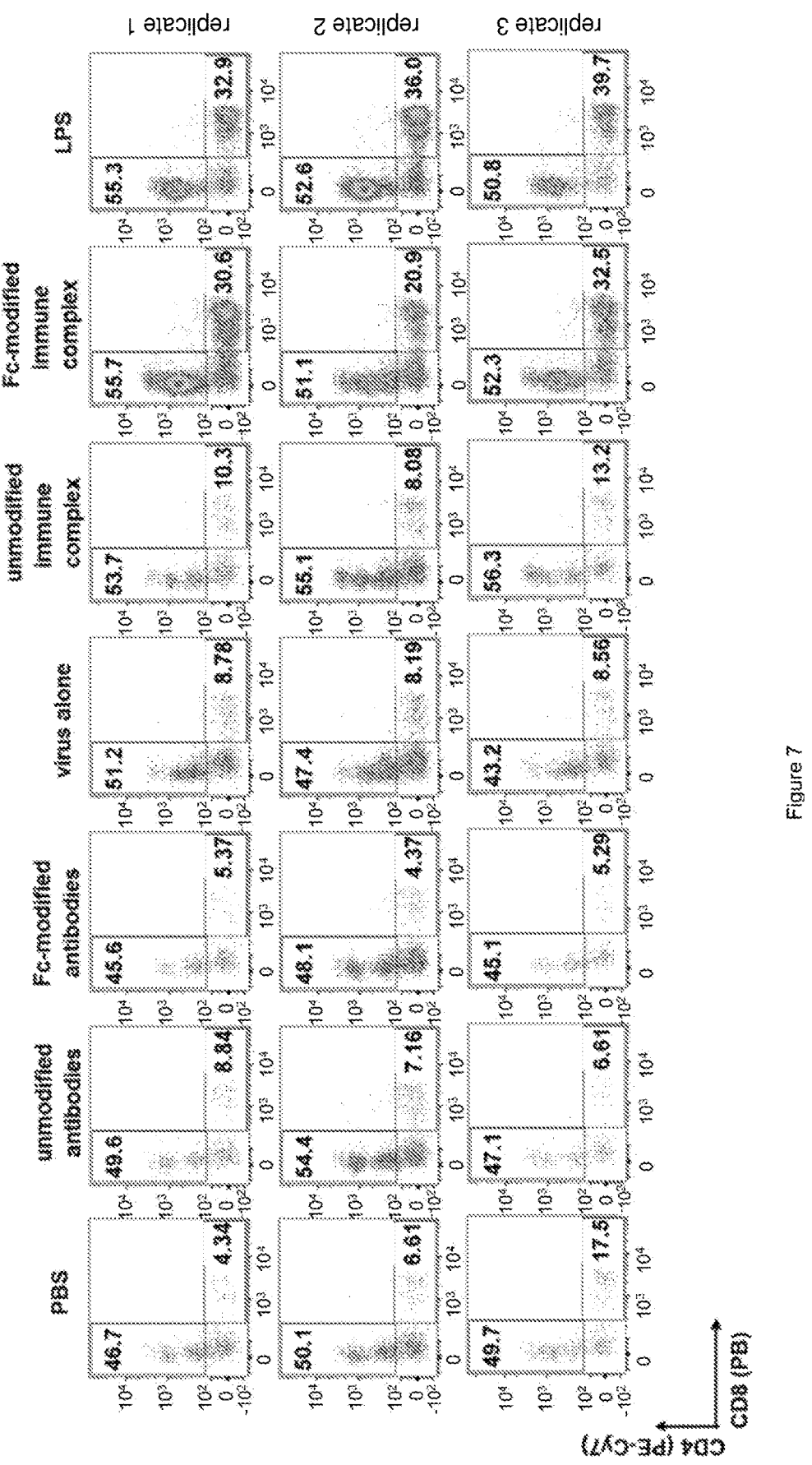
FIG. 7. Scatterplots showing CD4 and CD8 T cell responses of donor LCY02 following co-culture for 11 days of CD14–PBMCs with MoDCs which pre-treated with PBS, antibodies, virus alone or immune complexes. After 11 days, co-cultures that received the modified-Fc immune complex treatment display significant increase in the percentage of CD8 T cells.

2.6 Increasing Fc Affinity for TRIM21 Increases Antigen-Specific CD8 T Cell Proliferation Induced by moDC Incubated with Immune Complexes To understand the extent to which the CD8 T cell response was antigen-specific, the inventors further investigated the response of donor LCY02; this donor was HLA-A24– and HLA-A2-positive, and exhibited a 2.7-fold increase in the percentage of CD8 T cells in moDC:CD14– PBMC co-cultures in response to PN04-90 Fc immune complexes (FIG. 7). 11 day old moDC-CD14– PBMC co-cultures were re-stimulated with autologous moDCs that had been treated with TNF-α and pulsed with peptides representing an Adenovirus epitope for HLA-A24 haplotype (TYFSLNNKF), HLA-A2 haplotype (YVLFEVFDVV), and, as negative controls, a scrambled peptide (LAVFEDYVAF) or a HIV epitope (SLYNTVATL). The antigen-specific response was also investigated using a library of 15-mer peptides representing the hexon protein of Adenovirus or an irrelevant protein (Human NY-ESO-1 protein).

Figure 8A:
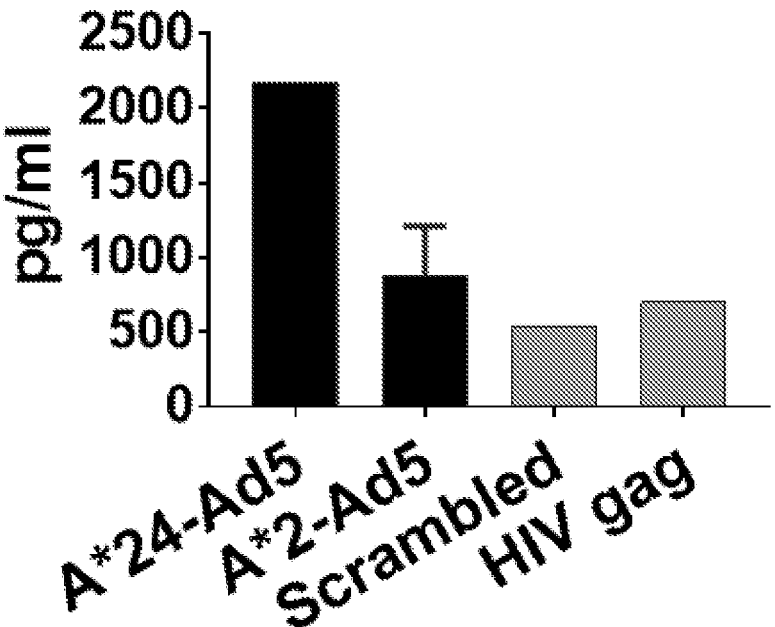
FIGS. 8A to 8D. Bar charts and scatterplots showing the results of analysis of the effect of Fc modification on ability of moDCs to stimulate expansion of antigen-specific CD8+ T cells. (8A and 8B) Results of an ELISA detecting the level of IFN-γ in the supernatant of moDC:CD14–PBMCs co-cultures that were re-stimulated for 16 h with autologous moDCs pulsed with peptides. Results show the means and SEM of duplicates, or of a single well (for A*24-Ad5, Scrambled and HIV gag) of donor LCYO2. (8A) A*24-Ad5 and A*2-Ad5 are peptides from Adenovirus that are presented by HLA-A24 and HLA-A2 haplotypes, respectively. Scrambled and HIV gag are negative controls. (8B) Results of ELISA detecting the level of IFN-γ in the supernatant when moDCs were pulsed with peptide library of 15-mer peptides from the hexon protein of Adenovirus (Ad5 hexon) or the human protein NY-ESO-1 (negative control). (8C) Results of analysis by flow cytometry of donor LCYO2's CD4 and CD8 T cells from CD14–PBMC co-cultures with autologous moDCs that were untreated or treated with modified Fc immune complexes for 11 days, re-stimulated with moDCs pulsed with different peptides for 16 h, and then treated for 5 h with Brefeldin A. Numbers at the bottom show percentages of CFSE-diluted cells in a population of CD8 or CD4 T cells. Numbers at the top show percentage of IFN-γ high cells (responding cells) in the population of CFSE-diluted CD8 or CD4 T cells. (8D) Results of analysis by flow cytometry analysis of CD4 and CD8 T cells from donors LCY10, PAT35, and LCY25, from CD14−PBMC co-cultures with autologous moDC that were treated with modified Fc immune complexes for 11 days, and then re-stimulated for 16 h with moDC pulsed with different peptides in the presence of Brefeldin A. Numbers at the top show percentage of IFN-γ high cells (responding cells) in a population of CFSE-diluted CD8 or CD4 T cells. Asterisks indicated responses that are specific to restimulation by the Ag. (8E) Results of analysis by flow cytometry analysis of CFSE-dilution in CD8 T cells following 11 d of coculture with moDC (Donor LCY25). The moDC were either pre-treated with medium alone or medium with MG132 for 1 h and then subjected to a 4-h treatment in medium with PBS, unmodified Abs (unmod Ab), or Fc-modified Abs (Fc-mod Ab) in the presence or absence of adenovirus. TransACT is used as a positive control for T cell proliferation.
Figure 8B:
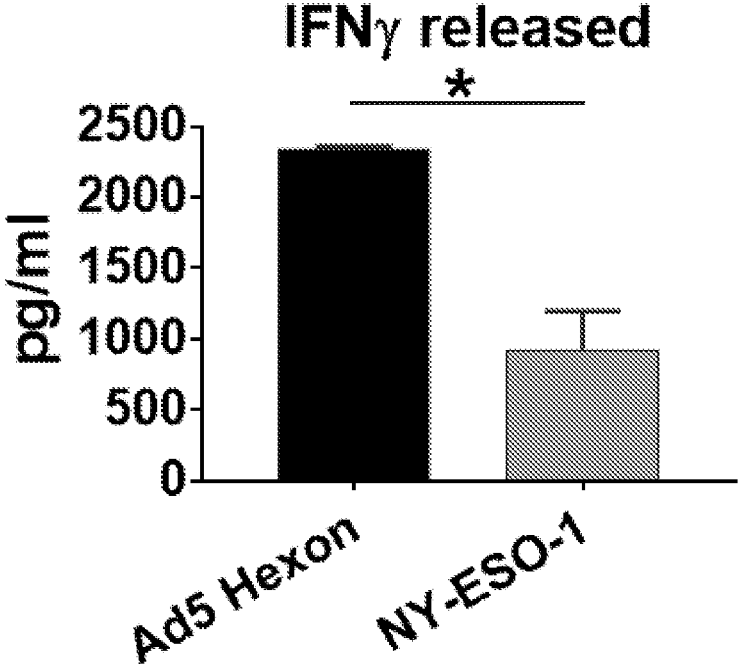

A marked and specific IFN-γ response to the HLA-A24-restricted-Adenovirus epitope was observed after 16 h of re-stimulation (FIG. 8A). A strong IFN-γ response was also detected to the peptide library generated from the Adenovirus-hexon protein was detected, but not to the peptide library of the NY-ESO-1 protein (FIG. 8B).

Figure 17A:
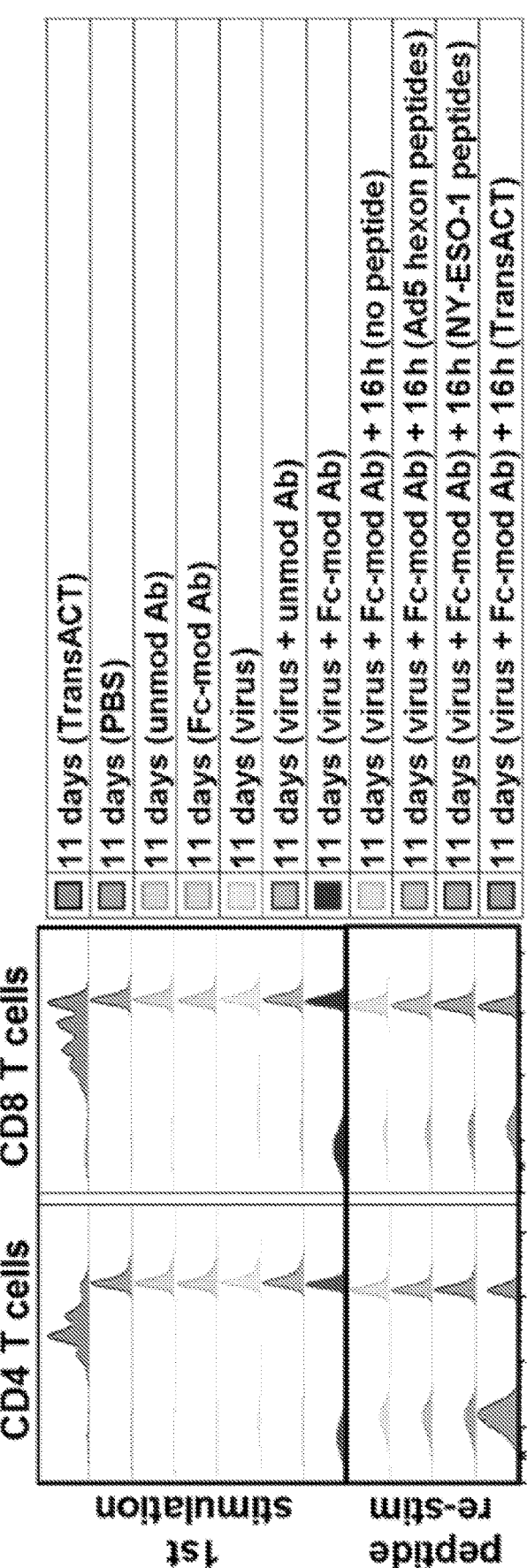

In the same experiment, CD14– PBMCs were labelled with CFSE to enable identification of proliferating cell populations. T cells that were cocultured with moDCs pretreated with the virus and Fc-modified Abs showed the most proliferation (FIG. 17A). No such proliferation is seen when moDC were treated with PBS, virus alone, Abs alone, or virus with unmodified Abs.

Figure 8C:
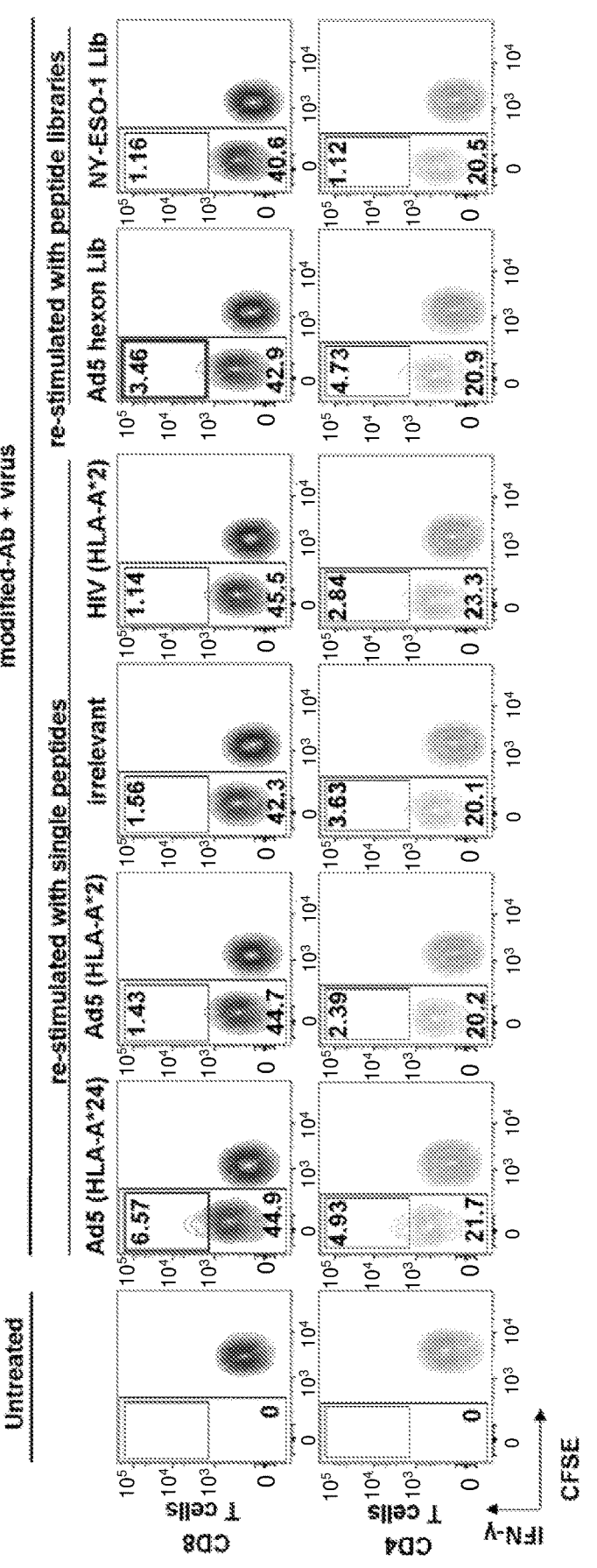

After 11 days, 43% of the CD8 T cells, and 21% of the CD4 T cells had proliferated (FIG. 8C). After 16 h of re-stimulation, Brefeldin A was added to the co-cultures to enable detection of individual cells that were producing IFN-γ, and also to understand their proliferative response to the different antigens. Both CD4 and CD8 T cell populations exhibited higher percentages of CFSE-diluted IFN-γ-producing cells when moDCs had been stimulated by the Ad5 hexon peptide library (4.73% and 3.46% respectively) than when stimulated by the NY-ESO-1 peptide library (1.12% and 1.16%).

In the single peptide experiments, the HLA-A24 adenovirus peptide stimulated 6.57% of the proliferated CD8 T cells to produce IFN-γ, while the response to the HLA-A2 adenovirus peptide was comparable to the negative controls (FIG. 8C). Since the single peptide experiment used 9-mer peptides, restimulation of CD4 T cells was not expected, however, there was a small increase in the frequency of IFN-γ-producing CD4 T cells in co-cultures where moDCs were treated with the HLA-A24 peptide relative to negative controls. This may have been a bystander effect resulting from the production of cytokines by the CD8 T cells that were truly responding to the 9-mer peptide.

Figure 8D:
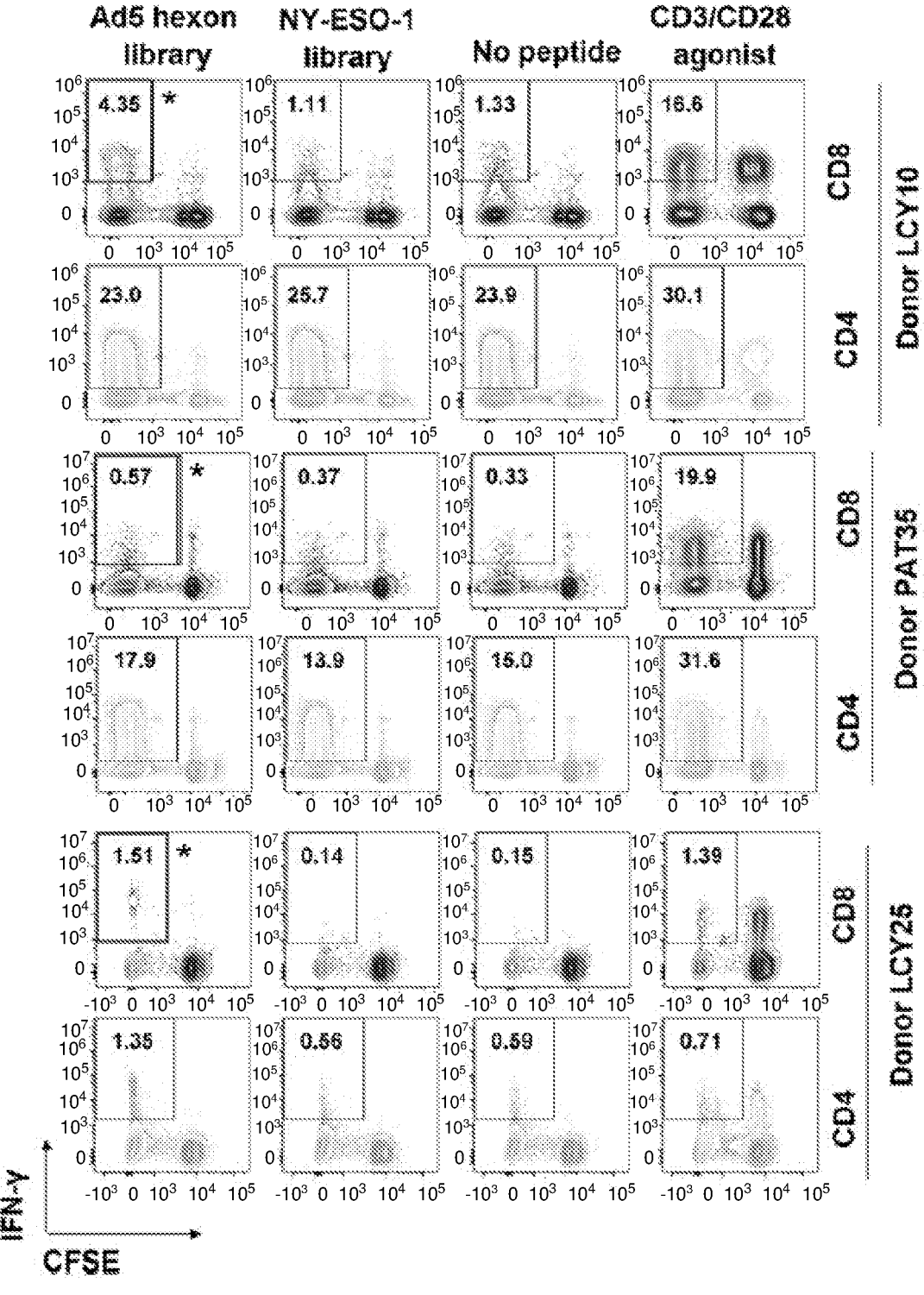

To eliminate the bystander effect of cytokines which could be released during re-stimulation, the experiment was repeated in the presence of Brefeldin A to stop cytokine release right at the start of re-stimulation. Only CD8 but not CD4 T cells were found to display antigen-specific re-stimulation (FIG. 8D). Controls using CD3/CD28 agonist confirmed that the CD4 T cells were capable of responding to stimulation and are not intoxicated by the overnight treatment with Brefeldin A.

Figure 17B:
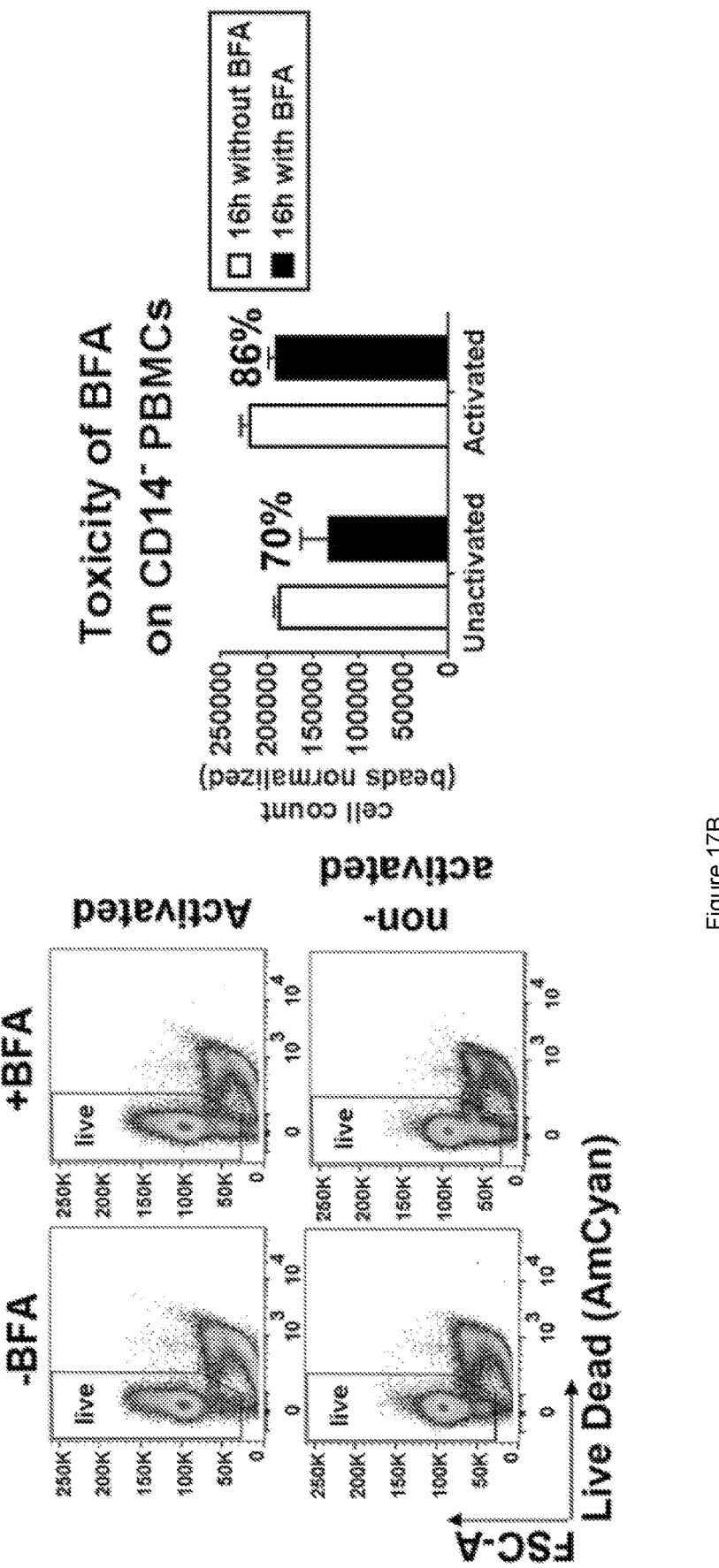

In a separate experiment, toxicity from overnight brefeldin A treatment was directly measured by comparing the number of live cells in CD14– PBMCs in the presence and absence of brefeldin A. LIVE/DEAD staining showed that after 16 h the viability of CD14– PBMCs with brefeldin A treatment was ~70 and 86% of that without brefeldin A treatment for inactivated and activated cells, respectively (FIG. 17B). Notwithstanding the toxicity of brefeldin A, our results indicate that with overnight brefeldin A treatment T cell proliferation stimulated by Fc-modified immune complexes appears to be driven by Ag-specific CD8 T cells.

Taken together, these results show that Fc-modified immune complexes increase moDC stimulation of antigen-specific IFN-γ production and CD8 T cell proliferation.

The inventors next investigated whether the CD8 T cell proliferation stimulated by moDCs treated with Fc-modified immune complex were dependent on proteasomal degradation in the moDCs.

MoDCs were pretreated with MG132 for 1 h, then subjected to treatment with immune complexes or various controls and then cocultured with autologous CFSE-labeled CD14– PBMCs for 11 days.

The results are shown in FIG. 8E, and demonstrate that pretreatment of moDC with the proteasomal inhibitor MG132 resulted in the loss of CD8 T cell proliferation.

To ensure that the loss of proliferation was not solely because of MG132-associated toxicity to moDC, moDC viability was analysed 1 d after MG132 treatment. At 22 h posttreatment, the viability of moDC with MG132 treatment was 61% of that without MG132 treatment (FIG. 17C). This indicated that there were still moDCs after MG132 pretreatment, but they were unable to mediate enhanced Ag cross-presentation because the Fc-modified immune complex is dependent on a proteasome-mediated pathway.

Example 3: Discussion

The inventors engineered the human IgG Fc region to increase its affinity for TRIM21 by 100-fold, and showed that the resulting antibodies directs viral antigens effectively into the cross-presentation pathway leading to the stimulation of antigen-specific CD8 T cells. This process is mediated by cross-presentation and not the classical MHC class I presentation of viral proteins because most of the endocytosed viruses are neutralized and therefore viral genes are not being expressed. Importantly, the cross-presentation process is remarkably enhanced by Fc-modification for increased TRIM binding, while the host-protective mechanism of ADIN is retained.

While both the Fcγ receptor (FcγR) and the neonatal Fc receptor (FcRn) have been shown to facilitate cross-presentation (Baker et al. 2011; Regnault et al. 1999), this is the first demonstration that TRIM21 also accesses this pathway. The involvement of TRIM21 with the proteasome has led to speculation that it regulates antigen-processing (signal 1) in DCs, but the inventors also found that TRIM21 ligation by Fc-modified immune complexes induces expression of co-stimulatory molecules (signal 2), and pro-inflammatory cytokine/chemokine release (signal 3) by moDCs. For cross-priming of CD8 T cells, all 3-signals are required. DC-targeted vaccine strategies often rely on TLR-stimulants, such as monophosphorylated lipid A, polyinosinic-polycytidylic acid, and CpG oligonucleotides, or a cocktail of four cytokines, IL1β, IL-6, TNF-α and Prostaglandin E2 (Castiello et al., 2011; de Jong et al., 2002; Han et al., 2009), to provide signals 2 and 3 to DCs. Fc-modified immune complexes could potentially provide all three signals, removing the need to optimize the timing for the adding of antigen (before or after the addition of the maturation cocktail, depending on whether antigen-internalization is required) and dosages of the different components; and also overcomes the issue of ensuring all four components reach the DCs with the correct timing in vivo. In other words, the modified Fc would render in vivo application of DC-targeted vaccines more feasible.

MoDCs treated with Fc-modified immune complexes consistently upregulated maturation marker expression in five out of six donors, and a sub-population of donors (60%) exhibit markedly increased CD8 T cell expansion. The differences are likely to be due to the level and timing of previous exposure to Ad5 for the donors. Donors with prior exposure to adenovirus may have memory T cells capable of responding to viral antigens in the absence of co-stimulatory molecule expression by DC. In this case, moDCs treated with virus alone would be expected to outperform moDCs treated with immune complexes, due to increased expression of viral proteins: at MOI 400 the replication-deficient Ad5 infects 69% of the moDC, likely leading to expression of viral proteins at a level equivalent to that of a replication-competent adenovirus at an MOI of 1 (Saha and Parks, 2017). Thus in the absence of antibodies (and therefore ADIN), there is a larger population of moDCs (69% versus 4% in the presence of antibody) producing viral proteins, albeit without upregulating their co-stimulatory markers, and able to stimulate memory CD8 T cells in the subpopulation of donors who have them. Importantly, prophylactic vaccines need to stimulate naïve T cells rather than memory T cells, since they are meant to protect individuals not having had prior exposure to the virus while therapeutic vaccines need to revive a virally-damped immune response, which means that the DC might need a 'boost' to upregulate their stimulatory status again. In both cases, the ability of the modified-Fc to enhance moDC-cross-priming of CD8 T cells is advantageous.

Ad5 immune complexes were used to demonstrate the potential of modified-Fc immune complexes to induce and enhance CD8 T cell responses to viral antigen, but these findings are of relevance to other pathogens and diseases. Ad5 immune complexes reach TRIM21 in the cytosol of moDC because adenoviruses release protein VI, which lyses the endosome (Wiethoff et al., 2005; Greber et al., 1993).

Antibody-antigen fusion proteins targeting DCs such as anti-DEC205-NY-ESO-1 (Dhodapkar et al., 2014) and anti-DEC-HIV gag (Bozzacco et al., 2007) have been shown to stimulate anti-cancer and anti-HIV CD8 T cell responses. Also, antibodies can simply be designed to target antigens of interest to form immune complexes that are taken into the DC via the Fc receptor. Fc receptor-mediated antigen internalization in DCs is known to be channelled to a special transport pathway which allows the antigen efficient access to the cytosol (Amigorena, 2002). HRP-anti-HRP immune complexes were detectable by HRP substrate (DAB) and anti-rabbit IgG Fabs suggesting that both antigen and antibody remains mostly intact in the cytosol (Rodriguez et al., 1999, Gros and Amigorena, 2019). Given that an Fc receptor (TRIM21) and an Ag-processing enzyme (proteasome) both exist in the cytosol, immune complexes may have privileged access to deliver themselves and their cargo completely intact to the cytosol.

In summary, the inventors have identified a readily-adaptable method of Fc modification for targeting endocytosed antigen in immune complexes to MHC class I cross-presentation pathway via TRIM21, and have shown its potential to provide all the signals necessary for the stimulation of a potent CD8 T cell and cytokine response to specific antigen.

Example 4: Further Fc Variants

Further variant Fc regions having improved affinity for TRIM21 as compared to wildtype human IgG1 Fc were identified.

Briefly, an Fc Phage display library was generated, essentially as described in Example 1.8, comprising 200 million Fc variants having amino acids randomised at positions 256, 433, 434, 436 and 440 of human IgG1.

The Fc Phage display was used in three biopanning experiments performed as described in Example 1.9, as summarised in Table 2 below. Binding to the PRYSPRY domain of TRIM21 was analysed by ELISA.

TABLE 2

Biopanning with an Fc Phage display library randomised at positions 256, 433, 434, 436 and 440 to identify variants with improved binding to TRIM21

| Expt | Biopanning conditions | Host cells for phage amplification | Host cells for Fc expression for ELISA | No. clones picked for ELISA | No. clones with improved binding to TRIM21 as determined by ELISA | No. of new sequences |
|---|---|---|---|---|---|---|
| 1 | Low stringency approach (3 rounds of panning) | TG1 | HB2151 | 94 | 4 (only 2 have PCR insert) | 2 |
| 2 | Low stringency approach (repeated pan 3) | TG1 | HB2151 | 24 | 11 | 8 |
| 3 | High stringency approach (2 rounds of panning) | XL1-Blue | XL1-Blue | 372 | 293 | 125 |

Figure 10:
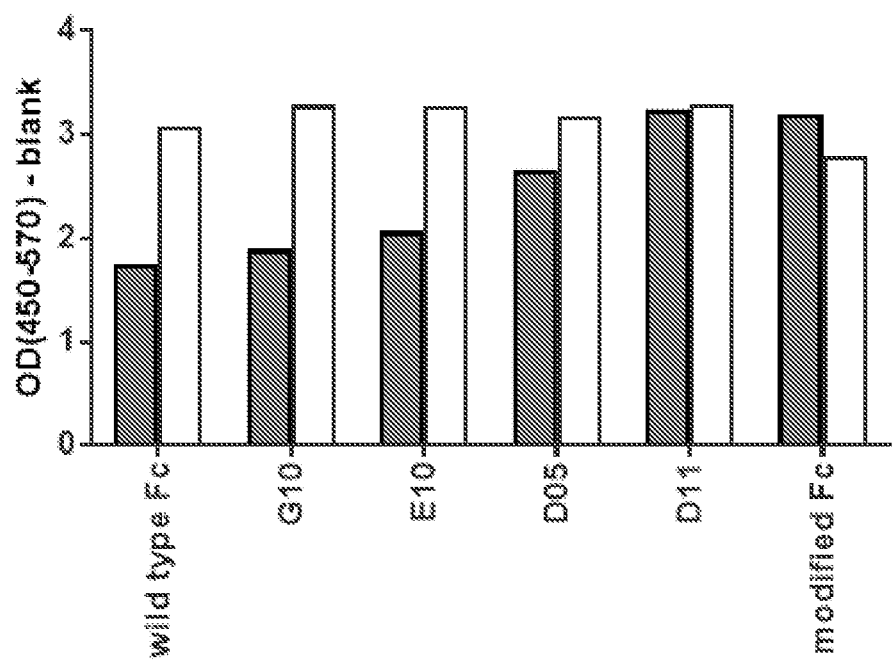
FIG. 10. Bar chart showing relative binding to TRIM21 PRYSPRY domain by Fc molecules having different sequences expressed from the indicated clones, as determined by ELISA. Binding by 4 clones identified by biopanning experiment 1 (see Example 4) to bind TRIM21 PRYSPRY domain with greater affinity than wildtype IgG1 Fc (wildtype Fc) is shown. Binding signal for PN04-90 Fc (modified Fc) is also shown. Filled bars show the signal for binding to 5 μg/ml biotinylated PRYSPRY domain. Open bars show the signal for binding to 5 μg/ml anti-FLAG.
Figure 11:
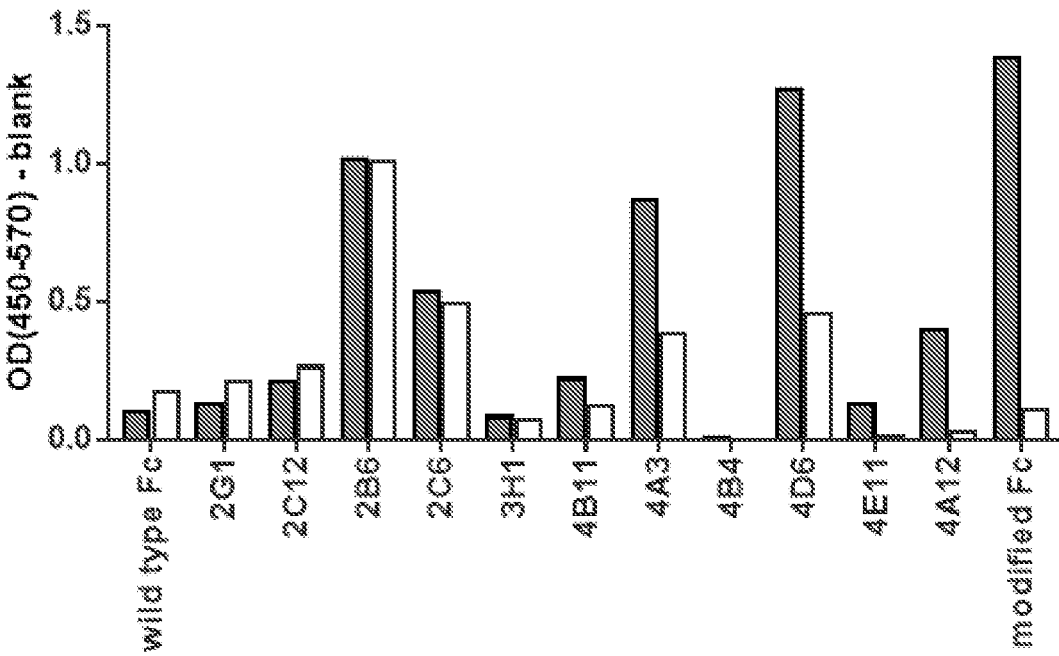
FIG. 11. Bar chart showing relative binding to TRIM21 PRYSPRY domain by Fc molecules having different sequences expressed from the indicated clones, as determined by ELISA. Binding by 11 clones identified by biopanning experiment 2 (see Example 4) to bind TRIM21 PRYSPRY domain with greater affinity than wildtype IgG1 Fc (wildtype Fc) is shown. Binding signal for PN04-90 Fc (modified Fc) is also shown. Filled bars show the signal for binding to 5 μg/ml biotinylated PRYSPRY domain. Open bars show the signal for binding to 5 μg/ml anti-FLAG.
Figure 12A:
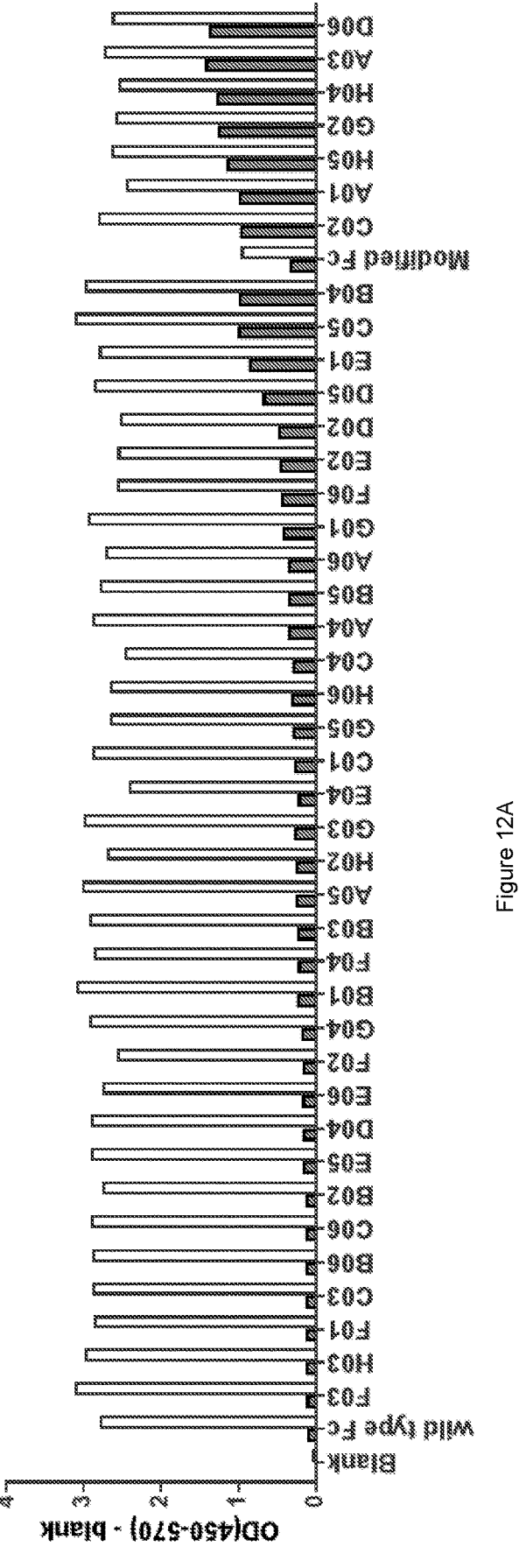
FIGS. 12A to 12H. Bar charts showing relative binding to TRIM21 PRYSPRY domain by Fc molecules having different sequences expressed from the indicated clones, as determined by ELISA. Binding by 293 clones identified by biopanning experiment 3 (see Example 4) to bind TRIM21 PRYSPRY domain with greater affinity than wildtype IgG1 Fc (wildtype Fc) is shown. Binding signal for PN04-90 Fc (modified Fc) is also shown. Filled bars show the signal for binding to 0.125 μg/ml biotinylated PRYSPRY domain. Open bars show the signal for binding to 5 μg/ml anti-FLAG. 12A to 12H show the results of different ELISAs.
Figure 12B:
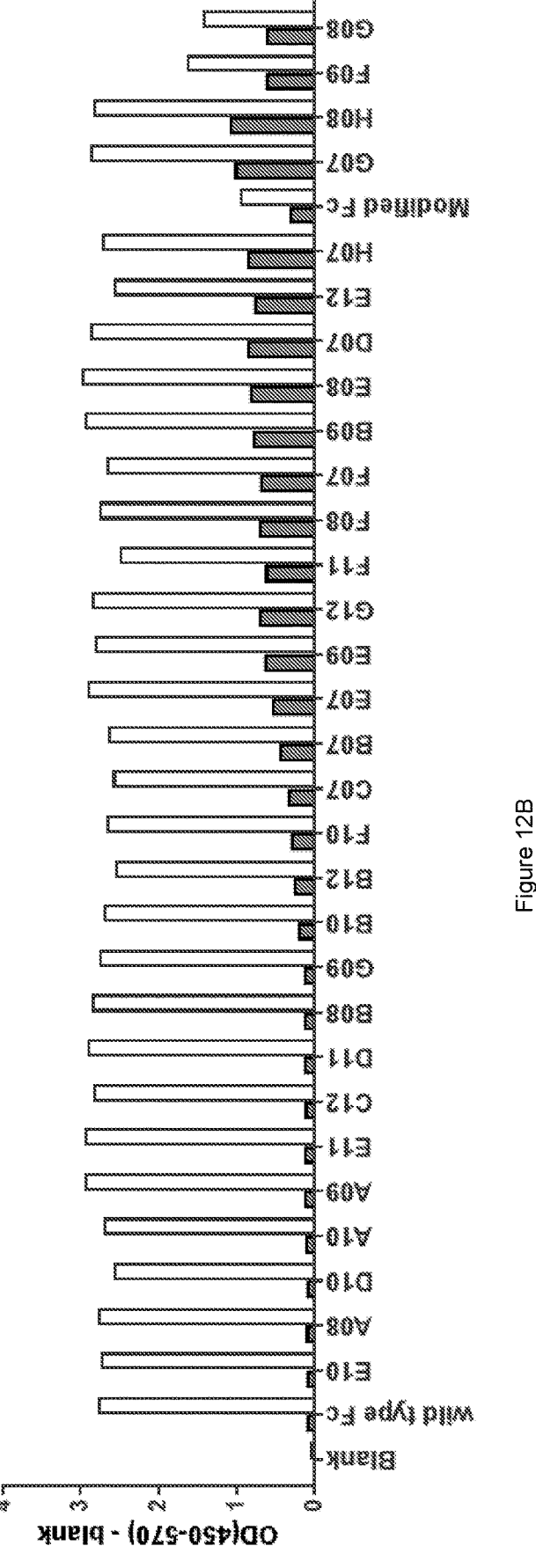
Figure 12C:
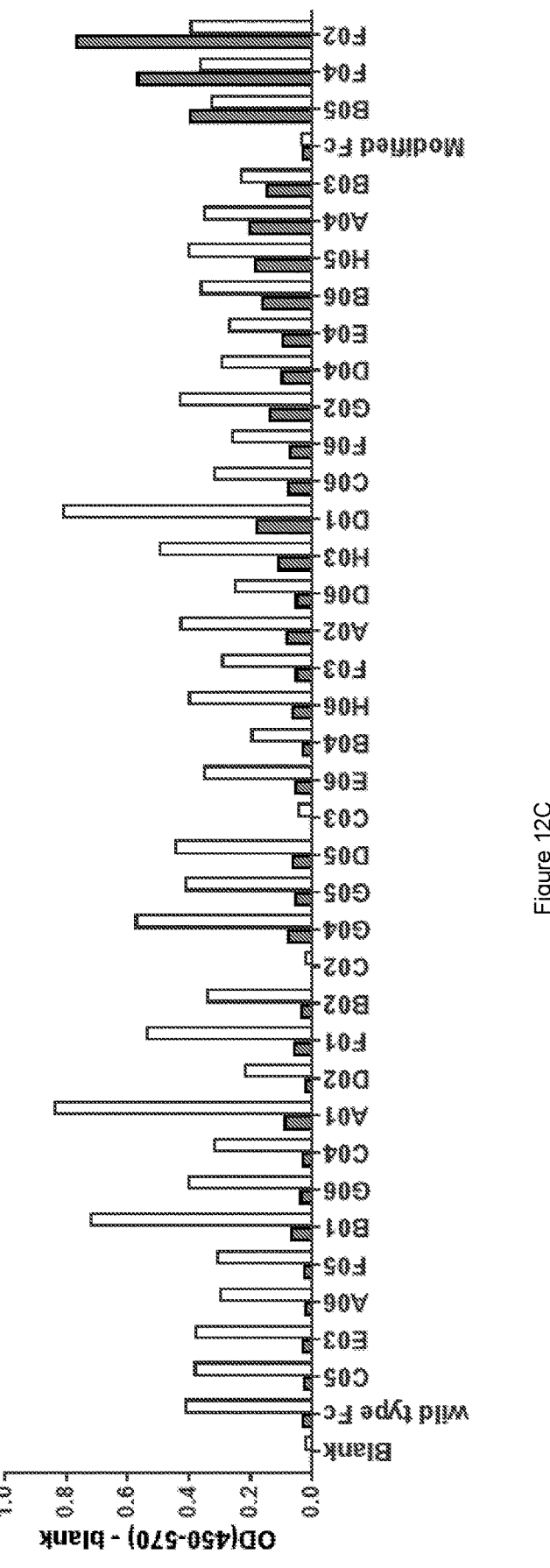
Figure 12D:
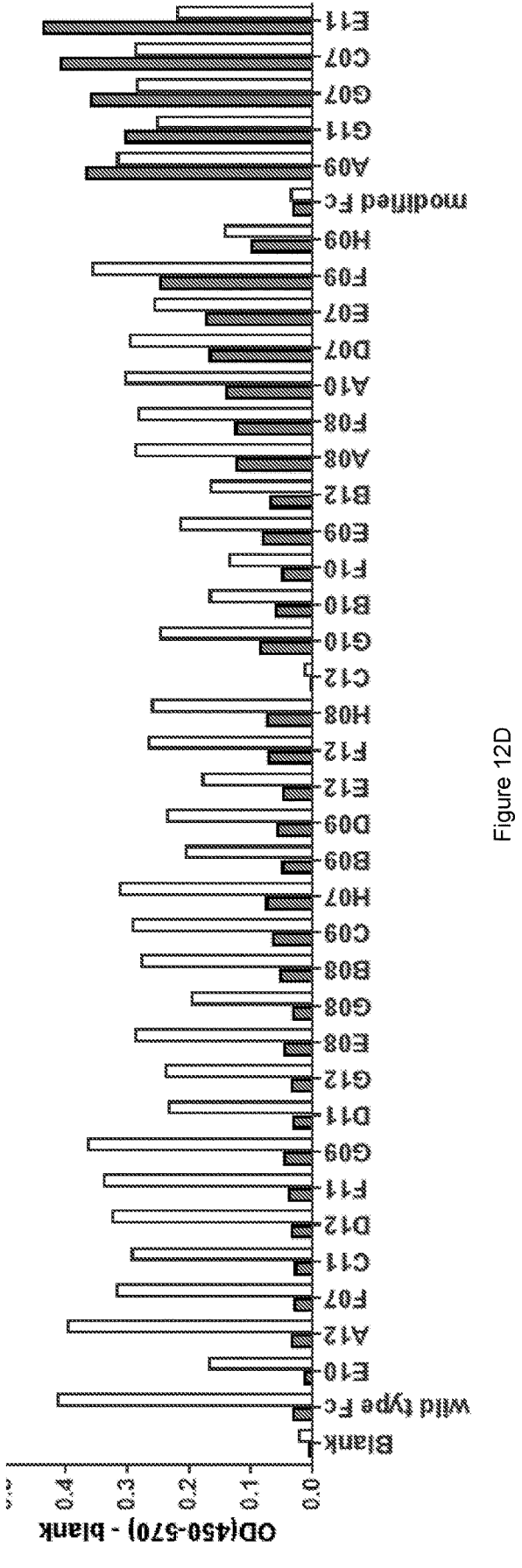
Figure 12E:
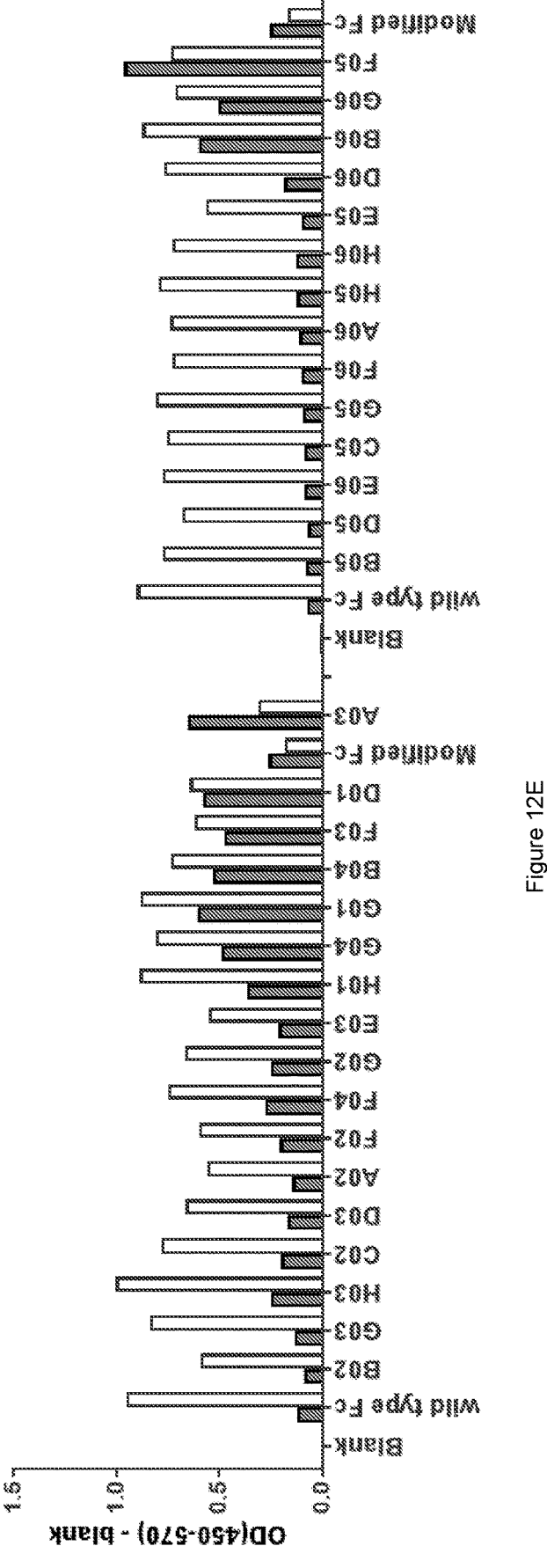
Figure 12F:
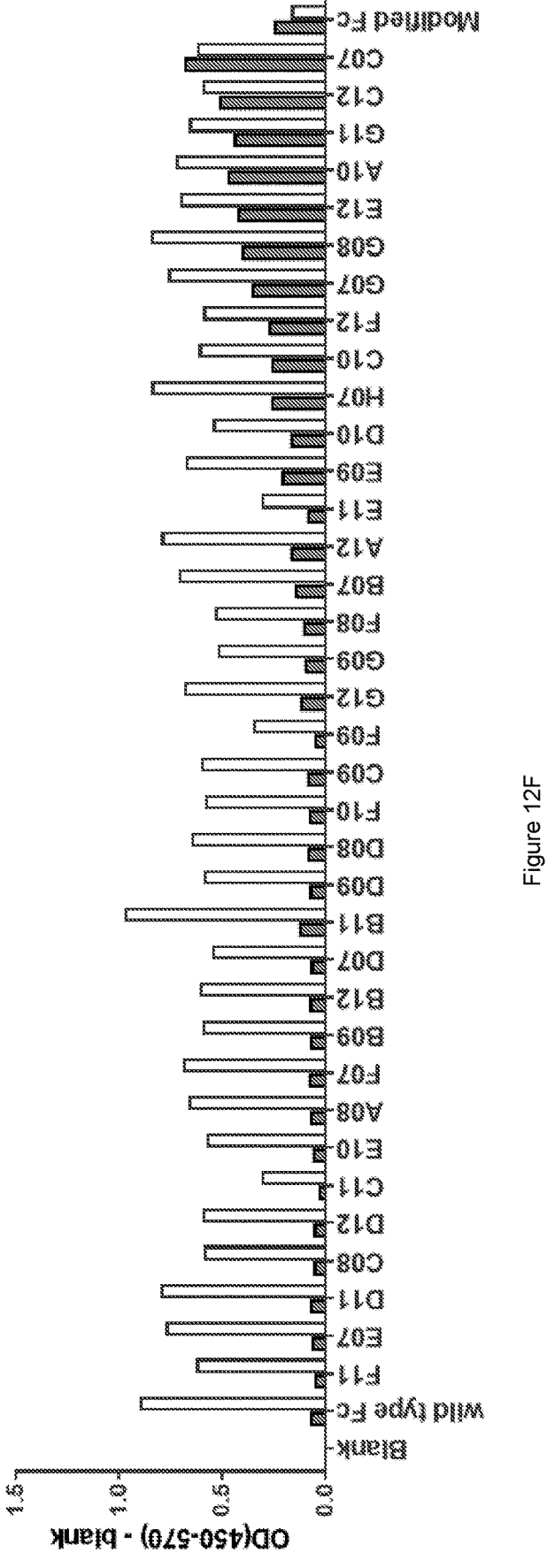
Figure 12G:
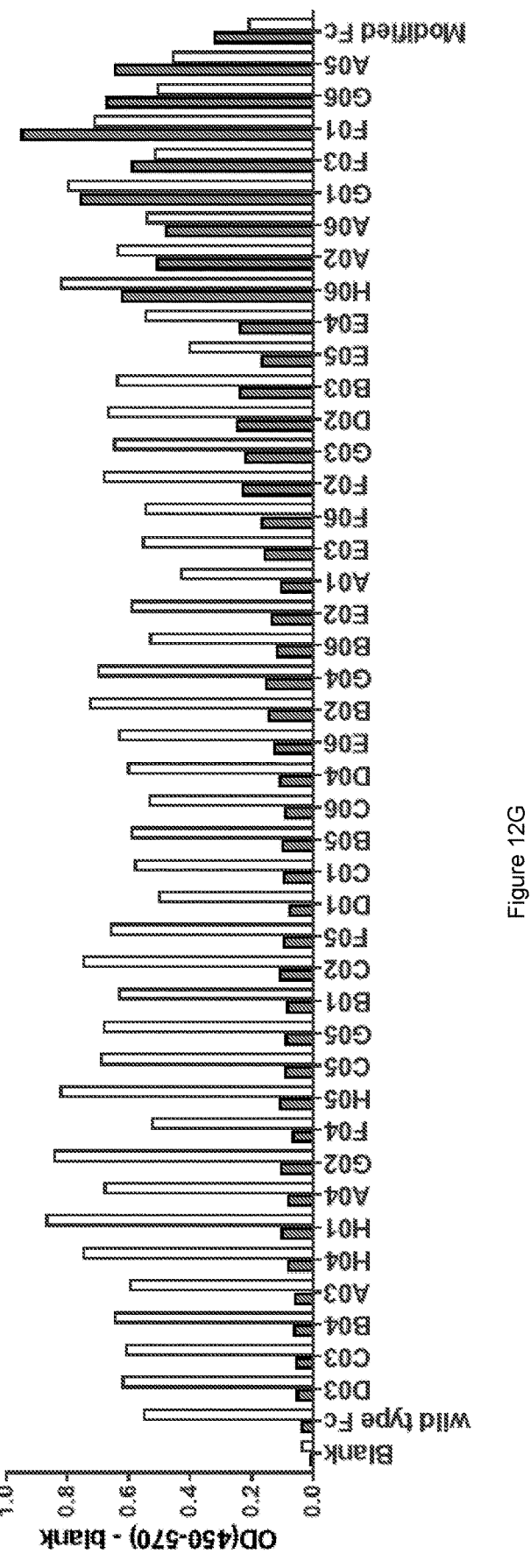
Figure 12H:
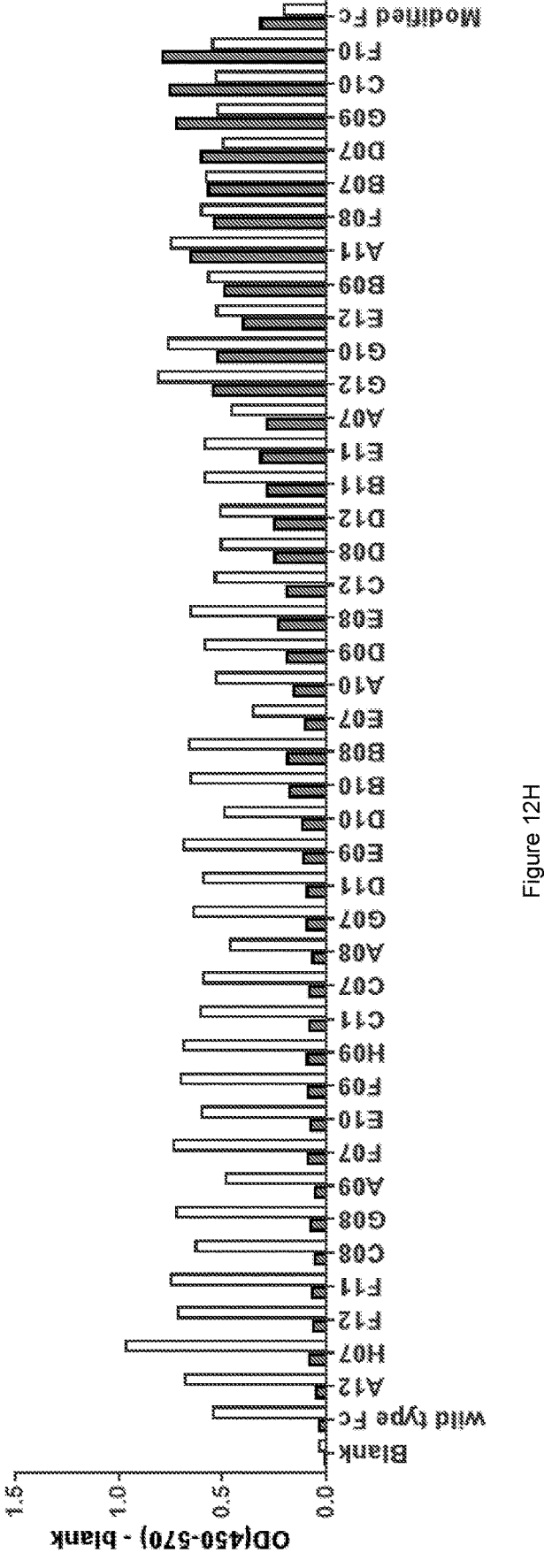

FIGS. 10 to 12 show the binding of the variant Fc regions to the PRYSPRY domain of TRIM21 (filled bars), and to anti-FLAG (open bars, the Fc regions include a FLAG tag).

FIG. 10 shows the results for the 4 clones obtained from biopanning experiment 1.

FIG. 11 shows the results for the 11 clones obtained from biopanning experiment 2.

FIGS. 12A to 12H show the results of the 293 clones obtained from biopanning experiment 3.

A total of 306 clones were identified as expressing Fc regions which bound to the PRYSPRY domain of TRIM21 with greater affinity to wildtype Fc.

The 306 clones were sequenced, and identifying 128 new, unique sequences (SNs. 1 to 8, 10 to 39, and 46 to 135 of FIG. 13A). A further sequence that was not identified in the biopanning experiments was also prepared (see SN.9 of FIG. 13A).

The 135 sequences were divided into 8 subgroups based on their sequence pattern (see FIGS. 13A and 13B). Sequences comprising the combinations of substitutions shown in Table 1 of Example 2.1 are also shown in FIG. 13 (SNs.40-45 of FIG. 13A).

Fc regions comprising sequences corresponding to 8 of the 129 new sequences were analysed for binding to TRIM21 PRYSPRY domain by Surface Plasmon Resonance, which was performed as described in Example 1.10.

The results are summarised below:

| SN (of FIG. 13) | Amino-acid (EU numbering system) | | | | | Ka (1/Ms) | Kd (1/s) | KD (M) |
|---|---|---|---|---|---|---|---|---|
| | 256 | 433 | 434 | 436 | 440 | | | |
| Wild-type IgG1 Fc | T | H | N | Y | S | $6.47 \times 10^5$ | $8.12 \times 10^{-2}$ | $1.26 \times 10^{-7}$ |
| 1 | P | S | H | Y | G | $7.05 \times 10^6$ | $3.88 \times 10^{-4}$ | $5.5 \times 10^{-11}$ |
| 2 | P | S | H | Y | S | $4.66 \times 10^6$ | $7.27 \times 10^{-4}$ | $1.56 \times 10^{-10}$ |
| 10 | P | V | H | Y | R | $5.15 \times 10^5$ | $4.60 \times 10^{-4}$ | $8.92 \times 10^{-10}$ |
| 9 | P | V | H | Y | S | $5.03 \times 10^6$ | $4.81 \times 10^{-4}$ | $9.57 \times 10^{-11}$ |
| 15 | P | H | H | Y | S | $7.84 \times 10^6$ | $1.65 \times 10^{-2}$ | $2.11 \times 10^{-9}$ |
| 32 | P | T | R | Y | S | $1.06 \times 10^6$ | $5.30 \times 10^{-4}$ | $4.98 \times 10^{-10}$ |

-continued

| SN (of FIG. | Amino-acid (EU numbering system) | | | | | Ka (1/Ms) | Kd (1/s) | KD (M) |
|---|---|---|---|---|---|---|---|---|
| 13) | 256 | 433 | 434 | 436 | 440 | (1/Ms) | (1/s) | (M) |
| 46 | P | V | R | Y | S | $7.30 \times 10^5$ | $1.24 \times 10^{-4}$ | $1.69 \times 10^{-10}$ |
| 92 | A | H | N | F | M | $3.94 \times 10^6$ | $1.45 \times 10^{-2}$ | $3.68 \times 10^{-9}$ |

Example 2.3 and FIG. 3 demonstrate that virus-antibody immune complexes comprising PN04-90 Fc, which binds to TRIM21 PRYSPRY domain with an affinity of $K_D$=4.25× $10^{-10}$ M, stimulate maturation of moDC to a greater extent than equivalent virus-antibody immune complexes comprising wildtype human IgG1 Fc.

The inventors next investigated whether the improved ability to stimulate moDC maturation was also possessed by virus-antibody immune complexes comprising variant Fc having a more modest improvement in the affinity of binding to TRIM21 PRYSPRY domain relative to wildtype human IgG1 Fc.

The inventors therefore investigated the co-stimulatory molecule expression by DCs following co-culture with immune complexes comprising V1 Fc. V1 Fc binds to TRIM21 PRYSPRY domain with an affinity of $K_D$=1.08× $10^{-8}$ M (see Example 2.1 above).

Figure 14:
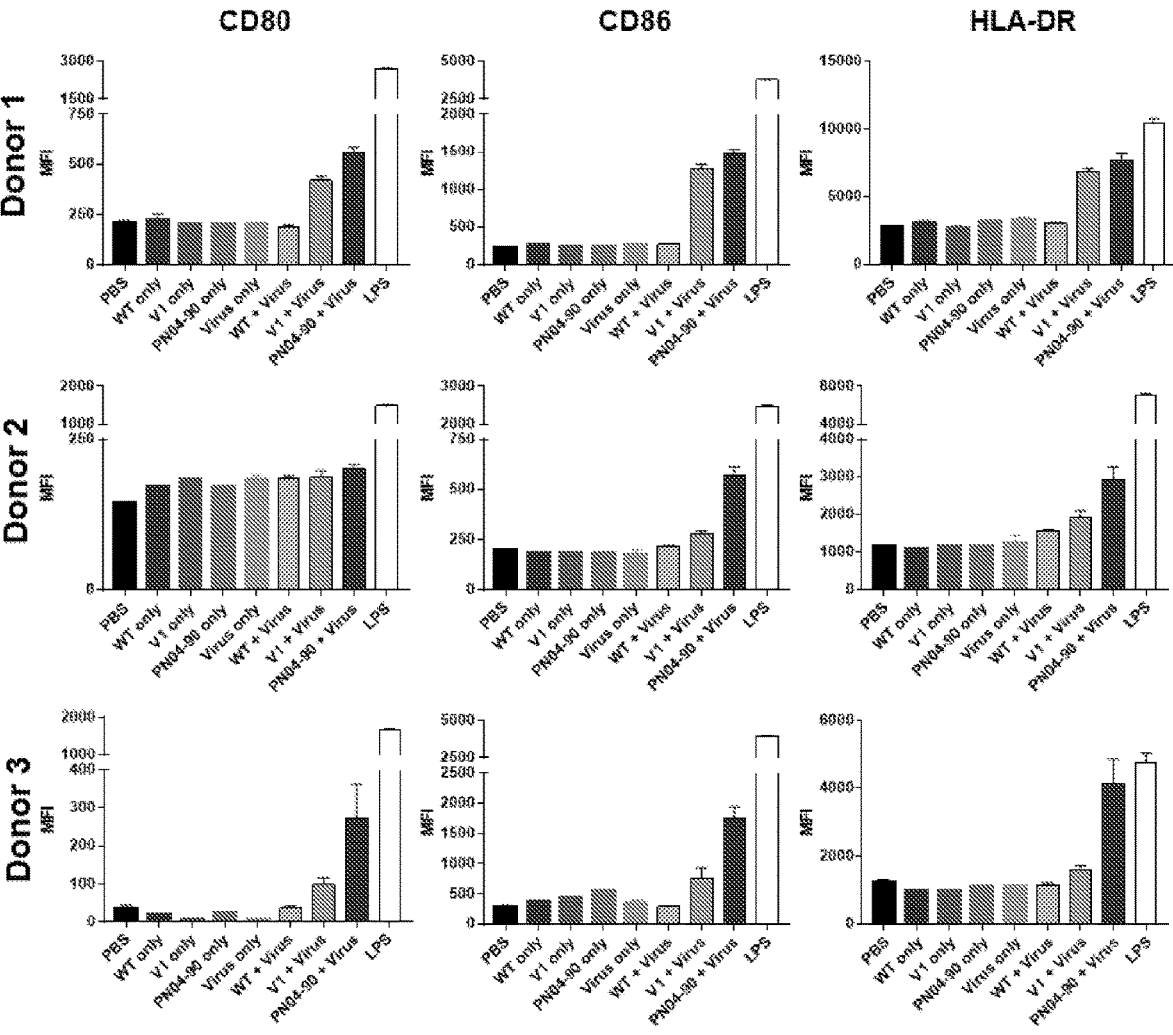
FIG. 14. Bar charts showing the results of analysis of the effect of Fc modification on moDC maturation. moDCs were treated with PBS, (PBS; negative control), Ad5-specific antibody comprising wildtype IgG1 Fc (WT only), Ad5-specific antibody comprising V1 Fc (V1 only), Ad5-specific antibody comprising PN04-90 Fc (PN04-90 only), Ad5 only (Virus only), Immunocomplex comprising Ad5-specific antibody comprising wildtype IgG1 Fc+Ad5 (WT+Virus), Immunocomplex comprising V1 Fc+Ad5 (V1+Virus), Immunocomplex comprising Ad5-specific antibody comprising PN04-90 Fc+Ad5 (PN04-90+Virus) or LPS only (LPS; positive control), and analysed 24 h after treatment for expression of moDC maturation markers. Bar chart showing the Median Fluorescent Intensities (MFIs) of the different maturation markers for 3 representative donors.

A moDC maturation assay was sperformed as described in Example 1.12, using moDCs from PBMCs obtained from three different donors. The following test conditions were investigated:

PBS only (PBS; negative control);
Ad5-specific antibody comprising wildtype IgG1 Fc (WT only)
Ad5-specific antibody comprising V1 Fc (V1 only)
Ad5-specific antibody comprising PN04-90 Fc (PN04-90 only)
Ad5 only (Virus only)
Immunocomplex comprising Ad5-specific antibody comprising wildtype IgG1 Fc+Ad5 (WT+Virus)
Immunocomplex comprising Ad5-specific antibody comprising V1 Fc+Ad5 (V1+Virus)
Immunocomplex comprising Ad5-specific antibody comprising PN04-90 Fc+Ad5 (PN04-90+Virus)
LPS only (LPS; positive control)
The results are shown in FIG. 14. V1 Fc+Ad5 complexes promoted significantly greater moDC maturation than wildtype IgG1 Fc+Ad5 complexes.

Based on these results it can be concluded that even a modest improvement in affinity for TRIM21 provides functional effects relevant to therapeutic and prophylactic applications of molecules and complexes comprising Fc regions.

REFERENCES

Amigorena, S. 2002. Fc Receptors and Cross-Presentation in Dendritic Cells. J. Exp. Med. 195:F1-F3. doi:10.1084/jem.20011925.

Baker, K., S.-W. Qiao, T. T. Kuo, V. G. Aveson, B. Platzer, J.-T. Andersen, I. Sandlie, Z. Chen, C. de Haar, W. I. Lencer, E. Fiebiger, and R. S. Blumberg. 2011. Neonatal Fc receptor for IgG (FcRn) regulates cross-presentation of IgG immune complexes by CD8-CD11 b+ dendritic cells. Proc. Natl. Acad. Sci. 108:9927-9932. doi:10.1073/pnas.1019037108.

Bozzacco, L., C. Trumpfheller, F. P. Siegal, S. Mehandru, M. Markowitz, M. Carrington, M. C. Nussenzweig, A. G. Piperno, and R. M. Steinman. 2007. DEC-205 receptor on dendritic cells mediates presentation of HIV gag protein to CD8+ T cells in a spectrum of human MHC I haplotypes. Proc Natl Acad Sci USA. 104:1289-1294. doi:10.1073/pnas.0610383104.

Castiello, L., M. Sabatino, P. Jin, C. Clayberger, F. M. Marincola, A. M. Krensky, and D. F. Stroncek. 2011. Monocyte-derived DC maturation strategies and related pathways: a transcriptional view. Cancer Immunol. Immunother. CII. 60:457-466. doi:10.1007/s00262-010-0954-6.Monocyte-derived.

Cheong, C., J. Choi, L. Vitale, L.-Z. He, C. Trumpfheller, L. Bozzacco, Y. Do, G. Nchinda, S. H. Park, D. B. Dandamudi, E. Shrestha, M. Pack, H.-W. Lee, T. Keler, R. M. Steinman, and C. G. Park. 2010. Improved cellular and humoral immune responses in vivo following targeting of HIV Gag to dendritic cells within human anti-human DEC205 monoclonal antibody. Blood. 116:3828-3838. doi:10.1182/blood-2010-06-288068.

Dhodapkar, M. V, M. Sznol, B. Zhao, D. Wang, R. D. Carvajal, M. L. Keohan, E. Chuang, R. E. Sanborn, J. Lutzky, J. Powderly, H. Kluger, S. Tejwani, J. Green, V. Ramakrishna, A. Crocker, L. Vitale, M. Yellin, T. Davis, and T. Keler. 2014. Induction of antigen-specific immunity with a vaccine targeting NY-ESO-1 to the dendritic cell receptor DEC-205. Sci. Transl. Med. 6:232ra51. doi:10.1126/scitranslmed.3008068.

Fan, W., D. Zhang, P. Qian, S. Qian, M. Wu, H. Chen, and X. Li. 2016. Swine TRIM21 restricts FMDV infection via an intracellular neutralization mechanism. Antiviral Res. 127:32-40. doi:10.1016/j.antiviral.2016.01.004.

Fechner, H., X. Wang, H. Wang, a Jansen, M. Pauschinger, H. Scherubl, J. M. Bergelson, H. P. Schultheiss, and W. Poller. 2000. Trans-complementation of vector replication versus Coxsackie-adenovirus-receptor overexpression to improve transgene expression in poorly permissive cancer cells. Gene Ther. 7:1954-68. doi:10.1038/sj.gt.3301321.

Fletcher, A. J., D. L. Mallery, R. E. Watkinson, C. F. Dickson, and L. C. James. 2015. Sequential ubiquitination and deubiquitination enzymes synchronize the dual sensor and effector functions of TRIM21. Proc. Natl. Acad. Sci. 112:10014-10019. doi:10.1073/pnas.1507534112.

Foss, S., R. E. Watkinson, A. Grevys, M. B. McAdam, M. Bern, L. S. Hoydahl, B. Dalhus, T. E. Michaelsen, I. Sandlie, L. C. James, and J. T. Andersen. 2016. TRIM21 Immune Signaling Is More Sensitive to Antibody Affinity Than Its Neutralization Activity. J. Immunol. 196:3452-3459. doi:10.4049/jimmunol.1502601.

Granelli-piperno, A., A. Golebiowska, C. Trumpfheller, F. P. Siegal, and R. M. Steinman. 2004. HIV-1-infected monocyte-derived dendritic cells do not undergo maturation but can elicit IL-10 production and T cell regulation. 101:7669-7674.

Greber, U. F., M. Willetts, P. Webster, and a Helenius. 1993. Stepwise dismantling of adenovirus 2 during entry into cells. Cell. 75:477-86.

Gros, M. and S. Amigorena. 2019. Regulation of Antigen Export to the Cytosol During Cross-Presentation. Front. Immunol. 10: 41. doi:10.3389/fimmu.2019.00041

Han, T. H., P. Jin, J. Ren, S. Slezak, F. M. Marincola, and D. F. Stroncek. 2009. Evaluation of Three Clinical Dendritic Cell Maturation Protocols Containing Lipopolysaccharide and Interferon-gamma. J. Immunother. 32:399-407. doi:10.1097/CJI.0b013e31819e1773.Evaluation.

James, L. C., A. H. Keeble, Z. Khan, D. a Rhodes, and J. Trowsdale. 2007. Structural basis for PRYSPRY-mediated tripartite motif (TRIM) protein function. Proc. Natl. Acad. Sci. U.S.A 104:6200-5. doi:10.1073/pnas.0609174104.

Joffre, O. P., E. Segura, A. Savina, and S. Amigorena. 2012. Cross-presentation by dendritic cells. Nat. Rev. Immunol. 12:557-569. doi:10.1038/nri3254.

de Jong, E. C., P. L. Vieira, P. Kalinski, J. H. N. Schuite-maker, Y. Tanaka, E. A. Wierenga, M. Yazdanbakhsh, and M. L. Kapsenberg. 2002. Microbial Compounds Selectively Induce Th1 Cell-Promoting or Th2 Cell-Promoting Dendritic Cells In Vitro with Diverse Th Cell-Polarizing Signals. J. Immunol. 168:1704-1709. doi:10.4049/jimmunol.168.4.1704.

Lebre, M. C., T. Burwell, P. L. Vieira, J. Lora, A. J. Coyle, M. L. Kapsenberg, B. E. Clausen, and E. C. De Jong. 2005. Differential expression of inflammatory chemokines by Th1- and Th2-cell promoting dendritic cells: A role for different mature dendritic cell populations in attracting appropriate effector cells to peripheral sites of inflammation. Immunol. Cell Biol. 83:525-535. doi: 10.1111/j.1440-1711.2005.01365.x.

Lenart, M., M. Rutkowska-Zapata, R. Szatanek, K. Weglarczyk, M. Stec, K. Bukowska-Strakova, A. Gruca, J. Czyz, and M. Siedlar. 2017. Alterations of TRIM21-mRNA expression during monocyte maturation. Immunobiology. 222:494-498. doi:10.1016/j.imbio.2016.10.016.

Liu, B., A. M. Woltman, H. L. A. Janssen, and A. Boonstra. 2009. Modulation of dendritic cell function by persistent viruses. J. Leukoc. Biol. 85:205-214. doi:10.1189/jlb.0408241.

Mallery, D. L., W. a McEwan, S. R. Bidgood, G. J. Towers, C. M. Johnson, and L. C. James. 2010. Antibodies mediate intracellular immunity through tripartite motif-containing 21 (TRIM21). Proc. Natl. Acad. Sci. U.S.A 107: 19985-90. doi:10.1073/pnas.1014074107.

McEwan, W. A., B. Falcon, M. Vaysburd, D. Clift, A. L. Oblak, B. Ghetti, M. Goedert, and L. C. James. 2017. Cytosolic Fc receptor TRIM21 inhibits seeded tau aggregation. Proc. Natl. Acad. Sci. 114:201607215. doi: 10.1073/pnas.1607215114.

McEwan, W. A., J. C. H. Tam, R. E. Watkinson, S. R. Bidgood, D. L. Mallery, and L. C. James. 2013. Intracellular antibody-bound pathogens stimulate immune signaling via the Fc receptor TRIM21. Nat. Immunol. 14:327-336. doi:10.1038/ni.2548.

McEwan, W. a, D. L. Mallery, D. a Rhodes, J. Trowsdale, and L. C. James. 2011. Intracellular antibody-mediated immunity and the role of TRIM21. Bioessays. 33:803-9. doi:10.1002/bies.201100093.

Newton, K. R., E. Sala-Soriano, H. Varsani, J. R. Stephenson, D. Goldblatt, and L. R. Wedderburn. 2008. Human dendritic cells infected with an adenoviral vector suppress proliferation of autologous and allogeneic T cells. Immunology. 125:469-479. doi:10.1111/j.1365-2567.2008.02860.x.

Rakebrandt, N., S. Lentes, H. Neumann, L. C. James, and P. Neumann-Staubitz. 2014. Antibody- and TRIM21-dependent intracellular restriction of Salmonella enterica. Pathog. Dis. 72:131-137. doi:10.11111/2049-632X.12192.

Regnault, A., D. Lankar, V. Lacabanne, A. Rodriguez, C. Thery, M. Rescigno, T. Saito, S. Verbeek, C. Bonnerot, P. Ricciardi-Castagnoli, and S. Amigorena. 1999. Fcgamma receptor-mediated induction of dendritic cell maturation and major histocompatibility complex class I-restricted antigen presentation after immune complex internalization. J Exp Med. 189:371-380. doi:9892619.

Rodriguez, A., A. Regnault, M. Kleijmeer, P. Ricciardi-Castagnoli, and S. Amigorena. 1999. Selective transport of internalized antigens to the cytosol for MHC class I presentation in dendritic cells. Nat. Cell Biol. 1:362-8. doi:10.1038/14058.

Saha, B., and R. J. Parks. 2017. Human adenovirus type 5 vectors deleted of early region 1 (E1) undergo limited expression of early replicative E2 proteins and DNA replication in non-permissive cells. PLoS One. 12:e0181012. doi:10.1371/journal.pone.0181012.

Saito, K., M. Ait-goughoulte, S. M. Truscott, K. Meyer, A. Blazevic, G. Abate, R. B. Ray, D. F. Hoft, and R. Ray. 2008. Hepatitis C Virus Inhibits Cell Surface Expression of HLA-DR, Prevents Dendritic Cell Maturation, and Induces Interleukin-10 Production. J. Virol. 82:3320-3328. doi:10.1128/JVI.02547-07.

Sallusto, F., C. Mackay, and A. Lanzavecchia. 2000. The role of chemokine receptors in primary, effector, and memory immune responses. Annu. Rev. Immunol. 18:529-560.

Sallusto, F., B. Palermo, D. Lenig, M. Miettinen, S. Matikainen, I. Julkunen, R. Forster, R. Burgstahler, M. Lipp, and A. Lanzavecchia. 1999. Distinct patterns and kinetics of chemokine production regulate dendritic cell function. Eur. J. Immunol. 29:1617-1625. doi:10.1002/(SICI)1521-4141(199905)29:05<1617::AID-IMMU1617>3.0.CO;2-3.

Tonikian, R., Y. Zhang, C. Boone, and S. S. Sidhu. 2007. Identifying specificity profiles for peptide recognition modules from phage-displayed peptide libraries. Nat. Protoc. 2:1368-1386. doi:10.1038/nprot.2007.151.

Varghese, R., Y. Mikyas, P. L. Stewart, and R. Ralston. 2004a. Postentry Neutralization of Adenovirus Type 5 by an Antihexon Antibody. J. Virol. 78:12320-12332. doi: 10.1128/JVI.78.22.12320.

Varghese, R., Y. Mikyas, P. L. Stewart, and R. Ralston. 2004b. Postentry Neutralization of Adenovirus Type 5 by an Antihexon Antibody Postentry Neutralization of Adenovirus Type 5 by an Antihexon Antibody. 78:12320-12332. doi:10.1128/JVI.78.22.12320.

Watkinson, R. E., W. A. McEwan, J. C. H. Tam, M. Vaysburd, and L. C. James. 2015. TRIM21 Promotes cGAS and RIG-1 Sensing of Viral Genomes during Infection by Antibody-Opsonized Virus. PLoS Pathog. 11:1-20. doi:10.1371/journal.ppat.1005253.

Wiethoff, C. M., H. Wodrich, L. Gerace, and G. R. Nemerow. 2005. Adenovirus Protein VI Mediates Membrane Disruption following Capsid Disassembly. 79:1992-2000. doi:10.1128/JVI.79.4.1992.

Xia, Z. P., L. Sun, X. Chen, G. Pineda, X. Jiang, A. Adhikari, W. Zeng, and Z. J. Chen. 2009. Direct activation of protein kinases by unanchored polyubiquitin chains. Nature. 461:114-119. doi:10.1038/nature08247.

Zhang, Z., M. Bao, N. Lu, L. Weng, B. Yuan, and Y.-J. Liu. 2013. The E3 ubiquitin ligase TRIM21 negatively regulates the innate immune response to intracellular double-stranded DNA. Nat. Immunol. 14:172-8. doi:10.1038/ni.2492.

Zimmermann, M., C. Flechsig, N. La Monica, M. Tripodi, G. Adler, N. Dikopoulos, and L. Sapienza. 2008. Hepatitis C virus core protein impairs in vitro priming of specific T cell responses by dendritic cells and hepatocytes q. 48:51-60. doi:10.1016/j.jhep.2007.08.008.

What is claimed is:

1. A polypeptide comprising: an amino acid sequence having at least 98% sequence identity to SEQ ID NO:71, wherein the polypeptide comprises the following residues at positions numbered relative to SEQ ID NO:71: P, A, T, V, G, I, K, N or S at the residue corresponding to position 29; S, V, H, A, D, P, Q, T or I at the residue corresponding to position 206; H, R, N, I, L or M at the residue corresponding to position 207; Y, F, T, L, W or S at the residue corresponding to position 209; and S, G, I, R, Y, N, V, T, P, D, W, M, A, K, F, E or C at the residue corresponding to position 213; wherein the amino acid sequence of the polypeptide is not identical to the amino acid sequence of a constituent polypeptide of an Fc region of a wildtype immunoglobulin.

2. The polypeptide according to claim 1, wherein the polypeptide is a constituent polypeptide of an Fc region.

3. A method of treating an infectious disease, cancer, or an autoimmune disease, comprising administering to a subject a therapeutically effective amount of:

an antigen-binding molecule comprising an antigen-binding domain capable of binding to a target antigen and an Fc region, wherein the Fc region comprises an Fc region according to claim 2; or an immunogen comprising an antigenic sequence of a target antigen and an Fc region, wherein the Fc region comprises an Fc region according to claim 2.

4. The polypeptide according to claim 1, wherein the polypeptide further comprises an I at position 26, and an H at position 208.

* * * * *